US011976096B2

(12) United States Patent
McCoy et al.

(10) Patent No.: US 11,976,096 B2
(45) **Date of Patent: *May 7, 2024**

(54) ANTIBODY-EVADING VIRUS VECTORS

(71) Applicant: Ginkgo Bioworks, Inc., Boston, MA (US)

(72) Inventors: Daniel McCoy, Durham, NC (US); Garrett E. Berry, Durham, NC (US)

(73) Assignee: Ginkgo Bioworks, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/372,833

(22) Filed: Sep. 26, 2023

(65) Prior Publication Data

US 2024/0051998 A1 Feb. 15, 2024

Related U.S. Application Data

(63) Continuation of application No. 17/045,091, filed as application No. PCT/US2019/025617 on Apr. 3, 2019.

(60) Provisional application No. 62/819,388, filed on Mar. 15, 2019, provisional application No. 62/776,814, filed on Dec. 7, 2018, provisional application No. 62/652,111, filed on Apr. 3, 2018.

(51) Int. Cl.

| | |
|---|---|
| *C07K 14/005* | (2006.01) |
| *A61K 31/7088* | (2006.01) |
| *A61K 38/46* | (2006.01) |
| *A61K 48/00* | (2006.01) |
| *A61P 1/16* | (2006.01) |
| *C12N 7/00* | (2006.01) |
| *C12N 15/86* | (2006.01) |

(52) U.S. Cl.
CPC ........ *C07K 14/005* (2013.01); *A61K 31/7088* (2013.01); *A61K 38/465* (2013.01); *A61P 1/16* (2018.01); *C12N 7/00* (2013.01); *C12N 15/86* (2013.01); *A61K 48/00* (2013.01); *C12N 2750/14122* (2013.01); *C12N 2750/14143* (2013.01); *C12N 2750/14171* (2013.01)

(58) Field of Classification Search
CPC ............. C07K 14/005; A61K 31/7088; A61K 38/465; A61K 48/00; A61P 1/16; C12N 7/00; C12N 15/86; C12N 2750/14122; C12N 2750/14143; C12N 2750/14171
See application file for complete search history.

(56) References Cited

U.S. PATENT DOCUMENTS

| | | | |
|---|---|---|---|
| 4,039,388 | A | 8/1977 | Gal et al. |
| 4,501,729 | A | 2/1985 | Boucher et al. |
| 4,968,603 | A | 11/1990 | Slamon et al. |
| 5,139,941 | A | 8/1992 | Muzyczka et al. |
| 5,328,470 | A | 7/1994 | Nabel et al. |
| 5,399,346 | A | 3/1995 | Anderson et al. |
| 5,478,745 | A | 12/1995 | Samulski et al. |
| 5,658,776 | A | 8/1997 | Flotte et al. |
| 5,686,240 | A | 11/1997 | Schuchman et al. |
| 5,863,541 | A | 1/1999 | Samulski et al. |
| 5,869,248 | A | 2/1999 | Yuan et al. |
| 5,877,022 | A | 3/1999 | Stinchcomb et al. |
| 5,882,652 | A | 3/1999 | Valdes et al. |
| 5,905,040 | A | 5/1999 | Mazzara et al. |
| 5,916,563 | A | 6/1999 | Young et al. |
| 5,962,313 | A | 10/1999 | Podsakoff et al. |
| 6,013,487 | A | 1/2000 | Mitchell |
| 6,040,183 | A | 3/2000 | Ferrari et al. |
| 6,083,702 | A | 7/2000 | Mitchell et al. |
| 6,093,570 | A | 7/2000 | Ferrari et al. |
| 6,156,303 | A | 12/2000 | Russell et al. |
| 6,180,613 | B1 | 1/2001 | Kaplitt et al. |
| 6,426,198 | B1 | 7/2002 | Carstea et al. |
| 6,468,524 | B1 | 10/2002 | Chiorini et al. |
| 6,468,798 | B1 | 10/2002 | Debs et al. |
| 6,503,888 | B1 | 1/2003 | Kaplitt et al. |
| 6,544,785 | B1 | 4/2003 | Palese et al. |
| 6,562,958 | B1 | 5/2003 | Breton et al. |
| 6,733,757 | B2 | 5/2004 | Patel et al. |
| 6,822,071 | B1 | 11/2004 | Stephens et al. |
| 6,962,815 | B2 | 11/2005 | Bartlett |
| 6,984,517 | B1 | 1/2006 | Chiorini et al. |
| 7,045,675 | B2 | 5/2006 | Carstea et al. |
| 7,071,172 | B2 | 7/2006 | McCown et al. |
| 7,105,345 | B2 | 9/2006 | Wilson et al. |

(Continued)

FOREIGN PATENT DOCUMENTS

| | | | |
|---|---|---|---|
| EP | 1033405 | A2 | 9/2000 |
| EP | 1777296 | A2 | 4/2007 |

(Continued)

OTHER PUBLICATIONS

ACS on STN, BD Registry, 1182714-10-8 [online] [retrieved on Apr. 30, 2019], 2009215879, Aug. 29, 2009, SEQ ID No. 7, 1 page.

ACS on STN, BD Registry, 1182714-97-1 [online] [retrieved on Apr. 30, 2019], 2009215879, Aug. 27, 2009, SEQ ID No. 210, 1 page.

(Continued)

*Primary Examiner* — Arthur S Leonard

*Assistant Examiner* — Josephine M Gonzales

(74) *Attorney, Agent, or Firm* — Foley Hoag LLP; Brendan T. Jones; Tracy L. Vrablik

(57) ABSTRACT

The present disclosure provides recombinant AAV capsid proteins comprising a modification in the amino acid sequence and virus vectors comprising the recombinant AAV capsid proteins. The disclosure also provides methods of administering the virus vectors and vims capsids of the disclosure to a cell or to a subject in vivo.

20 Claims, 8 Drawing Sheets

Specification includes a Sequence Listing.

(56) References Cited

U.S. PATENT DOCUMENTS

| | | |
|---|---|---|
| 7,198,951 B2 | 4/2007 | Gao et al. |
| 7,201,898 B2 | 4/2007 | Monahan et al. |
| 7,214,786 B2 | 5/2007 | Kovalic et al. |
| 7,252,997 B1 | 8/2007 | Hallek et al. |
| 7,259,151 B2 | 8/2007 | Arbetman et al. |
| 7,282,199 B2 | 10/2007 | Gao et al. |
| 7,314,912 B1 | 1/2008 | Hallek et al. |
| 7,473,531 B1 | 1/2009 | Domon et al. |
| 7,588,772 B2 | 9/2009 | Kay et al. |
| 7,712,893 B2 | 5/2010 | Dobashi |
| 7,718,424 B2 | 5/2010 | Chiorini et al. |
| 7,749,492 B2 | 7/2010 | Bartlett et al. |
| 7,777,097 B2 | 8/2010 | Glazebrook et al. |
| 7,790,449 B2 | 9/2010 | Gao et al. |
| 7,867,484 B2 | 1/2011 | Samulski et al. |
| 7,892,809 B2 * | 2/2011 | Bowles ............... A61P 9/04 435/235.1 |
| 7,906,111 B2 | 3/2011 | Wilson et al. |
| 8,067,014 B2 * | 11/2011 | Kay et al. |
| 8,299,321 B2 | 10/2012 | Cao |
| 8,318,480 B2 | 11/2012 | Gao et al. |
| 8,343,764 B2 | 1/2013 | Abad et al. |
| 8,445,267 B2 | 5/2013 | Zhong et al. |
| 8,628,966 B2 | 1/2014 | Chatterjee et al. |
| 8,664,475 B2 | 3/2014 | Puzio et al. |
| 8,679,837 B2 | 3/2014 | Zolotukhin et al. |
| 8,734,809 B2 | 5/2014 | Gao et al. |
| 8,802,440 B2 | 8/2014 | Zhong et al. |
| 8,889,641 B2 | 11/2014 | Asokan et al. |
| 8,906,387 B2 | 12/2014 | Kay et al. |
| 8,906,675 B2 | 12/2014 | Gao et al. |
| 8,927,514 B2 | 1/2015 | Chatterjee et al. |
| 8,952,217 B2 | 2/2015 | Puzio et al. |
| 8,962,332 B2 | 2/2015 | Gao et al. |
| 9,012,224 B2 | 4/2015 | Bowles et al. |
| 9,066,966 B2 | 6/2015 | Puccio et al. |
| 9,157,098 B2 | 10/2015 | Zhong et al. |
| 9,409,953 B2 | 8/2016 | Asokan et al. |
| 9,441,244 B2 | 9/2016 | Schaffer et al. |
| 9,475,845 B2 | 10/2016 | Asokan et al. |
| 9,567,376 B2 | 2/2017 | Cronin et al. |
| 9,585,971 B2 | 3/2017 | Deverman et al. |
| 9,587,250 B2 | 3/2017 | Gao et al. |
| 9,598,468 B2 | 3/2017 | Weigel-Van Aken et al. |
| 9,611,302 B2 | 4/2017 | Srivastava et al. |
| 9,623,120 B2 | 4/2017 | Chatterjee et al. |
| 9,677,088 B2 | 6/2017 | Nakai et al. |
| 9,677,089 B2 | 6/2017 | Gao et al. |
| 9,683,268 B2 | 6/2017 | Barouch et al. |
| 9,695,220 B2 | 7/2017 | Vandenberghe et al. |
| 9,719,070 B2 | 8/2017 | Vandenberghe et al. |
| 9,725,485 B2 | 8/2017 | Srivastava et al. |
| 9,737,618 B2 | 8/2017 | Wilson et al. |
| 9,737,619 B2 | 8/2017 | Ansell et al. |
| 9,775,918 B2 | 10/2017 | Zhong et al. |
| 9,777,291 B2 | 10/2017 | Chatterjee et al. |
| 9,783,825 B2 | 10/2017 | Chatterjee et al. |
| 9,790,472 B2 | 10/2017 | Gao et al. |
| 9,803,218 B2 | 10/2017 | Chatterjee et al. |
| 9,834,789 B2 | 12/2017 | Chatterjee et al. |
| 9,839,696 B2 | 12/2017 | Chatterjee et al. |
| 9,879,275 B2 | 1/2018 | Nadzan et al. |
| 9,890,396 B2 | 2/2018 | Chatterjee et al. |
| 9,909,142 B2 | 3/2018 | Yazicioglu et al. |
| 9,920,097 B2 | 3/2018 | Zhong et al. |
| 9,944,908 B2 | 4/2018 | Vatèn et al. |
| 9,976,157 B2 | 5/2018 | Poraty-Gavra et al. |
| 10,011,640 B2 | 7/2018 | Srivastava et al. |
| 10,072,251 B2 | 9/2018 | Gao et al. |
| 10,077,291 B2 | 9/2018 | Asokan et al. |
| 10,081,659 B2 | 9/2018 | Chiorini et al. |
| 10,119,125 B2 | 11/2018 | Vandenberghe et al. |
| 10,214,566 B2 | 2/2019 | Schaffer et al. |
| 10,337,027 B2 | 7/2019 | Puccio et al. |
| 10,369,193 B2 | 8/2019 | Passini et al. |
| 10,385,320 B2 | 8/2019 | Kay et al. |
| 10,392,632 B2 | 8/2019 | Wright et al. |
| 10,406,244 B2 | 9/2019 | Kay et al. |
| 10,414,803 B2 * | 9/2019 | Nathwani ............... C12N 15/86 |
| 10,426,844 B2 | 10/2019 | Agbandje-McKenna et al. |
| 10,526,627 B2 | 1/2020 | Skuratowicz et al. |
| 10,668,094 B2 | 6/2020 | Karlish et al. |
| 10,745,447 B2 | 8/2020 | Asokan et al. |
| 10,907,176 B2 | 2/2021 | Asokan et al. |
| 11,077,128 B2 | 8/2021 | Karlish et al. |
| 11,208,438 B2 | 12/2021 | Asokan et al. |
| 11,332,727 B2 * | 5/2022 | Mali ................... C12N 15/86 |
| 2002/0192189 A1 | 12/2002 | Xiao et al. |
| 2003/0017131 A1 | 1/2003 | Park et al. |
| 2003/0053990 A1 | 3/2003 | Rabinowitz et al. |
| 2003/0225017 A1 | 12/2003 | Murdin et al. |
| 2004/0013645 A1 | 1/2004 | Monahan et al. |
| 2004/0031072 A1 | 2/2004 | La Rosa et al. |
| 2004/0071659 A1 | 4/2004 | Chang et al. |
| 2004/0166519 A1 | 8/2004 | Cargill et al. |
| 2004/0214272 A1 | 10/2004 | La Rosa et al. |
| 2005/0287122 A1 | 12/2005 | Bartlett et al. |
| 2006/0107345 A1 | 5/2006 | Alexandrov et al. |
| 2006/0123505 A1 | 6/2006 | Kikuchi et al. |
| 2006/0171926 A1 | 8/2006 | Passini et al. |
| 2006/0236419 A1 | 10/2006 | La Rosa et al. |
| 2007/0015238 A1 | 1/2007 | Snyder et al. |
| 2007/0124833 A1 | 5/2007 | Abad et al. |
| 2007/0196338 A1 | 8/2007 | Samulski et al. |
| 2007/0243526 A1 | 10/2007 | Kay et al. |
| 2008/0229439 A1 | 9/2008 | La Rosa et al. |
| 2009/0215879 A1 | 8/2009 | Diprimio et al. |
| 2009/0221620 A1 | 9/2009 | Luke et al. |
| 2009/0275107 A1 | 11/2009 | Lock et al. |
| 2009/0317417 A1 | 12/2009 | Vandenberghe et al. |
| 2010/0037352 A1 | 2/2010 | Alexandrov et al. |
| 2010/0047174 A1 | 2/2010 | Kay et al. |
| 2010/0095387 A1 | 4/2010 | Smith et al. |
| 2011/0061124 A1 | 3/2011 | Nadzan et al. |
| 2011/0067143 A2 | 3/2011 | Rosa et al. |
| 2011/0124048 A1 | 5/2011 | Yun |
| 2011/0131679 A2 | 6/2011 | Rosa et al. |
| 2011/0209246 A1 | 8/2011 | Kovalic et al. |
| 2011/0214206 A1 | 9/2011 | La Rosa et al. |
| 2011/0236353 A1 | 9/2011 | Wilson et al. |
| 2011/0294218 A1 | 12/2011 | Chatterjee et al. |
| 2012/0009268 A1 | 1/2012 | Asokan et al. |
| 2012/0137379 A1 | 5/2012 | Gao et al. |
| 2012/0216318 A1 | 8/2012 | La Rosa et al. |
| 2012/0255046 A1 | 10/2012 | Kay et al. |
| 2012/0322861 A1 | 12/2012 | Byrne et al. |
| 2013/0096182 A1 | 4/2013 | Chatterjee et al. |
| 2013/0152224 A1 | 6/2013 | Abad et al. |
| 2013/0185831 A1 | 7/2013 | Kovalic et al. |
| 2013/0195801 A1 | 8/2013 | Gao et al. |
| 2013/0203841 A1 | 8/2013 | Zhong et al. |
| 2013/0216501 A1 | 8/2013 | Zhong et al. |
| 2013/0224836 A1 | 8/2013 | Muramatsu |
| 2013/0225666 A1 | 8/2013 | Kaspar et al. |
| 2013/0326723 A1 | 12/2013 | La Rosa et al. |
| 2014/0017212 A1 | 1/2014 | Rebar |
| 2014/0037585 A1 | 2/2014 | Wright et al. |
| 2014/0050701 A1 | 2/2014 | Zhong et al. |
| 2014/0056854 A1 | 2/2014 | Asokan et al. |
| 2014/0057969 A1 | 2/2014 | Frost et al. |
| 2014/0130203 A1 | 5/2014 | La Rosa et al. |
| 2014/0162319 A2 | 6/2014 | Hareendran et al. |
| 2014/0199313 A1 | 7/2014 | Plesch et al. |
| 2014/0223605 A1 | 8/2014 | Puzio et al. |
| 2014/0259218 A1 | 9/2014 | Kovalic et al. |
| 2014/0296486 A1 | 10/2014 | Gao et al. |
| 2014/0335054 A1 | 11/2014 | Gao et al. |
| 2014/0341852 A1 | 11/2014 | Srivastava et al. |
| 2015/0050302 A1 | 2/2015 | Thess |
| 2015/0079038 A1 | 3/2015 | Deverman et al. |
| 2015/0082481 A1 | 3/2015 | La Rosa et al. |
| 2015/0126588 A1 | 5/2015 | Nakai et al. |
| 2015/0133530 A1 | 5/2015 | Srivastava et al. |
| 2015/0184189 A1 | 7/2015 | Abad et al. |

(56) References Cited

U.S. PATENT DOCUMENTS

| | | |
|---|---|---|
| 2015/0191739 A1 | 7/2015 | La Rosa et al. |
| 2015/0197763 A1 | 7/2015 | La Rosa et al. |
| 2015/0238550 A1 | 8/2015 | McCown et al. |
| 2015/0344911 A1 | 12/2015 | Chatterjee et al. |
| 2016/0017295 A1 | 1/2016 | Schaffer et al. |
| 2016/0025657 A1 | 1/2016 | Shahbazmohamadi et al. |
| 2016/0106865 A1 | 4/2016 | Zhong et al. |
| 2016/0215024 A1 | 7/2016 | Vandenberghe et al. |
| 2016/0222067 A1 | 8/2016 | Gao et al. |
| 2016/0256571 A1 | 9/2016 | Corral-Debrinski et al. |
| 2016/0264984 A1 | 9/2016 | La Rosa et al. |
| 2016/0289275 A1 | 10/2016 | Chiorini et al. |
| 2016/0319294 A1 | 11/2016 | Kovalic et al. |
| 2016/0333372 A1 | 11/2016 | Srivastava et al. |
| 2016/0361439 A1 | 12/2016 | Agbandje-Mckenna et al. |
| 2016/0369299 A1 | 12/2016 | Boye et al. |
| 2017/0007720 A1 | 1/2017 | Boye et al. |
| 2017/0028082 A1 | 2/2017 | Wilson et al. |
| 2017/0049910 A1 | 2/2017 | Cronin et al. |
| 2017/0067908 A1 | 3/2017 | Nakai et al. |
| 2017/0088852 A1 | 3/2017 | Dangoor et al. |
| 2017/0088858 A1 | 3/2017 | Gao et al. |
| 2017/0096683 A1 | 4/2017 | Scaria et al. |
| 2017/0130245 A1 | 5/2017 | Kotin et al. |
| 2017/0159027 A1 | 6/2017 | Wilson et al. |
| 2017/0166926 A1 | 6/2017 | Deverman et al. |
| 2017/0204144 A1 | 7/2017 | Deverman et al. |
| 2017/0211092 A1 | 7/2017 | Chatterjee et al. |
| 2017/0211093 A1 | 7/2017 | Chatterjee et al. |
| 2017/0211094 A1 | 7/2017 | Chatterjee et al. |
| 2017/0211095 A1 | 7/2017 | Chatterjee et al. |
| 2017/0240885 A1 | 8/2017 | Deverman et al. |
| 2017/0275337 A1 | 9/2017 | Srivastava et al. |
| 2017/0298323 A1 | 10/2017 | Vandenberghe et al. |
| 2017/0349911 A1 | 12/2017 | Gao et al. |
| 2018/0002722 A1 | 1/2018 | Asokan et al. |
| 2018/0030096 A1 | 2/2018 | Aslanidi et al. |
| 2018/0030479 A1 | 2/2018 | Gao et al. |
| 2018/0036428 A1 | 2/2018 | Zhong et al. |
| 2018/0066022 A1 | 3/2018 | Chalberg et al. |
| 2018/0066285 A1 | 3/2018 | Ojala et al. |
| 2018/0104289 A1 | 4/2018 | Venditti et al. |
| 2018/0105559 A1 | 4/2018 | Srivastava et al. |
| 2018/0112229 A1 | 4/2018 | Nadzan et al. |
| 2018/0119167 A1 | 5/2018 | Abad et al. |
| 2018/0135074 A1 | 5/2018 | Srivastava et al. |
| 2018/0135076 A1 | 5/2018 | Linden |
| 2018/0163227 A1 | 6/2018 | Chatterjee et al. |
| 2018/0214576 A1 | 8/2018 | Fitzgerald et al. |
| 2018/0244727 A1 | 8/2018 | Zhong et al. |
| 2018/0265863 A1 | 9/2018 | Esteves et al. |
| 2018/0355376 A1 | 12/2018 | Chiorini et al. |
| 2018/0362592 A1 | 12/2018 | Gao et al. |
| 2018/0371024 A1 | 12/2018 | Asokan et al. |
| 2019/0048041 A1 | 2/2019 | Asokan et al. |
| 2019/0055524 A1 | 2/2019 | Vandenberghe et al. |
| 2019/0085301 A1 | 3/2019 | Gao et al. |
| 2019/0100560 A1 | 4/2019 | Vandenberghe et al. |
| 2019/0249195 A1 | 8/2019 | Marsic et al. |
| 2019/0255192 A1 | 8/2019 | Kirn et al. |
| 2019/0262373 A1 | 8/2019 | Woodard et al. |
| 2019/0284576 A1 | 9/2019 | Qu et al. |
| 2019/0292561 A1 | 9/2019 | Qu et al. |
| 2019/0367562 A1 | 12/2019 | Asokan et al. |
| 2020/0109418 A1 | 4/2020 | Li et al. |
| 2020/0399321 A1 | 12/2020 | Asokan et al. |
| 2021/0115474 A1 | 4/2021 | Mccoy et al. |
| 2021/0128652 A1 | 5/2021 | Dismuke |
| 2021/0324418 A1 | 10/2021 | Thomas et al. |
| 2021/0371469 A1 | 12/2021 | McCoy et al. |
| 2021/0371471 A1 | 12/2021 | McCoy et al. |
| 2022/0056478 A1 | 2/2022 | O'Banion |
| 2022/0064675 A1 | 3/2022 | McCoy et al. |
| 2022/0088152 A1 | 3/2022 | Mikati et al. |
| 2022/0089651 A1 | 3/2022 | Asokan et al. |

FOREIGN PATENT DOCUMENTS

| | | |
|---|---|---|
| EP | 1887081 A2 | 2/2008 |
| EP | 2194140 A2 | 6/2010 |
| EP | 2359869 A2 | 8/2011 |
| EP | 2492347 A1 | 8/2012 |
| EP | 2660325 A2 | 11/2013 |
| EP | 2315833 B1 | 4/2015 |
| EP | 1453547 B1 | 9/2016 |
| EP | 2007795 B1 | 11/2016 |
| EP | 2675484 B1 | 5/2018 |
| EP | 2263692 B1 | 9/2018 |
| EP | 2206728 B9 | 10/2018 |
| EP | 1633767 B1 | 11/2018 |
| EP | 3459965 A1 | 3/2019 |
| EP | 3511021 A1 | 7/2019 |
| JP | 2014-534245 A | 12/2014 |
| RU | 2457252 C2 | 7/2012 |
| WO | WO-90/05142 A1 | 5/1990 |
| WO | WO-98/11244 A2 | 3/1998 |
| WO | WO-99/01555 A1 | 1/1999 |
| WO | WO-99/61601 A2 | 12/1999 |
| WO | WO-00/17377 A2 | 3/2000 |
| WO | WO-99/61601 A9 | 3/2000 |
| WO | WO-00/23477 A2 | 4/2000 |
| WO | WO-00/28004 A1 | 5/2000 |
| WO | WO-00/28061 A2 | 5/2000 |
| WO | WO-00/28061 A9 | 11/2000 |
| WO | WO-01/11034 A2 | 2/2001 |
| WO | WO-01/81581 A2 | 11/2001 |
| WO | WO-2001/92551 A2 | 12/2001 |
| WO | WO-02/10210 A2 | 2/2002 |
| WO | WO-03/000906 A2 | 1/2003 |
| WO | WO-03/008540 A2 | 1/2003 |
| WO | WO-03/033515 A1 | 4/2003 |
| WO | WO-03/042361 A2 | 5/2003 |
| WO | WO-2003/052051 A2 | 6/2003 |
| WO | WO-03/095647 A2 | 11/2003 |
| WO | WO-2004/027019 A2 | 4/2004 |
| WO | WO-2005/033321 A2 | 4/2005 |
| WO | WO-2006/021724 A2 | 3/2006 |
| WO | WO-2006/029319 A2 | 3/2006 |
| WO | WO-2006/066066 A2 | 6/2006 |
| WO | WO-2006/073052 A1 | 7/2006 |
| WO | WO-2006/119137 A1 | 11/2006 |
| WO | WO-2006/119432 A2 | 11/2006 |
| WO | WO-2007/084773 A2 | 7/2007 |
| WO | WO-2007/089632 A2 | 8/2007 |
| WO | WO-2007/092563 A2 | 8/2007 |
| WO | WO-2007/100465 A2 | 9/2007 |
| WO | WO-2007/120542 A2 | 10/2007 |
| WO | WO-2007/127264 A2 | 11/2007 |
| WO | WO-2008/088895 A2 | 7/2008 |
| WO | WO-2009/037279 A1 | 3/2009 |
| WO | WO-2009/043936 A1 | 4/2009 |
| WO | WO-2009/105612 A2 | 8/2009 |
| WO | WO-2009/108274 A2 | 9/2009 |
| WO | WO-2010/093784 A2 | 8/2010 |
| WO | WO-2010/129021 A1 | 11/2010 |
| WO | WO-2010/138263 A2 | 12/2010 |
| WO | WO-2011/020118 A1 | 2/2011 |
| WO | WO-2011/020710 A2 | 2/2011 |
| WO | WO-2011/122950 A1 | 10/2011 |
| WO | WO-2011/133890 A1 | 10/2011 |
| WO | WO-2012/061744 A2 | 5/2012 |
| WO | WO-2012/064960 A2 | 5/2012 |
| WO | WO-2012/112578 A2 | 8/2012 |
| WO | WO-2012/178173 A2 | 12/2012 |
| WO | WO-2013/016315 A1 | 1/2013 |
| WO | WO-2013/027223 A2 | 2/2013 |
| WO | WO-2013/158879 A1 | 10/2013 |
| WO | WO-2013/170078 A1 | 11/2013 |
| WO | WO-2013/173512 A2 | 11/2013 |
| WO | WO-2013/190059 A1 | 12/2013 |
| WO | WO-2014/007858 A1 | 1/2014 |
| WO | WO-2014/045674 A1 | 3/2014 |
| WO | WO-2014/124282 A1 | 8/2014 |
| WO | WO-2014/144229 A1 | 9/2014 |
| WO | WO-2014/153083 A1 | 9/2014 |

(56) References Cited

FOREIGN PATENT DOCUMENTS

| | | |
|---|---|---|
| WO | WO-2014/193716 A2 | 12/2014 |
| WO | WO-2014/194132 A1 | 12/2014 |
| WO | WO-2015/013313 A2 | 1/2015 |
| WO | WO-2015/038958 A1 | 3/2015 |
| WO | WO-2015/054653 A2 | 4/2015 |
| WO | WO-2015/121501 A1 | 8/2015 |
| WO | WO-2015/164757 A1 | 8/2015 |
| WO | WO-2015/168666 A2 | 10/2015 |
| WO | WO-2015/181823 A1 | 11/2015 |
| WO | WO-2015/191508 A1 | 12/2015 |
| WO | WO-2016/054557 A1 | 4/2016 |
| WO | WO-2016/065001 A1 | 4/2016 |
| WO | WO-2016/081811 A1 | 5/2016 |
| WO | WO-2016/115382 A1 | 5/2016 |
| WO | WO-2016/115503 A1 | 7/2016 |
| WO | WO-2016/128558 A1 | 7/2016 |
| WO | WO-2016/128559 A1 | 8/2016 |
| WO | WO-2016/134338 A1 | 8/2016 |
| WO | WO-2016/150964 A1 | 8/2016 |
| WO | WO-2016/164642 A1 | 9/2016 |
| WO | WO-2016/172008 A1 | 10/2016 |
| WO | WO-2016/172155 A1 | 10/2016 |
| WO | WO-2016/179644 A1 | 10/2016 |
| WO | WO-2017/015102 A1 | 11/2016 |
| WO | WO-2017/058892 A2 | 1/2017 |
| WO | WO-2017/066764 A2 | 4/2017 |
| WO | WO-2017/070516 A1 | 4/2017 |
| WO | WO-2017/077451 A1 | 5/2017 |
| WO | WO-2017/096164 A1 | 6/2017 |
| WO | WO-2017/106236 A1 | 6/2017 |
| WO | WO-2017/139643 A1 | 8/2017 |
| WO | WO-2017/143100 A1 | 8/2017 |
| WO | WO-2017/147123 A1 | 8/2017 |
| WO | WO-2017/180854 A1 | 10/2017 |
| WO | WO-2017/192750 A1 | 11/2017 |
| WO | WO-2017/201248 A1 | 11/2017 |
| WO | WO-2018/022608 A2 | 2/2018 |
| WO | WO-2018/035213 A1 | 2/2018 |
| WO | WO-2018/049226 A1 | 3/2018 |
| WO | WO-2018/064624 A1 | 4/2018 |
| WO | WO-2018/075798 A1 | 4/2018 |
| WO | WO-2018/119330 A2 | 6/2018 |
| WO | WO-2018/152333 A1 | 8/2018 |
| WO | WO-2018/160582 A1 | 9/2018 |
| WO | WO-2018/170310 A1 | 9/2018 |
| WO | WO-2018/204764 A1 | 11/2018 |
| WO | WO-2018/209154 A1 | 11/2018 |
| WO | WO-2018/226785 A1 | 12/2018 |
| WO | WO-2018/237066 A1 | 12/2018 |
| WO | WO-2019/006418 A2 | 1/2019 |
| WO | WO-2019/025984 A1 | 2/2019 |
| WO | WO-2019/141765 A1 | 7/2019 |
| WO | WO-2019/168961 A1 | 9/2019 |
| WO | WO-2019/169004 A1 | 9/2019 |
| WO | WO-2019/169132 A1 | 9/2019 |
| WO | WO-2019/173434 A1 | 9/2019 |
| WO | WO-2019/173538 A1 | 9/2019 |
| WO | WO-2019/178412 A1 | 9/2019 |
| WO | WO-2019/195423 A1 | 10/2019 |
| WO | WO-2019/195444 A1 | 10/2019 |
| WO | WO-2019/195449 A1 | 10/2019 |
| WO | WO-2019/222444 A2 | 10/2019 |
| WO | WO-2020/016318 A1 | 11/2019 |
| WO | WO-2020/106916 A1 | 1/2020 |
| WO | WO-2020/142653 A1 | 5/2020 |
| WO | WO-2020/191300 A1 | 7/2020 |
| WO | WO-2020/232297 A1 | 9/2020 |
| WO | WO-2021/076911 A1 | 11/2020 |
| WO | WO-2021/076925 A1 | 4/2021 |

OTHER PUBLICATIONS

Adachi et al., "Drawing a high-resolution functional map of adeno-associated virus capsid by massively parallel sequencing," Nature Communications 5(1): 14 pages (2013).

Agbandje et al. "The Structure of Human Parvovirus B19 at 8 A; Resolution" Virology 203(1):106-115 (1994).

Agbandje-Mckenna et al. "AAV Capsid Structure and Cell Interactions" Methods in Molecular Biology, 807:47-92 (2011).

Albright et al., "Mapping the Structural Determinants Required for AAVrh .10 Transport across the Blood-Brain Barrier," Molecular Therapy 26(2), p. 1-14 (2017).

Albright, "Modulation of Sialic Acid Dependence Influences the Central Nervous System Transduction Profile of Adeno-associated Viruses," Journal of Virology 93(11), pp. 1-15 (2019).

Altschul et al. "Basic Local Alignment Search Tool" Journal of Molecular Biology 215:403-410 (1990).

Altschul et al. "Local Alignment Statistics" Methods in Enzymology 266:460-480 (1996).

Altschul et al., "Gapped BLAST and PSI-BLAST: a new generation of protein database search programs," Nucleic Acids Research 25(17):3389-3402 (1997).

Altschul, SF et al., 'Issues in searching molecular sequence databases,' Nat. Genet., vol. 6, pp. 119-129, (Feb. 1994).

Andino et al. "AAV-mediated knockdown of phospholamban leads to improved contractility and calcium handling in cardiomyocytes" The Journal of Gene Medicine 10:132-142 (2008).

Arnold et al., "A calcium responsive element that regulates expression of two calcium binding proteins in Purkinje cells," Proc Natl Acad Sci USA 94(16):8842-8847 (1997).

Arruda et al., "Regional intravascular delivery of AAV-2-F.IX to skeletal muscle achieves long-term correction of hemophilia B in a large animal model," Blood 105:3458-3464 (2005).

Asokan et al. "Adeno-Associated Virus Type 2 Contains an Integrin a5 1 Binding Domain Essential for Viral Cell Entry" Journal of Virology, 80(18):8961-8969 (2006).

Asokan et al., "The AVV Vector Toolkit: Poised at the Clinical Crossroads," Molecular Therapy 20(4):699-708 (2012).

Asokan, et al., "Reengineering a receptor footprint of adeno-associated virus enables selective and systemic gene transfer to muscle", Nat Biotechnol, (Jan. 2010); 28(1): 79-82.

Asuri et al., Directed Evolution of adeno-associated Virus for Enhanced Gene Delivery and Gene Targeting in Human Pluripotent Stem Cells, Molecular Therapy, Nature Publishing Group GB 20(2):329-338 (2013).

Ballabh et al. "The blood-brain barrier: an overview: structure, regulation, and clinical implications" Neurobiology of Disease, 16:1-13 (2004).

Bantel-Schaal et al. "Human adeno-Associated Virus Type 5 Is Only Distantly Related to Other Known Primate Helper-Dependent Parvovirus" Journal of Virology 73(2):939-947 (1999).

Bantel-Schaal et al., "Adeno-associated virus type 5 exploits two different entry pathways in human embryo fibroblast," J Virology 73:939 (1999).

Bartlett, JS et al., 'Selective and Rapid Uptake of Adeno-Associated Virus Type 2 in Brain,' Hum. Gene Ther., 9(8):1181-1186, (May 1998).

Bell et al. "Identification of the Galactose Binding Domain of the Adeno-Associated Virus Serotype 9 Capsid" Journal of Virology, 86(13):7326-7333 (2012).

Bennett et al. "AAV6 K531 serves a dual function in selective receptor and antibody ADK6 recognition" Virology, 18:369-376 (2018).

Bleker et al. "Mutational Analysis of Narrow Pores at the Fivefold Symmetry Axes of Adeno-Associated Virus Type 2 Capsids Reveals a Dual Role in Genome Packaging and Activation of Phospholipase A2 Activity" Journal of Virology, 79(4):2528-2540 (2005).

Bordoli et al. "Protein structure homology modeling using SWISS-MODEL workspace" Nature Protocols, 4(1):1-13 (2008).

Bowie, et al., " Deciphering the Message in Protein Sequences: Tolerance to Amino Acid Substitutions." Science (1990); 247: 1306-1310.

Bowles et al. "Phase 1 Gene Therapy for Duchenne Muscular Dystrophy Using a Translational Optimized AAV Vector" Molecular Therapy, 20(2):443-455 (2012).

Brichard et al. «The Tyrosinase Gene Codes for an Antigen Recognized by Autologous Cytolytic T Lymphocytes on HLA-AZ

(56) References Cited

OTHER PUBLICATIONS

Melanomas»Journal of Experimental Medicine178:489-495 (1993).
Brown et al. "Chimeric Parvovirus 19 Capsids for the Presentation of Foreign Epitopes" Virology 198(2):477-488 (1994).
Brown et al. "Erythrocyte P Antigen: Cellular Receptor for B19 Parvovirus" Science 262(5130):114-117 (1993).
Carrillo-Tripp et al. "VIPERdb2: an enhanced and web API enabled relational database for structural virology" Nucleic Acids Research, 37:D436-D442 (2009).
Carstea, ED et al. 'Niemann-Pick C1 Disease Gene: Homology to Mediators of Cholesterol Homeostasis,' Science, 277(5323): 228-231 (Jul. 1997).
Cearley et al. "Transduction Characteristics of Adeno-associated Virus Vectors Expressing Cap Serotypes 7, 8, 9, and Rh10 in the Mouse Brain" Molecular Therapy, 13(3):528-537 (2006).
Cearley, C.N. et al. (2008). "Expanded repertoire of AAV vector serotypes mediate unique patterns of transduction in mouse brain," Mol. Ther. 16:1710-1718.
Chandler et al., "Systemic AAV9 gene therapy improves the lifespan of mice with Niemann-Pick disease, type C1 ," Human Molecular Genetics 26(1):52-64 (2017).
Chao et al. "Several Log Increase in Therapeutic Transgene Delivery by Distinct Adeno- Associated Viral Serotype Vectors" Molecular Therapy 2(6):619-623 (2000).
Chapman et al. "Structure, Sequence, and Function Correlations among Parvoviruses" Virology 194(2):491-508 (1993).
Chen et al. "Efficient Transduction of Vascular Endothelial Cells with Recombinant Adeno-Associated Virus Serotype 1 and 5 Vectors" Human Gene Therapy, 16(2):235-247 (2005).
Chen, SH et al., 'Gene therapy for brain tumors: Regression of experimental gliomas by adenovirus-mediated gene transfer in vivo,' Proc. Natl Acad. Sci. USA, vol. 91, pp. 3054-3057, (Apr. 1994).
Chiorini et al. "Cloning and Characterization of adeno-Associated Virus Type 5" Journal of Virology 73(2):1309-1319 (1999).
Chiorini et al. "Cloning of adeno-Associated Virus Type 4 (AAV4). and Generation of Recombinant AAV4 Particles" Journal of Virology 71 (9):6823-6833 (1997).
Chipman et al. «Cryo-electron microscopy studies of empty capsids of human parvovirus 819 complexed with its cellular receptor»Proceedings of the National Academy of Sciences 93:7502-7506 (1996).
Chirmule et al., "Humoral immunity to adeno-associated virus type 2 vectors following administration to murine and nonhuman primate muscle," Journal of Virology, The American Society for Microbiology, 74(5):2420-2425 (2000).
Choi et al., "Optimization of AAV expression cassettes to improve packaging capacity and transgene expression in neurons," Molecular Brain, Biomed Central Ltd, London UK, 7(1):17 pp. 1-10 (2014).
Clapcote et al., " Mutation I810N in the alpha3 isoform of Na+,K+-ATPase causes impairments in the sodium pump and hyperexcitability in the CNS," Proc Natl Acad Sci USA. 106(33):14085-14090 (2009).
Clark, KR et al., 'Highly Purified Recombinant Adeno-Associated Virus Vectors Are Biologically Active and Free of Detectable Helper and Wild-Type Viruses,' Hum. Gene Ther., 10(6):1031-1039, (Apr. 1999).
Cleves, "Protein transport: The nonclassical ins and outs" Current Biology 7:R318-R320 (1997).
Conway et al. "High-titer recombinant adeno-associated virus production utilizing a recombinant herpes simplex virus type 1 vector expressing AAV-2 Rep and Cap" Gene Therapy 6:986-993 (1999).
Corpet et al., 'Multiple sequence alignment with hierarchical clustering,' Nucleic Acids Research, vol. 16 No. 22, pp. 10881-10890, (Oct. 1988).
Cotmore et al.,"The Family Parvoviridae," Archives of Virology 159:1239-1247 (2014).
DataBase GenBank: ABS91093.1, Aug. 10, 2007, [online] [retrieved on Feb. 14, 2020] Retrieved from Internet: https://www.ncbi.nlm.nih.gov/protein/ABS91093.1.
DataBase GenBank: ACW56705.1, Sep. 24, 2009, [online] [retrieved on May 7, 2019] Retrieved from Internet:https://www.ncbi.nlm.nih.gov/protein/ACW56705.1?report=genbank&log$=prottop&bl ast_rank=1&RID=D2CZ8TP9014, 1 page.
De Jesus et al., "Telomerase gene therapy in adult and old mice delays aging and increases longevity without increasing cancer," EMBO Mol. Med. 4(8): 691-704 (2012).
Devereux et al. "A comprehensive set of sequence analysis programs for the VAX" Nucleic Acids Research 12(1):387-395 (1984).
Deverman, BE, Cre-dependent selection yields AAV variants for widespread gene transfer to the adult brain, Nat. Biotechnol., 34(2):204-209. doi: 10.1038/nbt.3440. PubMed PMID: 26829320 (Epub Feb. 1, 2016).
Dimattia et al. "Structural Insight into the Unique Properties of Adeno-Associated Virus Serotype 9," Journal of Virology, 86(12):6947-6958 (2012).
Dipasquale et al. "Identification of PDGFR as a receptor for MV-5 transduction" Nature Medicine, 9:1306-1312 (2003). (Abstract only).
Diprimio, et al., "Surface loop dynamics in adeno-associated virus capsid assembly", Journal of Virology (2008); vol. 82, No. 11, pp. 5178-5189.
Emsley et al. "Features and development of Coot" Acta Crystallographica Section D: Biological Crystallography, D66:486-501 (2010).
Extended European Search Report corresponding to European Patent Application No. 20212583.7, dated May 3, 2021, 10 pages.
Extended European Search Report corresponding to European Patent Application No. 16737901.5 (6 pages). (dated May 15, 2018).
Extended European Search Report for European Application No. EP19760157.8 dated Nov. 8, 2021, 6 pages.
Extended European Search Report issued by the European Patent Office for Application No. 16852471.8, dated Jul. 29, 2019, 13 pages.
Extended European Search Report issued by the European Patent Office for Application No. 18754551, dated Jun. 4, 2021, 11 pages.
Fang et al., "Stable antibody expression at therapeutic levels using the 2A peptide," Nature Biotechnology 23:584-590 (2005).
Felsenstein, Joseph "Confidence Limits on Phylogenies: An Approach Using the Bootstrap" Evolution, 39 (4):783-791 (1985).
Ferrari et al. "New developments in the generation of Ad-free high-titer rAAV gene therapy vectors" Nature Medicine 3(11):1295-1297 (1997).
Fields et al., Virology, vol. 2, chapter 69 (4th ed., Lippincott-Raven Publishers).
Fisher, KJ et al., 'Transduction with Recombinant Adeno-Associated Virus for Gene Therapy Is Limited by Leading-Strand Synthesis,' J. Virol., 70(1):520-532 (LFU assay) (Jan. 1996).
Foster et al., "Emerging Immunotherapies for Autoimmune Kidney Disease," Hyman Vaccines & Immunotherapeutics 15(4):876-890 (2019).
Foust et al. "Intravascular AAV9 preferentially targets neonatal neurons and adult astrocytes" Nature Biotechnology, 27(1):59-65 (2009).
Gao et al. "Adeno-associated viruses undergo substantial evolution in primates during natural infections" Proceedings of the National Academy of Sciences, 100(10):6081-6086 (2003).
Gao et al. "Novel adeno-associated viruses from Rhesus Monkeys as Vectors for human gene therapy," Proceedings of the National Academy of Sciences 99(18):11854-11859 (2002).
Genbank Accession No. AAR26465, Bovine Adeno-Associated Virus, dated May 25, 2004, 2 pages.
Genbank Accession No. AAT46339, capsid protein [Adeno-associated virus 11], dated Nov. 30, 2004, 2 pages.
Genbank Accession No. ABI16639, VP1 [Adeno-associated virus 12, dated Feb. 20, 2008, 2 pages.
GenBank Accession No. AF028704 "adeno-associated Virus 6, complete genome" NCBI (2 pages). (Jan. 12, 1998).
GenBank Accession No. AF028705 "adeno-associated Virus 3B, complete genome" NCBI (2 pages). (Jan. 12, 1998).
GenBank Accession No. AF043303 "adeno-Associated Virus 2, complete genome" NCBJ (4 pages). (May 20, 2010).
Genbank Accession No. AF063497, Adeno-associated virus 1, complete genome, dated Apr. 27, 1999, 3 pages.

(56) References Cited

OTHER PUBLICATIONS

Genbank Accession No. AF085716, Adeno-associated virus 5 DNA binding trs helicase (Rep22) and capsid protein (VP1) genes, complete cds., dated Feb. 9, 1999, 3 pages.
GenBank Accession No. AF258783.1 'Felis catus Niemann-Pick type C1 disease protein (NPC1) mRNA, complete eds' (2000).
GenBank Accession No. AF288061 "Hamster parvovirus 5' terminal hairpin gene sequence" NCBI (1 page). (Apr. 13, 2001), replaced by AH009962.
GenBank Accession No. AF513851 "adeno-associated Virus 7 nonstructural protein and capsid protein genes, complete eds." NCBI (2 pages). (Sep. 5, 2002/).
GenBank Accession No. AF513852 "adeno-associated Virus 8 nonstructural protein and capsid protein genes, complete eds" NCBI (2 pages). (Sep. 5, 2002/).
GenBank Accession No. AH009962 "Hamster parvovir" NCBI (1 page). (Aug. 25, 2016), replaced AF288061.
GenBank Accession No. AY028223 "B19 Virus isolate patient_A.1.1 genomic sequence" NCB/ (1 page). (Apr. 16, 2001).
GenBank Accession No. AY028226 "819 Virus isolate patient_A.2.1 genomic sequence" NCB/ (1 page). (Apr. 16, 2001).
Genbank Accession No. AY186198, Avian adeno-associated virus ATCC VR-865, complete genome, dated Jun. 5, 2003, 3 pages.
Genbank Accession No. AY242997, Non-Human primate Adeno-associated virus isolate AAVrh.8 capsid protein (VP1) gene, complete cds, dated May 14, 2003, 2 pages.
Genbank Accession No. AY242998, Non-Human primate Adeno-associated virus isolate AAVrh.37 capsid protein (VP1) gene, complete cds, dated May 14, 2003, 2 pages.
Genbank Accession No. AY242999, Non-Human primate Adeno-associated virus isolate AAVrh.36 capsid protein (VP1) gene, complete cds, dated May 14, 2003, 2 pages.
Genbank Accession No. AY243000, Non-Human primate Adeno-associated virus isolate AAVrh.35 capsid protein (VP1) gene, complete cds, dated May 14, 2003, 2 pages.
Genbank Accession No. AY243001, Non-Human Primate Adeno-associated Virus Isolate AAVrh.34 capsid protein (VP1) gene, complete cds., dated May 14, 2003, 2 pages.
Genbank Accession No. AY243002, Non-Human Primate Adeno-associated Virus Isolate AAVrh.33 capsid protein (VP1) gene, complete cds. dated May 14, 2003, 2 pages.
Genbank Accession No. AY243003, Non-Human Primate Adeno-associated Virus Isolate AAVrh.32 cpsid protein (VP1) gene, complete cds, dated May 14, 2003, 2 pages.
Genbank Accession No. AY243007, Non-Human Primate Adeno-associated Virus Isolate AAVrh.2 capsid protein (VP1) gene, complete cds, dated May 14, 2003, 2 pages.
Genbank Accession No. AY243013, Non-Human primate Adeno-associated virus isolate AAVrh.13 capsid protein (VP1) gene, complete cds, dated May 14, 2003, 2 pages.
Genbank Accession No. AY243015, Non-Human primate Adeno-associated virus isolate AAVrh.10 capsid protein (VP1) gene, complete cds dated May 14, 2003, 2 pages.
Genbank Accession No. AY243016, Non-Human primate Adeno-associated virus isolate AAVcy.6 capsid protein (VP1) gene, complete cds dated May 14, 2003, 2 pages.
Genbank Accession No. AY243017, Non-Human primate Adeno-associated virus isolate AAVcy.5 capsid protein (VP1) gene, complete cds, dated May 14, 2003, 2 pages.
Genbank Accession No. AY243018, Non-Human primate Adeno-associated virus isolate AAVcy.4 capsid protein (VP1) gene, complete cds, dated May 14, 2003, 2 pages.
Genbank Accession No. AY243019, Non-Human primate Adeno-associated virus isolate AAVcy.3 capsid protein (VP1) gene, complete cds, dated May 14, 2003, 2 pages.
Genbank Accession No. AY243020, Non-Human primate Adeno-associated virus isolate AAVcy.2 capsid protein (VP1) gene, complete cds, dated May 14, 2003, 2 pages.
Genbank Accession No. AY243021, Non-Human primate Adeno-associated virus isolate AAVch.5 capsid protein (VP1) gene, complete cds, dated May 14, 2003, 2 pages.
Genbank Accession No. AY243022, Non-Human primate Adeno-associated virus isolate AAVbb.2 capsid protein (VP1) gene, complete cds, dated May 14, 2003, 2 pages.
Genbank Accession No. AY243023, Non-Human primate Adeno-associated virus isolate AAVbb.1 capsid protein (VP1) gene, complete cds, dated May 14, 2003, 2 pages.
GenBank Accession No. AY388617, Bovine adeno-associated virus, complete genome, dated May 25, 2004, 3 pages.
Genbank Accession No. AY530553, Adeno-associated virus isolate pi.1 capsid protein VP1 9cap) gene, complete cds, dated Jun. 24, 2004, 2 pages.
Genbank Accession No. AY530554, Adeno-associated virus isolate pi.2 capsid protein VP1 9cap) gene, complete cds, dated Jun. 24, 2004, 2 pages.
Genbank Accession No. AY530555, Adeno-associated virus isolate pi.3 capsid protein VP1 9cap) gene, complete cds, dated Jun. 24, 2004, 2 pages.
Genbank Accession No. AY530556, Adeno-associated virus isolate rh.1 capsid protein VP1 9cap) gene, complete cds, dated Jun. 24, 2004, 2 pages.
Genbank Accession No. AY530557, Adeno-associated virus isolate rh.25 capsid protein VP1 9cap) gene, complete cds, dated Jun. 24, 2004, 2 pages.
Genbank Accession No. AY530558, Adeno-associated virus isolate rh.38 capsid protein VP1 (cap) gene, complete cds, dated Jun. 24, 2004, 2 pages.
Genbank Accession No. AY530559, Adeno-associated virus isolate rh.40 capsid protein VP1 (cap) gene, complete cds, dated Jun. 24, 2004, 2 pages.
Genbank Accession No. AY530560, Adeno-associated virus isolate rh.43 capsid protein VP1 (cap) gene, complete cds, dated Jun. 24, 2004, 2 pages.
Genbank Accession No. AY530561, Genbank Accession No. AY530560, Adeno-associated virus isolate rh.48 capsid protein VP1 (cap) gene, complete cds, dated Jun. 24, 2004, 2 pages.
Genbank Accession No. AY530562, Adeno-associated virus isolate rh.49 capsid protein VP1 (cap) gene, complete cds, dated Jun. 24, 2004, 2 pages.
Genbank Accession No. AY530563, Adeno-associated virus isolate rh.50 capsid protein VP1 (cap) gene, complete cds, dated Jun. 24, 2004, 2 pages.
Genbank Accession No. AY530564, Adeno-associated virus isolate rh.51 capsid protein VP1 (cap) gene, complete cds, dated Jun. 24, 2004, 2 pages.
Genbank Accession No. AY530565, Adeno-associated virus isolate rh.52 capsid protein VP1 (cap) gene, complete cds, dated Jun. 24, 2004, 2 pages.
Genbank Accession No. AY530566, Adeno-associated virus isolate rh.53 capsid protein VP1 (cap) gene, complete cds, dated Jun. 24, 2004, 2 pages.
Genbank Accession No. AY530567, Adeno-associated virus isolate rh.54 capsid protein VP1 (cap) gene, complete cds, dated Jun. 24, 2004, 2 pages.
Genbank Accession No. AY530568, Adeno-associated virus isolate rh.55 capsid protein VP1 (cap) gene, complete cds, dated Jun. 24, 2004, 2 pages.
Genbank Accession No. AY530569, Adeno-associated virus isolate rh.57 capsid protein VP1 (cap) gene, complete cds, dated Jun. 24, 2004, 2 pages.
Genbank Accession No. AY530570, Adeno-associated virus isolate rh.58 capsid protein VP1 (cap) gene, complete cds, dated Jun. 24, 2004, 2 pages.
Genbank Accession No. AY530572, Adeno-associated virus isolate rh.61 capsid protein VP1 (cap) gene, complete cds, dated Jun. 24, 2004, 2 pages.
Genbank Accession No. AY530573, Adeno-associated virus isolate rh.62 capsid protein VP1 (cap) gene, complete cds, dated Jun. 24, 2004, 2 pages.

(56) References Cited

OTHER PUBLICATIONS

Genbank Accession No. AY530574, Adeno-associated virus isolate rh.64 capsid protein VP1 (cap) gene, complete cds, dated Jun. 24, 2004, 2 pages.
Genbank Accession No. AY530575, Adeno-associated virus isolate hu.1 capsid protein VP1 (cap) gene, complete cds, dated Jun. 24, 2004, 2 pages.
Genbank Accession No. AY530576, Adeno-associated virus isolate hu.10 capsid protein VP1 (cap) gene, complete cds, dated Jun. 24, 2004, 2 pages.
Genbank Accession No. AY530577, Adeno-associated virus isolate hu.11 capsid protein VP1 (cap) gene, complete cds, dated Jun. 24, 2004, 2 pages.
Genbank Accession No. AY530578, Adeno-associated virus isolate hu.13 capsid protein VP1 (cap) gene, complete cds, dated Jun. 24, 2004, 2 pages.
Genbank Accession No. AY530579, Adeno-associated virus isolate hu.14 capsid protein VP1 (cap) gene, complete cds, dated Jun. 24, 2004, 2 pages.
Genbank Accession No. AY530580, Adeno-associated virus isolate hu.15 capsid protein VP1 (cap) gene, complete cds, dated Jun. 24, 2004, 2 pages.
Genbank Accession No. AY530581, Adeno-associated virus isolate hu.16 capsid protein VP1 (cap) gene, complete cds, dated Jun. 24, 2004, 2 pages.
Genbank Accession No. AY530582, Adeno-associated virus isolate hu.17 capsid protein VP1 (cap) gene, complete cds, dated Jun. 24, 2004, 2 pages.
Genbank Accession No. AY530583, Adeno-associated virus isolate hu.18 capsid protein VP1 (cap) gene, complete cds, dated Jun. 24, 2004, 2 pages.
Genbank Accession No. AY530584, Adeno-associated virus isolate hu.19 capsid protein VP1 (cap) gene, complete cds, dated Jun. 24, 2004, 2 pages.
Genbank Accession No. AY530585, Adeno-associated virus isolate hu.2 capsid protein VP1 (cap) gene, complete cds, dated Jun. 24, 2004, 2 pages.
Genbank Accession No. AY530586, Adeno-associated virus isolate hu.20 capsid protein VP1 (cap) gene, complete cds, dated Jun. 24, 2004, 2 pages.
Genbank Accession No. AY530587, Adeno-associated virus isolate hu.21 capsid protein VP1 (cap) gene, complete cds, dated Jun. 24, 2004, 2 pages.
Genbank Accession No. AY530588, Adeno-associated virus isolate hu.22 capsid protein VP1 (cap) gene, complete cds, dated Jun. 24, 2004, 2 pages.
Genbank Accession No. AY530589, Adeno-associated virus isolate hu.23 capsid protein VP1 (cap) gene, complete cds, dated Jun. 24, 2004, 2 pages.
Genbank Accession No. AY530590, Adeno-associated virus isolate hu.24 capsid protein VP1 (cap) gene, complete cds, dated Jun. 24, 2004, 2 pages.
Genbank Accession No. AY530591, Adeno-associated virus isolate hu.25 capsid protein VP1 (cap) gene, complete cds, dated Jun. 24, 2004, 2 pages.
Genbank Accession No. AY530592, Adeno-associated virus isolate hu.27 capsid protein VP1 (cap) gene, complete cds, dated Jun. 24, 2004, 2 pages.
Genbank Accession No. AY530593, Adeno-associated virus isolate hu.28 capsid protein VP1 (cap) gene, complete cds, dated Jun. 24, 2004, 2 pages.
Genbank Accession No. AY530594, Adeno-associated virus isolate hu.29 capsid protein VP1 (cap) gene, complete cds, dated Jun. 24, 2004, 2 pages.
Genbank Accession No. AY530595, Adeno-associated virus isolate hu.3 capsid protein VP1 (cap) gene, complete cds, dated Jun. 24, 2004, 2 pages.
Genbank Accession No. AY530596, Adeno-associated virus isolate hu.31 capsid protein VP1 (cap) gene, complete cds, dated Jun. 24, 2004, 2 pages.
Genbank Accession No. AY530597, Adeno-associated virus isolate hu.32 capsid protein VP1 (cap) gene, complete cds, dated Jun. 24, 2004, 2 pages.
Genbank Accession No. AY530598, Adeno-associated virus isolate hu.34 capsid protein VP1 (cap) gene, complete cds, dated Jun. 24, 2004, 2 pages.
Genbank Accession No. AY530599, Adeno-associated virus isolate hu.35 capsid protein VP1 (cap) gene, complete cds, dated Jun. 24, 2004, 2 pages.
Genbank Accession No. AY530600, Adeno-associated virus isolate hu.37 capsid protein VP1 (cap) gene, complete cds, dated Jun. 24, 2004, 2 pages.
Genbank Accession No. AY530601, Adeno-associated virus isolate hu.39 capsid protein VP1 (cap) gene, complete cds, dated Jun. 24, 2004, 2 pages.
Genbank Accession No. AY530602, Adeno-associated virus isolate hu.4 capsid protein VP1 (cap) gene, complete cds, dated Jun. 24, 2004, 2 pages.
Genbank Accession No. AY530603, Adeno-associated virus isolate hu.40 capsid protein VP1 (cap) gene, complete cds, dated Jun. 24, 2004, 2 pages.
Genbank Accession No. AY530604, Adeno-associated virus isolate hu.41 capsid protein VP1 (cap) gene, complete cds, dated Jun. 24, 2004, 2 pages.
Genbank Accession No. AY530605, Adeno-associated virus isolate hu.42 capsid protein VP1 (cap) gene, complete cds, dated Jun. 24, 2004, 2 pages.
Genbank Accession No. AY530606, Adeno-associated virus isolate hu.43 capsid protein VP1 (cap) gene, complete cds, dated Jun. 24, 2004, 2 pages.
Genbank Accession No. AY530607, Adeno-associated virus isolate hu.44 capsid protein VP1 (cap) gene, complete cds, dated Jun. 24, 2004, 2 pages.
Genbank Accession No. AY530608, Adeno-associated virus isolate hu.45 capsid protein VP1 (cap) gene, complete cds, dated Jun. 24, 2004, 2 pages.
Genbank Accession No. AY530609, Adeno-associated virus isolate hu.46 capsid protein VP1 (cap) gene, complete cds, dated Jun. 24, 2004, 2 pages.
Genbank Accession No. AY530610, Adeno-associated virus isolate hu.47 capsid protein VP1 (cap) gene, complete cds, dated Jun. 24, 2004, 2 pages.
Genbank Accession No. AY530611, Adeno-associated virus isolate hu.48 capsid protein VP1 (cap) gene, complete cds, dated Jun. 24, 2004, 4 pages.
Genbank Accession No. AY530612, Adeno-associated virus isolate hu.49 capsid protein VP1 (cap) gene, complete cds, dated Jun. 24, 2004, 2 pages.
Genbank Accession No. AY530613, Adeno-associated virus isolate hu.51 capsid protein VP1 (cap) gene, complete cds, dated Jun. 24, 2004, 2 pages.
Genbank Accession No. AY530614, Adeno-associated virus isolate hu.52 capsid protein VP1 (cap) gene, complete cds, dated Jun. 24, 2004, 2 pages.
Genbank Accession No. AY530615, Adeno-associated virus isolate hu.53 capsid protein VP1 (cap) gene, complete cds, dated Jun. 24, 2004, 2 pages.
Genbank Accession No. AY530616, Adeno-associated virus isolate hu.54 capsid protein VP1 (cap) gene, complete cds, dated Jun. 24, 2004, 2 pages.
Genbank Accession No. AY530617, Adeno-associated virus isolate hu.55 capsid protein VP1 (cap) gene, complete cds, dated Jun. 24, 2004, 2 pages.
Genbank Accession No. AY530618, Adeno-associated virus isolate hu.56 capsid protein VP1 (cap) gene, complete cds, dated Jun. 24, 2004, 2 pages.
Genbank Accession No. AY530619, Adeno-associated virus isolate hu.57 capsid protein VP1 (cap) gene, complete cds, dated Jun. 24, 2004, 2 pages.
Genbank Accession No. AY530620, Adeno-associated virus isolate hu.58 capsid protein VP1 (cap) gene, complete cds, dated Jun. 24, 2004, 2 pages.

(56) References Cited

OTHER PUBLICATIONS

Genbank Accession No. AY530621, Adeno-associated virus isolate hu.6 capsid protein VP1 (cap) gene, complete cds, dated Jun. 24, 2004, 2 pages.
Genbank Accession No. AY530622, Adeno-associated virus isolate hu.60 capsid protein VP1 (cap) gene, complete cds, dated Jun. 24, 2004, 2 pages.
Genbank Accession No. AY530623, Adeno-associated virus isolate hu.61 capsid protein VP1 (cap) gene, complete cds, dated Jun. 24, 2004, 2 pages.
Genbank Accession No. AY530624, Adeno-associated virus isolate hu.63 capsid protein VP1 (cap) gene, complete cds, dated Jun. 24, 2004, 2 pages.
Genbank Accession No. AY530625, Adeno-associated virus isolate hu.64 capsid protein VP1 (cap) gene, complete cds, dated Jun. 24, 2004, 2 pages.
Genbank Accession No. AY530626, Adeno-associated virus isolate hu.66 capsid protein VP1 (cap) gene, complete cds, dated Jun. 24, 2004, 2 pages.
Genbank Accession No. AY530627, Adeno-associated virus isolate hu.67 capsid protein VP1 (cap) gene, complete cds, dated Jun. 24, 2004, 2 pages.
Genbank Accession No. AY530628, Adeno-associated virus isolate hu.7 capsid protein VP1 (cap) gene, complete cds, dated Jun. 24, 2004, 2 pages.
Genbank Accession No. AY530629, Adeno-associated virus isolate hu.9 capsid protein VP1 (cap) gene, complete cds, dated Jun. 24, 2004, 2 pages.
Genbank Accession No. AY629583, Avian adeno-associated virus strain DA-1, complete genome, dated Sep. 10, 2004, 3 pages.
Genbank Accession No. AY631966, Adeno-associated virus 11 nonstructural protein and capsid protein genes, complete cds, dated Nov. 30, 2004, 3 pages.
Genbank Accession No. AY695370, Adeno-associated virus isolate hu.T17 capsid protein VP1 (cap) gene, complete cds, dated Nov. 15, 2005, 3 pages.
Genbank Accession No. AY695371, Adeno-associated virus isolate hu.T32 Rep 78 protein and capsid protein VP1 (cap) genes, complete cds, dated Nov. 15, 2005, 3 pages.
Genbank Accession No. AY695372, Adeno-associated virus isolate hu.T40 Rep 78 protein and capsid protein VP1 (cap) genes, complete cds, dated Nov. 15, 2005, 3 pages.
Genbank Accession No. AY695373, Adeno-associated virus isolate hu.T70 Rep 78 protein and capsid protein VP1 (cap) genes, complete cds, dated Nov. 15, 2005, 3 pages.
Genbank Accession No. AY695374, Adeno-associated virus isolate hu.T32 Rep 71 protein and capsid protein VP1 (cap) genes, complete cds, dated Nov. 15, 2005, 3 pages.
Genbank Accession No. AY695375, Adeno-associated virus isolate hu.T88 Rep 78 protein and capsid protein VP1 (cap) genes, complete cds, dated Nov. 15, 2005, 3 pages.
Genbank Accession No. AY695376, Adeno-associated virus isolate hu.S17 Rep 78 protein and capsid protein VP1 (cap) genes, complete cds, dated Nov. 15, 2005, 3 pages.
Genbank Accession No. AY695377, Adeno-associated virus isolate hu.LG15 capsid protein VP1 (cap) gene, complete cds, dated Nov. 15, 2005, 3 pages.
Genbank Accession No. AY695378, Adeno-associated virus isolate hu.T41 capsid protein VP1 (cap) gene, complete cds, dated Nov. 15, 2005, 2 pages.
GenBank Accession No. BC002532 'Homo sapiens Niemann-Pick disease, type C2, mRNA (cDNA clone MGC:1333 IMAGE:3140870), complete eds' (2006).
GenBank Accession No. BC045895 'Dania rerio Niemann-Pick disease, type C2, mRNA (cDNA clone MGC:56070 IMAGE:5409780), complete eds' (2003).
GenBank Accession No. BC054539 'Mus musculus Niemann Pick type C1, mRNA (cDNA clone MGC:62352 IMAGE:6405214), complete eds' (2006).
GenBank Accession No. BC090541 'Dania rerio Niemann-Pick disease, type C1, mRNA (cDNA clone IMAGE:7149020), partial eds' (2016).
GenBank Accession No. BC102504 'Bos taurus Niemann-Pick disease, type C2, mRNA (cDNA clone MGC:127986 IMAGE:7954223), complete eds' (2007).
GenBank Accession No. BC117178 'Homo sapiens NPC1 (Niemann-Pickdisease, type C1, gene)-like 1, mRNA (cDNA clone MGC:150787 IMAGE:40125729), complete eds' (2006).
GenBank Accession No. BC143756 'Homo sapiens NPC1 (Niemann-Pickdisease, type C1, gene)-like 1, mRNA (cDNA clone MGC:177287 IMAGE:9052270), complete eds' (2009).
GenBank Accession No. BC151276 'Bos taurus Niemann-Pick disease, type C1, mRNA (cDNA clone MGC:152602 IMAGE:8433293), complete eds '(2007).
Genbank Accession No. DQ813647, Adeno-Associated Virus 12 Rep 78 and VP1 genes, complete cds., dated Feb. 20, 2008, 3 pages.
GenBank Accession No. J00306 "Human somatostatin I gene and flanks" NCBJ (2 pages). (Jan. 13, 1995).
GenBank Accession No. J01901 "adeno-associated Virus 2, complete genome" NCBJ (3 pages). (Apr. 27, 1993).
GenBank Accession No. J02275 "Minute Virus of mice, complete genome" NCBJ (4 pages). (May 22, 1995).
GenBank Accession No. KJ893081 'Synthetic construct Homo sapiens clone cosb BroadEn_02475 NPC2 gene, encodes complete protein' (2015).
Genbank Accession No. MI332400.1, Sequence 20 from U.S. Pat. No. 9,839,696, dated Feb. 12, 2018, 2 pages.
Genbank Accession No. MI332401.1, Sequence 21 from U.S. Pat. No. 9,839,696, dated Feb. 12, 2018, 2 pages.
Genbank Accession No. MI332402.1, Sequence 22 from U.S. Pat. No. 9,839,696, dated Feb. 12, 2018, 2 pages.
Genbank Accession No. MI332403.1, Sequence 23 from U.S. Pat. No. 9,839,696, dated Feb. 12, 2018, 2 pages.
Genbank Accession No. MI332404.1, Sequence 24 from U.S. Pat. No. 9,839,696, dated Feb. 12, 2018, 2 pages.
Genbank Accession No. MI332405.1, Sequence 25 from U.S. Pat. No. 9,839,696, dated Feb. 12, 2018, 2 pages.
Genbank Accession No. MI332406.1, Sequence 26 from U.S. Pat. No. 9,839,696, dated Feb. 12, 2018, 2 pages.
Genbank Accession No. MI332407.1, Sequence 27 from U.S. Pat. No. 9,839,696, dated Feb. 12, 2018, 2 pages.
Genbank Accession No. MI332408.1, Sequence 28 from U.S. Pat. No. 9,839,696, dated Feb. 12, 2018, 2 pages.
Genbank Accession No. MI332409.1, Sequence 29 from U.S. Pat. No. 9,839,696, dated Feb. 12, 2018, 2 pages.
Genbank Accession No. MI332410.1, Sequence 30 from U.S. Pat. No. 9,839,696, dated Feb. 12, 2018, 2 pages.
Genbank Accession No. MI332411.1, Sequence 31 from U.S. Pat. No. 9,839,696, dated Feb. 12, 2018, 2 pages.
Genbank Accession No. MI332412.1, Sequence 32 from U.S. Pat. No. 9,839,696, dated Feb. 12, 2018, 2 pages.
Genbank Accession No. MI332413.1, Sequence 33 from U.S. Pat. No. 9,839,696, dated Feb. 12, 2018, 2 pages.
Genbank Accession No. MI332414.1, Sequence 34 from U.S. Pat. No. 9,839,696, dated Feb. 12, 2018, 2 pages.
Genbank Accession No. MI332415.1, Sequence 35 from U.S. Pat. No. 9,839,696, dated Feb. 12, 2018, 2 pages.
GenBank Accession No. NC_000883 "Human parvoVirus 819, complete genome" NCBI (4 pages). (Feb. 10, 2015).
GenBank Accession No. NC_001358 "ParvoVirus H1, complete genome" NCBI (3 pages). (Feb. 10, 2015).
Genbank Accession No. NC_001401, Adeono-associated virus-2, complete genome, dated Aug. 13, 2018, 6 pages.
GenBank Accession No. NC_001510 "Minute Virus of mice, complete genome" NCBI (5 pages). (Mar. 28, 2016).
GenBank Accession No. NC_001540 "Bovine parvovir, complete genome" NCBI (4 pages). (Nov. 30, 2009).
GenBank Accession No. NC_001701 "Goose parvovir, complete genome" NCBI (4 pages). (Jan. 28, 2010).
Genbank Accession No. NC_001729, Adeno-associated virus-3, complete genome, dated Aug. 13, 2018, 3 pages.

(56) References Cited

OTHER PUBLICATIONS

Genbank Accession No. NC_001829, Adeno-associated virus-4, complete genome, dated Aug. 13, 2018, 3 pages.
Genbank Accession No. NC_001862, Adeno-associated virus-6, complete genome, dated Jan. 12, 2004, 4 pages.
Genbank Accession No. NC_001863, Adeno-associated virus 3B, complete genome, dated Jan. 12, 2004, 4 pages.
Genbank Accession No. NC_002077, Adeno-associated virus-1, dated Aug. 13, 2018, 3 pages.
Genbank Accession No. NC_004828, Avian adeno-associated virus ATCC VR-865, complete genome, dated Aug. 13, 2018, 3 pages.
Genbank Accession No. NC_005889, Bovine adeno-associated virus, complete genome, dated Aug. 13, 2018, 3 pages.
Genbank Accession No. NC_006148.1, Snake parvovirus 1, complete genome, dated Aug. 13, 2018, 3 pages.
GenBank Accession No. NC_006152 "adeno-associated Virus 5, complete genome" NCBI (3 pages). (Dec. 8, 2008).
GenBank Accession No. NC_006261 "adeno-associated Virus-8, complete genome" NCBI (3 pages). (Mar. 11, 2010).
Genbank Accession No. NC_006263, Avian adeno-associated virus strain DA-1, complete genome, dated Aug. 13, 2018, 3 pages.
GenBank Accession No. NM 000271.4 *Homo sapiens* cholesterol transporter 1 (NPC1), mRNA (2017).
GenBank Accession No. NM 008720.2 Mus musculus cholesterol transporter 1 (Npc1), mRNA (2017).
GenBank Accession No. NM 023409.4 'Mus musculus NPC intracellular cholesterol transporter 2 (Npc2 mRNA' (2017).
GenBank Accession No. NM 173918 Bos taurus NPC intracellular cholesterol transporter 2 (NPC2), mRNA -;- (2017).
GenBank Accession No. NM_006432.3 '*Homo sapiens* NPC intracellular cholesterol transporter 2 (NPC2), mRNA' (2017).
GenBank Accession No. NM_214206 "Sus scrofa NPC intracellular cholesterol transporter 2 (NPC2), mRNA," dated Jun. 20, 2021, 2 pages.
GenBank Accession No. NP_044927 "capsid [Adeno-associated Virus-4]" NCBI (2 pages). (Jan. 28, 2010).
GenBank Accession No. P01166 "Somatostatin precursor [Contains: Somatostatin 28; Somatostatin-14]" NCBI (2 pages). (Sep. 15, 2003).
GenBank Accession No. P61278 "Somatostatin precursor [Contains: Somatostatin 28; Somatostatin-14]" NCBI (2 pages). (Nov. 13, 2019).
GenBank Accession No. U89790 "Adeno-associated Virus 4, complete genome" NCBI (2 pages). (Aug. 21, 1997).
GenBank Accession No. X01457 "Parvovirus h-1, complete genome" NCBI (3 pages). (Apr. 18, 2005).
Genbank Accession No. Y18065, adeno-associated virus type 5 partial genome (cap and rep genes complete), dated Jan. 15, 1999, 3 pages.
Ghusayni, R. et al., "Magnetic resonance imaging volumetric analysis in patients with Alternating hemiplegia of childhood: A pilot study," Eur J Paediatr Neurol. 26:15-19 (2020).
Gonzales, "Cross-Species Evolution of Synthetic AAV Strains for clinical Translation," ASGCT, 23 pages. (2020).
Gorman et al. "Stable alteration of pre-mRNA splicing patterns by modified U7 small nuclear RNAs" Proceedings of the National Academy of Sciences 95:4929:4934 (1998).
Govindasamy et al., "Structurally mapping the diverse phenotype of adeno-associated virus serotype 4," J. Virology 80:11556-11570 (2006).
Govindasamy et al., "Structural Insights into Adeno-Associated Virus Serotype 5," J. Virology 87: 11187-11199 (2013).
Gray et al. "Preclinical Differences of Intravascular MV9 Delivery to Neurons and Glia: A Comparative Study of Adult Mice and Nonhuman Primates" Molecular Therapy, 19(6):1058-1069 (2011).
Gregorevic et al. "Systemic Microdystrophin Gene Delivery Improves Skeletal Muscle Structure and Function in Old Dystrophic mdx Mice" Molecular Therapy 16(4):657-664 (2008).

Grieger, et al., "Separate Basic Region Motifs within the Adeno-Associated Virus Capsid Proteins Are Essential for infectivity and Assembly." J. Virol. (2006), 80(11):5199-5210.
Grifman et al. "Incorporation of Tumor-Targeting Peptides into Recombinant Adeno-Associated Virus Capsids" Molecular Therapy 3(6):964-975 (2001).
Grimm D., et al., "In Vitro and in Vivo Gene Therapy Vector Evolution Via Multispecies Interbreeding and Retargeting of Adeno-Associated Viruses," Journal of Virology, Jun. 2008, vol. 82(12), pp. 5887-5911, XP002610286.
Gurda et al. "Capsid Antibodies to Different adeno-Associated Virus Serotypes Bind Common Regions" Journal of Virology, 87(16):9111-9124 (2013).
Gurda et al., "Mapping a Neutralizing Epitope onto the Capsid of Adeno-Associated Virus Serotype 8," Journal of Virology 86(15): 7739-7751 (2012).
Hadaczek et al. "Transduction of Nonhuman Primate Brain with Adeno-Associated Virus Serotype 1: Vector Trafficking and Immune Response" Human Gene Therapy, 20(3):225-237 (2009).
Hajitou et al., "Vascular targeting: recent advances and therapeutic perspectives," TCM 16:80-88 (2006).
Hauck et al. "Characterization of Tissue Tropism Determinants of Adeno-Associated Virus Type 1" Journal of Virology 77(4):2768-2774 (2003).
Havlik et al., "Co-Evolution of AAV Capsid Antigenicity and Tropism Through a Structure-Guided Approach," ASGCT, 39 pages (2020).
Havlik, Engineering A Humanized AAV8 Capsid Through Iterative Structure-Guided Evolution ASGCT, 24 pages. (2019).
Heinzen EL, et al., "De nova mutations in ATP1A3 cause alternating hemiplegia of childhood," Nat Genet. 44 (9):1030-1034 (2012).
Helseth AR, et al., "Novel E815K knock-in mouse model of alternating hemiplegia of childhood," Neurobiol Dis. 119:100-112 (2018).
Higgins et al., "CLUSTAL: a package for performing multiple sequence alignment on a microcomputer." Gene (1988); 73.1: 237-244.
Higgins, DG et al., 'Fast and sensitive multiple sequence alignments on a microcomputer,' Comput Appl Biosci., 5(2):151-3, (Apr. 1989).
Holm R, et al., " B. Neurological disease mutations of a3 Na+, K+-ATPase: Structural and functional perspectives and rescue of compromised function," Biochim Biophys Acta. 1857(11):1807-1828 (2016).
Hoshijima et al. «Chronic suppression of heart-failure progression by a pseudophosphorylated mutant of phospholamban via in vivo cardiac rAAV gene delivery» Nature Medicine 8:864-871 (2002).
Huang et al. "Characterization of the adeno-Associated Virus 1 and 6 Sialic Acid Binding Site" Journal of Virology, 9 (11 ):5219-5230 (2016).
Huang et al. "ParvoVirus glycan interactions" Current Opinion in Virology 7:108-118 (2014).
Huang, X et al., 'Dynamic programming algorithms for restriction map comparison,' Cabios, Vo1.8, No. 5., pp. 511-520, (1992).
Hughes et al., "AAV9 intracerebroventricular gene therapy improves lifespan, locomotor function and pathology in a mouse model of Niemann-Pick type C1 disease," Human Molecular Genetics 27(17)3079-3098 (2018).
Hunanyan AS, et al., Knock-in mouse model of alternating hemiplegia of childhood: behavioral and electrophysiologic characterization. Epilepsia. 56(1):82-93 (2015).
Hunanyan AS, et al., "Mechanisms of increased hippocampal excitability in the Mashl+/− mouse model of Na+ /K+ -ATPase dysfunction," Epilepsia 59(7):1455-1468 (2018).
Ikeda K, et al., «Knockout of sodium pump a3 subunit gene (Atp1a3-/-) results in perinatal seizure and defective respiratory rhythm generation,» Brain Res. 1666:27-37 (2017).
International Search Report and the Written Opinion of the International Searching Authority corresponding to International Patent Application No. PCT/US2019/020053 (10 pages) (mailed Jun. 6, 2019).

(56) References Cited

OTHER PUBLICATIONS

International Search Report and the Written Opinion of the International Searching Authority corresponding to International Patent Application No. PCT/2018/018381 (14 pages) (mailed Jul. 5, 2018).
International Search Report and Written Opinion for International Application No. PCT/US2021/046699 dated Jan. 12, 2022, 17 pages.
International Search Report and Written Opinion issued by the International Searching Authority for Application No. PCT/2016/013460, dated May 12, 2016, 11 pages.
International Search Report and Written Opinion issued by the International Searching Authority for Application No. PCT/2016/054143, dated Mar. 23, 2017, 33 pages.
International Search Report and Written Opinion issued by the International Searching Authority for Application No. PCT/2020/023877, dated Aug. 3, 2020, 21 pages.
International Search Report and Written Opinion issued by the International Searching Authority for Application No. PCT/US20/15386, dated Apr. 27, 2020, 14 pages.
International Search Report and Written Opinion issued by the International Searching Authority for Application No. PCT/US2016/026524, dated Jan. 9, 2016, 10 pages.
International Search Report and Written Opinion issued by the International Searching Authority for Application No. PCT/US2018/038584 dated Aug. 24, 2018, 11 pages.
International Search Report and Written Opinion issued by the International Searching Authority for Application No. PCT/US2019/062531, dated Apr. 1, 2020, 12 pages.
International Search Report and Written Opinion issued by the International Searching Authority for Application No. PCT/US2020/032978, dated Oct. 15, 2020, 5 pages.
International Search Report and Written Opinion issued by the International Searching Authority for Application No. PCT/US2020/056015, dated Feb. 12, 2021, 16 pages.
International Search Report and Written Opinion issued by the International Searching Authority for Application No. PCT/US2020/056031, dated Feb. 15, 2021, 18 pages.
International Search Report and Written Opinion issued by the International Searching Authority for Application No. PCT/US2021/030937, dated Oct. 29, 2021, 14 pages.
International Search Report and Written Opinion issued by the International Searching Authority for Application No. PCT/US2022/012542, dated Jun. 3, 2022, 10 pages.
International Search Report of International PCT/US2016/026524, mailed Sep. 1, 2016.
Invitation to Pay issued by the International Searching Authority for Application No. PCT/US2019/062531, dated Feb. 3, 2020, 2 pages.
Invitation to Pay issued by the International Searching Authority for Application No. PCT/US21/30937, dated Aug. 16, 2021, 3 pages.
Isaksen TJ, et al., "Hypothermia-induced dystonia and abnormal cerebellar activity in a mouse model with a single disease-mutation in the sodium-potassium pump," PLoS Genet. 13(5):e1006763, pp. 1-23 (2017).
Janson, C. et al., 'Clinical protocol. Gene therapy of Canavan disease: AAV-2 vector for neurosurgical delivery of aspartoacylase gene (ASPA) to the human brain,' Hum. Gene Ther., 13(11 ):1391-1412 (Jul. 2002).
Kailasan et al., "Structure of an enteric pathogen, bovine parvovirus," Virology 89:2603-2614 (2015).
Kaplitt, M.G. et al. (1994). "Long-term gene expression and phenotypic correction using adenoassociated virus vectors in the mammalian brain," Nature Genetics 6:148-154.
Karlin et al. "Applications and statistics for multiple high-scoring segments in molecular sequences" Proceedings of National Academy of Sciences 90:5873-5877 (1993).
Kashiwakura et al. "Hepatocyte Growth Factor Receptor Is a Coreceptor for Adeno-Associated Virus Type 2 Infection" Journal of Virology, 79(1).609-614 (2005).

Kauffman et al., "Mechanism Matters: A Taxonomy of Cell Penetrating Peptides," Trends in Biochemical Sciences, Elsevier, Amsterdam, NL 40(12):749-764 (2015).
Kawakami et al. "Cloning of the gene coding for a shared human melanoma antigen recognized by autologous T cells infiltrating into tumor" Proceedings of the National Academy of Sciences 91:3515-3519 (1994).
Kawakami et al. "Identification of the Immunodominant Peptides of the MART-1 Human Melanoma Antigen Recognized by the Majority of HLA-A2-restricted Tumor Infiltrating Lymphocytes" The Journal of Experimental Medicine 180:347-352 (1994).
Kells, A.P., et al., "AAV-Mediated Gene Delivery of BDNF or GDNF is Neuroprotective in a Model of Huntington Disease," Molecular Therapy, May 2004, vol. 9(5), pp. 682-688.
Kirshenbaum GS, et al., "Alternating hemiplegia of childhood-related neural and behavioural phenotypes in Na +, K+-ATPase a3 missense mutant mice," PLoS One. 8(3):e60141, pp. 1-15 (2013).
Koivunen et al., "Identification of Receptor Ligands with Phase Display Peptide Libraries," J. Nucl. Med. 40:883-888 (1999).
Krissinel et al. "Secondary-structure matching (SSM)., a new tool for fast protein structure alignment in three dimensions" Acta Crystallographica Section D: Biological Crystallography, D60:2256-2268 (2004).
Kuck et al. "Development of AAV serotype-specific ELISAs using novel monoclonal antibodies" Journal of Virological Methods, 140(1-2):17-24 (2007) (Abstract only).
Kumar et al. "MEGA7: Molecular Evolutionary Genetics Analysis Version 7.0 for Bigger Datasets" Molecular Biology and Evolution, 33(7):1870-1874 (2016).
Lein et al. "Genome-wide atlas of gene expression in the adult mouse brain" Nature, 445(7124):168-176 (2007). (Abstract only).
Lerch et al., "The structure of adeno-associated virus serotype 3B (AAV-3B): insights into receptor binding and immune evasion," Virology 403(1):26-36 (2010).
Levine et al. "The Tumor Suppressor Genes" Annual Review of Biochemistry 62:623-651 (1993).
Li et al. "Construction of phospholamban antisense RNA recombinant adeno-associated Virus vector and its effects in rat cardiomyocytes" Acta Pharmalogica Sinica 26(1).51-55 (2005).
Li et al. "Development of Patient-specific AAV Vectors After Neutralizing Antibody Selection for Enhanced Muscle Gene Transfer" Molecular Therapy, 24(1):53-65 (2016).
Li et al. "Engineering and Selection of Shuffled AAV Genomes: A New Strategy for Producing Targeted Biological Nanoparticles" Molecular Therapy, 16(7):1252-1260 (2008).
Li et al. "Single Amino Acid Modification of adeno-Associated Virus Capsid Changes Transduction and Humeral Immune Profiles" Journal of Virology, 86(15):7752-7759 (2012).
Lisowski L., et al., "Selection and Evaluation of Clinically Relevant AAV Variants in a Xenograft Liver Model," Nature, Feb. 2014, vol. 506 (7488), pp. 382-386, XP055573596.
Loftus, SK et al., 'Murine Model of Niemann-Pick C Disease: Mutation in a Cholesterol Homeostasis Gene,' Science, 277(5323):232-235 (Jul. 1997).
Lux et al. "Green Fluorescent Protein-Tagged Adeno-Associated Virus Particles Allow the Study of Cytosolic and Nuclear Trafficking" Journal of Virology, 79(18):11776-11787 (2005).
Madigan et al. "Engineering AAV receptor footprints for gene therapy" Current Opinion in Virology, 18:89-96 (2016).
Margolskee, R. F. "Epstein-Barr Virus Based Expression Vectors" Current Topics in Microbiology and Immunology 158:67-95 (1992).
Masoud M, et al., "Diagnosis and Treatment of Alternating Hemiplegia of Childhood," Curr Treat Options Neurol. 19(2):8 (2017).
Mauro et al., "A critical analysis of codon optimization in human therapeutics," Trends in Molecular Medicine, Nov. 2014, vol. 20, No. 11, pp. 604-613.
Mccarty et al., "Self-complementary recombinant adeno-associated virus (scAAV) vectors promote efficient transduction independently of DNA synthesis," Gene Therapy 8:1248-1254 (2001).
Mccraw et al. "structurE of adeno-associated virus-2 In Complex with Neutralizing Monoclonal antibody A20" Virology, 431 (1-2):40-49 (2012).

(56) References Cited

OTHER PUBLICATIONS

Mclaughlin et al., "Adeno-associated virus general transduction vectors: analysis of proviral structures," J. Virol., (1988) 62:1963-1973.
Mikati MA, et al., " Alternating hemiplegia of childhood: clinical manifestations and long-term outcome," Pediatr Neurol. 23(2):134-141 (2000).
Miller et al. "Production, purification and preliminary X-ray crystallographic studies of adenoassociated virus serotype 1" Acta Crystallographica Section F: Structural Biology and Crystallization Communications, 62(Pt 12):1271-1274 (2006).
Mingozzi et al. "Immune responses to AAV vectors: overcoming barriers to successful gene therapy" Blood, 122 (1):23-36 (2013).
Mingozzi et al., "Overcoming the Host Immune Response to Adeno-Associated Virus Gene Delivery Vectors: The Race Between Clearance, Tolerance, Neutralization, and Escape," Annual Review of Virology 1(1):511-534 (2017).
Miyamura et al. "ParvoVirus particles at platforms for protein presentation" Proceedings of National Academy of Sciences 91:8507-8511 (1995).
Mori et al. "Two novel adeno-associated vires from cynomolgus monkey:pseudotyping characterization of capsid protein," Virology 330:375-383 (2004).
Muller et al. "Random peptide libraries displayed on adeno-associated virus to select for targeted gene therapy vectors", Nat Biotechnol, Sep. 2003; 21(9):1040-6. Epub Aug. 3, 2003.
Muramatsu et al. "Nucleotide Sequencing and Generation of an Infectious Clone of Adeno-Associated Virus 3," Virology 22(0367):208-217 (1996).
Murlidharan et al. "265. Polysialic Acid as a Novel Regulator of AAV Tropism in the Developing Brain" Molecular Therapy 23(Supplement 1 ):S106 (2015), 1 page.
Murlidharan et al. "Biology of adeno-associated viral vectors in the central nervous system" Frontiers in Molecular Neuroscience, 7(76):1-9 (2014).
Murlidharan et al. "CNS-restricted Transduction and CRISPR/Cas9-mediated Gene Deletion with an Engineered AAV Vector" Molecular Therapy: Nucleic Acids, 5:e338 (2016).
Murlidharan et al. "Glymphatic fluid transport controls paravascular clearance of MV vectors from the brain" JCI Insight, 1 (14):e88034 (2016).
Murlidharan et al. "Unique Glycan Signatures Regulate adeno-Associated Virus Tropism in the Developing Brain" Journal of Virology 89(7):3976-3987 (2015).
Muzyczka, N. "Use of adeno-Associated Virus as a General Transduction Vector for Mammalian Cells," Current Topics in Microbiology and Immunology 158:97-129 (1992).
Nam et al. "Structure of Adeno-Associated Virus Serotype 8, a Gene Therapy Vector" Journal of Virology, 81 (22):12260-12271 (2007).
Nathwani et al. "Long-Term Safety and Efficacy of Factor IX Gene Therapy in Hemophilia B" The New England Journal of Medicine, 371 (21):1994-2004 (2014).
Needleman et al., "A general method applicable to the search for similarities in the amino acid sequence of two proteins." J Mol Biol. (1970); 48(3): 443-453.
Newton et al., Phage Peptide Display in Handbook of Experimental Pharmacology, pp. 145-163, Springer-Verlag, Berlin (2008).
Ng et al. "Structural Characterization of the Dual Glycan Binding adeno-Associated Virus Serotype 6" Journal of Virology, 84(24):12945-12957 (2010).
Nguyen Vu et al., "Cerebellar Purkinje cell activity drives motor learning", Nature Neuroscience 16(12):1734-1736 (2013).
Padron et al. "Structure of adeno-Associated Virus Type 4" Journal of Virology 79(8):5047-5058 (2005).
Palombo et al. "Site-Specific Integration in Mammalian Cells Mediated by a New Hybrid Baculoviru-Adeno-Associated Virus Vector" Journal of Virology72(6):5025-5034 (1998).
Papadakis, ED et al., 'Promoters and Control Elements: Designing Expression Cassettes for Gene Therapy,' Curr. Gene Therapy, vol. 4, No. 1, pp. 89-113, (Mar. 2004).

Partial Supplementary European Search Report issued by the European Patent Office for Application No. 16852471.8, dated Apr. 24, 2019, 17 pages.
Passini, Ma et al., 'Distribution of a Lysosomal Enzyme in the Adult Brain by Axonal Transport and by Cells of the Rostral Migratory Stream,' J. Neuroscience, 22(15):6437-6446 (Aug. 2002).
Paul, CA et al., 'Adenovirus Expressing an NPCI-GFP Fusion Gene Corrects Neuronal and Nonneuronal Defects Associated With Niemann Pick Type C Disease,' J. Neurosci. Res., vol. 81, No. 5, pp. 706-719 (Sep. 2005).
Piguet et al., "Rapid and Complete Reversal of Sensory Ataxia by Gene Therapy in a Novel Model of Friedreich Ataxia", Molecular Therapy, Nature Publishing Group, GB 26(8), pp. 1-13 (2018).
Pillay et al. "An essential receptor for adeno-associated virus infection" Nature, 530(7588):108-112 (2016).
Powell et al. Characterization of a Novel Adena-Associated Viral Vector with Preferential Oligodendrocyte Tropism. Gene Therapy, 2016. 23:807-814.
Pulicherla et al. "Engineering Liver-detargeted AAV9 Vectors for Cardiac and Musculoskeletal Gene Transfer" Molecular Therapy, 19(6):1070-1078 (2011).
Puttaraju et al. "Spliceosome-mediated RNA trans-splicing as a tool for gene therapy" Nature Biotechnology 17:246-252 (1999).
Robbins et al., "Recognition of tyrosinase by tumor-infiltrating lymphocytes from a patient responding to immunotherapy," Cancer Res. 54:3124-3126 (1994).
Rosenberg "The Immunotherapy of Solid Cancers Based on Cloning the Genes Encoding Tumor-Rejection Antigens" Annual Review of Medicine 47:481-491 (1996).
Rosenberg et al. "A New Era for Cancer Immunotherapy Based on the Genes that Encode Cancer Antigens" Immunity 10:281-287 (1999).
Rosenberg et al. "Comparative Efficacy and Safety of Multiple Routes of Direct CNS Administration of Adeno-Associated Virus Gene Transfer Vector Serotype rh.10 Expressing the Human Arylsulfatase A cDNA to Nonhuman Primates" Human Gene Therapy Clinical Development, 25(3):164-177 (2014).
Saitou, N. et al. (1987). "The neighbor-joining method: A new method for reconstructing phylogenetic trees," Mol. Biol. Evol. 4:406-425.
Salinas et al. "A hitchhiker's guide to the nervous system: the complex journey of viruses and toxins" Nature Reviews Microbiology, 8(9):645-655 (2010). (Abstract only).
Selot et al., "Developing Immunologically Inert Adeno-Associated Virus (AAV). Vectors for Gene Therapy: Possibilities and Limitations," Current Pharmaceutical Biotechnology, Bentham Science Publishers, NL 14(12). 1072-1082 (2013).
Severino M, et al., "White matter and cerebellar involvement in alternating hemiplegia of childhood," J Neurol. 267 (5):1300-1311 (2020).
Shade et al. "Nucleotide Sequence and Genome Organization of Human Parvovirus B19 Isolated from the Serum of a Child during Aplastic Crisis" Journal of Virology 28(3):921-936 (1986).
Sharp et al. "RNA Interference" Science 287(5462):2431-2433 (2000).
Shen et al. "Engraftment of a Galactose Receptor Footprint onto adeno-associated Viral Capsids Improves Transduction Efficiency" The Journal of Biological Chemistry, 288(40):28814-28823 (2013).
Shen et al., Multiple Roles for Sialylated Glycans in Determining the Cardiopulmonary Tropism of Adeno-Associated Virus 4, Journal of Virology 87(24):13206-13213 (2013).
Shi et al. "Insertional Mutagenesis at Positions 520 and 584 of adeno-Associated Virus Type 2 (AAV2). Capsid Gene and Generation of AAV2 Vectors with Eliminated Heparin-Binding Ability and Introduced Novel Tropism" Human Gene Therapy 17:353-361 (2006).
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.
Smith et al., "Comparison of Biosequences", Advances in Applied Mathematics, vol. 2, Issue 4, Dec. 1981, pp. 482-489.
Smith et al., "Structural Mapping of AAV9 Antigenic Sites and the Engineering of Immune Escape Variants," Molecular Therapy; 20th

(56) References Cited

OTHER PUBLICATIONS

Annual Meeting of the American Society of Gene and Cell Therapy (ASGCT) .; Washington, DC, A; May 10-13, 2017, Nature Publishing Group, GB vol. 25, No. 5, Suppl 1 (2017).

Smith, TF et al., 'Identification of Common Molecular Subsequences,' Journal of Molecular Biology, 147:195-197, PMID 7265238. doi:10.1016/0022-2836(81)90087-5, (1981).

Sonntag et al. "Adeno-Associated Virus Type 2 Capsids with Externalized VP1NP2 Trafficking Domains Are Generated prior to Passage through the Cytoplasm and Are Maintained until Uncoating Occurs in the Nucleus" Journal of Virology, 80(22):11040-11054 (2006).

Srivastava et al. "Nucleotide Sequence and Organization of the adeno-Associated Virus 2 Genome" Journal of Virology 45(2):555-564 (1983).

Summerford et al. "Membrane-Associated Heparan Sulfate Proteoglycan Is a Receptor for adeno-Associated Virus Type 2 Virions" Journal of Virology, 72(2):1438-1445 (1998).

Tellez et al. "Characterization of Naturally-Occurring Humoral Immunity to AAV in Sheep" PLoS ONE, 8(9):e75142 (2013).

Tinsley et al. "Amelioration of the dystrophic phenotype of mdx mice using a truncated utrophin transgene" Nature 384(6607):349-353 (1996).

Titeux et al., "SIN Retroviral Vectors Expressing COL7A1 Under Human Promoters for Ex Vivo Gene Therapy of Recessive Dystrophic Epidermolysis Bullosa," Mol. Ther., 2010 18:1509-1518.

Tsao et al. The Three-Dimensional Structure of Canine ParvoVirus and Its Functional Implications Science 251 (5000):1456-1464 (1991).

Tse et al., "Strategies to Circumvent Humoral Immunity to Adeno-Associated Viral Vectors," Expert Opinion on Biological Therapy 15(6):845-855 (2015).

Tse et al., "Structure-guided evolution of antigenically distinct adeno-associated Virus variants for immune evasion", Proceedings of the National Academy of Sciences of The United States of America 114(24):E4812-E4821 (2017).

Tseng et al. "Adeno-Associated Virus Serotype 1 (AAV1).- and AAV5-Antibody Complex Structures Reveal Evolutionary Commonalities in ParvoVirus Antigenic Reactivity" Journal of Virology, 89(3):1794-1808 (2015).

Tseng et al. "Generation and characterization of anti-adeno-associated Virus serotype 8 (AAV8). and anti-AAV9 monoclonal antibodies" Journal of Virological Methods, 236:105-110 (2016).

Tseng et al. "Mapping the AAV capsid host antibody response toward the development of second generation gene delivery vectors" Frontiers in Immunology, 5(9):1-11 (2014).

UniProt Accession No. 015118, dated May 30, 2000, 21 pages.

University College London (UCL) School of Pharmacy website "Therapy for Niemann-Pick Type C Disease", (Apr. 2014).

Urabe et al. "Insect Cells as a Factory to Produce adeno-Associated Virus Type 2 Vectors" Human Gene Therapy 13:1935-1943 (2002).

Various: Abstracts , 20th Annual Meeting of the American-Society-of-Gene-and-Cell-Therapy (ASGCT); Washington, DC, USA; May 10-13. 2017 , Molecular Therapy: the Journal of the American Society of Gene Therapy 25:1-363 (2017).

Veldwijk, MR et al., 'Development and optimization of a real-time quantitative PCR-based method for the titration of AAV-2 vector stocks,' Mol. Ther.,6(2):272-8 (Aug. 2002).

Veron et al. «Humeral and Cellular Capsid-Specific Immune Responses to Adena-Associated Virus Type 1 in andomized Healthy Donors» The Journal of Immunology, 188:6418-6424 (2012).

Vincent et al. "Long-term correction of mouse dystrophin degeneration by adenovirusmediated transfer of a minidystrophin gene" Nature Genetics 5:130-134 (1993).

Walters et al. "Structure of adeno-Associated Virus Serotype 5" Journal of Virology 78(7):3361-3371 (2004).

Wang et al. "Adeno-associated Virus vector carrying human minidystrophin genes effectively ameliorates muscular dystrophy in mdx mouse model" Proceedings of the National Academy of Sciences 97(25):13714-13719 (2000).

Wang et al. "Expanding the genetic code" Annual Review of Biophysics and Biomolecular Structure 35:225-249 (2006).

Wang et al., "Identification of an adeno-associated Virus binding epitope for AVB sepharose affinity resin," Molecular Therapy-Methods & Clinical Development vol. 2, pp. 1-6 (2015).

Wang et al., "Selection of neutralizing antibody-resistant AAV8 variants with structure-guided site-specific saturated mutagenesis," Molecular Therapy, 2011, vol. 19 Suppl. 1, S129.

Wassif, CA et al., 'High Incidence of Unrecognized Visceral/Neurological Lateonset Niemann-Pick Disease, type C1 Predicted by Analysis of Massively Parallel Sequencinq Data Sets,' Genet Med., 18(1):41-48 (Jan. 2016).

Weller et al. "Epidermal growth factor receptor is a co-receptor for adeno-associated virus serotype 6" Nature Medicine, 16(6):662-664 (2010).

Williams et al. «Monocyte maturation, HIV susceptibility, and transmigration across the blood brain barrier are critical in HIV neuropathogenesis» Journal of Leukocyte Biology, 91 (3):401-415 (2012).

Winkler et al., "Changing the Antigen Binding Specificity by Single Point Mutations of an Antip24 (HIV-1) Antibody", The Journal of Immunology, 165: 4505-4514 (2000).

Wobus et al. "Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection," J. of Virology, 74(19):9281-9293 (2000).

Work et al., "Vascular bed-targeted in vivo gene delivery using tropism-modified adeno-associated viruses," Molecular Therapy 13(4):683-693 (2006).

Wu et al. "alpha2,3 and alpha2,6 N-Linked Sialic Acids Facilitate Efficient Binding and Transduction by Adeno-Associated Virus Types 1 and 6" Journal of Virology, 80(18):9093- 9103 (2006).

Wu et al. "Single Amino Acid Changes Can Influence Titer, Heparin Binding, and Tissue Tropism in Different adeno-Associated Virus Serotypes" Journal of Virology, 80(22):11393-11397 (2006).

Xiao et al. "Gene Therapy Vectors Based on adeno-Associated Virus Type 1" Journal of Virology 73(5):3994-4003 (1999).

Xiao et al. "Interpretation of Electron Density with Stereographic Roadmap Projections" Journal of Structural Biology, 158(2):182-187 (2007).

Xiao et al., "Gene transfer by adeno-associated virus vectors into the central nervous system," Exp. Neurobiol., (1997) 144:113-124.

Xie et al. "Canine ParvoVirus Capsid Structure, Analyzed at 2.9 A Resolution" Journal of Molecular Biology 264(3):497-420 (1996).

Xie et al. "The atomic structure of adeno-associated Virus (AAV-2)., a vector for human gene therapy" Proceeding of the National Academy of Sciences 99(16):10405-10410 (2002).

Xie, J. et al., "Short DNA Hairpins Compromise Recombinant Adeno-Associated Virus Genome Homogeneity," Mol. Ther., 25(6): 1363-1374 (2017).

Yang et al. "Global CNS Transduction of Adult Mice by Intravenously Delivered rAAVrh.8 and rAAVrh. 10 and Nonhuman Primates by rAAVrh.10" Molecular Therapy, 22(7):1299-1309 (2014).

Ye Q, et al., "The AAA+ ATPase TRIP13 remodels HORMA domains through N-terminal engagement and unfolding," EMBO J. 36(16):2419-2434 (2017).

Zhang et al. "Recombinant adenoVirus expressing adeno-associated Virus cap and rep proteins supports production of high-titer recombinant adeno-associated virus" Gene Therapy 8:704-712 (2001).

Zhang et al. "Several rAAV Vectors Efficiently Cross the Blood-brain Barrier and Transduce Neurons and Astrocytes in the Neonatal Mouse Central Nervous System" Molecular Therapy, 19(8):1440-1448 (2011 ).

Zhang, "Endocytic mechanisms and drug discovery in neurodegenerative diseases," Frontiers in Bioscience 13:6086-6105 (2008).

Zhong et al. "Next generation of adeno-associated virus 2 vectors: Point mutations in tyrosines lead to high-efficienc ransduction at lower doses" Proceedings of the National Academy of Sciences USA, 105(22):7827-7832 (2008).

Zhong et al. "Tyrosine-phosphorylation of AAV2 vectors and its consequences on viral intracellular trafficking and transgene expression" Virology, 381(2):194-202 (2008).

(56) References Cited

OTHER PUBLICATIONS

Zinn, E. et al., "In Silico Reconstruction of the Viral Evolutionary Lineage Yields a Potent Gene Therapy Vector," Cell Reports, Aug. 2015; 12:1056-1068.
Zolotukhin et al. "Production and purification of serotype 1, 2, and 5 recombinant adeno-associated viral vectors" Methods, 28(2):158-167 (2002) (Abstract only).
Zolotukhin, et al., "Recombinant adeno-associated virus purification using novel methods improves infectious titer and yield." Gene Therapy (1999); vol. 6, pp. 973-985.

* cited by examiner

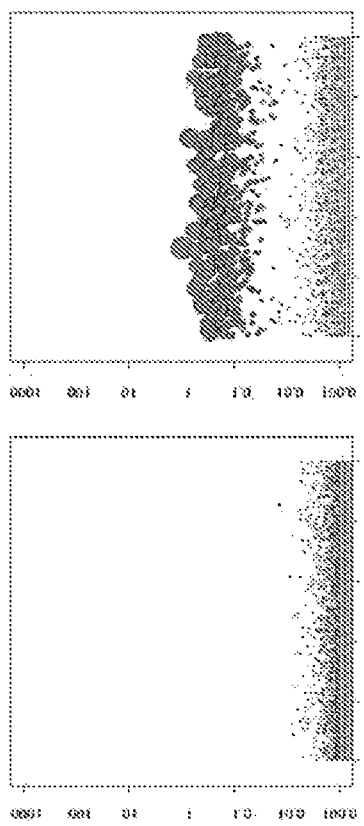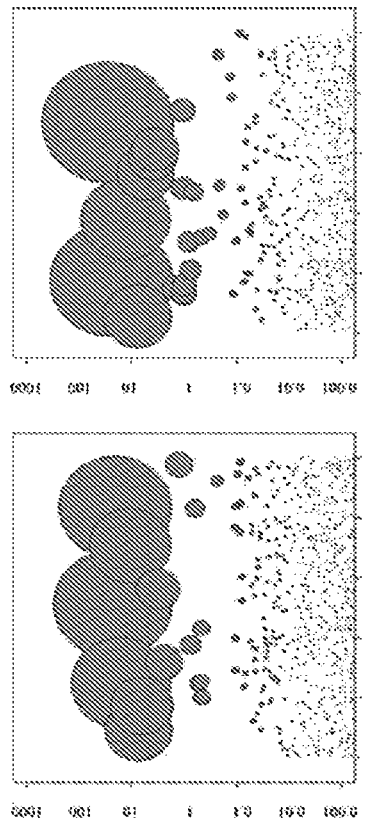
Fig. 2A Round 1 Input
Fig. 2B Round 2 Input
Fig. 2C Round 3 Input
Fig. 2D Round 3 Output

ANTIBODY-EVADING VIRUS VECTORS

CROSS REFERENCE TO RELATED APPLICATIONS

This application is a continuation of U.S. patent application Ser. No. 17/045,091, filed Oct. 2, 2020, which is a national phase of International Application No. PCT/US2019/025617, filed Apr. 3, 2019, which claims priority to U.S. Provisional Application Ser. No. 62/819,388, filed Mar. 15, 2019, U.S. Provisional Application Ser. No. 62/776,814, filed Dec. 7, 2018, U.S. Provisional Application Ser. No. 62/652,111, filed Apr. 3, 2018, each of which is incorporated by reference herein in its entirety for all purposes.

FIELD OF THE DISCLOSURE

The present disclosure relates to modified capsid proteins from adeno-associated virus (AAV) and virus capsids and virus vectors comprising the same. In particular, the disclosure relates to modified AAV capsid proteins and capsids comprising the same that can be incorporated into virus vectors to confer a phenotype of evasion of neutralizing antibodies without decreased transduction efficiency.

SEQUENCE LISTING

The instant application contains a Sequence Listing which has been submitted electronically in XML format and is hereby incorporated by reference in its entirety. Said XML format copy, created on Oct. 17, 2023, is identified as GSB-00602 and is 1,104,723 bytes in size.

BACKGROUND

Host-derived pre-existing antibodies generated upon natural encounter of AAV or recombinant AAV vectors prevent first time as well as repeat administration of AAV vectors as vaccines and/or for gene therapy. Serological studies reveal a high prevalence of antibodies in the human population worldwide with about 67% of people having antibodies against AAV1, 72% against AAV2, and about 40% against AAV5 through AAV9.

Furthermore, in gene therapy, certain clinical scenarios involving gene silencing or tissue degeneration may require multiple AAV vector administrations to sustain long term expression of the transgene. To circumvent these issues, recombinant AAV vectors which evade antibody recognition (AAVe) are required. Such vectors will help a) expand the eligible cohort of patients suitable for AAV-based gene therapy and b) allow multiple, repeat administrations of AAV-based gene therapy vectors.

The present disclosure provides methods and compositions comprising an adeno-associated virus (AAV) capsid protein, comprising one or more amino acid substitutions, wherein the substitutions introduce into an AAV vector comprising these modified capsid proteins the ability to evade host antibodies.

BRIEF SUMMARY

The present disclosure provides an adeno-associated virus (AAV) capsid proteins, comprising one or more amino acid modifications, wherein the one or more amino acid modifications modify one or more antigenic sites on the AAV capsid protein. In some embodiments wherein the AAV capsid proteins are incorporated into AAV vectors, the modification of the one or more antigenic sites results in evasion of neutralizing antibodies.

In some embodiments, the disclosure provides a recombinant adeno-associated virus (AAV) capsid protein, wherein the capsid protein comprises a substitution in an antigenic site of the AAV capsid protein, wherein the substitution has a sequence of any one of SEQ ID NO: 9, 10, 11, 12, 13, 14, 15, 16, 17, 297, 298, 299, or 411-421. In some embodiments, the AAV capsid protein is of an AAV serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, the AAV capsid protein is chimeric.

In some embodiments, the disclosure provides a recombinant AAV capsid protein, wherein the AAV capsid protein comprises an amino acid sequence that has at least 90%, at least 95%, at least 96%, at least 97%, at least 98%, at least 99%, or 100% sequence identity, with any one of SEQ ID NOs: 18-80, 300-612, or 783-785.

The present disclosure also provides a nucleotide sequence, or an expression vector comprising the same, that encodes one or more of the AAV capsid proteins of the disclosure. The present disclosure also provides a cell that comprises one or more nucleotide sequences or expression vectors of the disclosure.

The present disclosure also provides an AAV capsid comprising the AAV capsid protein of this disclosure. Further provided herein is a viral vector comprising the AAV capsid of this disclosure as well as a composition comprising the AAV capsid protein, AAV capsid and/or viral vector of this disclosure in a pharmaceutically acceptable carrier.

The present disclosure additionally provides a method of introducing a nucleic acid into a cell in the presence of antibodies against the AAV capsid, comprising contacting the cell with the viral vector of this disclosure. The cell can be in a subject and in some embodiments, the subject can be a human subject.

In some embodiments, a method of treating a patient in need thereof is provided, the method comprising administering to the patient a therapeutically effective amount of an AAV viral vector of the disclosure.

These and other aspects are addressed in more detail in the detailed description set forth below.

BRIEF DESCRIPTION OF THE DRAWINGS

FIG. 1A and FIG. 1B. Bubble plots showing analysis of library diversity, directed evolution and enrichment of novel antigenic footprints. Parental (FIG. 1A) and evolved (FIG. 1B) AAV libraries were subjected to high-throughput sequencing using the Illumina MiSeq platform. Following analysis with a custom Perl script, enriched amino acid sequences were plotted. Each bubble represents a distinct capsid amino acid sequence with the radius of the bubble proportional to the number of reads for that variant in the respective library. The y-axis represents the absolute number of reads, transformed to log base 2. Data are spread along the x-axis for ease of visualization. The percent reduction in unique clones (93.4%) demonstrates that numerous "un-fit" sequences were removed after a first round of evolution.

FIG. 2A, FIG. 2B, FIG. 2C, and FIG. 2D. FIG. 2A is a bubble plot showing the parental (input) library for the first round of evolution. FIG. 2B is a bubble plot showing the output library for the first round of evolution, which was used as the input library for the second round of evolution. FIG. 2C is a bubble blot showing the output library for the second round of evolution, which was used as the input library for the third round of evolution. FIG. 2D is a bubble plot showing the output library for the third round of evolution, which represents a 97.3% overall reduction in unique clones compared to the parental library shown in FIG. 2A. Notably, FIGS. 2A and 2B show the same data as in FIG. 1A and FIG. 1B, respectively, but the data has been normalized to percent total reads, allowing for longitudinal comparison across subsequent rounds of evolution.

FIG. 3. Luciferase expression in human hepatocytes (HepG2, Huh7) after infection by recombinant AAVs (AAV-SB1, AAV-SB2, AAV-SB3, AAV-SB4, AAV-SB5) at a dose of 10,000 vg/cell.

FIG. 4. Neutralization of recombinant AAVs (AAV-SB1, AAV-SB2, AAV-SB3, AAV-SB4, AAV-SB5) by human intravenous immunoglobulin (IVIG) compared to neutralization of parental AAV8. Data are presented as transduction after IVIG treatment as a percentage of transduction without IVIG treatment.

FIG. 5. Curve showing percent transduction (i.e. extent of neutralization) of parental AAV8 and AAV-SB1 after treatment with various doses of IVIG (0-4 mg/mL).

FIG. 6A. Percentage of donor samples (100 samples total) that were neutralizing and non-neutralizing to the indicated capsids. FIG. 6B. Breakdown of seropositive donor samples by age groups.

FIG. 7. Representative immunohistochemistry (IHC) images of liver from normal mice after infection with either parental AAV8 or AAV-SB1 at a $3 \times 10^{12}$ vg/mL dose.

FIG. 8. Representative fluorescent microscopy images of U87 cells 48 hours after transduction with parental AAV8, AAV-SB1 or AAV-SB6 vectors packaging GFP at an MOI of 40,000. A representative light microscopy image is also shown for reference.

DETAILED DESCRIPTION

Figures 1A, 1B:
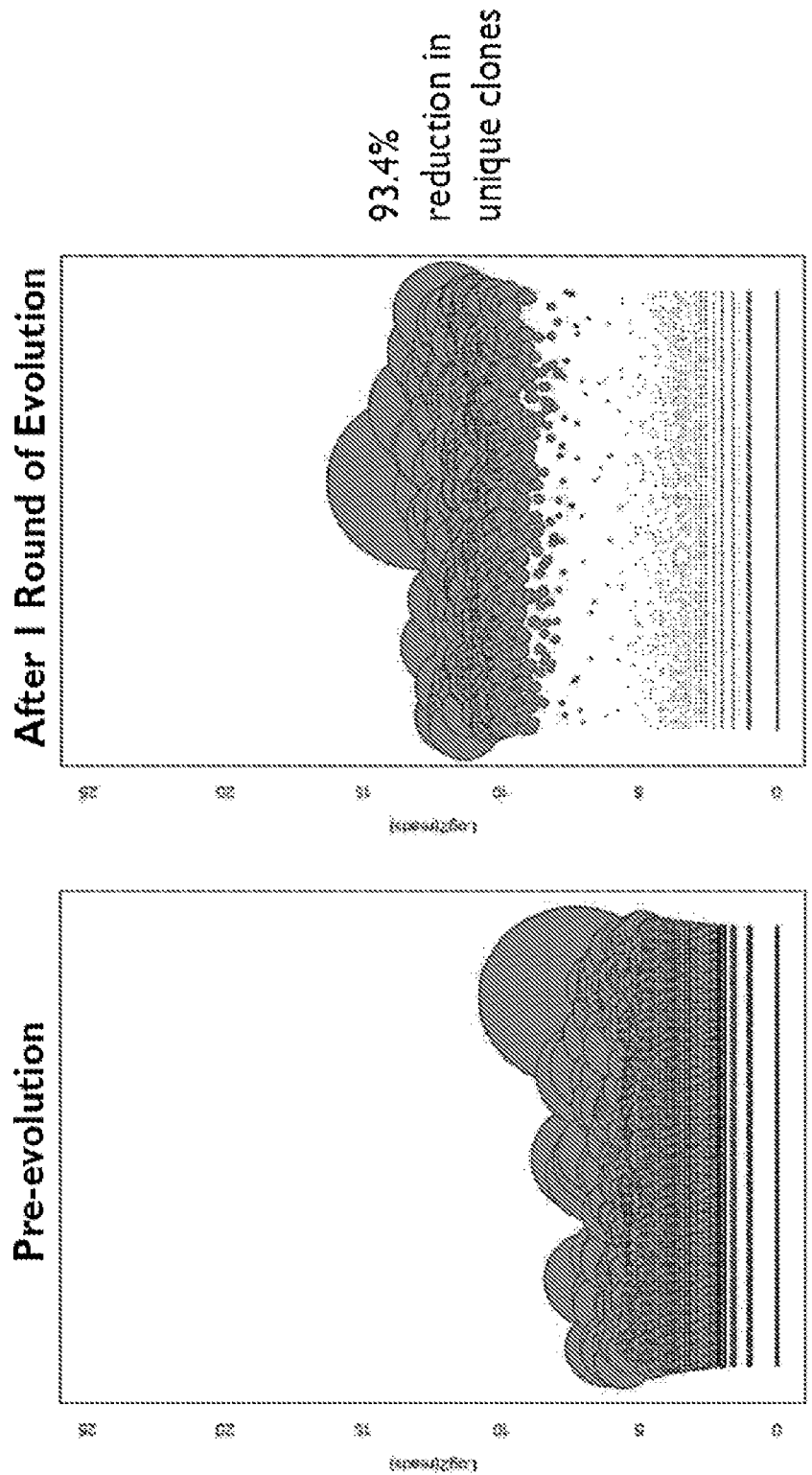

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

All publications, patent applications, patents, GenBank or other accession numbers and other references mentioned herein are incorporated by reference herein in their entirety.

The designation of all amino acid positions in the AAV capsid proteins in the disclosure and the appended claims is with respect to VP1 capsid subunit numbering. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3).

Definitions

The following terms are used in the description herein and the appended claims:

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features described herein can be used in any combination.

Moreover, the present disclosure also contemplates that in some embodiments, any feature or combination of features set forth herein can be excluded or omitted. To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc., as if each such subcombination is expressly set forth herein. Moreover, such language also indicates that one or more of the specified amino acids can be disclaimed. For example, in particular embodiments the amino acid is not A, G or I; is not A; is not G or V; etc., as if each such possible disclaimer is expressly set forth herein.

As used herein, the terms "reduce," "reduces," "reduction" and similar terms mean a decrease of at least about 10%, about 15%, about 20%, about 25%, about 35%, about 50%, about 75%, about 80%, about 85%, about 90%, about 95%, about 97% or more.

As used herein, the terms "enhance," "enhances," "enhancement" and similar terms indicate an increase of at least about 10%, about 15%, about 20%, about 25%, about 50%, about 75%, about 100%, about 150%, about 200%, about 300%, about 400%, about 500% or more.

The term "parvovirus" as used herein encompasses the family Parvoviridae, including autonomously replicating parvoviruses and dependoviruses. The autonomous parvoviruses include members of the genera Protoparvovirus, Erythroparvovirus, Bocaparvovirus, and Densovirus subfamily. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al, VIROLOGY, volume 2, chapter 69 (4th ed., Lippincott-Raven Publishers; Cotmore et al. Archives of Virology DOI 10.1007/s00705-013-1914-1).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, AAV type rh74, AAV type hu.68, avian AAV, bovine AAV, canine AAV, equine AAV, ovine AAV, snake AAV, bearded dragon AAV, AAV2i8, AAV2g9, AAV-LK03, AAV7m8, AAV Anc80, AAV PHP.B, and any other AAV now known or later discovered. See, e.g., BERNARD N. FIELDS et al., VIROLOGY, volume 2, chapter 69 (4th ed., Lippincott-Raven Publishers). A number of AAV serotypes and clades have been identified (see, e.g., Gao et al, (2004) J. Virology 78:6381-6388; Moris et al, (2004) Virology 33-:375-383; and Table 2).

As used herein, the term "chimeric AAV" refers to an AAV comprising a capsid protein with regions, domains, individual amino acids that are derived from two or more different serotypes of AAV. In some embodiments, a chimeric AAV comprises a capsid protein comprised of a first region that is derived from a first AAV serotype and a second region that is derived from a second AAV serotype. In some embodiments, a chimeric AAV comprises a capsid protein comprised of a first region that is derived from a first AAV serotype, a second region that is derived from a second AAV serotype, and a third region that is derived from a third AAV serotype. In some embodiments, the chimeric AAV may comprise regions, domains, individual amino acids derived from two or more of AAV1, AAV2, AAV3, AAV4, AAV5, AAV6, AAV7, AAV8, AAV9, AAV10, AAV11, and/or AAV12. For example, the chimeric AAV may include regions, domains, and/or individual amino acids from a first and a second AAV serotype as shown below (Table 1), wherein AAVX+Y indicates a chimeric AAV including sequences derived from AAVX and AAVY.

TABLE 1

Chimeric AAVs

| | | Second AAV Serotype | | | | | |
|---|---|---|---|---|---|---|---|
| | | AAV1 | AAV2 | AAV3 | AAV4 | AAV5 | AAV6 |
| First AAV Sertoype | AAV1 | x | AAV1 + 2 | AAV1 + 3 | AAV1 + 4 | AAV1 + 5 | AAV1 + 6 |
| | AAV2 | AAV2 + 1 | x | AAV2 + 3 | AAV2 + 4 | AAV2 + 5 | AAV2 + 6 |
| | AAV3 | AAV3 + 1 | AAV3 + 2 | x | AAV3 + 4 | AAV3 + 5 | AAV3 + 6 |
| | AAV4 | AAV4 + 1 | AAV4 + 2 | AAV4 + 3 | x | AAV4 + 5 | AAV4 + 6 |
| | AAV5 | AAV5 + 1 | AAV5 + 2 | AAV5 + 3 | AAV5 + 4 | x | AAV5 + 6 |
| | AAV6 | AAV6 + 1 | AAV6 + 2 | AAV6 + 3 | AAV6 + 4 | AAV6 + 5 | x |
| | AAV7 | AAV7 + 1 | AAV7 + 2 | AAV7 + 3 | AAV7 + 4 | AAV7 + 5 | AAV7 + 6 |
| | AAV8 | AAV8 + 1 | AAV8 + 2 | AAV8 + 3 | AAV8 + 4 | AAV8 + 5 | AAV8 + 6 |
| | AAV9 | AAV9 + 1 | AAV9 + 2 | AAV9 + 3 | AAV9 + 4 | AAV9 + 5 | AAV9 + 6 |
| | AAV10 | AAV10 + 1 | AAV10 + 2 | AAV10 + 3 | AAV10 + 4 | AAV10 + 5 | AAV10 + 6 |
| | AAV11 | AAV11 + 1 | AAV11 + 2 | AAV11 + 3 | AAV11 + 4 | AAV11 + 5 | AAV11 + 6 |
| | AAV12 | AAV12 + 1 | AAV12 + 2 | AAV12 + 3 | AAV12 + 4 | AAV12 + 5 | AAV12 + 6 |

| | | Second AAV Serotype | | | | | |
|---|---|---|---|---|---|---|---|
| | | AAV7 | AAV8 | AAV9 | AAV10 | AAV11 | AAV12 |
| First AAV Sertoype | AAV1 | AAV1 + 7 | AAV1 + 8 | AAV1 + 9 | AAV1 + 10 | AAV1 + 11 | AAV1 + 12 |
| | AAV2 | AAV2 + 7 | AAV2 + 8 | AAV2 + 9 | AAV2 + 10 | AAV2 + 11 | AAV2 + 12 |
| | AAV3 | AAV3 + 7 | AAV3 + 8 | AAV3 + 9 | AAV3 + 10 | AAV3 + 11 | AAV3 + 12 |
| | AAV4 | AAV4 + 7 | AAV4 + 8 | AAV4 + 9 | AAV4 + 10 | AAV4 + 11 | AAV4 + 12 |
| | AAV5 | AAV5 + 7 | AAV5 + 8 | AAV5 + 9 | AAV5 + 10 | AAV5 + 11 | AAVS + 12 |
| | AAV6 | AAV6 + 7 | AAV6 + 8 | AAV6 + 9 | AAV6 + 10 | AAV6 + 11 | AAV6 + 12 |
| | AAV7 | x | AAV7 + 8 | AAV7 + 9 | AAV7 + 10 | AAV7 + 11 | AAV7 + 12 |
| | AAV8 | AAV8 + 7 | x | AAV8 + 9 | AAV8 + 10 | AAV8 + 11 | AAV8 + 12 |
| | AAV9 | AAV9 + 7 | AAV9 + 8 | x | AAV9 + 10 | AAV9 + 11 | AAV9 + 12 |
| | AAV10 | AAV10 + 7 | AAV10 + 8 | AAV10 + 9 | x | AAV10 + 11 | AAV10 + 12 |
| | AAV11 | AAV11 + 7 | AAV11 + 8 | AAV11 + 9 | AAV11 + 10 | x | AAV11 + 12 |
| | AAV12 | AAV12 + 7 | AAV12 + 8 | AAV12 + 9 | AAV12 + 10 | AAV12 + 11 | x |

By including individual amino acids or regions from multiple AAV serotypes in one capsid protein, capsid proteins that have multiple desired properties that are separately derived from the multiple AAV serotypes may be obtained.

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) J. Virology 45:555; Chiorini et al, (1998) J Virology 71:6823; Chiorini et al., (1999) J. Virology 73: 1309; Bantel-Schaal et al., (1999) J Virology 73:939; Xiao et al, (1999) J Virology 73:3994; Muramatsu et al., (1996) Virology 221:208; Shade et al, (1986) J. Virol. 58:921; Gao et al, (2002) Proc. Nat. Acad. Sci. USA 99:11854; Moris et al, (2004) Virology 33:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 2. The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) Proc. Nat. Acad. Sci. 99: 10405-10), AAV9 (DiMattia et al., (2012) J. Virol. 86:6947-6958), AAV8 (Nam et al, (2007) J. Virol. 81:12260-12271), AAV6 (Ng et al., (2010) J. Virol. 84:12945-12957), AAV5 (Govindasamy et al. (2013) J. Virol. 87, 11187-11199), AAV4 (Govindasamy et al. (2006) J. Virol. 80:11556-11570), AAV3B (Lerch et al., (2010) Virology 403:26-36), BPV (Kailasan et al., (2015) J. Virol. 89:2603-2614) and CPV (Xie et al, (1996) J. Mol. Biol. 6:497-520 and Tsao et al, (1991) Science 251:1456-64).

TABLE 2

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617, AAR26465 |
| AAV11 | AAT46339, AY631966 |
| AAV12 | ABI16639, DQ813647 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |

TABLE 2-continued

| | GenBank Accession Number |
|---|---|
| HSC1 | MI332400.1 |
| HSC2 | MI332401.1 |
| HSC3 | MI332402.1 |
| HSC4 | MI332403.1 |
| HSC5 | MI332405.1 |
| HSC6 | MI332404.1 |
| HSC7 | MI332407.1 |
| HSC8 | MI332408.1 |
| HSC9 | MI332409.1 |
| HSC11 | MI332406.1 |
| HSC12 | MI332410.1 |
| HSC13 | MI332411.1 |
| HSC14 | MI332412.1 |
| HSC15 | MI332413.1 |
| HSC16 | MI332414.1 |
| HSC17 | MI332415.1 |
| Hu68 Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |
| Others Rh74 Bearded Dragon AAV | |
| Snake AAV | NC_006148.1 |

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest.

Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used here, "systemic tropism" and "systemic transduction" (and equivalent terms) indicate that the virus capsid or virus vector of the disclosure exhibits tropism for or transduces, respectively, tissues throughout the body (e.g., brain, lung, skeletal muscle, heart, liver, kidney and/or pancreas). In embodiments, systemic transduction of muscle tissues (e.g., skeletal muscle, diaphragm and cardiac muscle) is observed. In other embodiments, systemic transduction of skeletal muscle tissues achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically).

Alternatively, in other embodiments, the capsid or virus vector is delivered locally (e.g., to the footpad, intramuscularly, intradermally, subcutaneously, topically).

Unless indicated otherwise, "efficient transduction" or "efficient tropism," or similar terms, can be determined by reference to a suitable control (e.g., at least about 50%, about 60%, about 70%, about 80%, about 85%, about 90%, about 95% or more of the transduction or tropism, respectively, of the control). In particular embodiments, the virus vector efficiently transduces or has efficient tropism for skeletal muscle, cardiac muscle, diaphragm muscle, pancreas (including p-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, viral vectors can be identified that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable vector may represent some tradeoffs. To illustrate, a virus vector of the disclosure may be less efficient than AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, undesirable transduction of tissue(s) (e.g., liver) is about 20% or less, about 10% or less, about 5% or less, about 1% or less, about 0.1% or less of the level of transduction of the desired target tissue(s) (e.g., skeletal muscle, diaphragm muscle, cardiac muscle and/or cells of the central nervous system).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, about 100-fold, about 1000-fold, about 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, about 100-fold, about 1000-fold, about 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, about 100-fold, about 1000-fold, about 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the disclosure. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present disclosure.

"Therapeutically effective amount" as used herein refers to an amount that, when administered to a subject for treating a disease, or at least one of the clinical symptoms of a disease, is sufficient to affect such treatment of the disease or symptom thereof. The "therapeutically effective amount" may vary depending, for example, on the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka, (1992) Curr. Topics Microbiol. Immunol. 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments, the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11, 12, 13 or any other AAV now known or later discovered (see, e.g., Table 2). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the disclosure can further be "targeted" virus vectors (e.g., having a directed tropism) and/or a "hybrid" parvovirus (i.e., in which the viral TRs and viral capsid are from different parvoviruses) as described in international patent publication WO00/28004 and Chao et al, (2000) Molecular Therapy 2:619.

The virus vectors of the disclosure can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the disclosure. Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 3.

TABLE 3

Amino acid residues and abbreviations.

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |

TABLE 3-continued

Amino acid residues and abbreviations.

| Amino Acid Residue | Three-Letter Code | One-Letter Code |
|---|---|---|
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 4) and/or can be an amino acid that is modified by post-translation modification (e.g., acetylation, amidation, formylation, hydroxylation, methylation, phosphorylation or sulfatation).

TABLE 4

Modified Amino Acid Residues

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,21-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | alle |
| Methionine sulfoxide | MSO |
| N-Methylglycine, sarcosine | MeGly |
| N-Methyl isoleucine | MeIle |
| 6-N-Methyllysine | MeLys |

TABLE 4-continued

Modified Amino Acid Residues

| Modified Amino Acid Residue | Abbreviation |
|---|---|
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid (as described by Wang et al., Annu Rev Biophys Biomol Struct. 35:225-49 (2006)). These unnatural amino acids can advantageously be used to chemically link molecules of interest to the AAV capsid protein. Modified AAV Capsid Proteins and Virus Capsids and Virus Vectors Comprising the Same.

The present disclosure provides AAV capsid proteins (VP1, VP2 and/or VP3) comprising a modification (e.g., a substitution) in the amino acid sequence and virus capsids and virus vectors comprising the modified AAV capsid protein. The inventors have discovered that the modifications described herein can confer one or more desirable properties to virus vectors comprising the modified AAV capsid protein including without limitation, the ability to evade neutralizing antibodies. Thus, the present disclosure addresses some of the limitations associated with conventional AAV vectors.

Accordingly, in one aspect, the present disclosure provides an adeno-associated virus (AAV) capsid protein, comprising one or more amino acid substitutions, wherein the one or more substitutions modify one or more antigenic sites on the AAV capsid protein. The modification of the one or more antigenic sites results in inhibition of binding by an antibody to the one or more antigenic sites and/or inhibition of neutralization of infectivity of a virus particle comprising said AAV capsid protein. The one or more amino acid substitutions can be in one or more antigenic footprints identified by peptide epitope mapping and/or cryo-electron microscopy studies of AAV-antibody complexes containing AAV capsid proteins. In some embodiments, the one or more antigenic sites are common antigenic motifs or CAMs as described in WO 2017/058892, which is incorporated herein by reference in its entirety. In some embodiments, the antigenic sites are in a variable region (VR) of the AAV capsid protein, such as VR-I, VR-II, VR-III, VR-IV, VR-V, VR-VI, VR-VII, VR-VIII, VR-IX. In some embodiments, one or more antigenic sites is in the HI loop of the AAV capsid protein.

In some embodiments, the modified antigenic site can prevent antibodies from binding or recognizing or neutralizing AAV capsids, wherein the antibody is an IgG (including IgG1, IgG2a, IgG2b, IgG3), IgM, IgE or IgA.

In some embodiments, an AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, or Avian AAV capsid protein comprises an amino acid substitution in one or more of the regions identified in Table 5, below. In some embodiments, the amino acid substitution is selected from the group consisting of SEQ ID NO: 9, 10, 11, 12, 13, 14, 15, 16, 17, 297, 298, 299, and 411-421. In some embodiments, the amino acid substitution has at least 95%, 95%, 96%, 97%, 98%, or 99% sequence homology with SEQ ID NO: 9, 10, 11, 12, 13, 14, 15, 16, 17, 297, 298, 299, or 411-421.

TABLE 5

Exemplary antigenic or other regions on various AAV capsids that may be partially or fully substituted/replaced. Respective VP1 numbering of residues is shown.

| AAV1 Sequence (amino acid numbers) | SEQ ID NO | AAV2 Sequence (amino acid numbers) | SEQ ID NO | AAV3 Sequence (amino acid numbers) | SEQ ID NO | AAV4 Sequence (amino acid numbers) | SEQ ID NO | AAV5 Sequence (amino acid numbers) | SEQ ID NO |
|---|---|---|---|---|---|---|---|---|---|
| SASTGAS (262-268) | 613 | SQSGAS (262-267) | 623 | SQSGAS (262-267) | 633 | RLGESLQS (253-260) | 643 | EIKSGSVDGS (249-258) | 653 |
| VFMIPQYGYL (370-379) | 614 | VFMVPQYGYL (369-378) | 624 | VFMVPQYGYL (369-378) | 634 | VFMVPQYGYC (360-369) | 644 | VFTLPQYGYA (360-369) | 654 |
| NQSGSAQNK (451-459) | 615 | TPSGTTTQS (450-458) | 625 | TTSGTTNQS (451-459) | 635 | GTTLNAGTA (445-453) | 645 | STNNTGGVQ (440-448) | 655 |
| SV (472-473) | 616 | RD (471-472) | 626 | SL (472-473) | 636 | SN (466-467) | 646 | AN (458-459) | 656 |
| KTDNNNSN (493-500) | 617 | SADNNNSE (492-499) | 627 | ANDNNNSN (493-500) | 637 | ANQNYKIPATGS (487-498) | 647 | SGVNRAS (479-485) | 657 |
| KDDEDKF (528-534) | 618 | KDDEEKF (527-533) | 628 | KDDEEKF (528-534) | 638 | GPADSKF (527-533) | 648 | LQGSNTY (515-521) | 658 |
| SAGASN (547-552) | 619 | GSEKTN (546-551) | 629 | GTTASN (547-552) | 639 | QNGNTA (545-560) | 649 | ANPGTTAT (534-541) | 659 |
| STDPATGDVH (588-597) | 620 | NRQAATADVN (587-596) | 630 | NTAPTTGTVN (588-597) | 640 | SNLPTVDRLT (583-595) | 650 | T TABLE 5-continued Exemplary antigenic or other regions on various AAV capsids that may be partially or fully substituted/replaced. Respective VP1 numbering of residues is shown.

| | | | | | | | | | |
|---|---|---|---|---|---|---|---|---|---|
| STDPATG DVH (588-897) | 670 | NTAAQTQ VVN (589-598) | 680 | NTAPQIG TVNS (590-600) | 690 | QAQAQT GWVQ (588-597) | 700 | NTQAQTG LVH (588-597) | 710 |
| AN (709-710) | 671 | TG (710-711) | 681 | TS (711-712) | 691 | NN (709-710) | 701 | TN (709-710) | 711 |
| DNNGLY T (716-722) | 672 | DSQGVY S (717-723) | 682 | NTEGVY S (718-724) | 692 | NTEGVY S (716-722) | 702 | NTEGVYS (716-722) | 712 |

| AAVrh10 (amino acid numbers) | SEQ ID NO | AAV10 (amino acid numbers) | SEQ ID NO | AAV11 (amino acid numbers) | SEQ ID NO | AAV12 (amino acid numbers) | SEQ ID NO | AAVrh32.33 (amino acid numbers) | SEQ ID NO |
|---|---|---|---|---|---|---|---|---|---|
| NGTSGGS T (263-270) | 713 | NGTSGG ST (263-270) | 723 | RLGTTSS S (253-260) | 733 | RIGTTAN S (262-269) | 743 | RLGTTSNS (253-260) | 753 |
| VFMIPQY GYL (372-381) | 714 | VFMIPQY GYL (372-381) | 724 | VFMVPQ YGYC (360-369) | 734 | VFMVPQ YGYC (369-378) | 744 | VFMVPQYG YC (360-369) | 754 |
| STGGTAG TQ (453-461) | 715 | STGGTQ GTQ (453-461) | 725 | GETLNQ GNA (444-452) | 735 | GNSLNQ GTA (453-461) | 745 | GETLNQGN A (444-452) | 755 |
| SA (474-475) | 716 | SA (474-475) | 726 | AF (465-466) | 736 | AY (474-475) | 746 | AF (465-466) | 756 |
| LSQNNSN (495-502) | 717 | LSQNNSN (495-502) | 727 | ASQNYKI PASGG (486-497) | 737 | ANQNYKI PASGG (495-506) | 747 | ASQNYKIPA SGG (486-497) | 757 |
| KDDEERF (530-536) | 718 | KDDEERF (530-536) | 728 | GPSDGD F (526-532) | 738 | GAGDSD F (535-541) | 748 | GPSDGDF (526-532) | 758 |
| GAGKDN (549-554) | 719 | GAGRDN (549-554) | 729 | VTGNTT (544-549) | 739 | PSGNTT (553-558) | 749 | VTGNTT (544-549) | 759 |
| NAAPIVG AVN (590-599) | 720 | NTGPIVG NVN (590-599) | 730 | TTAPITG NVT (585-594) | 740 | TTAPHIA NLD (594-503) | 750 | TTAPITGNV T (585-594) | 760 |
| TN (711-712) | 721 | TN (711-712) | 731 | SS (706-707) | 741 | NS (715-716) | 751 | SS (706-707) | 761 |
| NTDGTYS (718-724) | 722 | NTEGTYS (718-724) | 732 | DTTGKYT (713-719) | 742 | DNAGNY H (722-728) | 752 | DTTGKYT (713-719) | 762 |

| Bovine AAV (amino acid numbers) | SEQ ID NO | Avian AAV (amino acid numbers) | SEQ ID NO |
|---|---|---|---|
| RLGSSN AS (255-262) | 763 | RIQGPSG G (265-272) | 773 |
| VFMVPQ YGYC (362-371) | 764 | IYTIPQYG YC (375-384) | 774 |
| GGTLNQ GNS (447-455) | 765 | VSQAGS SGR (454-462) | 775 |
| SG (468-469) | 766 | AA (475-476) | 776 |
| ASQNYKI PQGRN (489-500) | 767 | ASNITKN NVFSV (496-507) | 777 |

TABLE 5-continued

Exemplary antigenic or other regions on various AAV capsids that may be partially or fully substituted/replaced. Respective VP1 numbering of residues is shown.

| | | | |
|---|---|---|---|
| ANDATDF (529-535) | 768 | FSGEPDR (533-539) | 778 |
| ITGNTT (547-552) | 769 | VYDQTTAT (552-559) | 779 |
| TTVPTVDDVD (588-597) | 770 | VTPGTRAAVN (595-604) | 780 |
| DS (709-710) | 771 | AD (716-717) | 781 |
| DNAGAYK (716-722) | 772 | SDTGSYS (723-729) | 782 |

In some embodiments, the amino acid substitution replaces any six, seven, or eight amino acids in an AAV capsid protein from any one of the following serotypes: AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, or Avian AAV. For example, the amino acid substitution may replace the following amino acids (VP1 numbering) in any of the above-listed AAV serotypes: 280-286, 279-293, 294-300, 301-307, 308-314, 315-321, 322-328, 329-335, 336-342, 343-349, 350-356, 357-363, 364-370, 371-377, 378-384, 385-391, 392-398, 399-405, 406-412, 143-149, 420-426, 427-433, 434-440, 441-447, 448-454, 455-461, 462-468, 469-475, 476-482, 483-489, 490-496, 497-503, 504-510, 511-517, 518-524, 525-531, 532-538, 539-545, 546-552, 553-559, 560-566, 567-573, 574-580, 581-587, 588-594, 595-601, 602-608, 609-615, 616-622, 623-629, 630-636, 637-643, 644-650, 651-657, 658-664, 665-671, 672-678, 679-685, 686-692, 693-699. In embodiments, the amino acid substitution may replace the following amino acids (VP1 numbering) in any of the above-listed AAV serotypes: 294-301, 302-309, 310-317, 318-325, 326-333, 334-331, 342-349, 350-357, 358-365, 366-373, 374-381, 382-389, 390-397, 398-405, 406-413, 414-421, 422-429, 430-437, 438-445, 446-453, 454-461, 462-469, 470-477, 478-485, 486-493, 494-501, 502-509, 210-517, 518-525, 526-533, 534-541, 542-549, 550-557, 558-565, 566-573, 574-581, 582-589, 590-597, 598-605, 506-613, 614-621, 622-629, 630-637, 638-645, 646-653, 654-661, 662-669, 670-677, 678-685, 686-693, 694-701. In embodiments, the amino acid substitution may replace the following amino acids (VP1 numbering) in any of the above-listed AAV serotypes: 400-405, 406-411, 412-417, 418-423, 424-429, 430-435, 436-441, 442-447, 448-453, 454-459, 460-465, 466-471, 472-477, 478-483, 484-489, 490-495, 484-489, 490-495, 496-501, 502-507, 508-513, 514-519, 520-525, 526-531, 532-537, 538-543, 544-549, 550-555, 556-561, 562-567, 568-573, 574-579, 580-585, 586-591, 592-597, 598-603, 604-609, 610-615, 616-621, 622-627, 628-633, 634-639, 640-645, 646-651, 652-657, 658-663, 664-669, 670-675, 676-681, 682-687, 688-693, 694-699, 700-705.

In some embodiments, the substitution introduces a deletion into the AAV capsid sequence. For example, a sequence of 6, 7, 8, or 9 amino acids are substituted to replace 7, 8, 9, or 10 amino acids, respectively, of a native amino acid capsid sequence. In some embodiments, the substitution introduces an insertion into the AAV capsid sequence. For example, a sequence of 6, 7, 8, or 9 amino acids are substituted to replace 5, 6, 7, or 8 amino acids, respectively, of a native amino acid capsid sequence.

The capsid proteins of this disclosure are modified to produce an AAV capsid that is present in an AAV virus particle or AAV virus vector that has a phenotype of evading neutralizing antibodies. The AAV virus particle or vector of this disclosure can also have a phenotype of enhanced or maintained transduction efficiency in addition to the phenotype of evading neutralizing antibodies.

In some embodiments, the one or more substitutions of the one or more antigenic sites can introduce one or more antigenic sites from a capsid protein of a first AAV serotype into the capsid protein of a second AAV serotype that is different from said first AAV serotype.

The AAV capsid protein of this disclosure can be a capsid protein of an AAV serotype selected from AAV1, AAV2, AAV3, AAV3B, AAV4, AAV5, AAV6, AAV7, AAV8, AAV9, AAV10, AAV11, AAV12, AAVrh.8, AAVrh.10, AAVrh.32.33, AAVrh74, bovine AAV, avian AAV or any other AAV now known or later identified. In some embodiments, the AAV capsid protein is chimeric.

Several examples of a modified AAV capsid protein of this disclosure are provided herein. In the following examples, the capsid protein can comprise the specific substitutions described and in some embodiments can comprise fewer or more substitutions than those described. As used herein, "substitution" may refer to a single amino acid substitution, or a substitution of more than one amino acid. For example in some embodiments, a capsid protein of this disclosure can comprise at least 1, 2, 3, 4, 5, 6, 7, 8, 9, 10, etc., single amino acid substitutions. In some embodiments, a capsid protein of this disclosure can comprise one or more substitutions of multiple contiguous amino acids, such as one or more substitutions of 2, 3, 4, 5, 6, 7, 8, 9, 10, 11, or 12 contiguous amino acids.

Furthermore, in the embodiments described herein wherein an amino acid residue is substituted by any amino acid residue other than the amino acid residue present in the wild type or native amino acid sequence, said any other amino acid residue can be any natural or non-natural amino acid residue known in the art (see, e.g., Tables 3 and 4). In some embodiments, the substitution can be a conservative substitution and in some embodiments, the substitution can be a nonconservative substitution.

In some embodiments, an AAV capsid protein comprises one or more amino acid substitutions, wherein the amino acid substitutions are selected from the sequences listed in Table 6.1.

TABLE 6.1

AMINO ACID SUBSTITUTIONS

| Sequence Substitution | SEQ ID NO. |
|---|---|
| SNGRGV | 9 |
| NLAENFKY | 10 |
| VLSGDHSA | 11 |
| MSAASGSG | 12 |
| GTNLGKEQ | 13 |
| SSHSGTNQ | 14 |
| VATRDGQL | 15 |
| ALNADTGT | 16 |
| VMEPTR | 17 |
| VVGNGGVV | 297 |
| NFREMPIG | 298 |
| RRSEDMGTI | 299 |
| YPLQNNNS | 411 |
| YPLENFKY | 412 |
| YPLGDHSA | 413 |
| YPLASGSG | 414 |
| YPLLGKEQ | 415 |
| YPLSGTNQ | 416 |
| YPLRDGQL | 417 |
| YPLADTGT | 418 |
| YPLNGGVV | 419 |
| YPLEMPIG | 420 |
| YPLEDMGTI | 421 |

In some embodiments, the AAV capsid protein comprises a first amino acid substitution and a second amino acid substitution, wherein the first amino acid substitution and the second amino acid substitution each modify a different antigenic site on the AAV capsid protein. In some embodiments, the first amino acid substitution and the second amino acid substitution are each selected from SEQ ID NO: 9, 10, 11, 12, 13, 14, 15, 16, 17, 297, 298, 299, and 411-421.

In some embodiments, the AAV capsid protein comprises a first acid substitution, a second amino acid substitution, and a third amino acid substitution, wherein the first amino acid substitution, the second amino acid substitution, and the third amino acid substitution each modify a different antigenic site on the AAV capsid protein. In some embodiments, the first amino acid substitution, the second amino acid substitution and the third amino acid substitution are each selected from SEQ ID NO: 9, 10, 11, 12, 13, 14, 15, 16, 17, 297, 298, 299, and 411-421. In some embodiments, the first amino acid substitution comprises SEQ ID NO. 9; the second amino acid substitution comprises one of SEQ ID NO. 10, 11, 12, 13, 14, 15, 16, 297, 298, 299 or 411-421; and the third amino acid substitution comprises SEQ ID NO. 17. In some embodiments, the first amino acid substitution comprises SEQ ID NO. 9; the second amino acid substitution comprises one of SEQ ID NO. 10; and the third amino acid substitution comprises SEQ ID NO. 17. In some embodiments, the first amino acid substitution comprises SEQ ID NO. 9; the second amino acid substitution comprises one of SEQ ID NO. 14; and the third amino acid substitution comprises SEQ ID NO. 17.

In some embodiments, the AAV capsid protein comprises the sequence of any one of SEQ ID NOs: 18-80, 300-410, 422-612, or 783-785. In some embodiments, the AAV capsid protein comprises the sequence of any one of SEQ ID NO: 18-80, 300-410, 422-612, or 783-785. In some embodiments, the AAV capsid protein has at least 95%, 95%, 96%, 97%, 98%, or 99% sequence homology with any one of SEQ ID NOs: 18-80, 300-410, 422-612, or 783-785.

In some embodiments, the AAV capsid protein comprises SEQ ID NO: 49. In some embodiments, the AAV capsid protein has at least 95%, 95%, 96%, 97%, 98%, or 99% sequence homology with SEQ ID NO: 49. In some embodiments, the AAV capsid protein is modified by replacing the region spanning amino acids 454-460 of SEQ ID NO: 49 with SEQ ID NO: 9. In some embodiments, the AAV capsid protein is modified by replacing the region spanning amino acids 493-500 of SEQ ID NO: 49 with one of SEQ ID NO: 10, 11, 12, 13, 14, 15, 16, 297, 298, 299, or 411-421. In some embodiments, the AAV capsid protein is modified by replacing the region spanning amino acids 585-590 of SEQ ID NO: 49 with SEQ ID NO: 17. In some embodiments, the AAV capsid protein is modified by replacing the region spanning amino acids 454-460 of SEQ ID NO: 49 with SEQ ID NO: 9, the region spanning amino acids 493-500 of SEQ ID NO: 49 with one of SEQ ID NO: 10, 11, 12, 13, 14, 15, 16, 297, 298, 299, or 411-421, and the region spanning amino acids 585-590 of SEQ ID NO: 49 with SEQ ID NO: 17.

Any of the AAV capsids described herein may further comprise a modification (e.g., a substitution or a deletion) in the HI loop. The HI loop is a prominent domain on the AAV capsid surface, between β strands βH and βI, that extends from each viral protein (VP) subunit overlapping the neighboring fivefold VP. In some embodiments, an AAV capsid comprises one, two, three, four, five, six, seven, or eight amino acid substitutions in the HI loop. In some embodiments, the AAV capsid comprises one or more of the following substitutions in the HI loop: P661R, T662S, Q666G, S667D, wherein the numbering corresponds to the wildtype AAV8 capsid (SEQ ID NO: 6). In some embodiments, the AAV capsid comprises one or more of the following substitutions in the HI loop: P659R, T660S, A661T, K664G, wherein the numbering corresponds to the wildtype AAV9 capsid (SEQ ID NO: 7).

In some embodiments, an AAV capsid protein comprises one, two, three, or four amino acid substitutions, wherein each substitution modifies a different antigenic site on the AAV capsid protein, and wherein at least one of the amino acid substitutions modifies the HI loop of the capsid protein.

In some embodiments, an AAV capsid protein comprises a first, a second, a third, and a fourth amino acid substitution. In embodiments, the first amino acid substitution, the second amino acid substitution and the third amino acid substitution are each selected from SEQ ID NO: 9, 10, 11, 12, 13, 14, 15, 16, 17, 297, 298, 299, and 411-421, and the fourth amino acid substitution modifies the HI loop of the capsid protein.

In some embodiments, the first amino acid substitution comprises SEQ ID NO. 9; the second amino acid substitution comprises one of SEQ ID NO. 10, 11, 12, 13, 14, 15, 16, 297, 298, 299, or 411-421; the third amino acid substitution comprises SEQ ID NO. 17, and the fourth amino acid substitution modifies the HI loop of the capsid protein. In some embodiments, the AAV capsid comprises one or more of the following substitutions in the HI loop: P661R, T662S, Q666G, S667D, wherein the numbering corresponds to the wildtype AAV8 capsid (SEQ ID NO: 6); or P659R, T660S, A661T, K664G, wherein the numbering corresponds to the wildtype AAV9 capsid (SEQ ID NO: 7).

In some embodiments, an AAV capsid protein may comprise a first substitution, a second substitution, and optionally a third substitution, as shown in Table 6.2.

TABLE 6.2

COMBINATIONS OF AMINO ACID SUBSTITUTIONS

| First Substitution (SEQ ID NO) | Second Substitution (SEQ ID NO) | Third Substitution (SEQ ID NO) |
|---|---|---|
| 9 | 10 | 17 |
| 9 | 11 | 17 |
| 9 | 12 | 17 |
| 9 | 13 | 17 |
| 9 | 14 | 17 |
| 9 | 15 | 17 |
| 9 | 16 | 17 |
| 9 | 297 | 17 |
| 9 | 298 | 17 |
| 9 | 299 | 17 |
| 9 | 411 | 17 |
| 9 | 412 | 17 |
| 9 | 413 | 17 |
| 9 | 414 | 17 |
| 9 | 415 | 17 |
| 9 | 416 | 17 |
| 9 | 417 | 17 |
| 9 | 418 | 17 |
| 9 | 419 | 17 |
| 9 | 420 | 17 |
| 9 | 421 | 17 |
| 9 | 10 | |
| 9 | 11 | |
| 9 | 12 | |
| 9 | 13 | |
| 9 | 14 | |
| 9 | 15 | |
| 9 | 16 | |
| 9 | 297 | |
| 9 | 298 | |
| 9 | 299 | |
| 9 | 411 | |
| 9 | 412 | |
| 9 | 413 | |
| 9 | 414 | |
| 9 | 415 | |
| 9 | 416 | |
| 9 | 417 | |
| 9 | 418 | |
| 9 | 419 | |
| 9 | 420 | |
| 9 | 421 | |
| 9 | 17 | |
| 10 | 17 | |
| 11 | 17 | |
| 12 | 17 | |
| 13 | 17 | |
| 14 | 17 | |
| 15 | 17 | |
| 16 | 17 | |
| 297 | 17 | |
| 298 | 17 | |
| 299 | 17 | |
| 411 | 17 | |
| 412 | 17 | |
| 413 | 17 | |
| 414 | 17 | |
| 415 | 17 | |
| 416 | 17 | |
| 417 | 17 | |
| 418 | 17 | |
| 419 | 17 | |
| 420 | 17 | |
| 421 | 17 | |

In some embodiments, a recombinant capsid protein has a sequence that is at least 90%, at least 95%, at least 96%, at least 97%, at least 98%, at least 99% or 100% identical to SEQ ID NO: 6 (AAV8) or SEQ ID NO: 7 (AAV9) and comprises a first substitution, a second substitution, and optionally a third substitution, as shown in Table 6.2.

In some embodiments, a recombinant capsid protein has a sequence that is at least 90%, at least 95%, at least 96%, at least 97%, at least 98%, at least 99% or 100% identical to SEQ ID NO: 6 (AAV8) and comprises one or more of the following amino acid substitutions: G455S, G456N, G456S, T457G, T457N, A458R, A458G, N459G, N459R, T460V, T460G, N459R, Q461V, T494N, T494V, T494M, T494G, T494S, T494A, T494R, T494Y, T495L, T495S, T495T, T495S, T495V, T495F, T495R, T495P, G496A, G496S, G496N, G496H, G496T, G496N, G496R, G496L, Q497E, Q497G, Q497A, Q497L, Q497S, Q497R, Q497A, Q497N, Q497E, Q497E, N498D, N498S, N498G, N498M, N499F, N499H, N499G, N499K, N499T, N499P, N499M, N500K, N500S, N500E, N500N, N500Q, N500G, N500V, N500I, N500T, S501Y, S501A, S501G, S501Q, S501L, S501T, S501V, S501G, S501I, L586V, Q587M, Q588E, Q589P, N590T, T591R. In some embodiments, a recombinant capsid protein has a sequence that is at least 90%, at least 95%, at least 96%, at least 97%, at least 98%, at least 99% or 100% identical to SEQ ID NO: 6 (AAV8) and comprises the following amino acid substitutions: T494Y, T495P, and/or G496L.

In some embodiments, a recombinant capsid protein has a sequence that is at least 90%, at least 95%, at least 96%, at least 97%, at least 98%, at least 99% or 100% identical to the sequences of SEQ ID NO: 380, 384, 783, 784, or 785.

The present disclosure also provides a nucleotide sequence, or an expression vector comprising the same, that encodes one or more of the AAV capsid proteins of the disclosure. The nucleotide sequence may be a DNA sequence or an RNA sequence. The present disclosure also provides a cell that comprises one or more nucleotide sequences or expression vectors of the disclosure.

Also provided is an AAV capsid comprising an AAV capsid protein of this disclosure. Further provided herein is a viral vector comprising an AAV capsid of this disclosure as well as a composition comprising the AAV capsid protein, AAV capsid and/or viral vector of this disclosure in a pharmaceutically acceptable carrier.

In some embodiments, modification of the one or more antigenic sites results in inhibition of binding by an antibody to the one or more antigenic sites. In some embodiments, modification of the one or more antigenic sites results in inhibition of neutralization of infectivity of a virus particle comprising the AAV capsid protein.

As described herein, the nucleic acid and amino acid sequences of the capsid proteins from a number of AAV are known in the art. Thus, the amino acids "corresponding" to amino acid positions of the native AAV capsid protein can be readily determined for any other AAV (e.g., by using sequence alignments).

The disclosure contemplates that the modified capsid proteins can be produced by modifying the capsid protein of any AAV now known or later discovered.

Further, the AAV capsid protein that is to be modified can be a naturally occurring AAV capsid protein (e.g., an AAV2, AAV3a or 3b, AAV4, AAV5, AAV6, AAV7, AAV8, AAV9, AAV10 or AAV11 capsid protein or any of the AAV shown in Table 2) but is not so limited. Those skilled in the art will understand that a variety of manipulations to the AAV capsid proteins are known in the art and the disclosure is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11, AAV12 or any other AAV now known or later discovered). In some embodiments, the capsid protein may be a chimeric capsid protein. In some embodiments, the capsid protein may be an engineered AAV, such as AAV2i8, AAV2g9, AAV-LK03, AAV7m8, AAV Anc80, AAV PHP.B. Such AAV capsid proteins are also within the scope of the present disclosure.

Thus, in particular embodiments, the AAV capsid protein to be modified can be derived from a naturally occurring AAV but further comprises one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10 or AAV11 capsid protein or a capsid protein from any of the AAV shown in Table 2, etc.), it is intended to encompass the native capsid protein as well as capsid proteins that have alterations other than the modifications of the disclosure. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids inserted therein (other than the insertions of the present disclosure) as compared with the native AAV capsid protein sequence. In embodiments, the capsid protein comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acid substitutions (other than the amino acid substitutions according to the present disclosure) as compared with the native AAV capsid protein sequence, in embodiments of the disclosure, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids (other than the amino acid deletions of the disclosure) as compared with the native AAV capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection.

Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al. Methods in Enzymology, 266, 460-480 (1996). WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al, (1997) Nucleic Acids Res. 25, 3389-3402.

The disclosure also provides a virus capsid comprising, consisting essentially of, or consisting of the modified AAV capsid protein of the disclosure. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11, AAV12, AAVrh8, AAVrh10, AAVrh32.33, bovine AAV capsid, avian AAV capsid or any other AAV now known or later identified. A nonlimiting list of AAV serotypes is shown in Table 2, and an AAV capsid of this disclosure can be any AAV serotype listed in Table 2 or derived from any of the foregoing by one or more insertions, substitutions and/or deletions. The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the disclosure the therapeutically useful molecule is covalently linked (i.e., conjugated or chemically coupled) to the capsid proteins. Methods of covalently linking molecules are known by those skilled in the art.

The modified virus capsids of the disclosure also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal, cardiac and/or diaphragm muscle).

According to representative embodiments, modified virus capsids can be administered to a subject prior to and/or concurrently with a modified virus vector according to the present disclosure. Further, the disclosure provides compositions and pharmaceutical formulations comprising the inventive modified virus capsids; optionally, the composition also comprises a modified virus vector of the disclosure.

The disclosure also provides nucleic acids (optionally, isolated nucleic acids) encoding the modified virus capsids and capsid proteins of the disclosure. Further provided are vectors comprising the nucleic acids, and cells (in vivo or in culture) comprising the nucleic acids and/or vectors of the disclosure. As one example, the present disclosure provides a virus vector comprising: (a) a modified AAV capsid of this disclosure; and (b) a nucleic acid comprising at least one terminal repeat sequence, wherein the nucleic acid is encapsidated by the AAV capsid.

Other suitable vectors include without limitation viral vectors (e.g., adenovirus, AAV, herpesvirus, vaccinia, poxviruses, baculoviruses, and the like), plasmids, phage, YACs, BACs, and the like. Such nucleic acids, vectors and cells can be used, for example, as reagents (e.g., helper packaging constructs or packaging cells) for the production of modified virus capsids or virus vectors as described herein.

Virus capsids according to the disclosure can be produced using any method known in the art, e.g., by expression from a baculovirus (Brown et al., (1994) Virology 198:477-488).

The modifications to the AAV capsid protein according to the present disclosure are "selective" modifications. This approach is in contrast to previous work with whole subunit or large domain swaps between AAV serotypes (see, e.g., international patent publication WO 00/28004 and Hauck et al., (2003) J. Virology 77:2768-2774). In particular embodiments, a "selective" modification results in the insertion and/or substitution and/or deletion of less than or equal to about 20, 18, 15, 12, 10, 9, 8, 7, 6, 5, 4 or 3 contiguous amino acids.

The modified capsid proteins and capsids of the disclosure can further comprise any other modification, now known or later identified.

For example, the AAV capsid proteins and virus capsids of the disclosure can be chimeric in that they can comprise all or a portion of a capsid subunit from another virus, optionally another parvovirus or AAV, e.g., as described in international patent publication WO 00/28004.

In some embodiments of this disclosure, the virus capsid can be a targeted virus capsid, comprising a targeting sequence (e.g., substituted or inserted in the viral capsid) that directs the virus capsid to interact with cell-surface molecules present on desired target tissue(s) (see, e.g., International patent publication WO 00/28004 and Hauck et al., (2003) J. Virology 77:2768-2774); Shi et al., Human Gene Therapy 17:353-361 (2006) [describing insertion of the integrin receptor binding motif RGD at positions 520 and/or 584 of the AAV capsid subunit]; and U.S. Pat. No. 7,314,912 [describing insertion of the PI peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., Molecular Therapy 3:964-975 (2001)).

For example, a virus capsid of this disclosure may have relatively inefficient tropism toward certain target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another example, one or more non-naturally occurring amino acids as described by Wang et al., Annu Rev Biophys Biomol Struct. 35:225-49 (2006)) can be incorporated into an AAV capsid subunit of this disclosure at an orthogonal site as a means of redirecting a low-transduction vector to desired target tissue(s). These unnatural amino acids can advantageously be used to chemically link molecules of interest to the AAV capsid protein including without limitation: glycans (mannose-dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like.

Methods of chemically modifying amino acids are known in the art (see, e.g., Greg T. Hermanson, Bioconjugate Techniques, $1^{st}$ edition, Academic Press, 1996).

In some embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin or heparan sulfate binding domain (e.g., the respiratory syncytial virus heparin binding domain) may be inserted or substituted into a capsid subunit that does not typically bind HS receptors (e.g., AAV4, AAV5) to confer heparin and/or heparan sulfate binding to the resulting mutant.

B19 infects primary erythroid progenitor cells using globoside as its receptor (Brown et al, (1993) Science 262:114). The structure of B19 has been determined to 8 Å resolution (Agbandje-McKenna et al, (1994) Virology 203:106). The region of the B19 capsid that binds to globoside has been mapped between amino acids 399-406 (Chapman et al, (1993) Virology 194:419), a looped out region between β-barrel structures E and F (Chipman et al, (1996) Proc. Nat. Acad. Sci. USA 93:7502). Accordingly, the globoside receptor binding domain of the B19 capsid may be substituted into an AAV capsid protein of this disclosure to target a virus capsid or virus vector comprising the same to erythroid cells.

In some embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as ROD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., a, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadolibcrin, corticostatin, β-endorphin, leu-enkephalin, rimorphin, alpha-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as alpha-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (Current Biology 7:R318 (1997)) into the AAV capsid protein. Also encompassed are peptide motifs that direct uptake by specific cells, e.g., a FVFLP (SEQ ID NO: 83) peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC 1 glycoproteins, carbohydrate components found on membrane glycoproteins, including, mannose, N-acetyl-galactosamine, N-acetyl-glucosamine, fucose, galactose, and the like.

In particular embodiments, a heparan sulfate (HS) or heparin binding domain is substituted into the virus capsid (for example, in an AAV capsid that otherwise does not bind to HS or heparin). It is known in the art that HS/heparin binding is mediated by a "basic patch" that is rich in arginines and/or lysines. In exemplary embodiments, a sequence following the motif BXXB (SEQ ID NO: 84), where "B" is a basic residue and X is neutral and/or hydrophobic can be employed. As a nonlimiting example, BXXB can be RGNR (SEQ ID NO: 85). As another nonlimiting example, BXXB is substituted for amino acid positions 262 through 265 in the native AAV2 capsid protein or at the corresponding position(s) in the capsid protein of another AAV serotype.

Table 7 shows other nonlimiting examples of suitable targeting sequences.

TABLE 7

AAV Targeting sequences

| Sequence | SEQ ID NO | Reference |
| --- | --- | --- |
| NSVRDL(G/S) | 86 | Muller et al., Nature Biotechnology 21: 1040-1046 (2003) |
| PRSVTVP | 87 | Muller et al., Nature Biotechnology 21: 1040-1046 (2003) |
| NSVSSX(S/A) | 88 | Muller et al., Nature Biotechnology 21: 1040-1046 (2003) |
| NGRAHA | 89 | Grifman et al., Molecular Therapy 3:964-975 (2001) |
| QPEHSST | 90 | Work et al., Molecular Therapy 13:683-693 (2006) |
| VNTANST | 91 | Work et al., Molecular Therapy 13:683-693 (2006) |
| HGPMQS | 92 | Work et al., Molecular Therapy 13:683-693 (2006) |
| PHKPPLA | 93 | Work et al., Molecular Therapy 13:683-693 (2006) |
| IKNNEMW | 94 | Work et al., Molecular Therapy 13:683-693 (2006) |
| RNLDTPM | 95 | Work et al., Molecular Therapy 13:683-693 (2006) |
| VDSHRQS | 96 | Work et al., Molecular Therapy 13:683-693 (2006) |
| YDSKTKT | 97 | Work et al., Molecular Therapy 13:683-693 (2006) |
| SQLPHQK | 98 | Work et al., Molecular Therapy 13:683-693 (2006) |
| STMQQNT | 99 | Work et al., Molecular Therapy 13:683-693 (2006) |
| TERYMTQ | 100 | Work et al., Molecular Therapy 13:683-693 (2006) |
| QPEHSST | 101 | Work et al., Molecular Therapy 13:683-693 (2006) |
| DASLSTS | 102 | Work et al., Molecular Therapy 13:683-693 (2006) |
| DLPNKT | 103 | Work et al., Molecular Therapy 13:683-693 (2006) |
| DLTAARL | 104 | Work et al., Molecular Therapy 13:683-693 (2006) |
| EPHQFNY | 105 | Work et al., Molecular Therapy 13:683-693 (2006) |

TABLE 7-continued

AAV Targeting sequences

| Sequence | SEQ ID NO | Reference |
|---|---|---|
| EPQSNHT | 106 | Work et al., Molecular Therapy 13:683-693 (2006) |
| MSSWPSQ | 107 | Work et al., Molecular Therapy 13:683-693 (2006) |
| NPKHNAT | 108 | Work et al., Molecular Therapy 13:683-693 (2006) |
| PDGMRTT | 109 | Work et al., Molecular Therapy 13:683-693 (2006) |
| PNNNKTT | 110 | Work et al., Molecular Therapy 13:683-693 (2006) |
| QSTTHDS | 111 | Work et al., Molecular Therapy 13:683-693 (2006) |
| TGSKQKQ | 112 | Work et al., Molecular Therapy 13:683-693 (2006) |
| SLKHQAL | 113 | Work et al., Molecular Therapy 13:683-693 (2006) |
| SPIDGEQ | 114 | Work et al., Molecular Therapy 13:683-693 (2006) |
| WIFPWIQL | 115 | Hajitou et al., TCM 16:80-88 (2006) |
| CDCRGDCFC | 116 | Hajitou et al., TCM 16:80-88 (2006) |
| CNGRC | 117 | Hajitou et al., TCM 16:80-88 (2006) |
| CPRECES | 118 | Hajitou et al., TCM 16:80-88 (2006) |
| CTTHWGFTLC | 119 | Hajitou et al., TCM 16:80-88 (2006) |
| CGRRAGGSC | 120 | Hajitou et al., TCM 16:80-88 (2006) |
| CKGGRAKDC | 121 | Hajitou et al., TCM 16:80-88 (2006) |
| CVPELGHEC | 122 | Hajitou et al., TCM 16:80-88 (2006) |
| CRRETAWAK | 123 | Koivunen et al., J. Nucl. Med. 40:883-888 (1999) |
| VSWFSHRYSPFAVS | 124 | Koivunen et al., J. Nucl. Med. 40:883-888 (1999) |
| GYRDGYAGPILYN | 125 | Koivunen et al., J. Nucl. Med. 40:883-888 (1999) |
| XXXY*XXX | 126 | Koivunen et al., J. Nucl. Med. 40:883-888 (1999) |
| Y*E/MNW | 127 | Koivunen et al., J. Nucl. Med. 40:883-888 (1999) |
| RPLPPLP | 128 | Koivunen et al., J. Nucl. Med. 40:883-888 (1999) |
| APPLPPR | 129 | Koivunen et al., J. Nucl. Med. 40:883-888 (1999) |
| DVFYPYPYASGS | 130 | Koivunen et al., J. Nucl. Med. 40:883-888 (1999) |
| MYWYPY | 131 | Koivunen et al., J. Nucl. Med. 40:883-888 (1999) |
| DITWDQLWDLMK | 132 | Koivunen et al., J. Nucl. Med. 40:883-888 (1999) |
| CWDD(G/L)WLC | 133 | Koivunen et al., J. Nucl. Med. 40:883-888 (1999) |
| EWCEYLGGYLRCYA | 134 | Koivunen et al., J. Nucl. Med. 40:883-888 (1999) |
| YXCXXGPXTWXCXP | 135 | Koivunen et al., J. Nucl. Med. 40:883-888 (1999) |
| IEGPTLRQWLAARA | 136 | Koivunen et al., J. Nucl. Med. 40:883-888 (1999) |
| LWXX(Y/W/F/H) | 137 | Koivunen et al., J. Nucl. Med. 40:883-888 (1999) |
| XFXXYLW | 138 | Koivunen et al., J. Nucl. Med. 40:883-888 (1999) |
| RWGLCD | 139 | Koivunen et al., J. Nucl. Med. 40:883-888 (1999) |
| MSRPACPPNDKYE | 140 | Koivunen et al., J. Nucl. Med. 40:883-888 (1999) |
| CLRSGRGC | 141 | Koivunen et al., J. Nucl. Med. 40:883-888 (1999) |

TABLE 7-continued

AAV Targeting sequences

| Sequence | SEQ ID NO | Reference |
|---|---|---|
| CHWMFSPWC | 142 | Koivunen et al., J. Nucl. Med. 40:883-888 (1999) |
| WXXF | 143 | Koivunen et al., J. Nucl. Med. 40:883-888 (1999) |
| CSSRLDAC | 144 | Koivunen et al., J. Nucl. Med. 40:883-888 (1999) |
| CLPVASC | 145 | Koivunen et al., J. Nucl. Med. 40:883-888 (1999) |
| CGFECVRQCPERC | 146 | Koivunen et al., J. Nucl. Med. 40:883-888 (1999) |
| CVALCREACGEGC | 147 | Koivunen et al., J. Nucl. Med. 40:883-888 (1999) |
| SWCEPGWCR | 148 | Koivunen et al., J. Nucl. Med. 40:883-888 (1999) |
| YSGWGW | 149 | Koivunen et al., J. Nucl. Med. 40:883-888 (1999) |
| GLSGGRS | 150 | Koivunen et al., J. Nucl. Med. 40:883-888 (1999) |
| LMLPRAD | 151 | Koivunen et al., J. Nucl. Med. 40:883-888 (1999) |
| CSCFRDVCC | 152 | Koivunen et al., J. Nucl. Med. 40:883-888 (1999) |
| CRDVVSVIC | 153 | Koivunen et al., J. Nucl. Med. 40:883-888 (1999) |
| CNGRC | 154 | Koivunen et al., J. Nucl. Med. 40:883-888 (1999) |
| MARSGL | 155 | Newton & Deutscher, Phage Peptide Display in Handbook of Experimental Pharmacology, pages 145-163, Springer-Verlag, Berlin (2008) |
| MARAKE | 156 | Newton & Deutscher, Phage Peptide Display in Handbook of Experimental Pharmacology, pages 145-163, Springer-Verlag, Berlin (2008) |
| MSRTMS | 157 | Newton & Deutscher, Phage Peptide Display in Handbook of Experimental Pharmacology, pages 145-163, Springer-Verlag, Berlin (2008) |
| KCCYSL | 158 | Newton & Deutscher, Phage Peptide Display in Handbook of Experimental Pharmacology, pages 145-163, Springer-Verlag, Berlin (2008) |
| MYWGDSHWLQYWYE | 159 | Newton & Deutscher, Phage Peptide Display in Handbook of Experimental Pharmacology, pages 145-163, Springer-Verlag, Berlin (2008) |
| MQLPLAT | 160 | Newton & Deutscher, Phage Peptide Display in Handbook of Experimental Pharmacology, pages 145-163, Springer-Verlag, Berlin (2008) |
| EWLS | 161 | Newton & Deutscher, Phage Peptide Display in Handbook of Experimental Pharmacology, pages 145-163, Springer-Verlag, Berlin (2008) |
| SNEW | 162 | Newton & Deutscher, Phage Peptide Display in Handbook of Experimental Pharmacology, pages 145-163, Springer-Verlag, Berlin (2008) |
| TNYL | 163 | Newton & Deutscher, Phage Peptide Display in Handbook of Experimental Pharmacology, pages 145-163, Springer-Verlag, Berlin (2008) |
| WIFPWIQL | 164 | Newton & Deutscher, Phage Peptide Display in Handbook of Experimental Pharmacology, pages 145-163, Springer-Verlag, Berlin (2008) |
| WDLAWMFRLPVG | 165 | Newton & Deutscher, Phage Peptide Display in Handbook of Experimental Pharmacology, pages 145-163, Springer-Verlag, Berlin (2008) |
| CTVALPGGYVRVC | 166 | Newton & Deutscher, Phage Peptide Display in Handbook of Experimental Pharmacology, pages 145-163, Springer-Verlag, Berlin (2008) |

TABLE 7-continued

AAV Targeting sequences

| Sequence | SEQ ID NO | Reference |
|---|---|---|
| CVPELGHEC | 167 | Newton & Deutscher, Phage Peptide Display in Handbook of Experimental Pharmacology, pages 145-163, Springer-Verlag, Berlin (2008) |
| CGRRAGGSC | 168 | Newton & Deutscher, Phage Peptide Display in Handbook of Experimental Pharmacology, pages 145-163, Springer-Verlag, Berlin (2008) |
| CVAYCIEHHCWTC | 169 | Newton & Deutscher, Phage Peptide Display in Handbook of Experimental Pharmacology, pages 145-163, Springer-Verlag, Berlin (2008) |
| CVFAHNYDYLVC | 170 | Newton & Deutscher, Phage Peptide Display in Handbook of Experimental Pharmacology, pages 145-163, Springer-Verlag, Berlin (2008) |
| CVFTSNYAFC | 171 | Newton & Deutscher, Phage Peptide Display in Handbook of Experimental Pharmacology, pages 145-163, Springer-Verlag, Berlin (2008) |
| VHSPNKK | 172 | Newton & Deutscher, Phage Peptide Display in Handbook of Experimental Pharmacology, pages 145-163, Springer-Verlag, Berlin (2008) |
| CDCRGDCFC | 173 | Newton & Deutscher, Phage Peptide Display in Handbook of Experimental Pharmacology, pages 145-163, Springer-Verlag, Berlin (2008) |
| CRGDGWC | 174 | Newton & Deutscher, Phage Peptide Display in Handbook of Experimental Pharmacology, pages 145-163, Springer-Verlag, Berlin (2008) |
| XRGCDX | 175 | Newton & Deutscher, Phage Peptide Display in Handbook of Experimental Pharmacology, pages 145-163, Springer-Verlag, Berlin (2008) |
| PXX(S/T) | 176 | Newton & Deutscher, Phage Peptide Display in Handbook of Experimental Pharmacology, pages 145-163, Springer-Verlag, Berlin (2008) |
| CTTHWGFTLC | 177 | Newton & Deutscher, Phage Peptide Display in Handbook of Experimental Pharmacology, pages 145-163, Springer-Verlag, Berlin (2008) |
| SGKGPRQITAL | 178 | Newton & Deutscher, Phage Peptide Display in Handbook of Experimental Pharmacology, pages 145-163, Springer-Verlag, Berlin (2008) |
| A(A/Q)(N/A)(L/Y)(T/V/M/R)(R/K) | 179 | Newton & Deutscher, Phage Peptide Display in Handbook of Experimental Pharmacology, pages 145-163, Springer-Verlag, Berlin (2008) |
| VYMSPF | 180 | Newton & Deutscher, Phage Peptide Display in Handbook of Experimental Pharmacology, pages 145-163, Springer-Verlag, Berlin (2008) |
| MQLPLAT | 181 | Newton & Deutscher, Phage Peptide Display in Handbook of Experimental Pharmacology, pages 145-163, Springer-Verlag, Berlin (2008) |
| ATWLPPR | 182 | Newton & Deutscher, Phage Peptide Display in Handbook of Experimental Pharmacology, pages 145-163, Springer-Verlag, Berlin (2008) |
| HTMYYHHYQHHL | 183 | Newton & Deutscher, Phage Peptide Display in Handbook of Experimental Pharmacology, pages 145-163, Springer-Verlag, Berlin (2008) |
| SEVGCRAGPLQWLCEKYFG | 184 | Newton & Deutscher, Phage Peptide Display in Handbook of Experimental Pharmacology, pages 145-163, Springer-Verlag, Berlin (2008) |
| CGLLPVGRPDRNVWRWLC | 185 | Newton & Deutscher, Phage Peptide Display in Handbook of Experimental Pharmacology, pages 145-163, Springer-Verlag, Berlin (2008) |

TABLE 7-continued

AAV Targeting sequences

| Sequence | SEQ ID NO | Reference |
|---|---|---|
| CKGQCDRFKGLPWEC | 186 | Newton & Deutscher, Phage Peptide Display in Handbook of Experimental Pharmacology, pages 145-163, Springer-Verlag, Berlin (2008) |
| SGRSA | 187 | Newton & Deutscher, Phage Peptide Display in Handbook of Experimental Pharmacology, pages 145-163, Springer-Verlag, Berlin (2008) |
| WGFP | 188 | Newton & Deutscher, Phage Peptide Display in Handbook of Experimental Pharmacology, pages 145-163, Springer-Verlag, Berlin (2008) |
| LWXXAr | 189 | Newton & Deutscher, Phage Peptide Display in Handbook of Experimental Pharmacology, pages 145-163, Springer-Verlag, Berlin (2008) |
| XFXXYLW | 190 | Newton & Deutscher, Phage Peptide Display in Handbook of Experimental Pharmacology, pages 145-163, Springer-Verlag, Berlin (2008) |
| AEPMPHSLNFSQYLWYT | 191 | Newton & Deutscher, Phage Peptide Display in Handbook of Experimental Pharmacology, pages 145-163, Springer-Verlag, Berlin (2008) |
| WAY(W/F)SP | 192 | Newton & Deutscher, Phage Peptide Display in Handbook of Experimental Pharmacology, pages 145-163, Springer-Verlag, Berlin (2008) |
| IELLQAR | 193 | Newton & Deutscher, Phage Peptide Display in Handbook of Experimental Pharmacology, pages 145-163, Springer-Verlag, Berlin (2008) |
| DITWDQLWDLMK | 194 | Newton & Deutscher, Phage Peptide Display in Handbook of Experimental Pharmacology, pages 145-163, Springer-Verlag, Berlin (2008) |
| AYTKCSRQWRTCMTTH | 195 | Newton & Deutscher, Phage Peptide Display in Handbook of Experimental Pharmacology, pages 145-163, Springer-Verlag, Berlin (2008) |
| PQNSKIPGPTFLDPH | 196 | Newton & Deutscher, Phage Peptide Display in Handbook of Experimental Pharmacology, pages 145-163, Springer-Verlag, Berlin (2008) |
| SMEPALPDWWVKMFK | 197 | Newton & Deutscher, Phage Peptide Display in Handbook of Experimental Pharmacology, pages 145-163, Springer-Verlag, Berlin (2008) |
| ANTPCGPYTHDCPVKR | 198 | Newton & Deutscher, Phage Peptide Display in Handbook of Experimental Pharmacology, pages 145-163, Springer-Verlag, Berlin (2008) |
| TACHQHVRMVRP | 199 | Newton & Deutscher, Phage Peptide Display in Handbook of Experimental Pharmacology, pages 145-163, Springer-Verlag, Berlin (2008) |
| VPWMEPAYQRFL | 200 | Newton & Deutscher, Phage Peptide Display in Handbook of Experimental Pharmacology, pages 145-163, Springer-Verlag, Berlin (2008) |
| DPRATPGS | 201 | Newton & Deutscher, Phage Peptide Display in Handbook of Experimental Pharmacology, pages 145-163, Springer-Verlag, Berlin (2008) |
| FRPNRAQDYNTN | 202 | Newton & Deutscher, Phage Peptide Display in Handbook of Experimental Pharmacology, pages 145-163, Springer-Verlag, Berlin (2008) |
| CTKNSYLMC | 203 | Newton & Deutscher, Phage Peptide Display in Handbook of Experimental Pharmacology, pages 145-163, Springer-Verlag, Berlin (2008) |
| C(R/Q)L/RT(G/N)XXG(A/V)GC | 204 | Newton & Deutscher, Phage Peptide Display in Handbook of Experimental Pharmacology, pages 145-163, Springer-Verlag, Berlin (2008) |

TABLE 7-continued

AAV Targeting sequences

| Sequence | SEQ ID NO | Reference |
|---|---|---|
| CPIEDRPMC | 205 | Newton & Deutscher, Phage Peptide Display in Handbook of Experimental Pharmacology, pages 145-163, Springer-Verlag, Berlin (2008) |
| HEWSYLAPYPWF | 206 | Newton & Deutscher, Phage Peptide Display in Handbook of Experimental Pharmacology, pages 145-163, Springer-Verlag, Berlin (2008) |
| MCPKHPLGC | 207 | Newton & Deutscher, Phage Peptide Display in Handbook of Experimental Pharmacology, pages 145-163, Springer-Verlag, Berlin (2008) |
| RMWPSSTVNLSAGRR | 208 | Newton & Deutscher, Phage Peptide Display in Handbook of Experimental Pharmacology, pages 145-163, Springer-Verlag, Berlin (2008) |
| SAKTAVSQRVWLPSHRGGEP | 209 | Newton & Deutscher, Phage Peptide Display in Handbook of Experimental Pharmacology, pages 145-163, Springer-Verlag, Berlin (2008) |
| KSREHVNNSACPSKRITAAL | 210 | Newton & Deutscher, Phage Peptide Display in Handbook of Experimental Pharmacology, pages 145-163, Springer-Verlag, Berlin (2008) |
| EGFR | 211 | Newton & Deutscher, Phage Peptide Display in Handbook of Experimental Pharmacology, pages 145-163, Springer-Verlag, Berlin (2008) |
| AGLGVR | 212 | Newton & Deutscher, Phage Peptide Display in Handbook of Experimental Pharmacology, pages 145-163, Springer-Verlag, Berlin (2008) |
| GTRQGHTMRLGVSDG | 213 | Newton & Deutscher, Phage Peptide Display in Handbook of Experimental Pharmacology, pages 145-163, Springer-Verlag, Berlin (2008) |
| IAGLATPGWSHWLAL | 214 | Newton & Deutscher, Phage Peptide Display in Handbook of Experimental Pharmacology, pages 145-163, Springer-Verlag, Berlin (2008) |
| SMSIARL | 215 | Newton & Deutscher, Phage Peptide Display in Handbook of Experimental Pharmacology, pages 145-163, Springer-Verlag, Berlin (2008) |
| HTFEPGV | 216 | Newton & Deutscher, Phage Peptide Display in Handbook of Experimental Pharmacology, pages 145-163, Springer-Verlag, Berlin (2008) |
| NTSLKRISNKR1RRK | 217 | Newton & Deutscher, Phage Peptide Display in Handbook of Experimental Pharmacology, pages 145-163, Springer-Verlag, Berlin (2008) |
| LRIKRKRRKRKKTRK | 218 | Newton & Deutscher, Phage Peptide Display in Handbook of Experimental Pharmacology, pages 145-163, Springer-Verlag, Berlin (2008) |

As yet a further embodiment, the targeting sequence may be a peptide that can be used for chemical coupling (e.g., can comprise arginine and/or lysine residues that can be chemically coupled through their R groups) to another molecule that targets entry into a cell.

As another embodiment, the AAV capsid protein or virus capsid of the disclosure can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV serotype.

Additionally, or alternatively, in representative embodiments, the capsid protein, virus capsid or vector comprises a selective amino acid insertion directly following amino acid position 264 of the AAV2 capsid protein or a corresponding change in the capsid protein from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.).

Furthermore, in representative embodiments, the capsid protein, virus capsid or vector of this disclosure can comprise amino acid modifications such as described in PCT Publication No. WO 2010/093784 (e.g., 2i8) and/or in PCT Publication No. WO 2014/144229 (e.g., dual glycan).

In some embodiments of this disclosure, the capsid protein, virus capsid or vector of this disclosure can have equivalent or enhanced transduction efficiency relative to the transduction efficiency of the AAV serotype from which the capsid protein, virus capsid or vector of this disclosure originated. In some embodiments of this disclosure, the capsid protein, virus capsid or vector of this disclosure can have reduced transduction efficiency relative to the transduction efficiency of the AAV serotype from which the capsid protein, virus capsid or vector of this disclosure originated. In some embodiments of this disclosure, the capsid protein, virus capsid or vector of this disclosure can have equivalent or enhanced tropism relative to the tropism of the AAV serotype from which the capsid protein, virus capsid or vector of this disclosure originated. In some embodiments of this disclosure, the capsid protein, virus capsid or vector of this disclosure can have an altered or different tropism relative to the tropism of the AAV serotype from which the capsid protein, virus capsid or vector of this disclosure originated. In some embodiments of this disclosure, the capsid protein, virus capsid or vector of this disclosure can have or be engineered to have tropism for brain tissue. In some embodiments of this disclosure, the capsid protein, virus capsid or vector of this disclosure can have or be engineered to have tropism for liver tissue.

The foregoing embodiments can be used to deliver a heterologous nucleic acid to a cell or subject as described herein. For example, the modified vector can be used to treat a lysosomal storage disorder such as a mucopolysaccharidosis disorder (e.g., Sly syndrome [β-glucuronidase], Hurler Syndrome [alpha-L-iduronidase], Scheie Syndrome [alpha-L-iduronidase], Hurler-Scheie Syndrome [alpha-L-iduronidase], Hunter's Syndrome [iduronate sulfatase], Sanfilippo Syndrome A [heparan sulfamidase], B [N-acetylglucosaminidase], C [acetyl-CoA:alpha-glucosaminide acetyl-transferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (a-galactosidase), Gaucher's disease (glucocerebrosidase), or a glycogen storage disorder (e.g., Pompe disease; lysosomal acid alpha-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent. As discussed elsewhere herein, the corresponding amino acid position(s) will be readily apparent to those skilled in the art using well-known techniques.

The disclosure also encompasses virus vectors comprising the modified capsid proteins and capsids of the disclosure. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the disclosure and a vector genome.

For example, in representative embodiments, the virus vector comprises: (a) a modified virus capsid (e.g., a modified AAV capsid) comprising a modified capsid protein of the disclosure; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid encoding a polypeptide or functional RNA of interest. Recombinant virus vectors are described in more detail below.

In particular embodiments, the virus vectors of the disclosure (i) have reduced transduction of liver as compared with the level of transduction by a virus vector without the modified capsid protein; (ii) exhibit enhanced systemic transduction by the virus vector in an animal subject as compared with the level observed by a virus vector without the modified capsid protein; (iii) demonstrate enhanced movement across endothelial cells as compared with the level of movement by a virus vector without the modified capsid protein, and/or (iv) exhibit a selective enhancement in transduction of muscle tissue (e.g., skeletal muscle, cardiac muscle and/or diaphragm muscle), (v) exhibit a selective enhancement in transduction of liver tissue, and/or (vi) reduced transduction of brain tissues (e.g., neurons) as compared with the level of transduction by a virus vector without the modified capsid protein. In particular embodiments, the virus vector has systemic transduction toward liver.

It will be understood by those skilled in the art that the modified capsid proteins, virus capsids and virus vectors of the disclosure exclude those capsid proteins, capsids and virus vectors that have the indicated amino acids at the specified positions in their native state (i.e., are not mutants).

Methods of Producing Virus Vectors

The present disclosure further provides methods of producing the inventive virus vectors. Thus, in one embodiment, the present disclosure provides a method of producing an AAV vector that evades neutralizing antibodies, comprising: a) identifying contact amino acid residues that form a three dimensional antigenic footprint on an AAV capsid protein; b) generating a library of AAV capsid proteins comprising amino acid substitutions of the contact amino acid residues identified in (a); c) producing AAV particles comprising capsid proteins from the library of AAV capsid proteins of (b); d) contacting the AAV particles of (c) with cells under conditions whereby infection and replication can occur; e) selecting AAV particles that can complete at least one infectious cycle and replicate to titers similar to control AAV particles: 1) contacting the AAV particles selected in (e) with neutralizing antibodies and cells under conditions whereby infection and replication can occur; and g) selecting AAV particles that are not neutralized by the neutralizing antibodies of (f). Nonlimiting examples of methods for identifying contact amino acid residues include peptide epitope mapping and/or cryo-electron microscopy.

Resolution and identification of the antibody contact residues within the three dimensional antigenic footprint allows for their subsequent modification through random, rational and/or degenerate mutagenesis to generate antibody-evading AAV capsids that can be identified through further selection and/or screening.

Thus, in a further embodiment, the present disclosure provides a method of producing an AAV vector that evades neutralizing antibodies, comprising: a) identifying contact amino acid residues that form a three dimensional antigenic footprint on an AAV capsid protein; b) generating AAV capsid proteins comprising amino acid substitutions of the contact amino acid residues identified in (a) by random, rational and/or degenerate mutagenesis; c) producing AAV particles comprising capsid proteins from the AAV capsid proteins of (b); d) contacting the AAV particles of (c) with cells under conditions whereby infection and replication can occur; e) selecting AAV particles that can complete at least one infectious cycle and replicate to titers similar to control AAV particles; f) contacting the AAV particles selected in (e) with neutralizing antibodies and cells under conditions whereby infection and replication can occur; and g) selecting AAV particles that are not neutralized by the neutralizing antibodies of (f).

Nonlimiting examples of methods for identifying contact amino acid residues include peptide epitope mapping and/or cryo-electron microscopy. Methods of generating AAV capsid proteins comprising amino acid substitutions of contact amino acid residues by random, rational and/or degenerate mutagenesis are known in the art.

This comprehensive approach presents a platform technology that can be applied to modifying any AAV capsid. Application of this platform technology yields AAV antigenic variants derived from the original AAV capsid template without loss of transduction efficiency. As one advantage and benefit, application of this technology will expand the cohort of patients eligible for gene therapy with AAV vectors.

In one embodiment, the present disclosure provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the disclosure). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158: 67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a noninfectious adenovirus miniplasmid that carries all of the helper genes that promote efficient AAV production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al., ((2001) Gene Ther. 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) Gene Therapy 6:986 and WO 00/17377.

As a further alternative, the virus vectors of the disclosure can be produced in insect cells using baculovirus vectors to deliver the rep/cap genes and rAAV template as described, for example, by Urabe et al., (2002) Human Gene Therapy 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) Gene Therapy 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors

The virus vectors of the present disclosure are useful for the delivery of nucleic acids to cells in vitro, ex vivo, and in vivo. In particular, the virus vectors can be advantageously employed to deliver or transfer nucleic acids to animal, including mammalian, cells. Thus, in some embodiments, a nucleic acid ("cargo nucleic acid") may be encapsidated by a capsid protein of the disclosure.

In some embodiments, the disclosure provides an AAV vector comprising a recombinant capsid protein with at least 90%, at least 95%, at least 96%, at least 97%, at least 98%, at least 99%, or 100% sequence identity, with any one of SEQ ID NO: 18-80, 300-410, 422-612, or 783-785. In some embodiments, an AAV vector comprises a recombinant capsid protein with at least 90%, at least 95%, at least 96%, at least 97%, at least 98%, at least 99%, or 100% sequence identity, with SEQ ID NO: 380 or 384. In some embodiments, an AAV viral vector comprises a recombinant capsid protein with at least 90%, at least 95%, at least 96%, at least 97%, at least 98%, at least 99%, or 100% sequence identity, with any one of SEQ ID NO: 18-80, 300-410, 422-612, or 783-785 and further comprises a cargo nucleic acid encapsidated by the capsid protein. In some embodiments, an AAV viral vector comprises a recombinant capsid protein with at least 90%, at least 95%, at least 96%, at least 97%, at least 98%, at least 99%, or 100% sequence identity, with SEQ ID NO: 380 or 384 and further comprises a cargo nucleic acid encapsidated by the capsid protein.

The cargo nucleic acid sequence delivered in the virus vectors of the present disclosure may be any heterologous nucleic acid sequence(s) of interest. Nucleic acids of interest include nucleic acids encoding polypeptides, including therapeutic (e.g., for medical or veterinary uses) or immunogenic (e.g., for vaccines) polypeptides or RNAs.

Therapeutic polypeptides include, but are not limited to, cystic fibrosis transmembrane regulator protein (CFTR), dystrophin (including mini- and micro-dystrophins, see, e.g., Vincent et al, (1993) Nature Genetics 5:130; U.S. Patent Publication No. 2003/017131; International publication WO/2008/088895, Wang et al., Proc. Natl. Acad. Sci. USA 97:1 3714-13719 (2000); and Gregorevic et al., Mol. Ther. 16:657-64 (2008)), myostatin propeptide, follistatin, activin type 11 soluble receptor, IGF-1, apolipoproteins such as apoA (apoA1, apoA2, apoA4, apoA-V), apoB (apoB100, ApoB48), apoC (apoCI, apoCII, apoCIII, apoCIV), apoD, apoE, apoH, apoL, apo(a), anti-inflammatory polypeptides such as the Ikappa B dominant mutant, sarcospan, utrophin (Tinsley et al, (1996) Nature 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, progranulin, ornithine transcarbamylase, β-globin, a-globin, spectrin, alpha-1-antitrypsin, adenosine deaminase, hypoxanthine guanine phosphoribosyl transferase, glucocerebrosidase, amyloid beta, tau, batenin, sphingomyelinase, lysosomal hexosaminidase A, branched-chain keto acid dehydrogenase, frataxin, RP65 protein, cytokines (e.g., alpha-interferon, beta-interferon, gamma-interferon, interleukin-2, interleukin-4, alpha synuclein, parkin, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), huntingtin, lysosomal acid alpha-glucosidase, iduronate-2-sulfatase, N-sulfoglucosamine sulfohydrolase, alpha-galactosidase A, receptors (e.g., the tumor necrosis growth factor soluble receptor), S100A1, ubiquitin protein ligase E3, parvalbumin, adenylyl cyclase type 6, a molecule that modulates calcium handling (e.g., SERCA$_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins that enhance or inhibit transcription of host factors (e.g., nuclease-dead Cas9 linked to a transcription enhancer or inhibitor element, zinc-finger proteins linked to a transcription enhancer or inhibitor element, transcription activator-like (TAL) effectors linked to a transcription enhancer or inhibitor element), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., Nature Biotechnology 23:584-590 (2005)). Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this disclosure, the heterologous nucleic acid may encode an antisense nucleic acid, a ribozyme (e.g., as described in U.S. Pat. No. 5,877,022), RNAs that effect spliceosome-mediated/ramsplicing (see, Puttaraju et al, (1999) Nature Biotech. 17:246; U.S. Pat. Nos. 6,013,487; 6,083,702), interfering RNAs (RNAi) including siRNA, shRNA or miRNA that mediate gene silencing (see, Sharp et al, (2000) Science 287:2431), and other non-translated RNAs, such as "guide" RNAs (Gorman et al., (1998) Proc. Nat. Acad. Sci. USA 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., J. Gene Med. 10:132-142 (2008) and Li et al., Acta Pharmacol Sin. 26:51-55 (2005)); phospholamban inhibitory or dominant-negative molecules such as phospholamban S16E (e.g., to treat cardiovascular disease, see, e.g., Hoshijima et al. Nat. Med. 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the disclosure.

In some embodiments, a nucleic acid sequence that directs gene editing can be delivered. For example, the nucleic acid may encode a guide RNA. In some embodiments, the guide RNA is a single guide RNA (sgRNA) comprising a crRNA sequence and a tracrRNA sequence. In some embodiments, the nucleic acid may encode a nuclease. In some embodiments, the nuclease is a zinc-finger nuclease, a homing endonuclease, a TALEN (transcription activator-like effector nuclease), a NgAgo (agronaute endonuclease), a SGN (structure-guided endonuclease), a RGN (RNA-guided nuclease), or modified or truncated variants thereof. In some embodiments, the RNA-guided nuclease is a Cas9 nuclease, a Cas12(a) nuclease (Cpf1), a Cas12b nuclease, a Cas12c nuclease, a TrpB-like nuclease, a Cas13a nuclease (C2c2), a Cas13b nuclease, or modified or truncated variants thereof. In some embodiments, the Cas9 nuclease is isolated or derived from *S. pyogenes* or *S. aureus*.

In some embodiments, a nucleic acid sequence that directs gene knockdown can be delivered. For example, the nucleic acid sequence may encode a siRNA, an shRNA, a microRNA, or an antisense nucleic acid.

The virus vector may also comprise a heterologous nucleic acid that shares homology with and recombines with a locus on a host chromosome. This approach can be utilized, for example, to correct a genetic defect in the host cell.

The present disclosure also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura el al, (1994) Proc. Nat. Acad. Sci USA 91:8507; U.S. Pat. No. 5,916,563 to Young et al, U.S. Pat. No. 5,905,040 to Mazzara et al, U.S. Pat. Nos. 5,882, 652, 5,863,541 to Samulski et al). The antigen may be presented in the parvovirus capsid.

Alternatively, the antigen may be expressed from a heterologous nucleic acid introduced into a recombinant vector genome. Any immunogen of interest as described herein and/or as is known in the art can be provided by the virus vector of the present disclosure.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) ora lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP 160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia LI or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens), a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell.

Exemplary cancer and tumor cell antigens are described in S. A. Rosenberg (Immunity 10:281 (1991)). Other illustrative cancer and tumor antigens include, but are not limited to: BRCA1 gene product, BRCA2 gene product, gp100, tyrosinase, GAGE-1/2, BALE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) Proc. Natl. Acad. Sci. USA 91:3515; Kawakami et al., (1994) J. Exp. Med., 180:347; Kawakami et al., (1994) Cancer Res. 54:3124), MART-1, gp100, MAGE-1, MAGE-2, MAGE-3, CEA, TRP-1, TRP-2, P-15, tyrosinase (Brichard et al., (1993) J Exp. Med. 178:489); HER-2/neu gene product (U.S. Pat. No. 4,968, 603), CA 125, LK26, FB5 (endosialin), TAG 72, AFP, CA 19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) Ann. Rev. Biochem. 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition or metastasis thereof now known or later identified (see, e.g., Rosenberg, (1996) Ann. Rev. Med. 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present disclosure provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present disclosure can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders. Alzheimer's disease (GDF; neprilysin), multiple sclerosis (β-interferon), Parkinson's disease (glial-cell line derived neurotrophic factor [GDNF]), Huntington's disease (RNAi to remove repeats), Canavan's disease, amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., a, β, γ], RNAi against myostatic myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (a-L-iduronidase), adenosine deaminase deficiency (adenosine deaminase), glycogen storage diseases (e.g., Fabry disease [a-galactosidase] and Pompe disease [lysosomal acid alpha-glucosidase]) and other metabolic disorders, congenital emphysema (alpha-1-antitrypsin), Lesch-Nyhan Syndrome (hypoxanthine guanine phosphoribosyl transferase), Niemann-Pick disease (sphingomyelinase), Tay-Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/ or RNAi against VEGF]), liver, kidney, heart including congestive heart failure or peripheral artery disease (PAD) (e.g., by delivering protein phosphatase inhibitor 1 (I-1) and fragments thereof (e.g., IIC), serca2a, zinc finger proteins that regulate the phospholamban gene, Barkct, [32-adrenergic receptor, 2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as I RAP and TNFa soluble receptor), hepatitis (a-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The disclosure can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

In some embodiments, the virus vectors of the present disclosure can be employed to deliver a heterologous nucleic acid encoding a polypeptide or functional RNA to treat and/or prevent a liver disease or disorder. The liver disease or disorder may be, for example, primary biliary cirrhosis, nonalcoholic fatty liver disease (NAFLD), non-alcoholic steatohepatitis (NASH), autoimmune hepatitis, hepatitis B, hepatitis C, alcoholic liver disease, fibrosis, jaundice, primary sclerosing cholangitis (PSC), Budd-Chiari syndrome, hemochromatosis, Wilson's disease, alcoholic fibrosis, non-alcoholic fibrosis, liver steatosis, Gilbert's syndrome, biliary atresia, alpha-1-antitrypsin deficiency, alagille syndrome, progressive familial intrahepatic cholestasis, Hemophilia B, Hereditary Angioedema (HAE), Homozygous Familial Hypercholesterolemia (HoFH), Heterozygous Familial Hypercholesterolemia (HeFH), Von Gierke's Disease (GSD I), Hemophilia A, Methylmalonic Acidemia, Propionic Acidemia, Homocystinuria, Phenylketonuria (PKU), Tyrosinemia Type 1, Arginase 1 Deficiency, Argininosuccinate Lyase Deficiency, Carbamoyl-phosphate synthetase 1 deficiency, Citrullinemia Type 1, Citrin Deficiency, Crigler-Najjar Syndrome Type 1, Cystinosis, Fabry Disease, Glycogen Storage Disease 1b, LPL Deficiency, N-Acetylglutamate Synthetase Deficiency, Ornithine Transcarbamylase Deficiency, Ornithine Translocase Deficiency, Primary Hyperoxaluria Type 1, or ADA SCID.

The disclosure can also be used to produce induced pluripotent stem cells (iPS). For example, a virus vector of the disclosure can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like.

Nucleic acids encoding factors associated with stem cells are known in the art. Nonlimiting examples of such factors associated with stem cells and pluripotency include Oct-3/4, the SOX family (e.g., SOX 1, SOX2, SOX3 and/or SOX 15), the Klf family (e.g., Klf1, KHZ Klf4 and/or Klf5), the Myc family (e.g., C-myc, L-myc and/or N-myc), NANOG and/or LIN28.

The disclosure can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [alpha-L-iduronidase], Scheie Syndrome [alpha-L-iduronidase], Hurler-Scheie Syndrome [alpha-L-iduronidase], Hunter's Syndrome [iduronate sulfatase], Sanfilippo Syndrome A [heparan sulfamidase], B [N-acetylglucosaminidase], C [acetyl-CoA:alpha-glucosaminide acetyltransferase], D [N-acetylglucosamine 6-sulfatase], Morquio Syndrome A [galactoses-sulfate sulfatase], B [β-galactosidase], Maroteaux-Lamy Syndrome [N-acetylgalactosamine-4-sulfatase], etc.), Fabry disease (alpha-galactosidase), Gaucher's disease (glucocerebrosidase), or a glycogen storage disorder (e.g., Pompe disease; lysosomal acid alpha-glucosidase).

Gene transfer has substantial use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present disclosure permit the treatment and/or prevention of genetic diseases.

The virus vectors according to the present disclosure may also be employed to provide a functional RNA to a cell in vitro or in vivo. The functional RNA may be, for example, a non-coding RNA. In some embodiments, expression of the functional RNA in the cell can diminish expression of a particular target protein by the cell. Accordingly, functional RNA can be administered to decrease expression of a particular protein in a subject in need thereof. In some embodiments, expression of the functional RNA in the cell can increase expression of a particular target protein by the cell. Accordingly, functional RNA can be administered to increase expression of a particular protein in a subject in need thereof. In some embodiments, expression of the functional RNA can regulate splicing of a particular target RNA in a cell. Accordingly, functional RNA can be administered to regulate splicing of a particular RNA in a subject in need thereof. In some embodiments, expression of the functional RNA in the cell can regulate the function of a particular target protein by the cell. Accordingly, functional RNA can be administered to regulate the function of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant disclosure find use in diagnostic and screening methods, whereby a nucleic acid of interest is transiently or stably expressed in a cell culture system, or alternatively, a transgenic animal model.

The virus vectors of the present disclosure can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present disclosure may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, Immunophysiology: Cell Function and Cellular Interactions in Antibody Formation, in IMMUNOLOGY: BASIC PROCESSES 1 17 (Joseph A. Bellanti ed., 1985). Alternatively stated, an active immune response is mounted by the host after exposure to an immunogen by infection or by vaccination. Active immunity can be contrasted with passive immunity, which is acquired through the transfer of preformed substances (antibody, transfer factor, thymic graft, interleukin-2) from an actively immunized host to a non-immune host.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present disclosure can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein.

Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the disclosure provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant disclosure. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., alpha-interferon, beta-interferon, gamma-interferon, omega-interferon, tau-interferon, interleukin-1-alpha, interleukin-1β, interleukin-2, interleukin-3, interleukin-4, interleukin 5, interleukin-6, interleukin-7, interleukin-8, interleukin-9, interleukin-10, interleukin-11, interleukin-12, interleukin-13, interleukin-14, interleukin-18, B cell Growth factor, CD40 Ligand, tumor necrosis factor-alpha, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector. Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present disclosure find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammals" as used herein includes, but is not limited to, humans, non-human primates, bovines, ovines, caprines, equines, felines, canines, lagomorphs, etc. Human subjects include neonates, infants, juveniles, adults and geriatric subjects. In some embodiments, a human subject can be less than 6 months old, less than 2 years old, less than 5 years old, less than 10 years old, 10-18 years old, 19-29 years old, 30-35 years old, 36-40 years old, or older than 40 years old.

In representative embodiments, the subject is "in need" of the methods described herein.

In particular embodiments, a pharmaceutical composition is provided comprising a virus vector and/or capsid and/or capsid protein and/or virus particle of the disclosure in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present disclosure is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a therapeutically effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

Thus, the present disclosure provides a method of administering a nucleic acid to a cell, the method comprising contacting the cell with the virus vector, virus particle and/or composition of this disclosure.

A further aspect of the disclosure is a method of administering the virus vector, virus particle and/or virus capsid of this disclosure to a subject. Thus, the present disclosure also provides a method of delivering a nucleic acid to a subject, comprising administering to the subject a virus particle, virus vector and/or composition of this disclosure. Administration of the virus vectors, virus particles and/or capsids according to the present disclosure to a human subject or an animal in need thereof can be by any means known in the art. Optionally, the virus vector, virus particle and/or capsid is delivered in a therapeutically effective dose in a pharmaceutically acceptable carrier. In preferred embodiments, a therapeutically effective amount of the virus vector, virus particle and/or capsid is delivered.

The virus vectors and/or capsids of the disclosure can further be administered to elicit an immunogenic response (e.g., as a vaccine). Typically, immunogenic compositions of the present disclosure comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, about $10^6$, about $10^7$, about $10^8$, about $10^9$, about $10^{10}$, about $10^{11}$, about $10^{12}$, about $10^{13}$, about $10^{14}$, about $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present disclosure includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficial is, flexor hallucis brevis, flexor hallucis longus, flexor pollicis brevis. flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see, e.g. Arruda et al., (2005) Blood 105:3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the disclosure, the virus vectors and/or capsids of the disclosure can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the disclosure can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome. Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present disclosure is administered to skeletal muscle, diaphragm muscle and/or cardiac muscle (e.g., to treat and/or prevent muscular dystrophy, heart disease [for example, PAD or congestive heart failure]).

In representative embodiments, the disclosure is used to treat and/or prevent disorders of skeletal, cardiac and/or diaphragm muscle.

In a representative embodiment, a method of treating and/or preventing muscular dystrophy in a subject in need thereof is provided, the method comprising: administering a treatment or prevention effective amount of a virus vector of the disclosure to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-a2, alpha-sarcoglycan, beta-sarcoglycan, gamma-sarcoglycan, delta-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the disclosure can be practiced to deliver a nucleic acid to skeletal, cardiac or diaphragm muscle, which is used as a platform for production of a polypeptide (e.g., an enzyme) or functional RNA (e.g., RNAi, micro RNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [a-galactosidase A] or a glycogen storage disorder such as Pompe disease [lysosomal acid alpha glucosidase]). Other suitable proteins for treating and/or preventing metabolic disorders are described herein. The use of muscle as a platform to express a nucleic acid of interest is described in U.S. Patent publication US 2002/0192189.

Thus, as one aspect, the disclosure further encompasses a method of treating and/or preventing a metabolic disorder in a subject in need thereof, the method comprising: administering a treatment or prevention effective amount of a virus vector of the disclosure to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the disclosure, according to this embodiment, administration to the skeletal muscle can result in secretion of the polypeptide into the systemic circulation and delivery to target tissue(s). Methods of delivering virus vectors to skeletal muscle is described in more detail herein.

The disclosure can also be practiced to produce noncoding RNA, such as antisense RNA, RNAi or other functional RNA (e.g., a ribozyme) for systemic delivery.

The disclosure also provides a method of treating and/or preventing congenital heart failure or PAD in a subject in need thereof, the method comprising administering a treatment or prevention effective amount of a virus vector of the disclosure to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor 1 (I-1) and fragments thereof (e.g., I1C), RNAi against phospholamban; a phospholamban inhibitory or dominant-negative molecule such as phospholamban S16E, a zinc finger protein that regulates the phospholamban gene, beta-2-adrenergic receptor, beta-2-adrenergic receptor kinase (BARK), PI3 kinase, calsarcan, a β-adrenergic receptor kinase inhibitor (PARKct), inhibitor 1 of protein phosphatase 1 and fragments thereof (e.g., I1 C), S100A1, parvalbumin, adenylyl cyclase type 6, a molecule that effects G-protein coupled receptor kinase type 2 knockdown such as a truncated constitutively active bARKct, Pim-1, PGC-I α, SOD-1, SOD-2, EC-SOD, kallikrein, HIF, thymosin-p4, mir-I, mir-I 33, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids of the disclosure in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the CNS (e.g., brain, eye) and may advantageously result in broader distribution of the virus vector or capsid than would be observed in the absence of the present disclosure.

In particular embodiments, the delivery vectors described herein may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyhan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present disclosure can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the disclosure.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present disclosure may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the disclosure can also be used to treat epilepsy, which is marked by multiple seizures over time.

In one representative embodiment, somatostatin (or an active fragment thereof) is administered to the brain using a delivery vector of the disclosure to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the disclosure, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons. In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Numbered Embodiments

The following numbered embodiments are included within the scope of the disclosure.

1. A recombinant adeno-associated virus (AAV) capsid protein, wherein the capsid protein comprises a substitution in an antigenic site of the AAV capsid protein, wherein the substitution has a sequence of any one of SEQ ID NO: 9, 10, 11, 12, 13, 14, 15, 16, 17, 297, 298, 299, or 411-421.

2. The recombinant AAV capsid protein of embodiment 1, wherein the substitution comprises a sequence of any one of SEQ ID NO: 9, 10, 14, or 17.

3. The recombinant AAV capsid protein of embodiment 1 or 2, wherein the AAV capsid protein comprises a first amino acid substitution and a second amino acid substitution, wherein the first amino acid substitution and the second amino acid substitution each modify a different antigenic site on the AAV capsid protein, wherein the first amino acid substitution and the second amino acid substitution each comprise any one of SEQ ID NO: 9, 10, 11, 12, 13, 14, 15, 16, 17, 297, 298, 299, or 411-421.

4. The recombinant AAV capsid protein of embodiment 1 or 2, wherein the AAV capsid protein comprises a first acid substitution, a second amino acid substitution, and a third amino acid substitution, wherein the first amino acid substitution, the second amino acid substitution, and the third amino acid substitution each modify a different antigenic site on the AAV capsid protein, wherein the first amino acid substitution, the second amino acid substitution and the third amino acid substitution each comprise any one of SEQ ID NO: 9, 10, 11, 12, 13, 14, 15, 16, 17, 297, 298, 299, or 411-421.

5. The recombinant AAV capsid of embodiment 4, wherein the first amino acid substitution comprises SEQ ID NO. 9; the second amino acid substitution comprises any one of SEQ ID NO. 10, 11, 12, 13, 14, 15, 16, 297, 298, 299, or 411-421; and the third amino acid substitution comprises SEQ ID NO. 17.

6. The recombinant AAV capsid of embodiment 5, wherein the first amino acid substitution comprises SEQ ID NO. 9; the second amino acid substitution comprises SEQ ID NO. 10; and the third amino acid substitution comprises SEQ ID NO. 17.

7. The recombinant AAV capsid of embodiment 5, wherein the first amino acid substitution comprises SEQ ID NO. 9; the second amino acid substitution comprises SEQ ID NO. 14; and the third amino acid substitution comprises SEQ ID NO. 17.

8. The recombinant AAV capsid protein of any one of embodiments 1-7, wherein the AAV capsid protein further comprises a substitution that modifies the HI loop of the capsid.

9. The recombinant AAV capsid protein of embodiment 8, wherein the AAV capsid comprises one or more of the following substitutions in the HI loop:

P661R, T662S, Q666G, S667D, wherein the numbering corresponds to the wildtype AAV8 capsid (SEQ ID NO: 6); or P659R, T660S, A661T, K664G, wherein the numbering corresponds to the wildtype AAV9 capsid (SEQ ID NO: 7).

10. The recombinant AAV capsid protein of any one of embodiment 1 to 9, wherein the AAV capsid protein is of an AAV serotype selected from AAV1, AAV2, AAV3, AAV4, AAVS, AAV6, AAV7, AAV8, AAV9, AAV10, AAV11, AAV12, AAVrh.8, AAVrh.10, AAVrh32.33, AAVrh74, bovine AAV and avian AAV.

11. The recombinant AAV capsid protein of any one of embodiments 1 to 9, wherein the AAV capsid protein is chimeric.

12. The recombinant AAV capsid protein of embodiment 11, wherein the AAV capsid protein comprises sequences derived from two or more AAV serotypes.

13. The recombinant AAV capsid protein of embodiment 12, wherein the AAV capsid protein comprises sequences derived from three or more AAV serotypes.

14. The recombinant AAV capsid protein of any one of embodiments 1-10, wherein the AAV capsid protein comprises an amino acid sequence that has at least 90% sequence identity with any one of SEQ ID NOs: 18-80, 300-410, 422-612, or 783-785.

15. The recombinant AAV capsid protein of embodiment 14, wherein the AAV capsid protein comprises an amino acid sequence of any one of SEQ ID NOs: 18-80, 300-410, 422-612, or 783-785.

16. The recombinant AAV capsid protein of embodiment 15, wherein the AAV capsid protein comprises an amino acid sequence of SEQ ID NO: 380 or SEQ ID NO: 384.

17. The recombinant AAV capsid protein of any one of embodiments 1 to 16, wherein the modification of the one or more antigenic sites results in inhibition of binding by an antibody to the one or more antigenic sites.

18. The recombinant AAV capsid protein of any one of embodiments 1 to 17, wherein the modification of the one or more antigenic sites results in inhibition of neutralization of infectivity of a virus particle comprising said AAV capsid protein.

19. A recombinant AAV capsid protein comprising the amino acid sequence of SEQ ID NO: 49.

20. The recombinant AAV capsid protein of embodiment 19, wherein the AAV capsid protein is modified by replacing the region spanning amino acids 454-460 of SEQ ID NO: 49 with SEQ ID NO: 9.

21. The recombinant AAV capsid protein of any one of embodiments 19 or 20, wherein the AAV capsid protein is modified by replacing the region spanning amino acids 493-500 of SEQ ID NO: 49 with any one of SEQ ID NO: 10, 11, 12, 13, 14, 15, 16, 297, 298, 299, or 411-421.

22. The recombinant AAV capsid protein of any one of embodiments 19 to 21, wherein the AAV capsid protein is modified by replacing the region spanning amino acids 585-590 of SEQ ID NO: 49 with SEQ ID NO: 17.

23. The recombinant AAV capsid protein of any one of embodiments 19 to 22, wherein the AAV capsid protein is modified by replacing the region spanning amino acids 454-460 of SEQ ID NO: 49 with SEQ ID NO: 9, the region spanning amino acids 493-500 of SEQ ID NO: 49 with any one of SEQ ID NO: 10, 11, 12, 13, 14, 15, 16, 297, 298, 299, or 411-421, and the region spanning amino acids 585-590 of SEQ ID NO: 49 with SEQ ID NO: 17.

24. The recombinant AAV capsid protein of any one of embodiments 19 to 23, wherein the modification results in inhibition of binding by an antibody to the AAV capsid protein.

25. The recombinant AAV capsid protein of any one of embodiments 19 to 24, wherein the modification results in inhibition of neutralization of infectivity of a virus particle comprising the AAV capsid protein.

26. A recombinant AAV capsid protein comprising the amino acid sequence of any one of SEQ ID NO: 18-80, 300-410, 422-612, or 783-785.

27. A recombinant AAV capsid protein comprising the amino acid sequence of SEQ ID NO: 380 or SEQ ID NO: 384.

28. A nucleotide sequence encoding a recombinant AAV capsid protein of any one of embodiments 1 to 27.

29. The nucleotide sequence of embodiment 28, wherein the nucleotide sequence is a DNA sequence.

30. The nucleotide sequence of embodiment 28, wherein the nucleotide sequence is an RNA sequence.

31. An expression vector comprising the nucleotide sequence of any one of embodiments 28-30.

32. A cell comprising the nucleotide sequence of any one of embodiments 28-30, or the expression vector of embodiment 31.

33. An AAV viral vector comprising the recombinant capsid protein of any one of embodiments 1 to 27.

34. The AAV viral vector of embodiment 33, further comprising a cargo nucleic acid encapsidated by the capsid protein.

35. The AAV viral vector of embodiment 34, wherein the cargo nucleic acid encodes a therapeutic protein or RNA.

36. The AAV viral vector of any one of embodiments 34-35, wherein the cargo nucleic acid encodes a gene-editing molecule.

37. The AAV viral vector of embodiment 36, wherein the gene-editing molecule is a nuclease.

38. The AAV viral vector of embodiment 37, wherein the gene-editing molecule is a Cas9 nuclease.

39. The AAV viral vector of embodiment 37, wherein the gene-editing molecule is a Cpf1 nuclease.

40. The AAV viral vector of embodiment 36, wherein the gene-editing molecule is a single guide RNA.

41. A pharmaceutical composition comprising the AAV viral vector of any one of embodiment 33 to 40.

42. The pharmaceutical composition of embodiment 41, wherein the composition further comprises a pharmaceutically acceptable carrier.

43. A pharmaceutical composition comprising the cell of embodiment 32 or the expression vector of embodiment 31.

44. The pharmaceutical composition of embodiment 43 wherein the composition further comprises a pharmaceutically acceptable carrier.

45. A method of treating a patient in need thereof comprising administering to the patient a therapeutically effective amount of an AAV viral vector of any one of embodiments 33-40 or the pharmaceutical composition of any one of embodiments 41-44.

46. The method of embodiment 45, wherein the patient has a liver disease or disorder.

47. The method of embodiment 46, wherein the liver disease or disorder is primary biliary cirrhosis, nonalcoholic fatty liver disease (NAFLD), non-alcoholic steatohepatitis (NASH), autoimmune hepatitis, hepatitis B, hepatitis C, alcoholic liver disease, fibrosis, jaundice, primary sclerosing cholangitis (PSC), Budd-Chiari syndrome, hemochromatosis, Wilson's disease, alcoholic fibrosis, non-alcoholic fibrosis, liver steatosis, Gilbert's syndrome, biliary atresia, alpha-1-antitrypsin deficiency, alagille syndrome, progressive familial intrahepatic cholestasis, Hemophilia B, Hereditary Angioedema (HAE), Homozygous Familial Hypercholesterolemia (HoFH), Heterozygous Familial Hypercholesterolemia (HeFH), Von Gierke's Disease (GSD I), Hemophilia A, Methylmalonic Acidemia, Propionic Acidemia, Homocystinuria, Phenylketonuria (PKU), Tyrosinemia Type I, Arginase I Deficiency, Argininosuccinate Lyase Deficiency, Carbamoyl-phosphate synthetase 1 deficiency, Citrullinemia Type 1, Citrin Deficiency, Crigler-Najjar Syndrome Type 1, Cystinosis, Fabry Disease, Glycogen Storage Disease Ib, LPL Deficiency, N-Acetylglutamate Synthetase Deficiency, Ornithine Transcarbamylase Deficiency, Ornithine Translocase Deficiency, Primary Hyperoxaluria Type I, or ADA SCID.

48. The method of embodiment 46, wherein the liver disease or disorder is liver cancer or metastasis.

49. The method of any one of embodiments 45-48, wherein the patient is a mammal.

50. The method of embodiment 49, wherein the patient is a human.

51. A method of introducing a nucleic acid molecule into a cell, comprising contacting the cell with the AAV viral vector of any one of embodiments 33-40.

52. An AAV viral vector of any one of embodiments 33-40 for use as a medicament.

53. An AAV viral vector of any one of embodiments 33-40 for use in a method of treatment.

EXAMPLES

The following examples, which are included herein for illustration purposes only, are not intended to be limiting.

Example 1. Combinatorial Engineering and Selection of Antibody-Evading AAV Vectors The method for generating antibody evading AAV mutants is as follows. The first step involves identification of conformational 3D antigenic epitopes on the AAV capsid surface, for example using cryo-electron microscopy. Selected residues within antigenic motifs are then subjected to mutagenesis using degenerate primers with each codon substituted by nucleotides NNK and gene fragments combined together by Gibson assembly and/or multistep PCR. Capsid-encoding genes containing a degenerate library of mutated antigenic motifs are cloned into a wild type AAV genome to replace the original Cap encoding DNA sequence, yielding a plasmid library. Plasmid libraries are then transfected into 293 producer cell lines with an adenoviral helper plasmid to generate AAV libraries (i.e. libraries of AAVs comprising the mutated AAV capsids described above), which can then be subjected to selection. Successful generation of AAV libraries is confirmed via DNA sequencing.

In order to select for new AAV strains that can escape neutralizing antibodies (NAbs), AAV libraries are subjected to multiple rounds of infection in non-human primates. At each stage, tissues of interest are isolated from animal subjects. Cell lysates harvested from the tissues of interest are sequenced to identify AAV isolates escaping antibody neutralization. After multiple rounds of infection in non-human primates, the isolated sequences from each mutagenized region are combined in all permutations and combinations. Each round of infection, tissue isolation, and sequencing is referred to herein as a round of evolution.

As a nonlimiting specific example, common antigenic motifs on an AAV capsid protein were subjected to mutagenesis as described above. The degenerate libraries of recombinant AAVs comprising the mutated capsids were then subjected to a first round of infection in non-human primates (FIG. 1A, FIG. 2A). Liver was harvested at day 7 post-infection and sequenced to identify single recombinant AAV isolates (FIG. 1B, FIG. 2B).

The AAVs isolated during this first round of evolution (FIG. 2B) where then reintroduced into a second non-human primate. Liver was harvested at day 7 post-infection and sequenced to identify single recombinant AAV isolates (FIG. 2C).

The AAVs isolated during the second round of evolution (FIG. 2C) where then reintroduced into a third non-human primate. Liver was harvested at day 7 post-infection and sequenced to identify single recombinant AAV isolates (FIG. 2D).

After each round of evolution, various recombinant AAV isolates were identified in liver samples. A description of various isolates is provided in Table 8 and in Table 6.1, above.

TABLE 8

Recombinant AAV Isolated from Liver

| Sequence Replacing Antigenic Sequence | Full Capsid Sequence |
|---|---|
| SNGRGV (SEQ ID NO: 9) | SEQ ID NO: 18 |
| NLAENFKY (SEQ ID NO: 10) | SEQ ID NO: 19 |
| VLSGDHSA (SEQ ID NO: 11) | SEQ ID NO: 20 |
| MSAASGSG (SEQ ID NO: 12) | SEQ ID NO: 21 |
| GTNLGKEQ (SEQ ID NO: 13) | SEQ ID NO: 22 |

TABLE 8-continued

Recombinant AAV Isolated from Liver

| Sequence Replacing Antigenic Sequence | Full Capsid Sequence |
|---|---|
| SSHSGTNQ (SEQ ID NO: 14) | SEQ ID NO: 23 |
| VATRDGQL (SEQ ID NO: 15) | SEQ ID NO: 24 |
| ALNADTGT (SEQ ID NO: 16) | SEQ ID NO: 25 |
| VMEPTR (SEQ ID NO: 17) | SEQ ID NO: 26 |
| VVGNGGVV (SEQ ID NO: 297) | SEQ ID NO: 300 |
| NFREMPIG (SEQ ID NO: 298) | SEQ ID NO: 301 |
| RRSEDMGTI (SEQ ID NO: 299) | SEQ ID NO: 302 |

Example 2. Recombinant AAV Vectors Transduce Cells in Culture

To confirm whether various AAV vectors isolated from liver in Example 1 are generally infective and able to transduce cells in culture, various AAV vectors packaging a GFP transgene were prepared (AAV8, AAV-SB1 (SEQ ID NO. 380), AAV-SB6 (SEQ ID NO: 437). The AAV vectors were contacted with U87 cells (primary glioblastoma cell line) maintained under standard culture conditions. The cells were infected at a multiplicity of infection (MOI) of 40,000 vg/cell. 48 hours later, the cells were imaged using a fluorescent microscope.

Figure 8:
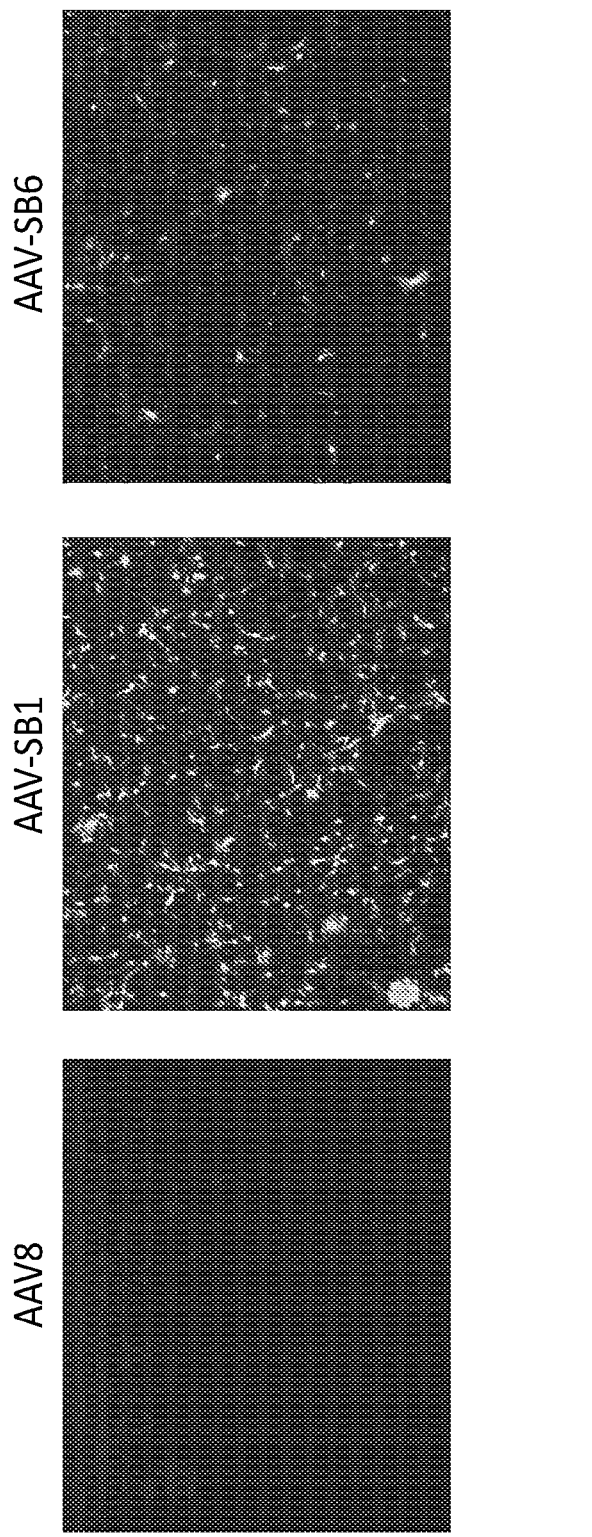

As shown in FIG. 8, all AAV vectors tested were able to successfully transduce U87 cells in culture, resulting in expression of their packaged transgene (GFP) in the cells. This data confirms that the recombinant AAV vectors are infective and can be used to deliver a transgene to a cell of interest.

Example 3. In Vitro Characterization of Recombinant AAVs Targeting Liver

Five recombinant capsid proteins comprising one or more of the substitutions identified in Example 1, above, were selected for in vitro characterization following in vivo evolution: SB1 (SEQ ID NO: 380), SB2 (SEQ ID NO: 384), SB3 (SEQ ID NO: 783), SB4 (SEQ ID NO: 784), SB5 (SEQ ID NO: 785). Recombinant AAV vectors were prepared that comprised the recombinant capsid proteins and packaged a luciferase transgene. These AAV vectors (AAV-SB1, AAV-SB2, AAV-SB3, AAV-SB4, and AAV-SB5) were derived from a parental AAV8 strain.

Figure 3:
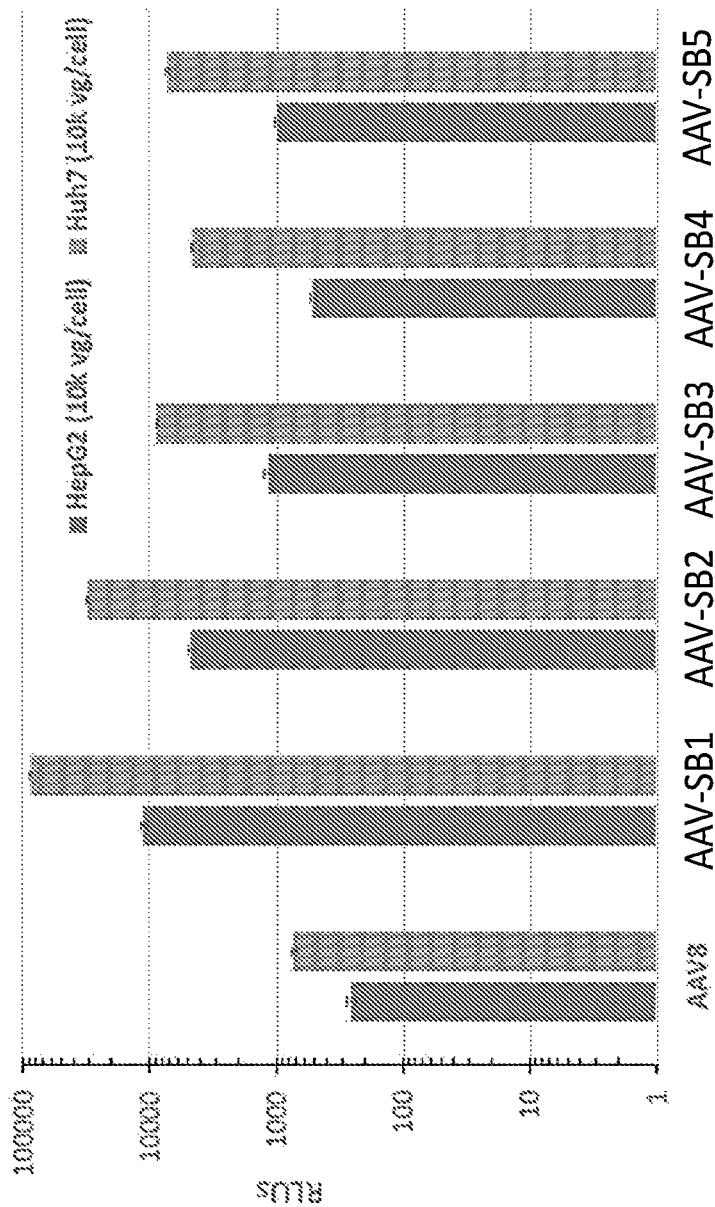

The five recombinant AAV vectors were contacted with HepG2 cells and Huh7 cells in culture, at a multiplicity of infection (MOI) of 10,000 vg/cell. Subsequently, the cells were lysed, and the lysate was contacted with a bioluminescent substrate, and RFUs were measured. As shown in FIG. 3, all five AAVs had improved tropism for human hepatocytes in vitro compared to the parental AAV8 strain, with AAV-SB1 showing up to 2-logs increase in luciferase expression.

Figure 4:
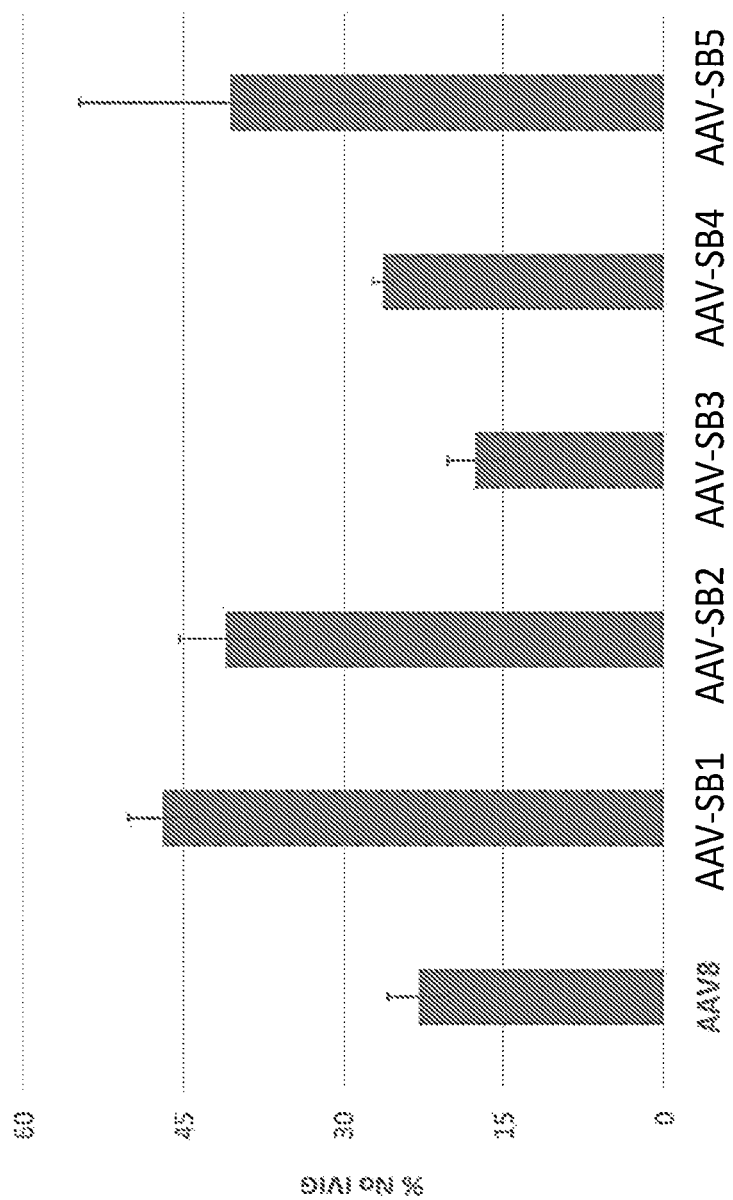
Figure 5:
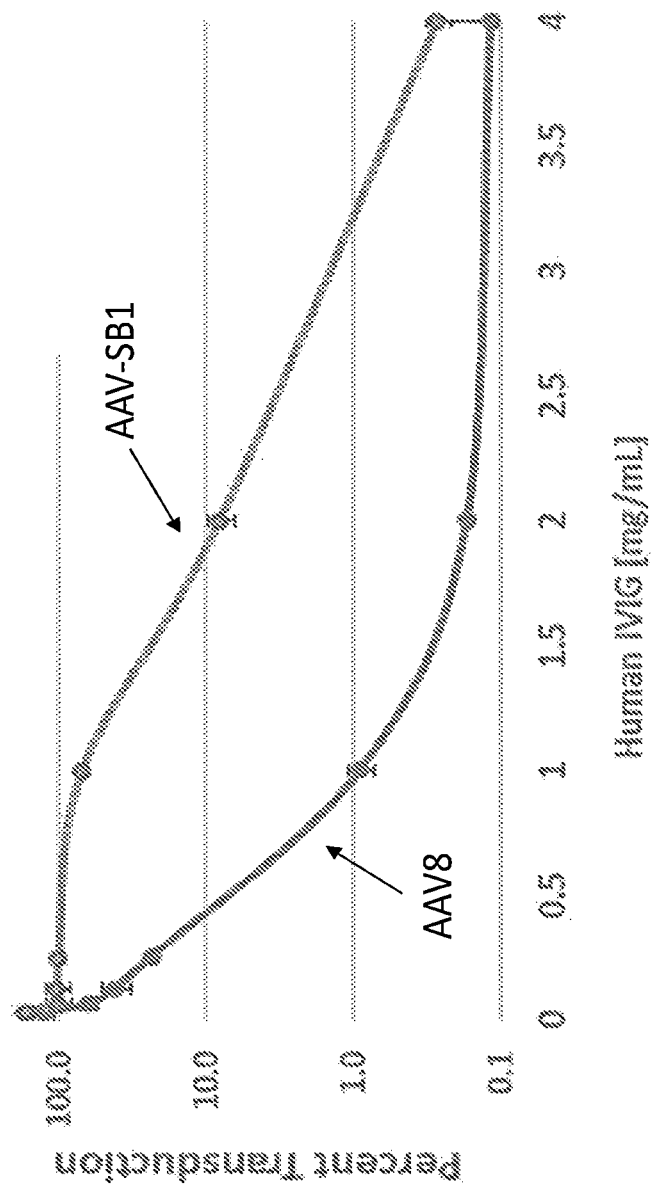

To test for improved escape of neutralizing antibodies over the parental AAV8, the five AAV-luciferase constructs were incubated with or without 0.25 mg/mL human intravenous immunoglobulin (IVIG) prior to transduction of U87 human glioblastoma cells. Shown in FIG. 4 is the percent transduction as compared to no IVIG incubation as measured by luciferase expression. AAV-SB1, AAV-SB2, and AAV-SB5 showed the greatest improvement in transduction efficiency in the presence of IVIG compared with parental AAV8. Further IVIG dose ranging analyses demonstrated that higher concentrations of IVIG are necessary to neutralize AAV-SB1 compared to parental AAV8 (FIG. 5).

Together, these data confirm the significant improvement in liver cell tropism in vitro and improvement in antibody escape of the recombinant AAVs compared with the parental AAV8 serotype.

Example 4. Human Serum Screen for AAV Neutralizing Antibodies

Parental AAV8, AAV-SB1, AAV-SB2, and three other liver-targeting capsids (AAV5, HSC15, and LK03) were tested in a neutralization assay against 100 samples of donor serum. The transduction efficiency of each AAV on U87 cells in the presence of a 1:5 dilution of serum was compared to transduction efficiency without serum as measured by levels of luciferase expression. A serum sample that reduced luciferase expression of an AAV vector to less than 50% of luciferase levels without serum was considered neutralizing.

Figure 6A:
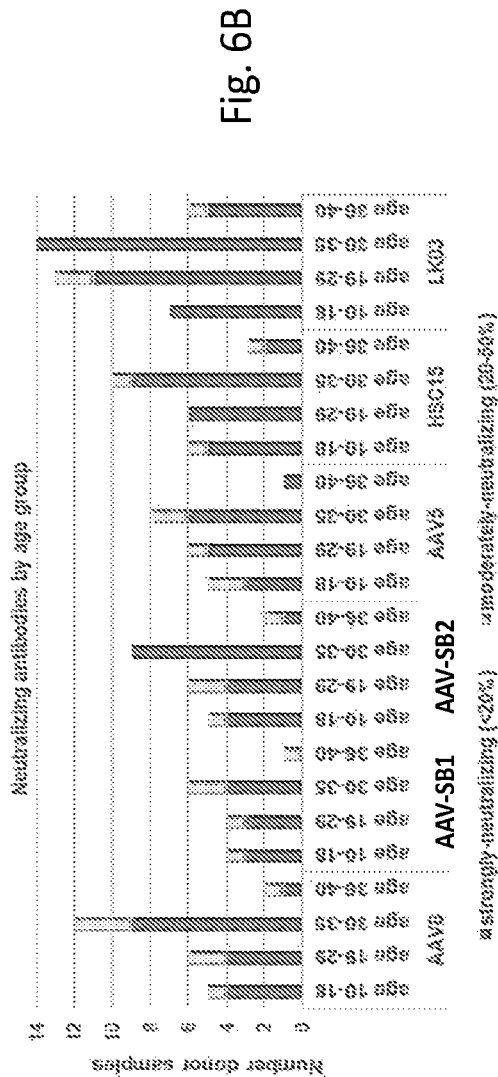

FIG. 6A shows the percentage of samples that were neutralizing (strongly-neutralizing, <20% transduction efficiency; moderately-neutralizing, 20-50% transduction efficiency) to the indicated AAV. AAV-SB1 was neutralized by the fewest samples (15%), whereas the parental AAV8 capsid was neutralized by 25% of samples. Of the other capsids, LK03 was neutralized by the greatest number of samples (40%) and AAV5 by the fewest (20%). Notably, with one exception, all samples that were seropositive for AAV-SB01 were seropositive for all of the other capsids. The one exception had a percent-transduction efficiency of 49.58% (just slightly below the 50% cut-off).

Figure 6B:
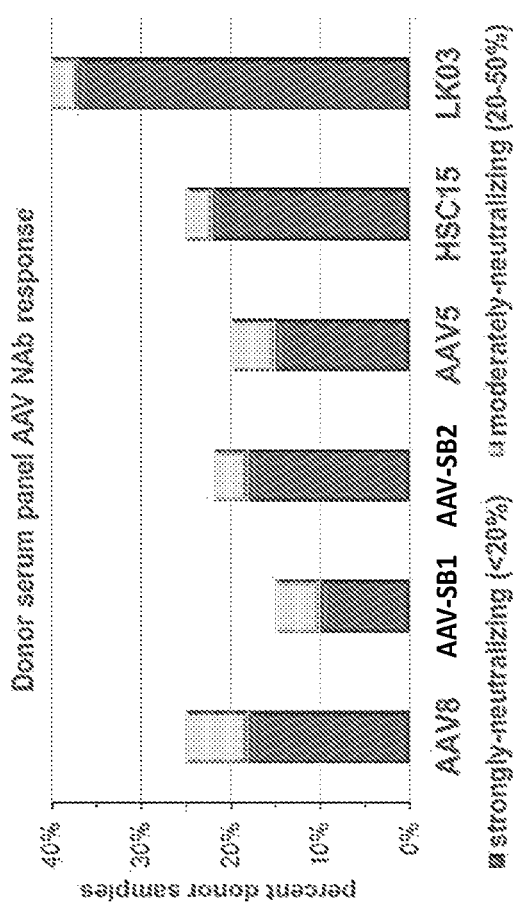

The breakdown of donors who are seropositive for the indicated capsid by age groups is shown below in FIG. 6B. A similar pattern of distribution among the age groups is seen with the age 30-35 group having the greatest number of seropositive donors and the age 36-40 group having the least number.

Example 5. Biodistribution of Recombinant AAVs in Normal Mice

This study was performed to assess whether evolution of capsid tropism to liver in non-human primates (NHP) would impact liver tropism in mice, which is important for the execution of proof-of-concept studies in available mouse models. A small study was conducted in normal Bl/6 mice. The study design is illustrated in Table 9 below. Mice were injected IV with one of two doses, and tissues were collected 30 days post-injection for immunohistochemistry (IHC) analysis for GFP expression, and for vector genome (vg) quantification by qPCR.

TABLE 9

Mouse biodistribution study design

| Group Number | AAV | Dose Level (vg/kg) | Number of Animals Male | Female |
|---|---|---|---|---|
| 1 | AAB-SB1-GFP | $3 \times 10^{12}$ | 2 | 2 |
| 2 | AAV8 (parental)-GFP | $3 \times 10^{12}$ | 2 | 2 |

Figure 7:
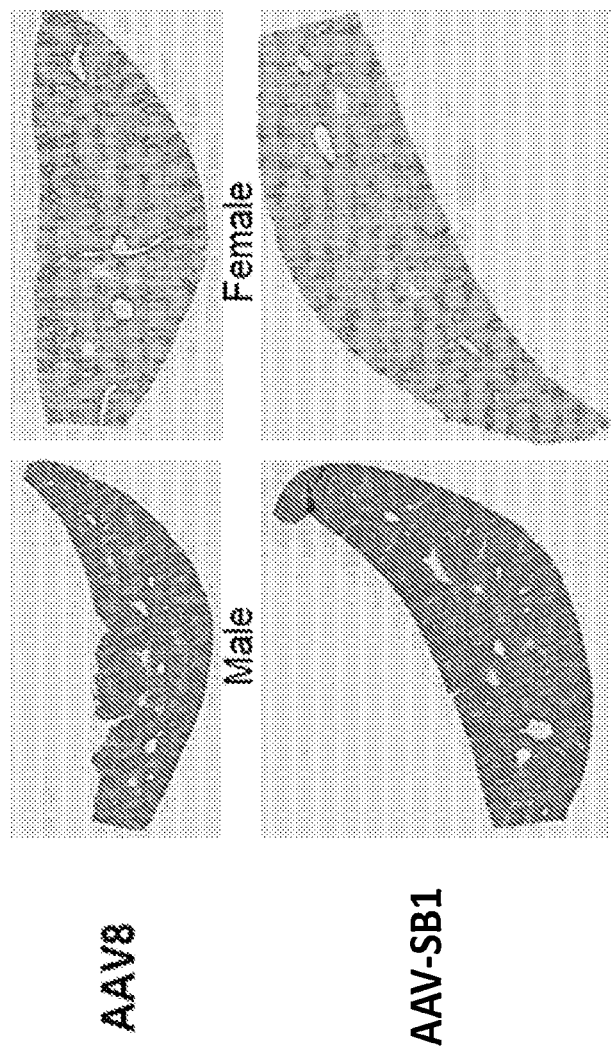

Tropism of AAV-SB1-GFP for mouse liver was confirmed to be similar to that of the parental AAV8 vector. IHC staining (FIG. 7) demonstrated similar levels of GFP expression between AAV8 and AAV-SB1, but expected differences between genders. Table 10 below shows the vg copy number per pg total DNA for each tissue. Each column represents a different mouse.

TABLE 10

Vector genome (per µg DNA) distribution in normal mice

| tissues | Group 1 (AAV-SB1-GFP, $3 \times 10^{12}$ vg/mL) | | | |
|---|---|---|---|---|
| Pancreas | $1.03 \times 10^{-03}$ | $3.35 \times 10^{-04}$ | $1.86 \times 10^{-03}$ | $2.19 \times 10^{-03}$ |
| Spleen | 0.017 | 0.142 | 0.015 | 0.017 |
| Brain (cortex) | $3.70 \times 10^{-04}$ | $2.00 \times 10^{-04}$ | $6.15 \times 10^{-04}$ | $8.40 \times 10^{-04}$ |
| Heart | $6.49 \times 10^{-03}$ | $3.23 \times 10^{-03}$ | 0.013 | 0.014 |
| Kidney, left | $8.47 \times 10^{-03}$ | $2.25 \times 10^{-03}$ | 0.027 | 0.021 |
| Muscle* | 0.013 | 0.013 | 0.018 | 0.021 |
| Liver, pooled | 1.730 | 0.477 | 0.627 | 0.573 |
| | Group 2 (AAV8-GFP, $3 \times 10^{12}$ vg/mL) | | | |
| Pancreas | $3.65 \times 10^{-04}$ | $5.85 \times 10^{-04}$ | $1.03 \times 10^{-03}$ | $1.52 \times 10^{-03}$ |
| Spleen | $5.87 \times 10^{-03}$ | $5.78 \times 10^{-03}$ | $5.94 \times 10^{-03}$ | $8.55 \times 10^{-03}$ |
| Brain (cortex) | $3.05 \times 10^{-04}$ | $5.75 \times 10^{-04}$ | $5.50 \times 10^{-04}$ | $4.20 \times 10^{-04}$ |
| Heart | $4.93 \times 10^{-03}$ | $4.41 \times 10^{-03}$ | $7.64 \times 10^{-03}$ | $7.36 \times 10^{-03}$ |
| Kidney, left | $3.68 \times 10^{-03}$ | $4.63 \times 10^{-03}$ | 0.014 | $8.55 \times 10^{-03}$ |
| Muscle* | $8.34 \times 10^{-03}$ | $3.23 \times 10^{-03}$ | $7.98 \times 10^{-03}$ | $8.71 \times 10^{-03}$ |
| Liver, pooled | 0.993 | 0.887 | 0.454 | 0.342 |

*muscle, gastrocnemius
BLOD - below limit of detection

The foregoing is illustrative of the present invention, and is not to be construed as limiting thereof. The invention is defined by the following claims, with equivalents of the claims to be included therein.

The invention claimed is:

1. An adeno-associated virus (AAV) vector comprising an AAV capsid protein, wherein the AAV capsid protein comprises the amino acid sequence of SEQ ID NO: 380.

2. The AAV vector of claim 1, wherein the AAV vector comprises an encapsidated nucleic acid, wherein the encapsidated nucleic acid is encapsidated by the AAV capsid protein.

3. The AAV vector of claim 2, wherein the encapsidated nucleic acid comprises at least one terminal repeat sequence.

4. The AAV vector of claim 3, wherein the encapsidated nucleic acid further comprises a heterologous nucleic acid sequence.

5. The AAV vector of claim 4, wherein the encapsidated nucleic acid comprises a first inverted terminal repeat (ITR) sequence located 3' of the heterologous nucleic acid sequence and a second inverted terminal repeat (ITR) sequence located 5' of the heterologous nucleic acid sequence.

6. The AAV vector of claim 4, wherein the heterologous nucleic acid sequence encodes a polypeptide.

7. The AAV vector of claim 6, wherein the polypeptide is a therapeutic polypeptide.

8. The AAV vector of claim 6, wherein the polypeptide is an immunogenic polypeptide.

9. The AAV vector of claim 6, wherein the polypeptide is nuclease.

10. The AAV vector of claim 9, wherein the nuclease is a Cas9 nuclease or a Cpf1 nuclease.

11. The AAV vector of claim 4, wherein the heterologous nucleic acid sequence encodes an untranslated RNA.

12. The AAV vector of claim 11, wherein the untranslated RNA is a guide RNA.

13. The AAV vector of claim 11, wherein the untranslated RNA is an antisense RNA, a ribozyme, or an interfering RNA.

14. A pharmaceutical composition comprising the AAV vector of claim 2 and a pharmaceutically acceptable carrier.

15. A method of introducing a nucleic acid into a cell, comprising contacting the cell with the AAV vector of claim 2.

16. An adeno-associated virus (AAV) capsid protein comprising the amino acid sequence of SEQ ID NO: 380.

17. A nucleic acid comprising a nucleic acid sequence encoding the AAV capsid protein of claim 16.

18. An expression vector comprising a nucleic acid sequence encoding the AAV capsid protein of claim 17.

19. A cell comprising the nucleic acid of claim 17.

20. A method of producing an adeno-associated virus (AAV) vector, the method comprising:
   a. culturing a cell that comprises (i) the nucleic acid of claim 17, (ii) a nucleic acid comprising 5' inverted terminal repeat (ITR), a heterologous nucleic acid sequence, and a 3' ITR, and (iii) AAV sequences sufficient for replication and encapsidation of nucleic acid, wherein the cell is cultured under conditions such that it produces the AAV vector; and
   b. collecting the AAV vector from the cell.

* * * * *

SEQUENCE LISTING

```
Sequence total quantity: 785
SEQ ID NO: 1            moltype = AA  length = 736
FEATURE                 Location/Qualifiers
source                  1..736
                        mol_type = protein
                        note = Dependovirus adeno-associated virus 1
                        organism = unidentified
SEQUENCE: 1
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
```

```
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPPFADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 2           moltype = AA   length = 735
FEATURE                Location/Qualifiers
source                 1..735
                       mol_type = protein
                       note = Dependovirus adeno-associated virus 2
                       organism = unidentified
SEQUENCE: 2
MAADGYLPDW LEDTLSEGIR QWWKLKPGPP PPKPAERHKD DSRGLVLPGY KYLGPFNGLD   60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDSE  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 3           moltype = AA   length = 736
FEATURE                Location/Qualifiers
source                 1..736
                       mol_type = protein
                       note = Dependovirus adeno-associated virus 3
                       organism = unidentified
SEQUENCE: 3
MAADGYLPDW LEDNLSEGIR EWWALKPGVP QPKANQQHQD NRRGLVLPGY KYLGPGNGLD   60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGIG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQT TSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTRTVNDQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                 736

SEQ ID NO: 4           moltype = AA   length = 736
FEATURE                Location/Qualifiers
source                 1..736
                       mol_type = protein
                       note = Dependovirus adeno-associated virus 6
                       organism = unidentified
SEQUENCE: 4
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPPFADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD KDKFFPMSGV  540
MIFGKESAGA SNTALDNVMI TDEEEIKATN PVATERFGTV AVNLQSSSTD PATGDVHVMG  600
ALPGMVWQDR DVYLQGPIWA KIPHTDGHFH PSPLMGGFGL KHPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 5           moltype = AA   length = 737
FEATURE                Location/Qualifiers
source                 1..737
                       mol_type = protein
```

```
                        note = Dependovirus adeno-associated virus 7
                        organism = unidentified
SEQUENCE: 5
MAADGYLPDW LEDNLSEGIR EWWDLKPGAP KPKANQQKQD NGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP AKKRPVEPSP QRSPDSSTGI GKKGQQPARK RLNFGQTGDS   180
ESVPDPQPLG EPPAAPSSVG SGTVAAGGGA PMADNNEGAD GVGNASGNWH CDSTWLGDRV   240
ITTSTRTWAL PTYNNHLYKQ ISSETAGSTN DNTYFGYSTP WGYFDFNRFH CHFSPRDWQR   300
LINNNWGFRP KKLRFKLFNI QVKEVTTNDG VTTIANNLTS TIQVFSDSEY QLPYVLGSAH   360
QGCLPPFPAD VFMIPQYGYL TLNNGSQSVG RSSFYCLEYF PSQMLRTGNN FEFSYSFEDV   420
PFHSSYAHSQ SLDRLMNPLI DQYLYYLART QSNPGGTAGN RELQFYQGGP STMAEQAKNW   480
LPGPCFRQQR VSKTLDQNNN SNFAWTGATK YHLNGRNSLV NPGVAMATHK DDEDRFFPSS   540
GVLIFGKTGA TNKTTLENVL MTNEEEIRPT NPVATEEYGI VSSNLQAANT AAQTQVVNNQ   600
GALPGMVWQN RDVYLQGPIW AKIPHTDGNF HPSPLMGGFG LKHPPPQILI KNTPVPANPP   660
EVFTPAKFAS FITQYSTGQV SVEIEWELQK ENSKRWNPEI QYTSNFEKQT GVDFAVDSQG   720
VYSEPRPIGT RYLTRNL                                                 737

SEQ ID NO: 6            moltype = AA  length = 738
FEATURE                 Location/Qualifiers
source                  1..738
                        mol_type = protein
                        note = Dependovirus adeno-associated virus 8
                        organism = unidentified
SEQUENCE: 6
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 7            moltype = AA  length = 736
FEATURE                 Location/Qualifiers
source                  1..736
                        mol_type = protein
                        note = Dependovirus adeno-associated virus 9
                        organism = unidentified
SEQUENCE: 7
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAQ   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 8            moltype = AA  length = 738
FEATURE                 Location/Qualifiers
source                  1..738
                        mol_type = protein
                        note = Dependovirus adeno-associated virus rh.10
                        organism = unidentified
SEQUENCE: 8
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEPSP QRSPDSSTGI GKKGQQPAKK RLNFGQTGDS   180
ESVPDPQPIG EPPAGPSGLG SGTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYQFED   420
VPFHSSYAHS QSLDRLMNPL IDQYLYYLSR TQSTGGTAGT QQLLFSQAGP NNMSAQAKNW   480
LPGPCYRQQR VSTTLSQNNN SNFAWTGATK YHLNGRDSLV NPGVAMATHK DDEERFFPSS   540
GVLMFGKQGA GKDNVDYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP   660
PTTFSQAKLA SFITQYSTGQ VSVEIEWELQ KENSKRWNPE IQYTSNYYKS TNVDFAVNTD   720
GTYSEPRPIG TRYLTRNL                                                738
```

```
SEQ ID NO: 9            moltype = AA   length = 6
FEATURE                 Location/Qualifiers
REGION                  1..6
                        note = AAV capsid protein amino acid substitution
source                  1..6
                        mol_type = protein
                        organism = synthetic construct
SEQUENCE: 9
SNGRGV                                                                    6

SEQ ID NO: 10           moltype = AA   length = 8
FEATURE                 Location/Qualifiers
REGION                  1..8
                        note = AAV capsid protein amino acid substitution
source                  1..8
                        mol_type = protein
                        organism = synthetic construct
SEQUENCE: 10
NLAENFKY                                                                  8

SEQ ID NO: 11           moltype = AA   length = 8
FEATURE                 Location/Qualifiers
REGION                  1..8
                        note = AAV capsid protein amino acid substitution
source                  1..8
                        mol_type = protein
                        organism = synthetic construct
SEQUENCE: 11
VLSGDHSA                                                                  8

SEQ ID NO: 12           moltype = AA   length = 8
FEATURE                 Location/Qualifiers
REGION                  1..8
                        note = AAV capsid protein amino acid substitution
source                  1..8
                        mol_type = protein
                        organism = synthetic construct
SEQUENCE: 12
MSAASGSG                                                                  8

SEQ ID NO: 13           moltype = AA   length = 8
FEATURE                 Location/Qualifiers
REGION                  1..8
                        note = AAV capsid protein amino acid substitution
source                  1..8
                        mol_type = protein
                        organism = synthetic construct
SEQUENCE: 13
GTNLGKEQ                                                                  8

SEQ ID NO: 14           moltype = AA   length = 8
FEATURE                 Location/Qualifiers
REGION                  1..8
                        note = AAV capsid protein amino acid substitution
source                  1..8
                        mol_type = protein
                        organism = synthetic construct
SEQUENCE: 14
SSHSGTNQ                                                                  8

SEQ ID NO: 15           moltype = AA   length = 8
FEATURE                 Location/Qualifiers
REGION                  1..8
                        note = AAV capsid protein amino acid substitution
source                  1..8
                        mol_type = protein
                        organism = synthetic construct
SEQUENCE: 15
VATRDGQL                                                                  8

SEQ ID NO: 16           moltype = AA   length = 8
FEATURE                 Location/Qualifiers
REGION                  1..8
                        note = AAV capsid protein amino acid substitution
source                  1..8
                        mol_type = protein
                        organism = synthetic construct
SEQUENCE: 16
```

```
ALNADTGT                                                             8

SEQ ID NO: 17           moltype = AA  length = 6
FEATURE                 Location/Qualifiers
REGION                  1..6
                        note = AAV capsid protein amino acid substitution
source                  1..6
                        mol_type = protein
                        organism = synthetic construct
SEQUENCE: 17
VMEPTR                                                               6

SEQ ID NO: 18           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 18
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STTTGQNNNS NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 19           moltype = AA  length = 738
FEATURE                 Location/Qualifiers
REGION                  1..738
                        note = AAV capsid variant
source                  1..738
                        mol_type = protein
                        organism = synthetic construct
SEQUENCE: 19
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTNLAENFK YNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 20           moltype = AA  length = 738
FEATURE                 Location/Qualifiers
REGION                  1..738
                        note = AAV capsid variant
source                  1..738
                        mol_type = protein
                        organism = synthetic construct
SEQUENCE: 20
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTVLSGDHS ANFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 21           moltype = AA  length = 738
```

| FEATURE | Location/Qualifiers |
|---|---|
| REGION | 1..738 |
| | note = AAV capsid variant |
| source | 1..738 |
| | mol_type = protein |
| | organism = synthetic construct |

SEQUENCE: 21
```
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTMSAASGS GNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738
```

| SEQ ID NO: 22 | moltype = AA length = 738 |
|---|---|
| FEATURE | Location/Qualifiers |
| REGION | 1..738 |
| | note = AAV capsid variant |
| source | 1..738 |
| | mol_type = protein |
| | organism = synthetic construct |

SEQUENCE: 22
```
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTGTNLGKE QNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738
```

| SEQ ID NO: 23 | moltype = AA length = 738 |
|---|---|
| FEATURE | Location/Qualifiers |
| REGION | 1..738 |
| | note = AAV capsid variant |
| source | 1..738 |
| | mol_type = protein |
| | organism = synthetic construct |

SEQUENCE: 23
```
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTSSHSGTN QNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738
```

| SEQ ID NO: 24 | moltype = AA length = 738 |
|---|---|
| FEATURE | Location/Qualifiers |
| REGION | 1..738 |
| | note = AAV capsid variant |
| source | 1..738 |
| | mol_type = protein |
| | organism = synthetic construct |

SEQUENCE: 24
```
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
```

```
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTVATRDGQ LNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 25           moltype = AA  length = 738
FEATURE                 Location/Qualifiers
REGION                  1..738
                        note = AAV capsid variant
source                  1..738
                        mol_type = protein
                        organism = synthetic construct
SEQUENCE: 25
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTALNADTG TNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 26           moltype = AA  length = 738
FEATURE                 Location/Qualifiers
REGION                  1..738
                        note = AAV capsid variant
source                  1..738
                        mol_type = protein
                        organism = synthetic construct
SEQUENCE: 26
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNVMEPT RAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 27           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 27
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTSNGRGV TLGFSQGGPN TMANQAKNWL  480
PGPCYRQRV STTTGQNNNS NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 28           moltype = AA  length = 737
FEATURE                 Location/Qualifiers
REGION                  1..737
                        note = AAV capsid variant
source                  1..737
```

```
                        mol_type = protein
                        organism = synthetic construct
SEQUENCE: 28
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STNLAENFKY NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 29           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 29
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STVLSGDHSA NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 30           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 30
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STMSAASGSG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 31           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 31
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STGTNLGKEQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
```

```
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 32           moltype = AA   length = 737
FEATURE                 Location/Qualifiers
REGION                  1..737
                        note = AAV capsid variant
source                  1..737
                        mol_type = protein
                        organism = synthetic construct
SEQUENCE: 32
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STSSHSGTNQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 33           moltype = AA   length = 737
FEATURE                 Location/Qualifiers
REGION                  1..737
                        note = AAV capsid variant
source                  1..737
                        mol_type = protein
                        organism = synthetic construct
SEQUENCE: 33
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STVATRDGQL NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 34           moltype = AA   length = 737
FEATURE                 Location/Qualifiers
REGION                  1..737
                        note = AAV capsid variant
source                  1..737
                        mol_type = protein
                        organism = synthetic construct
SEQUENCE: 34
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STALNADTGT NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 35           moltype = AA   length = 738
FEATURE                 Location/Qualifiers
REGION                  1..738
                        note = AAV capsid variant
source                  1..738
                        mol_type = protein
                        organism = synthetic construct
SEQUENCE: 35
MAADGYLPDW LEDNLSEGIR EWWALKPGAP KPKANQQKQD DGRGLVLPGY KYLGPFNGLD    60
```

```
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTNLAENFK YNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 36           moltype = AA   length = 738
FEATURE                 Location/Qualifiers
REGION                  1..738
                        note = AAV capsid variant
source                  1..738
                        mol_type = protein
                        organism = synthetic construct
SEQUENCE: 36
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTVLSGDHS ANFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 37           moltype = AA   length = 738
FEATURE                 Location/Qualifiers
REGION                  1..738
                        note = AAV capsid variant
source                  1..738
                        mol_type = protein
                        organism = synthetic construct
SEQUENCE: 37
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTMSAASGS GNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 38           moltype = AA   length = 738
FEATURE                 Location/Qualifiers
REGION                  1..738
                        note = AAV capsid variant
source                  1..738
                        mol_type = protein
                        organism = synthetic construct
SEQUENCE: 38
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTGTNLGKE QNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738
```

```
SEQ ID NO: 39              moltype = AA   length = 738
FEATURE                    Location/Qualifiers
REGION                     1..738
                           note = AAV capsid variant
source                     1..738
                           mol_type = protein
                           organism = synthetic construct
SEQUENCE: 39
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTSSHSGTN QNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 40              moltype = AA   length = 738
FEATURE                    Location/Qualifiers
REGION                     1..738
                           note = AAV capsid variant
source                     1..738
                           mol_type = protein
                           organism = synthetic construct
SEQUENCE: 40
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTVATRDGQ LNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 41              moltype = AA   length = 738
FEATURE                    Location/Qualifiers
REGION                     1..738
                           note = AAV capsid variant
source                     1..738
                           mol_type = protein
                           organism = synthetic construct
SEQUENCE: 41
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTALNADTG TNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 42              moltype = AA   length = 737
FEATURE                    Location/Qualifiers
REGION                     1..737
                           note = AAV capsid variant
source                     1..737
                           mol_type = protein
                           organism = synthetic construct
SEQUENCE: 42
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
```

```
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STNLAENFKY NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 43           moltype = AA   length = 737
FEATURE                 Location/Qualifiers
REGION                  1..737
                        note = AAV capsid variant
source                  1..737
                        mol_type = protein
                        organism = synthetic construct
SEQUENCE: 43
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STVLSGDHSA NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 44           moltype = AA   length = 737
FEATURE                 Location/Qualifiers
REGION                  1..737
                        note = AAV capsid variant
source                  1..737
                        mol_type = protein
                        organism = synthetic construct
SEQUENCE: 44
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STMSAASGSG NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 45           moltype = AA   length = 737
FEATURE                 Location/Qualifiers
REGION                  1..737
                        note = AAV capsid variant
source                  1..737
                        mol_type = protein
                        organism = synthetic construct
SEQUENCE: 45
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STGTNLGKEQ NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 46           moltype = AA   length = 737
FEATURE                 Location/Qualifiers
REGION                  1..737
                        note = AAV capsid variant
```

```
source                  1..737
                        mol_type = protein
                        organism = synthetic construct
SEQUENCE: 46
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STSSHSGTNQ NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 47           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 47
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STVATRDGQL NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 48           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 48
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STALNADTGT NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 49           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 49
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADV GSSSGNWHCD STWLGDRVI   240
TTSTRTWALP TYNNHLYKQI SNGTSGGATN DNTYFGYSTP WGYFDFNRFH CHFSPRDWQR   300
LINNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STTTGQNNNS NFAWTAGTKY HLNGRNSLAN PGIAMATHKD DEERFFPSNG   540
```

```
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 50           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 50
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TTTGQNNNSN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 51           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 51
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STNLAENFKY NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 52           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 52
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STVLSGDHSA NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 53           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 53
```

```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STMSAASGSG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 54           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 54
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STGTNLGKEQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 55           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 55
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STSSHSGTNQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 56           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 56
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STVATRDGQL NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737
```

```
SEQ ID NO: 57            moltype = AA   length = 737
FEATURE                  Location/Qualifiers
REGION                   1..737
                         note = AAV capsid variant
source                   1..737
                         mol_type = protein
                         organism = synthetic construct
SEQUENCE: 57
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STALNADTGT NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 58            moltype = AA   length = 737
FEATURE                  Location/Qualifiers
REGION                   1..737
                         note = AAV capsid variant
source                   1..737
                         mol_type = protein
                         organism = synthetic construct
SEQUENCE: 58
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STTGQNNNS NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 59            moltype = AA   length = 736
FEATURE                  Location/Qualifiers
REGION                   1..736
                         note = AAV capsid variant
source                   1..736
                         mol_type = protein
                         organism = synthetic construct
SEQUENCE: 59
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TTTGQNNSN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                   736

SEQ ID NO: 60            moltype = AA   length = 736
FEATURE                  Location/Qualifiers
REGION                   1..736
                         note = AAV capsid variant
source                   1..736
                         mol_type = protein
                         organism = synthetic construct
SEQUENCE: 60
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
```

```
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TNLAENFKYN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 61              moltype = AA  length = 736
FEATURE                    Location/Qualifiers
REGION                     1..736
                           note = AAV capsid variant
source                     1..736
                           mol_type = protein
                           organism = synthetic construct
SEQUENCE: 61
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TVLSGDHSAN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 62              moltype = AA  length = 736
FEATURE                    Location/Qualifiers
REGION                     1..736
                           note = AAV capsid variant
source                     1..736
                           mol_type = protein
                           organism = synthetic construct
SEQUENCE: 62
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TMSAASGSGN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 63              moltype = AA  length = 736
FEATURE                    Location/Qualifiers
REGION                     1..736
                           note = AAV capsid variant
source                     1..736
                           mol_type = protein
                           organism = synthetic construct
SEQUENCE: 63
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TGTNLGKEQN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 64              moltype = AA  length = 736
FEATURE                    Location/Qualifiers
REGION                     1..736
```

```
                        note = AAV capsid variant
source                  1..736
                        mol_type = protein
                        organism = synthetic construct
SEQUENCE: 64
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TSSHSGTNQN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 65           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 65
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TVATRDGQLN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 66           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 66
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TALNADTGTN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 67           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 67
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
```

```
PGPCYRQQRV STNLAENFKY NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 68           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 68
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STVLSGDHSA NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 69           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 69
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STMSAASGSG NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 70           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 70
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STGTNLGKEQ NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 71           moltype = AA  length = 737
FEATURE                 Location/Qualifiers
REGION                  1..737
                        note = AAV capsid variant
source                  1..737
                        mol_type = protein
                        organism = synthetic construct
```

```
SEQUENCE: 71
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STSSHSGTNQ NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 72           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 72
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STVATRDGQL NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 73           moltype = AA  length = 737
FEATURE                 Location/Qualifiers
REGION                  1..737
                        note = AAV capsid variant
source                  1..737
                        mol_type = protein
                        organism = synthetic construct
SEQUENCE: 73
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STALNADTGT NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 74           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 74
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TNLAENFKYN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
```

```
YSEPRPIGTR YLTRNL                                                            736

SEQ ID NO: 75           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 75
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TVLSGDHSAN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVADPPT    660
TFNQSKLNSF ITQYSTGQVS VEIEWELQKE NSKRWNPEIQ YTSNYYKSTS VDFAVNTEGV   720
YSEPRPIGTR YLTRNL                                                            736

SEQ ID NO: 76           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 76
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TMSAASGSGN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVADPPT    660
TFNQSKLNSF ITQYSTGQVS VEIEWELQKE NSKRWNPEIQ YTSNYYKSTS VDFAVNTEGV   720
YSEPRPIGTR YLTRNL                                                            736

SEQ ID NO: 77           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 77
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TGTNLGKEQN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVADPPT    660
TFNQSKLNSF ITQYSTGQVS VEIEWELQKE NSKRWNPEIQ YTSNYYKSTS VDFAVNTEGV   720
YSEPRPIGTR YLTRNL                                                            736

SEQ ID NO: 78           moltype = AA  length = 736
FEATURE                 Location/Qualifiers
REGION                  1..736
                        note = AAV capsid variant
source                  1..736
                        mol_type = protein
                        organism = synthetic construct
SEQUENCE: 78
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
```

```
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TSSHSGTNQN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 79            moltype = AA  length = 736
FEATURE                  Location/Qualifiers
REGION                   1..736
                         note = AAV capsid variant
source                   1..736
                         mol_type = protein
                         organism = synthetic construct
SEQUENCE: 79
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TVATRDGQLN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 80            moltype = AA  length = 736
FEATURE                  Location/Qualifiers
REGION                   1..736
                         note = AAV capsid variant
source                   1..736
                         mol_type = protein
                         organism = synthetic construct
SEQUENCE: 80
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TALNADTGTN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 81            moltype = AA  length = 734
FEATURE                  Location/Qualifiers
source                   1..734
                         mol_type = protein
                         note = Dependovirus adeno-associated virus 4
                         organism = unidentified
SEQUENCE: 81
MTDGYLPDWL EDNLSEGVRE WWALQPGAPK PKANQQHQDN ARGLVLPGYK YLGPGNGLDK     60
GEPVNAADAA ALEHDKAYDQ QLKAGDNPYL KYNHADAEFQ QRLQGDTSFG GNLGRAVFQA    120
KKRVLEPLGL VEQAGETAPG KKRPLIESPQ QPDSSTGIGK KGKQPAKKKL VFEDETGAGD    180
GPPEGSTSGA MSDDSEMRAA AGGAAVEGGQ GADGVGNASG DWHCDSTWSE GHVTTTSTRT    240
WVLPTYNNHL YKRLGESLQS NTYNGFSTPW GYFDFNRFHC HFSPRDWQRL INNNWGMRPK    300
AMRVKIFNIQ VKEVTTSNGE TTVANNLTST VQIFADSSYE LPYVMDAGQE GSLPPFPNDV    360
FMVPQYGYCG LVTGNTSQQQ TDRNAFYCLE YFPSQMLRTG NNFEITYSFE KVPFHSMYAH    420
SQSLDRLMNP LIDQYLWGLQ STTTGTTLNA GTATTNFTKL RPTNFSNFKK NWLPGPSIKQ    480
QGFSKTANQN YKIPATGSDS LIKYETHSTL DGRWSALTPG PPMATAGPAD SKFSNSQLIF    540
AGPKQNGNTA TVPGTLIFTS EEELAATNAT DTDMWGNLPG GDQSNSNLPT VDRLTALGAV    600
PGMVWQNRDI YYQGPIWAKI PHTDGHFHPS PLIGGFGLKH PPPQIFIKNT PVPANPATTF    660
SSTPVNSFIT QYSTGQVSVQ IDWEIQKERS KRWNPEVQFT SNYGQQNSLL WAPDAAGKYT    720
EPRAIGTRYL THHL                                                     734

SEQ ID NO: 82            moltype = AA  length = 724
FEATURE                  Location/Qualifiers
source                   1..724
```

```
                        mol_type = protein
                        note = Dependovirus adeno-associated virus 5
                        organism = unidentified
SEQUENCE: 82
MSFVDHPPDW LEEVGEGLRE FLGLEAGPPK PKPNQQHQDQ ARGLVLPGYN YLGPGNGLDR    60
GEPVNRADEV AREHDISYNE QLEAGDNPYL KYNHADAEFQ EKLADDTSFG GNLGKAVFQA   120
KKRVLEPFGL VEEGAKTAPT GKRIDDHFPK RKKARTEEDS KPSTSSDAEA GPSGSQQLQI   180
PAQPASSLGA DTMSAGGGGP LGDNNQGADG VGNASGDWHC DSTWMGDRVV TKSTRTWVLP   240
SYNNHQYREI KSGSVDGSNA NAYFGYSTPW GYFDFNRPHS HWSPRDWQRL INNYWGFRPR   300
SLRVKIFNIQ VKEVTVQDST TTIANNLTST VQVFTDDDYQ LPYVVGNGTE GCLPAFPPQV   360
FTLPQYGYAT LNRDNTENPT ERSSFFCLEY FPSKMLRTGN NFEFTYNFEE VPFHSSFAPS   420
QNLFKLANPL VDQYLYRFVS TNNTGGVQFN KNLAGRYANT YKNWFPGPMG RTQGWNLGSG   480
VNRASVSAFA TTNRMELEGA SYQVPPQPNG MTNNLQGSNT YALENTMIFN SQPANPGTTA   540
TYLEGNMLIT SESETQPVNR VAYNVGGQMA TNNQSSTTAP ATGTYNLQEI VPGSVWMERD   600
VYLQGPIWAK IPETGAHFHP SPAMGGFGLK HPPPMMLIKN TPVPGNITSF SDVPVSSFIT   660
QYSTGQVTVE MEWELKKENS KRWNPEIQYT NNYNDPQFVD FAPDSTGEYR TTRPIGTRYL   720
TRPL                                                                724

SEQ ID NO: 83           moltype = AA  length = 5
FEATURE                 Location/Qualifiers
REGION                  1..5
                        note = peptide motif triggers uptake by liver cells
source                  1..5
                        mol_type = protein
                        organism = synthetic construct
SEQUENCE: 83
FVFLP                                                                 5

SEQ ID NO: 84           moltype =    length =
SEQUENCE: 84
000

SEQ ID NO: 85           moltype = AA  length = 4
FEATURE                 Location/Qualifiers
REGION                  1..4
                        note = targeting peptide
source                  1..4
                        mol_type = protein
                        organism = synthetic construct
SEQUENCE: 85
RGNR                                                                  4

SEQ ID NO: 86           moltype = AA  length = 7
FEATURE                 Location/Qualifiers
REGION                  1..7
                        note = targeting peptide
VARIANT                 7
                        note = X can be G or S
source                  1..7
                        mol_type = protein
                        organism = synthetic construct
SEQUENCE: 86
NSVRDLX                                                               7

SEQ ID NO: 87           moltype = AA  length = 7
FEATURE                 Location/Qualifiers
REGION                  1..7
                        note = targeting peptide
source                  1..7
                        mol_type = protein
                        organism = synthetic construct
SEQUENCE: 87
PRSVTVP                                                               7

SEQ ID NO: 88           moltype = AA  length = 7
FEATURE                 Location/Qualifiers
REGION                  1..7
                        note = targeting peptide
VARIANT                 7
                        note = X can be S or A
source                  1..7
                        mol_type = protein
                        organism = synthetic construct
SEQUENCE: 88
NSVSSXX                                                               7

SEQ ID NO: 89           moltype = AA  length = 6
FEATURE                 Location/Qualifiers
REGION                  1..6
```

```
                        note = targeting peptide
source                  1..6
                        mol_type = protein
                        organism = synthetic construct
SEQUENCE: 89
NGRAHA                                                                         6

SEQ ID NO: 90           moltype = AA  length = 7
FEATURE                 Location/Qualifiers
REGION                  1..7
                        note = targeting peptide
source                  1..7
                        mol_type = protein
                        organism = synthetic construct
SEQUENCE: 90
QPEHSST                                                                        7

SEQ ID NO: 91           moltype = AA  length = 7
FEATURE                 Location/Qualifiers
REGION                  1..7
                        note = targeting peptide
source                  1..7
                        mol_type = protein
                        organism = synthetic construct
SEQUENCE: 91
VNTANST                                                                        7

SEQ ID NO: 92           moltype = AA  length = 6
FEATURE                 Location/Qualifiers
REGION                  1..6
                        note = targeting peptide
source                  1..6
                        mol_type = protein
                        organism = synthetic construct
SEQUENCE: 92
HGPMQS                                                                         6

SEQ ID NO: 93           moltype = AA  length = 7
FEATURE                 Location/Qualifiers
REGION                  1..7
                        note = targeting peptide
source                  1..7
                        mol_type = protein
                        organism = synthetic construct
SEQUENCE: 93
PHKPPLA                                                                        7

SEQ ID NO: 94           moltype = AA  length = 7
FEATURE                 Location/Qualifiers
REGION                  1..7
                        note = targeting peptide
source                  1..7
                        mol_type = protein
                        organism = synthetic construct
SEQUENCE: 94
IKNNEMW                                                                        7

SEQ ID NO: 95           moltype = AA  length = 7
FEATURE                 Location/Qualifiers
REGION                  1..7
                        note = targeting peptide
source                  1..7
                        mol_type = protein
                        organism = synthetic construct
SEQUENCE: 95
RNLDTPM                                                                        7

SEQ ID NO: 96           moltype = AA  length = 7
FEATURE                 Location/Qualifiers
REGION                  1..7
                        note = targeting peptide
source                  1..7
                        mol_type = protein
                        organism = synthetic construct
SEQUENCE: 96
VDSHRQS                                                                        7

SEQ ID NO: 97           moltype = AA  length = 7
FEATURE                 Location/Qualifiers
```

```
REGION                    1..7
                          note = targeting peptide
source                    1..7
                          mol_type = protein
                          organism = synthetic construct
SEQUENCE: 97
YDSKTKT                                                                  7

SEQ ID NO: 98             moltype = AA  length = 7
FEATURE                   Location/Qualifiers
REGION                    1..7
                          note = targeting peptide
source                    1..7
                          mol_type = protein
                          organism = synthetic construct
SEQUENCE: 98
SQLPHQK                                                                  7

SEQ ID NO: 99             moltype = AA  length = 7
FEATURE                   Location/Qualifiers
REGION                    1..7
                          note = targeting peptide
source                    1..7
                          mol_type = protein
                          organism = synthetic construct
SEQUENCE: 99
STMQQNT                                                                  7

SEQ ID NO: 100            moltype = AA  length = 7
FEATURE                   Location/Qualifiers
REGION                    1..7
                          note = targeting peptide
source                    1..7
                          mol_type = protein
                          organism = synthetic construct
SEQUENCE: 100
TERYMTQ                                                                  7

SEQ ID NO: 101            moltype = AA  length = 7
FEATURE                   Location/Qualifiers
REGION                    1..7
                          note = targeting peptide
source                    1..7
                          mol_type = protein
                          organism = synthetic construct
SEQUENCE: 101
QPEHSST                                                                  7

SEQ ID NO: 102            moltype = AA  length = 7
FEATURE                   Location/Qualifiers
REGION                    1..7
                          note = targeting peptide
source                    1..7
                          mol_type = protein
                          organism = synthetic construct
SEQUENCE: 102
DASLSTS                                                                  7

SEQ ID NO: 103            moltype = AA  length = 6
FEATURE                   Location/Qualifiers
REGION                    1..6
                          note = targeting peptide
source                    1..6
                          mol_type = protein
                          organism = synthetic construct
SEQUENCE: 103
DLPNKT                                                                   6

SEQ ID NO: 104            moltype = AA  length = 7
FEATURE                   Location/Qualifiers
REGION                    1..7
                          note = targeting peptide
source                    1..7
                          mol_type = protein
                          organism = synthetic construct
SEQUENCE: 104
DLTAARL                                                                  7

SEQ ID NO: 105            moltype = AA  length = 7
```

```
FEATURE               Location/Qualifiers
REGION                1..7
                      note = targeting peptide
source                1..7
                      mol_type = protein
                      organism = synthetic construct
SEQUENCE: 105
EPHQFNY                                                                 7

SEQ ID NO: 106        moltype = AA  length = 7
FEATURE               Location/Qualifiers
REGION                1..7
                      note = targeting peptide
source                1..7
                      mol_type = protein
                      organism = synthetic construct
SEQUENCE: 106
EPQSNHT                                                                 7

SEQ ID NO: 107        moltype = AA  length = 7
FEATURE               Location/Qualifiers
REGION                1..7
                      note = targeting peptide
source                1..7
                      mol_type = protein
                      organism = synthetic construct
SEQUENCE: 107
MSSWPSQ                                                                 7

SEQ ID NO: 108        moltype = AA  length = 7
FEATURE               Location/Qualifiers
REGION                1..7
                      note = targeting peptide
source                1..7
                      mol_type = protein
                      organism = synthetic construct
SEQUENCE: 108
NPKHNAT                                                                 7

SEQ ID NO: 109        moltype = AA  length = 7
FEATURE               Location/Qualifiers
REGION                1..7
                      note = targeting peptide
source                1..7
                      mol_type = protein
                      organism = synthetic construct
SEQUENCE: 109
PDGMRTT                                                                 7

SEQ ID NO: 110        moltype = AA  length = 7
FEATURE               Location/Qualifiers
REGION                1..7
                      note = targeting peptide
source                1..7
                      mol_type = protein
                      organism = synthetic construct
SEQUENCE: 110
PNNNKTT                                                                 7

SEQ ID NO: 111        moltype = AA  length = 7
FEATURE               Location/Qualifiers
REGION                1..7
                      note = targeting peptide
source                1..7
                      mol_type = protein
                      organism = synthetic construct
SEQUENCE: 111
QSTTHDS                                                                 7

SEQ ID NO: 112        moltype = AA  length = 7
FEATURE               Location/Qualifiers
REGION                1..7
                      note = targeting peptide
source                1..7
                      mol_type = protein
                      organism = synthetic construct
SEQUENCE: 112
TGSKQKQ                                                                 7
```

-continued

| | | |
|---|---|---|
| SEQ ID NO: 113<br>FEATURE<br>REGION<br>source | moltype = AA  length = 7<br>Location/Qualifiers<br>1..7<br>note = targeting peptide<br>1..7<br>mol_type = protein<br>organism = synthetic construct | |
| SEQUENCE: 113<br>SLKHQAL | | 7 |
| SEQ ID NO: 114<br>FEATURE<br>REGION<br>source | moltype = AA  length = 7<br>Location/Qualifiers<br>1..7<br>note = targeting peptide<br>1..7<br>mol_type = protein<br>organism = synthetic construct | |
| SEQUENCE: 114<br>SPIDGEQ | | 7 |
| SEQ ID NO: 115<br>FEATURE<br>REGION<br>source | moltype = AA  length = 8<br>Location/Qualifiers<br>1..8<br>note = targeting peptide<br>1..8<br>mol_type = protein<br>organism = synthetic construct | |
| SEQUENCE: 115<br>WIFPWIQL | | 8 |
| SEQ ID NO: 116<br>FEATURE<br>REGION<br>source | moltype = AA  length = 9<br>Location/Qualifiers<br>1..9<br>note = targeting peptide<br>1..9<br>mol_type = protein<br>organism = synthetic construct | |
| SEQUENCE: 116<br>CDCRGDCFC | | 9 |
| SEQ ID NO: 117<br>FEATURE<br>REGION<br>source | moltype = AA  length = 5<br>Location/Qualifiers<br>1..5<br>note = targeting peptide<br>1..5<br>mol_type = protein<br>organism = synthetic construct | |
| SEQUENCE: 117<br>CNGRC | | 5 |
| SEQ ID NO: 118<br>FEATURE<br>REGION<br>source | moltype = AA  length = 7<br>Location/Qualifiers<br>1..7<br>note = targeting peptide<br>1..7<br>mol_type = protein<br>organism = synthetic construct | |
| SEQUENCE: 118<br>CPRECES | | 7 |
| SEQ ID NO: 119<br>FEATURE<br>REGION<br>source | moltype = AA  length = 10<br>Location/Qualifiers<br>1..10<br>note = targeting peptide<br>1..10<br>mol_type = protein<br>organism = synthetic construct | |
| SEQUENCE: 119<br>CTTHWGFTLC | | 10 |
| SEQ ID NO: 120<br>FEATURE<br>REGION<br>source | moltype = AA  length = 9<br>Location/Qualifiers<br>1..9<br>note = targeting peptide<br>1..9<br>mol_type = protein<br>organism = synthetic construct | |
| SEQUENCE: 120<br>CGRRAGGSC | | 9 |

```
SEQ ID NO: 121          moltype = AA   length = 9
FEATURE                 Location/Qualifiers
REGION                  1..9
                        note = targeting peptide
source                  1..9
                        mol_type = protein
                        organism = synthetic construct
SEQUENCE: 121
CKGGRAKDC                                                                   9

SEQ ID NO: 122          moltype = AA   length = 9
FEATURE                 Location/Qualifiers
REGION                  1..9
                        note = targeting peptide
source                  1..9
                        mol_type = protein
                        organism = synthetic construct
SEQUENCE: 122
CVPELGHEC                                                                   9

SEQ ID NO: 123          moltype = AA   length = 9
FEATURE                 Location/Qualifiers
REGION                  1..9
                        note = targeting peptide
source                  1..9
                        mol_type = protein
                        organism = synthetic construct
SEQUENCE: 123
CRRETAWAK                                                                   9

SEQ ID NO: 124          moltype = AA   length = 14
FEATURE                 Location/Qualifiers
REGION                  1..14
                        note = targeting peptide
source                  1..14
                        mol_type = protein
                        organism = synthetic construct
SEQUENCE: 124
VSWFSHRYSP FAVS                                                            14

SEQ ID NO: 125          moltype = AA   length = 13
FEATURE                 Location/Qualifiers
REGION                  1..13
                        note = targeting peptide
source                  1..13
                        mol_type = protein
                        organism = synthetic construct
SEQUENCE: 125
GYRDGYAGPI LYN                                                             13

SEQ ID NO: 126          moltype =      length =
SEQUENCE: 126
000

SEQ ID NO: 127          moltype =      length =
SEQUENCE: 127
000

SEQ ID NO: 128          moltype = AA   length = 7
FEATURE                 Location/Qualifiers
REGION                  1..7
                        note = targeting peptide
source                  1..7
                        mol_type = protein
                        organism = synthetic construct
SEQUENCE: 128
RPLPPLP                                                                     7

SEQ ID NO: 129          moltype = AA   length = 7
FEATURE                 Location/Qualifiers
REGION                  1..7
                        note = targeting peptide
source                  1..7
                        mol_type = protein
                        organism = synthetic construct
SEQUENCE: 129
APPLPPR                                                                     7
```

```
SEQ ID NO: 130         moltype = AA   length = 12
FEATURE                Location/Qualifiers
REGION                 1..12
                       note = targeting peptide
source                 1..12
                       mol_type = protein
                       organism = synthetic construct
SEQUENCE: 130
DVFYPYPYAS GS                                                              12

SEQ ID NO: 131         moltype = AA   length = 6
FEATURE                Location/Qualifiers
REGION                 1..6
                       note = targeting peptide
source                 1..6
                       mol_type = protein
                       organism = synthetic construct
SEQUENCE: 131
MYWYPY                                                                      6

SEQ ID NO: 132         moltype = AA   length = 12
FEATURE                Location/Qualifiers
REGION                 1..12
                       note = targeting peptide
source                 1..12
                       mol_type = protein
                       organism = synthetic construct
SEQUENCE: 132
DITWDQLWDL MK                                                              12

SEQ ID NO: 133         moltype = AA   length = 8
FEATURE                Location/Qualifiers
REGION                 1..8
                       note = targeting peptide
VARIANT                5
                       note = X can be G or L
source                 1..8
                       mol_type = protein
                       organism = synthetic construct
SEQUENCE: 133
CWDDXWLC                                                                    8

SEQ ID NO: 134         moltype = AA   length = 14
FEATURE                Location/Qualifiers
REGION                 1..14
                       note = targeting peptide
source                 1..14
                       mol_type = protein
                       organism = synthetic construct
SEQUENCE: 134
EWCEYLGGYL RCYA                                                            14

SEQ ID NO: 135         moltype = AA   length = 14
FEATURE                Location/Qualifiers
REGION                 1..14
                       note = targeting peptide
source                 1..14
                       mol_type = protein
                       organism = synthetic construct
SEQUENCE: 135
YXCXXGPXTW XCXP                                                            14

SEQ ID NO: 136         moltype = AA   length = 14
FEATURE                Location/Qualifiers
REGION                 1..14
                       note = targeting peptide
source                 1..14
                       mol_type = protein
                       organism = synthetic construct
SEQUENCE: 136
IEGPTLRQWL AARA                                                            14

SEQ ID NO: 137         moltype =      length =
SEQUENCE: 137
000

SEQ ID NO: 138         moltype = AA   length = 7
FEATURE                Location/Qualifiers
REGION                 1..7
```

| | | |
|---|---|---|
| source | note = targeting peptide<br>1..7<br>mol_type = protein<br>organism = synthetic construct | |
| SEQUENCE: 138<br>XFXXYLW | | 7 |
| SEQ ID NO: 139<br>FEATURE<br>REGION<br>source | moltype = AA  length = 6<br>Location/Qualifiers<br>1..6<br>note = targeting peptide<br>1..6<br>mol_type = protein<br>organism = synthetic construct | |
| SEQUENCE: 139<br>RWGLCD | | 6 |
| SEQ ID NO: 140<br>FEATURE<br>REGION<br>source | moltype = AA  length = 13<br>Location/Qualifiers<br>1..13<br>note = targeting peptide<br>1..13<br>mol_type = protein<br>organism = synthetic construct | |
| SEQUENCE: 140<br>MSRPACPPND KYE | | 13 |
| SEQ ID NO: 141<br>FEATURE<br>REGION<br>source | moltype = AA  length = 8<br>Location/Qualifiers<br>1..8<br>note = targeting peptide<br>1..8<br>mol_type = protein<br>organism = synthetic construct | |
| SEQUENCE: 141<br>CLRSGRGC | | 8 |
| SEQ ID NO: 142<br>FEATURE<br>REGION<br>source | moltype = AA  length = 9<br>Location/Qualifiers<br>1..9<br>note = targeting peptide<br>1..9<br>mol_type = protein<br>organism = synthetic construct | |
| SEQUENCE: 142<br>CHWMFSPWC | | 9 |
| SEQ ID NO: 143<br>SEQUENCE: 143<br>000 | moltype =   length = | |
| SEQ ID NO: 144<br>FEATURE<br>REGION<br>source | moltype = AA  length = 8<br>Location/Qualifiers<br>1..8<br>note = targeting peptide<br>1..8<br>mol_type = protein<br>organism = synthetic construct | |
| SEQUENCE: 144<br>CSSRLDAC | | 8 |
| SEQ ID NO: 145<br>FEATURE<br>REGION<br>source | moltype = AA  length = 7<br>Location/Qualifiers<br>1..7<br>note = targeting peptide<br>1..7<br>mol_type = protein<br>organism = synthetic construct | |
| SEQUENCE: 145<br>CLPVASC | | 7 |
| SEQ ID NO: 146<br>FEATURE<br>REGION<br>source | moltype = AA  length = 13<br>Location/Qualifiers<br>1..13<br>note = targeting peptide<br>1..13<br>mol_type = protein<br>organism = synthetic construct | |
| SEQUENCE: 146 | | |

```
CGFECVRQCP ERC                                                              13

SEQ ID NO: 147          moltype = AA  length = 13
FEATURE                 Location/Qualifiers
REGION                  1..13
                        note = targeting peptide
source                  1..13
                        mol_type = protein
                        organism = synthetic construct
SEQUENCE: 147
CVALCREACG EGC                                                              13

SEQ ID NO: 148          moltype = AA  length = 9
FEATURE                 Location/Qualifiers
REGION                  1..9
                        note = targeting peptide
source                  1..9
                        mol_type = protein
                        organism = synthetic construct
SEQUENCE: 148
SWCEPGWCR                                                                    9

SEQ ID NO: 149          moltype = AA  length = 6
FEATURE                 Location/Qualifiers
REGION                  1..6
                        note = targeting peptide
source                  1..6
                        mol_type = protein
                        organism = synthetic construct
SEQUENCE: 149
YSGWGW                                                                       6

SEQ ID NO: 150          moltype = AA  length = 7
FEATURE                 Location/Qualifiers
REGION                  1..7
                        note = targeting peptide
source                  1..7
                        mol_type = protein
                        organism = synthetic construct
SEQUENCE: 150
GLSGGRS                                                                      7

SEQ ID NO: 151          moltype = AA  length = 7
FEATURE                 Location/Qualifiers
REGION                  1..7
                        note = targeting peptide
source                  1..7
                        mol_type = protein
                        organism = synthetic construct
SEQUENCE: 151
LMLPRAD                                                                      7

SEQ ID NO: 152          moltype = AA  length = 9
FEATURE                 Location/Qualifiers
REGION                  1..9
                        note = targeting peptide
source                  1..9
                        mol_type = protein
                        organism = synthetic construct
SEQUENCE: 152
CSCFRDVCC                                                                    9

SEQ ID NO: 153          moltype = AA  length = 9
FEATURE                 Location/Qualifiers
REGION                  1..9
                        note = targeting peptide
source                  1..9
                        mol_type = protein
                        organism = synthetic construct
SEQUENCE: 153
CRDVVSVIC                                                                    9

SEQ ID NO: 154          moltype = AA  length = 5
FEATURE                 Location/Qualifiers
REGION                  1..5
                        note = targeting peptide
source                  1..5
                        mol_type = protein
                        organism = synthetic construct
```

```
SEQUENCE: 154
CNGRC                                                                        5

SEQ ID NO: 155         moltype = AA   length = 6
FEATURE                Location/Qualifiers
REGION                 1..6
                       note = targeting peptide
source                 1..6
                       mol_type = protein
                       organism = synthetic construct
SEQUENCE: 155
MARSGL                                                                       6

SEQ ID NO: 156         moltype = AA   length = 6
FEATURE                Location/Qualifiers
REGION                 1..6
                       note = targeting peptide
source                 1..6
                       mol_type = protein
                       organism = synthetic construct
SEQUENCE: 156
MARAKE                                                                       6

SEQ ID NO: 157         moltype = AA   length = 6
FEATURE                Location/Qualifiers
REGION                 1..6
                       note = targeting peptide
source                 1..6
                       mol_type = protein
                       organism = synthetic construct
SEQUENCE: 157
MSRTMS                                                                       6

SEQ ID NO: 158         moltype = AA   length = 6
FEATURE                Location/Qualifiers
REGION                 1..6
                       note = targeting peptide
source                 1..6
                       mol_type = protein
                       organism = synthetic construct
SEQUENCE: 158
KCCYSL                                                                       6

SEQ ID NO: 159         moltype = AA   length = 14
FEATURE                Location/Qualifiers
REGION                 1..14
                       note = targeting peptide
source                 1..14
                       mol_type = protein
                       organism = synthetic construct
SEQUENCE: 159
MYWGDSHWLQ YWYE                                                             14

SEQ ID NO: 160         moltype = AA   length = 7
FEATURE                Location/Qualifiers
REGION                 1..7
                       note = targeting peptide
source                 1..7
                       mol_type = protein
                       organism = synthetic construct
SEQUENCE: 160
MQLPLAT                                                                      7

SEQ ID NO: 161         moltype = AA   length = 4
FEATURE                Location/Qualifiers
REGION                 1..4
                       note = targeting peptide
source                 1..4
                       mol_type = protein
                       organism = synthetic construct
SEQUENCE: 161
EWLS                                                                         4

SEQ ID NO: 162         moltype = AA   length = 4
FEATURE                Location/Qualifiers
REGION                 1..4
                       note = targeting peptide
source                 1..4
                       mol_type = protein
```

```
                              -continued organism = synthetic construct
SEQUENCE: 162
SNEW                                                                    4

SEQ ID NO: 163          moltype = AA   length = 4
FEATURE                 Location/Qualifiers
REGION                  1..4
                        note = targeting peptide
source                  1..4
                        mol_type = protein
                        organism = synthetic construct
SEQUENCE: 163
TNYL                                                                    4

SEQ ID NO: 164          moltype = AA   length = 8
FEATURE                 Location/Qualifiers
REGION                  1..8
                        note = targeting peptide
source                  1..8
                        mol_type = protein
                        organism = synthetic construct
SEQUENCE: 164
WIFPWIQL                                                                8

SEQ ID NO: 165          moltype = AA   length = 12
FEATURE                 Location/Qualifiers
REGION                  1..12
                        note = targeting peptide
source                  1..12
                        mol_type = protein
                        organism = synthetic construct
SEQUENCE: 165
WDLAWMFRLP VG                                                          12

SEQ ID NO: 166          moltype = AA   length = 13
FEATURE                 Location/Qualifiers
REGION                  1..13
                        note = targeting peptide
source                  1..13
                        mol_type = protein
                        organism = synthetic construct
SEQUENCE: 166
CTVALPGGYV RVC                                                         13

SEQ ID NO: 167          moltype = AA   length = 9
FEATURE                 Location/Qualifiers
REGION                  1..9
                        note = targeting peptide
source                  1..9
                        mol_type = protein
                        organism = synthetic construct
SEQUENCE: 167
CVPELGHEC                                                               9

SEQ ID NO: 168          moltype = AA   length = 9
FEATURE                 Location/Qualifiers
REGION                  1..9
                        note = targeting peptide
source                  1..9
                        mol_type = protein
                        organism = synthetic construct
SEQUENCE: 168
CGRRAGGSC                                                               9

SEQ ID NO: 169          moltype = AA   length = 13
FEATURE                 Location/Qualifiers
REGION                  1..13
                        note = targeting peptide
source                  1..13
                        mol_type = protein
                        organism = synthetic construct
SEQUENCE: 169
CVAYCIEHHC WTC                                                         13

SEQ ID NO: 170          moltype = AA   length = 12
FEATURE                 Location/Qualifiers
REGION                  1..12
                        note = targeting peptide
source                  1..12
```

```
                        mol_type = protein
                        organism = synthetic construct
SEQUENCE: 170
CVFAHNYDYL VC                                                           12

SEQ ID NO: 171          moltype = AA   length = 10
FEATURE                 Location/Qualifiers
REGION                  1..10
                        note = targeting peptide
source                  1..10
                        mol_type = protein
                        organism = synthetic construct
SEQUENCE: 171
CVFTSNYAFC                                                              10

SEQ ID NO: 172          moltype = AA   length = 7
FEATURE                 Location/Qualifiers
REGION                  1..7
                        note = targeting peptide
source                  1..7
                        mol_type = protein
                        organism = synthetic construct
SEQUENCE: 172
VHSPNKK                                                                 7

SEQ ID NO: 173          moltype = AA   length = 9
FEATURE                 Location/Qualifiers
REGION                  1..9
                        note = targeting peptide
source                  1..9
                        mol_type = protein
                        organism = synthetic construct
SEQUENCE: 173
CDCRGDCFC                                                               9

SEQ ID NO: 174          moltype = AA   length = 7
FEATURE                 Location/Qualifiers
REGION                  1..7
                        note = targeting peptide
source                  1..7
                        mol_type = protein
                        organism = synthetic construct
SEQUENCE: 174
CRGDGWC                                                                 7

SEQ ID NO: 175          moltype = AA   length = 6
FEATURE                 Location/Qualifiers
REGION                  1..6
                        note = targeting peptide
source                  1..6
                        mol_type = protein
                        organism = synthetic construct
SEQUENCE: 175
XRGCDX                                                                  6

SEQ ID NO: 176          moltype =    length =
SEQUENCE: 176
000

SEQ ID NO: 177          moltype = AA   length = 10
FEATURE                 Location/Qualifiers
REGION                  1..10
                        note = targeting peptide
source                  1..10
                        mol_type = protein
                        organism = synthetic construct
SEQUENCE: 177
CTTHWGFTLC                                                              10

SEQ ID NO: 178          moltype = AA   length = 11
FEATURE                 Location/Qualifiers
REGION                  1..11
                        note = targeting peptide
source                  1..11
                        mol_type = protein
                        organism = synthetic construct
SEQUENCE: 178
SGKGPRQITA L                                                            11
```

```
SEQ ID NO: 179           moltype =    length =
SEQUENCE: 179
000

SEQ ID NO: 180           moltype = AA   length = 6
FEATURE                  Location/Qualifiers
REGION                   1..6
                         note = targeting peptide
source                   1..6
                         mol_type = protein
                         organism = synthetic construct
SEQUENCE: 180
VYMSPF                                                                    6

SEQ ID NO: 181           moltype = AA   length = 7
FEATURE                  Location/Qualifiers
REGION                   1..7
                         note = targeting peptide
source                   1..7
                         mol_type = protein
                         organism = synthetic construct
SEQUENCE: 181
MQLPLAT                                                                   7

SEQ ID NO: 182           moltype = AA   length = 7
FEATURE                  Location/Qualifiers
REGION                   1..7
                         note = targeting peptide
source                   1..7
                         mol_type = protein
                         organism = synthetic construct
SEQUENCE: 182
ATWLPPR                                                                   7

SEQ ID NO: 183           moltype = AA   length = 12
FEATURE                  Location/Qualifiers
REGION                   1..12
                         note = targeting peptide
source                   1..12
                         mol_type = protein
                         organism = synthetic construct
SEQUENCE: 183
HTMYYHHYQH HL                                                            12

SEQ ID NO: 184           moltype = AA   length = 19
FEATURE                  Location/Qualifiers
REGION                   1..19
                         note = targeting peptide
source                   1..19
                         mol_type = protein
                         organism = synthetic construct
SEQUENCE: 184
SEVGCRAGPL QWLCEKYFG                                                     19

SEQ ID NO: 185           moltype = AA   length = 18
FEATURE                  Location/Qualifiers
REGION                   1..18
                         note = targeting peptide
source                   1..18
                         mol_type = protein
                         organism = synthetic construct
SEQUENCE: 185
CGLLPVGRPD RNVWRWLC                                                      18

SEQ ID NO: 186           moltype = AA   length = 15
FEATURE                  Location/Qualifiers
REGION                   1..15
                         note = targeting peptide
source                   1..15
                         mol_type = protein
                         organism = synthetic construct
SEQUENCE: 186
CKGQCDRFKG LPWEC                                                         15

SEQ ID NO: 187           moltype = AA   length = 5
FEATURE                  Location/Qualifiers
REGION                   1..5
                         note = targeting peptide
source                   1..5
```

```
                            mol_type = protein
                            organism = synthetic construct
SEQUENCE: 187
SGRSA                                                              5

SEQ ID NO: 188              moltype = AA   length = 4
FEATURE                     Location/Qualifiers
REGION                      1..4
                            note = targeting peptide
source                      1..4
                            mol_type = protein
                            organism = synthetic construct
SEQUENCE: 188
WGFP                                                               4

SEQ ID NO: 189              moltype =    length =
SEQUENCE: 189
000

SEQ ID NO: 190              moltype = AA   length = 7
FEATURE                     Location/Qualifiers
REGION                      1..7
                            note = targeting peptide
source                      1..7
                            mol_type = protein
                            organism = synthetic construct
SEQUENCE: 190
XFXXYLW                                                            7

SEQ ID NO: 191              moltype = AA   length = 17
FEATURE                     Location/Qualifiers
REGION                      1..17
                            note = targeting peptide
source                      1..17
                            mol_type = protein
                            organism = synthetic construct
SEQUENCE: 191
AEPMPHSLNF SQYLWYT                                                17

SEQ ID NO: 192              moltype = AA   length = 6
FEATURE                     Location/Qualifiers
REGION                      1..6
                            note = targeting peptide
VARIANT                     4
                            note = X can be W or F
source                      1..6
                            mol_type = protein
                            organism = synthetic construct
SEQUENCE: 192
WAYXSP                                                             6

SEQ ID NO: 193              moltype = AA   length = 7
FEATURE                     Location/Qualifiers
REGION                      1..7
                            note = targeting peptide
source                      1..7
                            mol_type = protein
                            organism = synthetic construct
SEQUENCE: 193
IELLQAR                                                            7

SEQ ID NO: 194              moltype = AA   length = 12
FEATURE                     Location/Qualifiers
REGION                      1..12
                            note = targeting peptide
source                      1..12
                            mol_type = protein
                            organism = synthetic construct
SEQUENCE: 194
DITWDQLWDL MK                                                     12

SEQ ID NO: 195              moltype = AA   length = 16
FEATURE                     Location/Qualifiers
REGION                      1..16
                            note = targeting peptide
source                      1..16
                            mol_type = protein
                            organism = synthetic construct
SEQUENCE: 195
```

```
AYTKCSRQWR TCMTTH                                                        16

SEQ ID NO: 196           moltype = AA   length = 15
FEATURE                  Location/Qualifiers
REGION                   1..15
                         note = targeting peptide
source                   1..15
                         mol_type = protein
                         organism = synthetic construct
SEQUENCE: 196
PQNSKIPGPT FLDPH                                                         15

SEQ ID NO: 197           moltype = AA   length = 15
FEATURE                  Location/Qualifiers
REGION                   1..15
                         note = targeting peptide
source                   1..15
                         mol_type = protein
                         organism = synthetic construct
SEQUENCE: 197
SMEPALPDWW WKMFK                                                         15

SEQ ID NO: 198           moltype = AA   length = 16
FEATURE                  Location/Qualifiers
REGION                   1..16
                         note = targeting peptide
source                   1..16
                         mol_type = protein
                         organism = synthetic construct
SEQUENCE: 198
ANTPCGPYTH DCPVKR                                                        16

SEQ ID NO: 199           moltype = AA   length = 12
FEATURE                  Location/Qualifiers
REGION                   1..12
                         note = targeting peptide
source                   1..12
                         mol_type = protein
                         organism = synthetic construct
SEQUENCE: 199
TACHQHVRMV RP                                                            12

SEQ ID NO: 200           moltype = AA   length = 12
FEATURE                  Location/Qualifiers
REGION                   1..12
                         note = targeting peptide
source                   1..12
                         mol_type = protein
                         organism = synthetic construct
SEQUENCE: 200
VPWMEPAYQR FL                                                            12

SEQ ID NO: 201           moltype = AA   length = 8
FEATURE                  Location/Qualifiers
REGION                   1..8
                         note = targeting peptide
source                   1..8
                         mol_type = protein
                         organism = synthetic construct
SEQUENCE: 201
DPRATPGS                                                                 8

SEQ ID NO: 202           moltype = AA   length = 12
FEATURE                  Location/Qualifiers
REGION                   1..12
                         note = targeting peptide
source                   1..12
                         mol_type = protein
                         organism = synthetic construct
SEQUENCE: 202
FRPNRAQDYN TN                                                            12

SEQ ID NO: 203           moltype = AA   length = 9
FEATURE                  Location/Qualifiers
REGION                   1..9
                         note = targeting peptide
source                   1..9
                         mol_type = protein
                         organism = synthetic construct
```

```
SEQUENCE: 203
CTKNSYLMC                                                                        9

SEQ ID NO: 204          moltype = AA   length = 11
FEATURE                 Location/Qualifiers
REGION                  1..11
                        note = targeting peptide
VARIANT                 2
                        note = X can be R or Q
VARIANT                 3
                        note = X can be L or R
VARIANT                 5
                        note = X can be G or N
VARIANT                 9
                        note = X can be A or V
source                  1..11
                        mol_type = protein
                        organism = synthetic construct
SEQUENCE: 204
CXXTXXXGXG C                                                                    11

SEQ ID NO: 205          moltype = AA   length = 9
FEATURE                 Location/Qualifiers
REGION                  1..9
                        note = targeting peptide
source                  1..9
                        mol_type = protein
                        organism = synthetic construct
SEQUENCE: 205
CPIEDRPMC                                                                        9

SEQ ID NO: 206          moltype = AA   length = 12
FEATURE                 Location/Qualifiers
REGION                  1..12
                        note = targeting peptide
source                  1..12
                        mol_type = protein
                        organism = synthetic construct
SEQUENCE: 206
HEWSYLAPYP WF                                                                   12

SEQ ID NO: 207          moltype = AA   length = 9
FEATURE                 Location/Qualifiers
REGION                  1..9
                        note = targeting peptide
source                  1..9
                        mol_type = protein
                        organism = synthetic construct
SEQUENCE: 207
MCPKHPLGC                                                                        9

SEQ ID NO: 208          moltype = AA   length = 15
FEATURE                 Location/Qualifiers
REGION                  1..15
                        note = targeting peptide
source                  1..15
                        mol_type = protein
                        organism = synthetic construct
SEQUENCE: 208
RMWPSSTVNL SAGRR                                                                15

SEQ ID NO: 209          moltype = AA   length = 20
FEATURE                 Location/Qualifiers
REGION                  1..20
                        note = targeting peptide
source                  1..20
                        mol_type = protein
                        organism = synthetic construct
SEQUENCE: 209
SAKTAVSQRV WLPSHRGGEP                                                           20

SEQ ID NO: 210          moltype = AA   length = 20
FEATURE                 Location/Qualifiers
REGION                  1..20
                        note = targeting peptide
source                  1..20
                        mol_type = protein
                        organism = synthetic construct
SEQUENCE: 210
```

KSREHVNNSA CPSKRITAAL 20

```
SEQ ID NO: 211         moltype = AA   length = 4
FEATURE                Location/Qualifiers
REGION                 1..4
                       note = targeting peptide
source                 1..4
                       mol_type = protein
                       organism = synthetic construct
SEQUENCE: 211
EGFR                                                                    4

SEQ ID NO: 212         moltype = AA   length = 6
FEATURE                Location/Qualifiers
REGION                 1..6
                       note = targeting peptide
source                 1..6
                       mol_type = protein
                       organism = synthetic construct
SEQUENCE: 212
AGLGVR                                                                  6

SEQ ID NO: 213         moltype = AA   length = 15
FEATURE                Location/Qualifiers
REGION                 1..15
                       note = targeting peptide
source                 1..15
                       mol_type = protein
                       organism = synthetic construct
SEQUENCE: 213
GTRQGHTMRL GVSDG                                                       15

SEQ ID NO: 214         moltype = AA   length = 15
FEATURE                Location/Qualifiers
REGION                 1..15
                       note = targeting peptide
source                 1..15
                       mol_type = protein
                       organism = synthetic construct
SEQUENCE: 214
IAGLATPGWS HWLAL                                                       15

SEQ ID NO: 215         moltype = AA   length = 7
FEATURE                Location/Qualifiers
REGION                 1..7
                       note = targeting peptide
source                 1..7
                       mol_type = protein
                       organism = synthetic construct
SEQUENCE: 215
SMSIARL                                                                 7

SEQ ID NO: 216         moltype = AA   length = 7
FEATURE                Location/Qualifiers
REGION                 1..7
                       note = targeting peptide
source                 1..7
                       mol_type = protein
                       organism = synthetic construct
SEQUENCE: 216
HTFEPGV                                                                 7

SEQ ID NO: 217         moltype = AA   length = 15
FEATURE                Location/Qualifiers
REGION                 1..15
                       note = targeting peptide
source                 1..15
                       mol_type = protein
                       organism = synthetic construct
SEQUENCE: 217
NTSLKRISNK RIRRK                                                       15

SEQ ID NO: 218         moltype = AA   length = 15
FEATURE                Location/Qualifiers
REGION                 1..15
                       note = targeting peptide
source                 1..15
                       mol_type = protein
                       organism = synthetic construct
```

```
SEQUENCE: 218
LRIKRKRRKR KKTRK                                                15

SEQ ID NO: 219           moltype =    length =
SEQUENCE: 219
000

SEQ ID NO: 220           moltype =    length =
SEQUENCE: 220
000

SEQ ID NO: 221           moltype =    length =
SEQUENCE: 221
000

SEQ ID NO: 222           moltype =    length =
SEQUENCE: 222
000

SEQ ID NO: 223           moltype =    length =
SEQUENCE: 223
000

SEQ ID NO: 224           moltype =    length =
SEQUENCE: 224
000

SEQ ID NO: 225           moltype =    length =
SEQUENCE: 225
000

SEQ ID NO: 226           moltype =    length =
SEQUENCE: 226
000

SEQ ID NO: 227           moltype =    length =
SEQUENCE: 227
000

SEQ ID NO: 228           moltype =    length =
SEQUENCE: 228
000

SEQ ID NO: 229           moltype =    length =
SEQUENCE: 229
000

SEQ ID NO: 230           moltype =    length =
SEQUENCE: 230
000

SEQ ID NO: 231           moltype =    length =
SEQUENCE: 231
000

SEQ ID NO: 232           moltype =    length =
SEQUENCE: 232
000

SEQ ID NO: 233           moltype =    length =
SEQUENCE: 233
000

SEQ ID NO: 234           moltype =    length =
SEQUENCE: 234
000

SEQ ID NO: 235           moltype =    length =
SEQUENCE: 235
000

SEQ ID NO: 236           moltype =    length =
SEQUENCE: 236
000

SEQ ID NO: 237           moltype =    length =
SEQUENCE: 237
000
```

| | | |
|---|---|---|
| SEQ ID NO: 238 SEQUENCE: 238 | moltype = | length = 000 |
| SEQ ID NO: 239 SEQUENCE: 239 | moltype = | length = 000 |
| SEQ ID NO: 240 SEQUENCE: 240 | moltype = | length = 000 |
| SEQ ID NO: 241 SEQUENCE: 241 | moltype = | length = 000 |
| SEQ ID NO: 242 SEQUENCE: 242 | moltype = | length = 000 |
| SEQ ID NO: 243 SEQUENCE: 243 | moltype = | length = 000 |
| SEQ ID NO: 244 SEQUENCE: 244 | moltype = | length = 000 |
| SEQ ID NO: 245 SEQUENCE: 245 | moltype = | length = 000 |
| SEQ ID NO: 246 SEQUENCE: 246 | moltype = | length = 000 |
| SEQ ID NO: 247 SEQUENCE: 247 | moltype = | length = 000 |
| SEQ ID NO: 248 SEQUENCE: 248 | moltype = | length = 000 |
| SEQ ID NO: 249 SEQUENCE: 249 | moltype = | length = 000 |
| SEQ ID NO: 250 SEQUENCE: 250 | moltype = | length = 000 |
| SEQ ID NO: 251 SEQUENCE: 251 | moltype = | length = 000 |
| SEQ ID NO: 252 SEQUENCE: 252 | moltype = | length = 000 |
| SEQ ID NO: 253 SEQUENCE: 253 | moltype = | length = 000 |
| SEQ ID NO: 254 SEQUENCE: 254 | moltype = | length = 000 |
| SEQ ID NO: 255 SEQUENCE: 255 | moltype = | length = 000 |
| SEQ ID NO: 256 SEQUENCE: 256 | moltype = | length = 000 |
| SEQ ID NO: 257 SEQUENCE: 257 | moltype = | length = 000 |

| | | |
|---|---|---|
| SEQ ID NO: 258 SEQUENCE: 258 | moltype = 000 | length = |
| SEQ ID NO: 259 SEQUENCE: 259 | moltype = 000 | length = |
| SEQ ID NO: 260 SEQUENCE: 260 | moltype = 000 | length = |
| SEQ ID NO: 261 SEQUENCE: 261 | moltype = 000 | length = |
| SEQ ID NO: 262 SEQUENCE: 262 | moltype = 000 | length = |
| SEQ ID NO: 263 SEQUENCE: 263 | moltype = 000 | length = |
| SEQ ID NO: 264 SEQUENCE: 264 | moltype = 000 | length = |
| SEQ ID NO: 265 SEQUENCE: 265 | moltype = 000 | length = |
| SEQ ID NO: 266 SEQUENCE: 266 | moltype = 000 | length = |
| SEQ ID NO: 267 SEQUENCE: 267 | moltype = 000 | length = |
| SEQ ID NO: 268 SEQUENCE: 268 | moltype = 000 | length = |
| SEQ ID NO: 269 SEQUENCE: 269 | moltype = 000 | length = |
| SEQ ID NO: 270 SEQUENCE: 270 | moltype = 000 | length = |
| SEQ ID NO: 271 SEQUENCE: 271 | moltype = 000 | length = |
| SEQ ID NO: 272 SEQUENCE: 272 | moltype = 000 | length = |
| SEQ ID NO: 273 SEQUENCE: 273 | moltype = 000 | length = |
| SEQ ID NO: 274 SEQUENCE: 274 | moltype = 000 | length = |
| SEQ ID NO: 275 SEQUENCE: 275 | moltype = 000 | length = |
| SEQ ID NO: 276 SEQUENCE: 276 | moltype = 000 | length = |
| SEQ ID NO: 277 SEQUENCE: 277 | moltype = | length = |

```
SEQ ID NO: 278          moltype =    length =
SEQUENCE: 278
000

SEQ ID NO: 279          moltype =    length =
SEQUENCE: 279
000

SEQ ID NO: 280          moltype =    length =
SEQUENCE: 280
000

SEQ ID NO: 281          moltype =    length =
SEQUENCE: 281
000

SEQ ID NO: 282          moltype =    length =
SEQUENCE: 282
000

SEQ ID NO: 283          moltype =    length =
SEQUENCE: 283
000

SEQ ID NO: 284          moltype =    length =
SEQUENCE: 284
000

SEQ ID NO: 285          moltype =    length =
SEQUENCE: 285
000

SEQ ID NO: 286          moltype =    length =
SEQUENCE: 286
000

SEQ ID NO: 287          moltype =    length =
SEQUENCE: 287
000

SEQ ID NO: 288          moltype =    length =
SEQUENCE: 288
000

SEQ ID NO: 289          moltype =    length =
SEQUENCE: 289
000

SEQ ID NO: 290          moltype =    length =
SEQUENCE: 290
000

SEQ ID NO: 291          moltype =    length =
SEQUENCE: 291
000

SEQ ID NO: 292          moltype =    length =
SEQUENCE: 292
000

SEQ ID NO: 293          moltype =    length =
SEQUENCE: 293
000

SEQ ID NO: 294          moltype =    length =
SEQUENCE: 294
000

SEQ ID NO: 295          moltype =    length =
SEQUENCE: 295
000

SEQ ID NO: 296          moltype =    length =
SEQUENCE: 296
000

SEQ ID NO: 297          moltype = AA  length = 8
```

| FEATURE | Location/Qualifiers |
|---|---|
| REGION | 1..8 |
| | note = AAV capsid protein amino acid substitution |
| source | 1..8 |
| | mol_type = protein |
| | organism = synthetic construct |

SEQUENCE: 297
VVGNGGVV                                                                8

| SEQ ID NO: 298 | moltype = AA   length = 8 |
|---|---|
| FEATURE | Location/Qualifiers |
| REGION | 1..8 |
| | note = AAV capsid protein amino acid substitution |
| source | 1..8 |
| | mol_type = protein |
| | organism = synthetic construct |

SEQUENCE: 298
NFREMPIG                                                                8

| SEQ ID NO: 299 | moltype = AA   length = 9 |
|---|---|
| FEATURE | Location/Qualifiers |
| REGION | 1..9 |
| | note = AAV capsid protein amino acid substitution |
| source | 1..9 |
| | mol_type = protein |
| | organism = synthetic construct |

SEQUENCE: 299
RRSEDMGTI                                                               9

| SEQ ID NO: 300 | moltype = AA   length = 738 |
|---|---|
| FEATURE | Location/Qualifiers |
| REGION | 1..738 |
| | note = AAV capsid variant |
| source | 1..738 |
| | mol_type = protein |
| | organism = synthetic construct |

SEQUENCE: 300
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTVVGNGGV VNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

| SEQ ID NO: 301 | moltype = AA   length = 738 |
|---|---|
| FEATURE | Location/Qualifiers |
| REGION | 1..738 |
| | note = AAV capsid variant |
| source | 1..738 |
| | mol_type = protein |
| | organism = synthetic construct |

SEQUENCE: 301
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTNFREMPI GNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

| SEQ ID NO: 302 | moltype = AA   length = 739 |
|---|---|
| FEATURE | Location/Qualifiers |
| REGION | 1..739 |
| | note = AAV capsid variant |
| source | 1..739 |
| | mol_type = protein |

```
                        organism = synthetic construct
SEQUENCE: 302
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTRRSEDMG TINFAWTAGT KYHLNGRNSL ANPGIAMATH KDDEERFFPS   540
NGILIFGKQN AARDNADYSD VMLTSEEEIK TTNPVATEEY GIVADNLQQQ NTAPQIGTVN   600
SQGALPGMVW QNRDVYLQGP IWAKIPHTDG NFHPSPLMGG FGLKHPPPQI LIKNTPVPAD   660
PPTTFNQSKL NSFITQYSTG QVSVEIEWEL QKENSKRWNP EIQYTSNYYK STSVDFAVNT   720
EGVYSEPRPI GTRYLTRNL                                                739

SEQ ID NO: 303          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 303
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQR STVVGNGGVV NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 304          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 304
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STNFREMPIG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 305          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 305
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STRRSEDMGT INFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
```

```
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 306         moltype = AA  length = 738
FEATURE                Location/Qualifiers
REGION                 1..738
                       note = AAV capsid variant
source                 1..738
                       mol_type = protein
                       organism = synthetic construct
SEQUENCE: 306
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTVVGNGGV VNFAWTAGTK YHLNGRNSLA NPGIAMATHK DDEERFFPSN  540
GILIFGKQNA ARDNADYSDV MLTSEEEIKT TNPVATEEYG IVADNVMEPT RAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 307         moltype = AA  length = 738
FEATURE                Location/Qualifiers
REGION                 1..738
                       note = AAV capsid variant
source                 1..738
                       mol_type = protein
                       organism = synthetic construct
SEQUENCE: 307
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTNFREMPI GNFAWTAGTK YHLNGRNSLA NPGIAMATHK DDEERFFPSN  540
GILIFGKQNA ARDNADYSDV MLTSEEEIKT TNPVATEEYG IVADNVMEPT RAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 308         moltype = AA  length = 739
FEATURE                Location/Qualifiers
REGION                 1..739
                       note = AAV capsid variant
source                 1..739
                       mol_type = protein
                       organism = synthetic construct
SEQUENCE: 308
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTRRSEDMG TINFAWTAGT KYHLNGRNSL ANPGIAMATH KDDEERFFPS  540
NGILIFGKQN AARDNADYSD VMLTSEEEIK TTNPVATEEY GIVADNVMEP TRAPQIGTVN  600
SQGALPGMVW QNRDVYLQGP IWAKIPHTDG NFHPSPLMGG FGLKHPPPQI LIKNTPVPAD  660
PPTTFNQSKL NSFITQYSTG QVSVEIEWEL QKENSKRWNP EIQYTSNYYK STSVDFAVNT  720
EGVYSEPRPI GTRYLTRNL                                              739

SEQ ID NO: 309         moltype = AA  length = 737
FEATURE                Location/Qualifiers
REGION                 1..737
                       note = AAV capsid variant
source                 1..737
                       mol_type = protein
                       organism = synthetic construct
SEQUENCE: 309
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
```

```
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STVVGNGGVV NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 310          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 310
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STNFREMPIG NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 311          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 311
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STRRSEDMGT INFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 312          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 312
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STVVGNGGVV NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 313          moltype = AA  length = 737
```

| FEATURE | Location/Qualifiers |
|---|---|
| REGION | 1..737 |
| | note = AAV capsid variant |
| source | 1..737 |
| | mol_type = protein |
| | organism = synthetic construct |

SEQUENCE: 313
```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STNFREMPIG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737
```

| SEQ ID NO: 314 | moltype = AA length = 738 |
|---|---|
| FEATURE | Location/Qualifiers |
| REGION | 1..738 |
| | note = AAV capsid variant |
| source | 1..738 |
| | mol_type = protein |
| | organism = synthetic construct |

SEQUENCE: 314
```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STRRSEDMGT INFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738
```

| SEQ ID NO: 315 | moltype = AA length = 736 |
|---|---|
| FEATURE | Location/Qualifiers |
| REGION | 1..736 |
| | note = AAV capsid variant |
| source | 1..736 |
| | mol_type = protein |
| | organism = synthetic construct |

SEQUENCE: 315
```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TVVGNGGVVN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736
```

| SEQ ID NO: 316 | moltype = AA length = 736 |
|---|---|
| FEATURE | Location/Qualifiers |
| REGION | 1..736 |
| | note = AAV capsid variant |
| source | 1..736 |
| | mol_type = protein |
| | organism = synthetic construct |

SEQUENCE: 316
```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
```

```
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTSNGRGVT LGFSQGGPNT MANQAKNWLP     480
GPCYRQQRVS TNFREMPIGN FAWTAGTKYH LNGRNSLANP GIAMATHKDD EERFFPSNGI     540
LIFGKQNAAR DNADYSDVML TSEEEIKTTN PVATEEYGIV ADNLQQQNTA PQIGTVNSQG     600
ALPGMVWQNR DVYLQGPIWA KIPHTDGNPH PSPLMGGFGL KHPPPQILIK NTPVPADPPT     660
TFNQSKLNSF ITQYSTGQVS VEIEWELQKE NSKRWNPEIQ YTSNYYKSTS VDFAVNTEGV     720
YSEPRPIGTR YLTRNL                                                    736

SEQ ID NO: 317          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 317
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDSE     180
SVPDPQPLGE PPAAPSGVGP NTMAAGGGAP MADNNEGADG VGSSSGNWHC DSTWLGDRVI     240
TTSTRTWALP TYNNHLYKQI SNGTSGGATN DNTYFGYSTP WGYFDFNRFH CHFSPRDWQR     300
LINNNWGFRP KRLSFKLFNI QVKEVTQNEG TKTIANNLTS TIQVFTDSEY QLPYVLGSAH     360
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTSNGRGVT LGFSQGGPNT MANQAKNWLP     480
GPCYRQQRVS TRRSEDMGTI NFAWTAGTKY HLNGRNSLAN PGIAMATHKD DEERFFPSNG     540
ILIFGKQNAA RDNADYSDVM LTSEEEIKTT NPVATEEYGI VADNLQQQNT APQIGTVNSQ     600
GALPGMVWQN RDVYLQGPIW AKIPHTDGNF HPSPLMGGFG LKHPPPQILI KNTPVPADPP     660
TTFNQSKLNS FITQYSTGQV SVEIEWELQK ENSKRWNPEI QYTSNYYKST SVDFAVNTEG     720
VYSEPRPIGT RYLTRNL                                                   737

SEQ ID NO: 318          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 318
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDSE     180
SVPDPQPLGE PPAAPSGVGP NTMAAGGGAP MADNNEGADG VGSSSGNWHC DSTWLGDRVI     240
TTSTRTWALP TYNNHLYKQI SNGTSGGATN DNTYFGYSTP WGYFDFNRFH CHFSPRDWQR     300
LINNNWGFRP KRLSFKLFNI QVKEVTQNEG TKTIANNLTS TIQVFTDSEY QLPYVLGSAH     360
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTGGTANTQ TLGFSQGGPN TMANQAKNWL     480
PGPCYRQQRV STVVGNGGVV NFAWTAGTKY HLNGRNSLAN PGIAMATHKD DEERFFPSNG     540
ILIFGKQNAA RDNADYSDVM LTSEEEIKTT NPVATEEYGI VADNVMEPTR APQIGTVNSQ     600
GALPGMVWQN RDVYLQGPIW AKIPHTDGNF HPSPLMGGFG LKHPPPQILI KNTPVPADPP     660
TTFNQSKLNS FITQYSTGQV SVEIEWELQK ENSKRWNPEI QYTSNYYKST SVDFAVNTEG     720
VYSEPRPIGT RYLTRNL                                                   737

SEQ ID NO: 319          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 319
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDSE     180
SVPDPQPLGE PPAAPSGVGP NTMAAGGGAP MADNNEGADG VGSSSGNWHC DSTWLGDRVI     240
TTSTRTWALP TYNNHLYKQI SNGTSGGATN DNTYFGYSTP WGYFDFNRFH CHFSPRDWQR     300
LINNNWGFRP KRLSFKLFNI QVKEVTQNEG TKTIANNLTS TIQVFTDSEY QLPYVLGSAH     360
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTGGTANTQ TLGFSQGGPN TMANQAKNWL     480
PGPCYRQQRV STNFREMPIG NFAWTAGTKY HLNGRNSLAN PGIAMATHKD DEERFFPSNG     540
ILIFGKQNAA RDNADYSDVM LTSEEEIKTT NPVATEEYGI VADNVMEPTR APQIGTVNSQ     600
GALPGMVWQN RDVYLQGPIW AKIPHTDGNF HPSPLMGGFG LKHPPPQILI KNTPVPADPP     660
TTFNQSKLNS FITQYSTGQV SVEIEWELQK ENSKRWNPEI QYTSNYYKST SVDFAVNTEG     720
VYSEPRPIGT RYLTRNL                                                   737

SEQ ID NO: 320          moltype = AA  length = 738
FEATURE                 Location/Qualifiers
REGION                  1..738
                        note = AAV capsid variant
source                  1..738
```

```
                        mol_type = protein
                        organism = synthetic construct
SEQUENCE: 320
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STRRSEDMGT INFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 321          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 321
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TVVGNGGVVN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNPH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                   736

SEQ ID NO: 322          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 322
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TNFREMPIGN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                   736

SEQ ID NO: 323          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 323
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TRRSEDMGTI NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
```

```
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 324           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 324
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STTTGQNNNS NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSG    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 325           moltype = AA   length = 738
FEATURE                  Location/Qualifiers
REGION                   1..738
                         note = AAV capsid variant
source                   1..738
                         mol_type = protein
                         organism = synthetic construct
SEQUENCE: 325
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTNLAENFK YNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 326           moltype = AA   length = 738
FEATURE                  Location/Qualifiers
REGION                   1..738
                         note = AAV capsid variant
source                   1..738
                         mol_type = protein
                         organism = synthetic construct
SEQUENCE: 326
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTVLSGDHS ANFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 327           moltype = AA   length = 738
FEATURE                  Location/Qualifiers
REGION                   1..738
                         note = AAV capsid variant
source                   1..738
                         mol_type = protein
                         organism = synthetic construct
SEQUENCE: 327
MAADGYLPDW LEDNLSEGIR EWWALKPGAP KPKANQQKQD DGRGLVLPGY KYLGPFNGLD    60
```

```
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTMSAASGS GNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 328          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 328
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTGTNLGKE QNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 329          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 329
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTSSHSGTN QNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 330          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 330
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTVATRDGQ LNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738
```

```
SEQ ID NO: 331           moltype = AA   length = 738
FEATURE                  Location/Qualifiers
REGION                   1..738
                         note = AAV capsid variant
source                   1..738
                         mol_type = protein
                         organism = synthetic construct
SEQUENCE: 331
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTALNADTG TNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 332           moltype = AA   length = 738
FEATURE                  Location/Qualifiers
REGION                   1..738
                         note = AAV capsid variant
source                   1..738
                         mol_type = protein
                         organism = synthetic construct
SEQUENCE: 332
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 333           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 333
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STTGQNNNS NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 334           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 334
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
```

```
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STNLAENFKY NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 335          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 335
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STVLSGDHSA NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 336          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 336
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STMSAASGSG NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 337          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 337
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STGTNLGKEQ NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 338          moltype = AA  length = 737
FEATURE                 Location/Qualifiers
REGION                  1..737
                        note = AAV capsid variant
```

```
source                  1..737
                        mol_type = protein
                        organism = synthetic construct
SEQUENCE: 338
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STSSHSGTNQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 339          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 339
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STVATRDGQL NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 340          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 340
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STALNADTGT NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 341          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 341
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTNLAENFK YNFAWTAGTK YHLNGRNSLA NPGIAMATHK DDEERFFPSN   540
```

```
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                  738

SEQ ID NO: 342         moltype = AA   length = 738
FEATURE                Location/Qualifiers
REGION                 1..738
                       note = AAV capsid variant
source                 1..738
                       mol_type = protein
                       organism = synthetic construct
SEQUENCE: 342
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTVLSGDHS ANFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                  738

SEQ ID NO: 343         moltype = AA   length = 738
FEATURE                Location/Qualifiers
REGION                 1..738
                       note = AAV capsid variant
source                 1..738
                       mol_type = protein
                       organism = synthetic construct
SEQUENCE: 343
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTMSAASGS GNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                  738

SEQ ID NO: 344         moltype = AA   length = 738
FEATURE                Location/Qualifiers
REGION                 1..738
                       note = AAV capsid variant
source                 1..738
                       mol_type = protein
                       organism = synthetic construct
SEQUENCE: 344
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTGTNLGKE QNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                  738

SEQ ID NO: 345         moltype = AA   length = 738
FEATURE                Location/Qualifiers
REGION                 1..738
                       note = AAV capsid variant
source                 1..738
                       mol_type = protein
                       organism = synthetic construct
SEQUENCE: 345
```

```
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTSSHSGTN QNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 346         moltype = AA  length = 738
FEATURE                Location/Qualifiers
REGION                 1..738
                       note = AAV capsid variant
source                 1..738
                       mol_type = protein
                       organism = synthetic construct
SEQUENCE: 346
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTVATRDGQ LNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 347         moltype = AA  length = 738
FEATURE                Location/Qualifiers
REGION                 1..738
                       note = AAV capsid variant
source                 1..738
                       mol_type = protein
                       organism = synthetic construct
SEQUENCE: 347
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTALNADTG TNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 348         moltype = AA  length = 737
FEATURE                Location/Qualifiers
REGION                 1..737
                       note = AAV capsid variant
source                 1..737
                       mol_type = protein
                       organism = synthetic construct
SEQUENCE: 348
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STNLAENFKY NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737
```

```
SEQ ID NO: 349          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 349
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STVLSGDHSA NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 350          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 350
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STMSAASGSG NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 351          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 351
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STGTNLGKEQ NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 352          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 352
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
```

```
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STSSHSGTNQ NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 353          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 353
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STVATRDGQL NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 354          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 354
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STALNADTGT NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 355          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 355
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STTTGQNNNS NFAWTAGTKY HLNGRNSLAN PGIAMATHKD DEERFFPSNG    540
ILIFGKQNAA RDNADYSDVM LTSEEEIKTT NPVATEEYGI VADNLQQNT  APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 356          moltype = AA   length = 736
FEATURE                 Location/Qualifiers
REGION                  1..736
```

```
                         note = AAV capsid variant
source                   1..736
                         mol_type = protein
                         organism = synthetic construct
SEQUENCE: 356
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TTTGQNNNSN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 357           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 357
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STNLAENFKY NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 358           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 358
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STVLSGDHSA NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 359           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 359
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
```

```
PGPCYRQQRV STMSAASGSG NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 360          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 360
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STGTNLGKEQ NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 361          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 361
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STSSHSGTNQ NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 362          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 362
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STVATRDGQL NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 363          moltype = AA  length = 737
FEATURE                 Location/Qualifiers
REGION                  1..737
                        note = AAV capsid variant
source                  1..737
                        mol_type = protein
                        organism = synthetic construct
```

```
SEQUENCE: 363
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STALNADTGT NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 364          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 364
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STTGQNNNS NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 365          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 365
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TTTGQNNSN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 366          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 366
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TNLAENFKYN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
```

```
SEQ ID NO: 367          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 367
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TVLSGDHSAN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 368          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 368
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TMSAASGSGN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 369          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 369
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TGTNLGKEQN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 370          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 370
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
```

```
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TSSHSGTNQN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 371          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 371
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TVATRDGQLN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 372          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 372
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TALNADTGTN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 373          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 373
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STNLAENFKY NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 374          moltype = AA  length = 737
FEATURE                 Location/Qualifiers
```

```
REGION                  1..737
                        note = AAV capsid variant
source                  1..737
                        mol_type = protein
                        organism = synthetic construct
SEQUENCE: 374
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STVLSGDHSA NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 375          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 375
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STMSAASGSG NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 376          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 376
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STGTNLGKEQ NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 377          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 377
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
```

```
PFHSSYAHSQ SLDRLMNPLI DQYLYYLSRT QTTGGTANTQ TLGFSQGGPN TMANQAKNWL   480
PGPCYRQQRV STSSHSGTNQ NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 378         moltype = AA  length = 737
FEATURE                Location/Qualifiers
REGION                 1..737
                       note = AAV capsid variant
source                 1..737
                       mol_type = protein
                       organism = synthetic construct
SEQUENCE: 378
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPPPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STVATRDGQL NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 379         moltype = AA  length = 737
FEATURE                Location/Qualifiers
REGION                 1..737
                       note = AAV capsid variant
source                 1..737
                       mol_type = protein
                       organism = synthetic construct
SEQUENCE: 379
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPPPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STALNADTGT NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 380         moltype = AA  length = 736
FEATURE                Location/Qualifiers
REGION                 1..736
                       note = AAV capsid variant
source                 1..736
                       mol_type = protein
                       organism = synthetic construct
SEQUENCE: 380
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPPPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TNLAENFKYN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 381         moltype = AA  length = 736
FEATURE                Location/Qualifiers
REGION                 1..736
                       note = AAV capsid variant
source                 1..736
                       mol_type = protein
```

```
                        organism = synthetic construct
SEQUENCE: 381
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TVLSGDHSAN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 382          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 382
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TMSAASGSGN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 383          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 383
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TGTNLGKEQN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 384          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 384
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TSSHSGTNQN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
```

```
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 385          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 385
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TVATRDGQLN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVADPRS     660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 386          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 386
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TALNADTGTN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVADPRS     660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 387          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 387
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT LGFSQGGGP NTMANQAKNW     480
LPGPCYRQQR VSTVVGNGGV VNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVADP     660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 388          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 388
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
```

```
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTNFREMPI GNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 389          moltype = AA  length = 739
FEATURE                 Location/Qualifiers
REGION                  1..739
                        note = AAV capsid variant
source                  1..739
                        mol_type = protein
                        organism = synthetic construct
SEQUENCE: 389
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTRRSEDMG TINFAWTAGT KYHLNGRNSL ANPGIAMATH KDDEERFFPS    540
NGILIFGKQN AARDNADYSD VMLTSEEEIK TTNPVATEEY GIVADNLQQQ NTAPQIGTVN    600
SQGALPGMVW QNRDVYLQGP IWAKIPHTDG NFHPSPLMGG FGLKHPPPQI LIKNTPVPAD    660
PRSTFNGDKL NSFITQYSTG QVSVEIEWEL QKENSKRWNP EIQYTSNYYK STSVDFAVNT    720
EGVYSEPRPI GTRYLTRNL                                                739

SEQ ID NO: 390          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 390
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNRGV TLGFSQGGPN TMANQAKNWL    480
PGPCYRQQRV STVVGNGGVV NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 391          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 391
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNRGV TLGFSQGGPN TMANQAKNWL    480
PGPCYRQQRV STNFREMPIG NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 392          moltype = AA  length = 738
```

```
FEATURE                 Location/Qualifiers
REGION                  1..738
                        note = AAV capsid variant
source                  1..738
                        mol_type = protein
                        organism = synthetic construct
SEQUENCE: 392
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STRRSEDMGT INFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 393          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 393
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTVVGNGGV VNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 394          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 394
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTNFREMPI GNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 395          moltype = AA  length = 739
FEATURE                 Location/Qualifiers
REGION                  1..739
                        note = AAV capsid variant
source                  1..739
                        mol_type = protein
                        organism = synthetic construct
SEQUENCE: 395
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
```

```
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTRRSEDMG TINFAWTAGT KYHLNGRNSL ANPGIAMATH KDDEERFFPS    540
NGILIFGKQN AARDNADYSD VMLTSEEEIK TTNPVATEEY GIVADNVMEP TRAPQIGTVN    600
SQGALPGMVW QNRDVYLQGP IWAKIPHTDG NFHPSPLMGG FGLKHPPPQI LIKNTPVPAD    660
PRSTFNGDKL NSFITQYSTG QVSVEIEWEL QKENSKRWNP EIQYTSNYYK STSVDFAVNT    720
EGVYSEPRPI GTRYLTRNL                                                739

SEQ ID NO: 396         moltype = AA  length = 737
FEATURE                Location/Qualifiers
REGION                 1..737
                       note = AAV capsid variant
source                 1..737
                       mol_type = protein
                       organism = synthetic construct
SEQUENCE: 396
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STVVGNGGVV NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 397         moltype = AA  length = 737
FEATURE                Location/Qualifiers
REGION                 1..737
                       note = AAV capsid variant
source                 1..737
                       mol_type = protein
                       organism = synthetic construct
SEQUENCE: 397
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STNFREMPIG NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 398         moltype = AA  length = 738
FEATURE                Location/Qualifiers
REGION                 1..738
                       note = AAV capsid variant
source                 1..738
                       mol_type = protein
                       organism = synthetic construct
SEQUENCE: 398
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STRRSEDMGT INFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 399         moltype = AA  length = 737
FEATURE                Location/Qualifiers
REGION                 1..737
                       note = AAV capsid variant
source                 1..737
```

```
                        mol_type = protein
                        organism = synthetic construct
SEQUENCE: 399
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STVVGNGGVV NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 400          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 400
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STNFREMPIG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 401          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 401
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STRRSEDMGT INFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 402          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 402
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TVVGNGGVVN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
```

```
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 403              moltype = AA  length = 736
FEATURE                     Location/Qualifiers
REGION                      1..736
                            note = AAV capsid variant
source                      1..736
                            mol_type = protein
                            organism = synthetic construct
SEQUENCE: 403
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TNFREMPIGN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 404              moltype = AA  length = 737
FEATURE                     Location/Qualifiers
REGION                      1..737
                            note = AAV capsid variant
source                      1..737
                            mol_type = protein
                            organism = synthetic construct
SEQUENCE: 404
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TRRSEDMGTI NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 405              moltype = AA  length = 737
FEATURE                     Location/Qualifiers
REGION                      1..737
                            note = AAV capsid variant
source                      1..737
                            mol_type = protein
                            organism = synthetic construct
SEQUENCE: 405
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STVVGNGGVV NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 406              moltype = AA  length = 737
FEATURE                     Location/Qualifiers
REGION                      1..737
                            note = AAV capsid variant
source                      1..737
                            mol_type = protein
                            organism = synthetic construct
SEQUENCE: 406
MAADGYLPDW LEDNLSEGIR EWWALKPGAP QPKANQQHQD NARGLVLPGY KYLGPGNGLD     60
```

```
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STNFREMPIG NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 407        moltype = AA  length = 738
FEATURE               Location/Qualifiers
REGION                1..738
                      note = AAV capsid variant
source                1..738
                      mol_type = protein
                      organism = synthetic construct
SEQUENCE: 407
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STRRSEDMGT INFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 408        moltype = AA  length = 736
FEATURE               Location/Qualifiers
REGION                1..736
                      note = AAV capsid variant
source                1..736
                      mol_type = protein
                      organism = synthetic construct
SEQUENCE: 408
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TVVGNGGVVN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 409        moltype = AA  length = 736
FEATURE               Location/Qualifiers
REGION                1..736
                      note = AAV capsid variant
source                1..736
                      mol_type = protein
                      organism = synthetic construct
SEQUENCE: 409
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TNFREMPIGN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736
```

```
SEQ ID NO: 410          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 410
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TRRSEDMGTI NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 411          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 411
YPLQNNNS                                                              8

SEQ ID NO: 412          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 412
YPLENFKY                                                              8

SEQ ID NO: 413          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 413
YPLGDHSA                                                              8

SEQ ID NO: 414          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 414
YPLASGSG                                                              8

SEQ ID NO: 415          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 415
YPLLGKEQ                                                              8

SEQ ID NO: 416          moltype = AA  length = 8
FEATURE                 Location/Qualifiers
REGION                  1..8
                        note = AAV capsid protein amino acid substitution
source                  1..8
                        mol_type = protein
                        organism = synthetic construct
```

```
SEQUENCE: 416
YPLSGTNQ                                                                        8

SEQ ID NO: 417          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 417
YPLRDGQL                                                                        8

SEQ ID NO: 418          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 418
YPLADTGT                                                                        8

SEQ ID NO: 419          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 419
YPLNGGVV                                                                        8

SEQ ID NO: 420          moltype = AA  length = 8
FEATURE                 Location/Qualifiers
REGION                  1..8
                        note = AAV capsid protein amino acid substitution
source                  1..8
                        mol_type = protein
                        organism = synthetic construct
SEQUENCE: 420
YPLEMPIG                                                                        8

SEQ ID NO: 421          moltype = AA  length = 9
FEATURE                 Location/Qualifiers
REGION                  1..9
                        note = AAV capsid protein amino acid substitution
source                  1..9
                        mol_type = protein
                        organism = synthetic construct
SEQUENCE: 421
YPLEDMGTI                                                                       9

SEQ ID NO: 422          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 422
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLQNNN SNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 423          moltype = AA  length = 737
FEATURE                 Location/Qualifiers
REGION                  1..737
                        note = AAV capsid variant
```

```
source                 1..737
                       mol_type = protein
                       organism = synthetic construct
SEQUENCE: 423
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLQNNNS NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 424         moltype = AA   length = 738
FEATURE                Location/Qualifiers
REGION                 1..738
                       note = AAV capsid variant
source                 1..738
                       mol_type = protein
                       organism = synthetic construct
SEQUENCE: 424
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLQNNN SNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 425         moltype = AA   length = 737
FEATURE                Location/Qualifiers
REGION                 1..737
                       note = AAV capsid variant
source                 1..737
                       mol_type = protein
                       organism = synthetic construct
SEQUENCE: 425
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLQNNNS NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 426         moltype = AA   length = 737
FEATURE                Location/Qualifiers
REGION                 1..737
                       note = AAV capsid variant
source                 1..737
                       mol_type = protein
                       organism = synthetic construct
SEQUENCE: 426
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADP VGSSSGNWHC DSTWLGDRVI   240
TTSTRTWALP TYNNHLYKQI SNGTSGGATN DNTYFGYSTP WGYFDFNRFH CHFSPRDWQR   300
LINNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLQNNNS NFAWTAGTKY HLNGRNSLAN PGIAMATHKD DEERFFPSNG   540
```

```
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 427          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 427
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLQNNNSN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 428          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 428
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLQNNNS NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 429          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 429
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLQNNNSN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 430          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 430
```

```
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTGGTANT QTLGFSQGGP NTMANQAKNW 480
LPGPCYRQQR VSTYPLQNNN SNFAWTAGTK YHLNGRNSLA NPGIAMATHK DDEERFFPSN 540
GILIFGKQNA ARDNADYSDV MLTSEEEIKT TNPVATEEYG IVADNLQQQN TAPQIGTVNS 600
QGALPGMVWQ NRDVYLQGPI WAKIPHTDGN FHPSPLMGGF GLKHPPPQIL IKNTPVPADP 660
RSTFNGDKLN SFITQYSTGQ VSVEIEWELQ KENSKRWNPE IQYTSNYYKS TSVDFAVNTE 720
GVYSEPRPIG TRYLTRNL                                               738

SEQ ID NO: 431          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 431
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTSNGRGV TLGFSQGGPN TMANQAKNWL 480
PGPCYRQQRV STYPLQNNNS NFAWTAGTKY HLNGRNSLAN PGIAMATHKD DEERFFPSNG 540
ILIFGKQNAA RDNADYSDVM LTSEEEIKTT NPVATEEYGI VADNLQQQNT APQIGTVNSQ 600
GALPGMVWQN RDVYLQGPIW AKIPHTDGNF HPSPLMGGFG LKHPPPQILI KNTPVPADPR 660
STFNGDKLNS FITQYSTGQV SVEIEWELQK ENSKRWNPEI QYTSNYYKST SVDFAVNTEG 720
VYSEPRPIGT RYLTRNL                                                737

SEQ ID NO: 432          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 432
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTGGTANT QTLGFSQGGP NTMANQAKNW 480
LPGPCYRQQR VSTYPLQNNN SNFAWTAGTK YHLNGRNSLA NPGIAMATHK DDEERFFPSN 540
GILIFGKQNA ARDNADYSDV MLTSEEEIKT TNPVATEEYG IVADNVMEPT RAPQIGTVNS 600
QGALPGMVWQ NRDVYLQGPI WAKIPHTDGN FHPSPLMGGF GLKHPPPQIL IKNTPVPADP 660
RSTFNGDKLN SFITQYSTGQ VSVEIEWELQ KENSKRWNPE IQYTSNYYKS TSVDFAVNTE 720
GVYSEPRPIG TRYLTRNL                                               738

SEQ ID NO: 433          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 433
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTSNGRGV TLGFSQGGPN TMANQAKNWL 480
PGPCYRQQRV STYPLQNNNS NFAWTAGTKY HLNGRNSLAN PGIAMATHKD DEERFFPSNG 540
ILIFGKQNAA RDNADYSDVM LTSEEEIKTT NPVATEEYGI VADNVMEPTR APQIGTVNSQ 600
GALPGMVWQN RDVYLQGPIW AKIPHTDGNF HPSPLMGGFG LKHPPPQILI KNTPVPADPR 660
STFNGDKLNS FITQYSTGQV SVEIEWELQK ENSKRWNPEI QYTSNYYKST SVDFAVNTEG 720
VYSEPRPIGT RYLTRNL                                                737
```

```
SEQ ID NO: 434          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 434
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STYPLQNNNS NFAWTAGTKY HLNGRNSLAN PGIAMATHKD DEERFFPSNG  540
ILIFGKQNAA RDNADYSDVM LTSEEEIKTT NPVATEEYGI VADNLQQQNT APQIGTVNSQ  600
GALPGMVWQN RDVYLQGPIW AKIPHTDGNF HPSPLMGGFG LKHPPPQILI KNTPVPADPR  660
STFNGDKLNS FITQYSTGQV SVEIEWELQK ENSKRWNPEI QYTSNYYKST SVDFAVNTEG  720
VYSEPRPIGT RYLTRNL                                                 737

SEQ ID NO: 435          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 435
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTSNGRGVT LGFSQGGPNT MANQAKNWLP  480
GPCYRQQRVS TYPLQNNNSN FAWTAGTKYH LNGRNSLANP GIAMATHKDD EERFFPSNGI  540
LIFGKQNAAR DNADYSDVML TSEEEIKTTN PVATEEYGIV ADNLQQQNTA PQIGTVNSQG  600
ALPGMVWQNR DVYLQGPIWA KIPHTDGNFH PSPLMGGFGL KHPPPQILIK NTPVPADPRS  660
TFNGDKLNSF ITQYSTGQVS VEIEWELQKE NSKRWNPEIQ YTSNYYKSTS VDFAVNTEGV  720
YSEPRPIGTR YLTRNL                                                  736

SEQ ID NO: 436          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 436
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STYPLQNNNS NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPR  660
STFNGDKLNS FITQYSTGQV SVEIEWELQK ENSKRWNPEI QYTSNYYKST SVDFAVNTEG  720
VYSEPRPIGT RYLTRNL                                                 737

SEQ ID NO: 437          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 437
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
```

```
TTSTRTWALP  TYNNHLYKQI  SNGTSGGATN  DNTYFGYSTP  WGYFDFNRFH  CHFSPRDWQR   300
LINNNWGFRP  KRLSFKLFNI  QVKEVTQNEG  TKTIANNLTS  TIQVFTDSEY  QLPYVLGSAH   360
QGCLPPFPAD  VFMIPQYGYL  TLNNGSQAVG  RSSFYCLEYF  PSQMLRTGNN  FQFTYTFEDV   420
PFHSSYAHSQ  SLDRLMNPLI  DQYLYYLSRT  QTTSNGRGVT  LGFSQGGPNT  MANQAKNWLP   480
GPCYRQQRVS  TYPLQNNNSN  FAWTAGTKYH  LNGRNSLANP  GIAMATHKDD  EERFFPSNGI   540
LIFGKQNAAR  DNADYSDVML  TSEEEIKTTN  PVATEEYGIV  ADNVMEPTRA  PQIGTVNSQG   600
ALPGMVWQNR  DVYLQGPIWA  KIPHTDGNFH  PSPLMGGFGL  KHPPPQILIK  NTPVPADPRS   660
TFNGDKLNSF  ITQYSTGQVS  VEIEWELQKE  NSKRWNPEIQ  YTSNYYKSTS  VDFAVNTEGV   720
YSEPRPIGTR  YLTRNL                                                      736

SEQ ID NO: 438           moltype = AA  length = 737
FEATURE                  Location/Qualifiers
REGION                   1..737
                         note = AAV capsid variant
source                   1..737
                         mol_type = protein
                         organism = synthetic construct
SEQUENCE: 438
MAADGYLPDW  LEDNLSEGIR  EWWALKPGAP  KPKANQQKQD  DGRGLVLPGY  KYLGPFNGLD   60
KGEPVNAADA  AALEHDKAYD  QQLQAGDNPY  LRYNHADAEF  QERLQEDTSF  GGNLGRAVFQ   120
AKKRVLEPLG  LVEEGAKTAP  GKKRPVEPSP  QRSPDSSTGI  GKKGQQPARK  RLNFGQTGDS   180
ESVPDPQPLG  EPPAAPSGVG  PNTMAAGGGA  PMADNNEGAD  GVGSSSGNWH  CDSTWLGDRV   240
ITTSTRTWAL  PTYNNHLYKQ  ISNGTSGGAT  NDNTYFGYST  PWGYFDFNRF  HCHFSPRDWQ   300
RLINNNWGFR  PKRLSFKLFN  IQVKEVTQNE  GTKTIANNLT  STIQVFTDSE  YQLPYVLGSA   360
HQGCLPPFPA  DVFMIPQYGY  LTLNNGSQAV  GRSSFYCLEY  FPSQMLRTGN  NFQFTYTFED   420
VPFHSSYAHS  QSLDRLMNPL  IDQYLYYLSR  TQTTSNGRGV  TLGFSQGGPN  TMANQAKNWL   480
PGPCYRQQRV  STYPLQNNNS  NFAWTAGTKY  HLNGRNSLAN  PGIAMATHKD  DEERFFPSNG   540
ILIFGKQNAA  RDNADYSDVM  LTSEEEIKTT  NPVATEEYGI  VADNVMEPTR  APQIGTVNSQ   600
GALPGMVWQN  RDVYLQGPIW  AKIPHTDGNF  HPSPLMGGFG  LKHPPPQILI  KNTPVPADPP   660
TTFNQSKLNS  FITQYSTGQV  SVEIEWELQK  ENSKRWNPEI  QYTSNYYKST  SVDFAVNTEG   720
VYSEPRPIGT  RYLTRNL                                                     737

SEQ ID NO: 439           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 439
MAADGYLPDW  LEDNLSEGIR  EWWALKPGAP  KPKANQQKQD  DGRGLVLPGY  KYLGPFNGLD   60
KGEPVNAADA  AALEHDKAYD  QQLQAGDNPY  LRYNHADAEF  QERLQEDTSF  GGNLGRAVFQ   120
AKKRVLEPLG  LVEEGAKTAP  GKKRPVEPSP  QRSPDSSTGI  GKKGQQPARK  RLNFGQTGDS   180
ESVPDPQPLG  EPPAAPSGVG  PNTMAAGGGA  PMADNNEGAD  GVGSSSGNWH  CDSTWLGDRV   240
ITTSTRTWAL  PTYNNHLYKQ  ISNGTSGGAT  NDNTYFGYST  PWGYFDFNRF  HCHFSPRDWQ   300
RLINNNWGFR  PKRLSFKLFN  IQVKEVTQNE  GTKTIANNLT  STIQVFTDSE  YQLPYVLGSA   360
HQGCLPPFPA  DVFMIPQYGY  LTLNNGSQAV  GRSSFYCLEY  FPSQMLRTGN  NFQFTYTFED   420
VPFHSSYAHS  QSLDRLMNPL  IDQYLYYLSR  TQTTGGTANT  QTLGFSQGGP  NTMANQAKNW   480
LPGPCYRQQR  VSTYPLENFK  YNFAWTAGTK  YHLNGRNSLA  NPGIAMATHK  DDEERFFPSN   540
GILIFGKQNA  ARDNADYSDV  MLTSEEEIKT  TNPVATEEYG  IVADNLQQQN  TAPQIGTVNS   600
QGALPGMVWQ  NRDVYLQGPI  WAKIPHTDGN  FHPSPLMGGF  GLKHPPPQIL  IKNTPVPADP   660
PTTFNQSKLN  SFITQYSTGQ  VSVEIEWELQ  KENSKRWNPE  IQYTSNYYKS  TSVDFAVNTE   720
GVYSEPRPIG  TRYLTRNL                                                    738

SEQ ID NO: 440           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 440
MAADGYLPDW  LEDNLSEGIR  EWWALKPGAP  KPKANQQKQD  DGRGLVLPGY  KYLGPFNGLD   60
KGEPVNAADA  AALEHDKAYD  QQLQAGDNPY  LRYNHADAEF  QERLQEDTSF  GGNLGRAVFQ   120
AKKRVLEPLG  LVEEGAKTAP  GKKRPVEPSP  QRSPDSSTGI  GKKGQQPARK  RLNFGQTGDS   180
ESVPDPQPLG  EPPAAPSGVG  PNTMAAGGGA  PMADNNEGAD  GVGSSSGNWH  CDSTWLGDRV   240
ITTSTRTWAL  PTYNNHLYKQ  ISNGTSGGAT  NDNTYFGYST  PWGYFDFNRF  HCHFSPRDWQ   300
RLINNNWGFR  PKRLSFKLFN  IQVKEVTQNE  GTKTIANNLT  STIQVFTDSE  YQLPYVLGSA   360
HQGCLPPFPA  DVFMIPQYGY  LTLNNGSQAV  GRSSFYCLEY  FPSQMLRTGN  NFQFTYTFED   420
VPFHSSYAHS  QSLDRLMNPL  IDQYLYYLSR  TQTTGGTANT  QTLGFSQGGP  NTMANQAKNW   480
LPGPCYRQQR  VSTYPLGDHS  ANFAWTAGTK  YHLNGRNSLA  NPGIAMATHK  DDEERFFPSN   540
GILIFGKQNA  ARDNADYSDV  MLTSEEEIKT  TNPVATEEYG  IVADNLQQQN  TAPQIGTVNS   600
QGALPGMVWQ  NRDVYLQGPI  WAKIPHTDGN  FHPSPLMGGF  GLKHPPPQIL  IKNTPVPADP   660
PTTFNQSKLN  SFITQYSTGQ  VSVEIEWELQ  KENSKRWNPE  IQYTSNYYKS  TSVDFAVNTE   720
GVYSEPRPIG  TRYLTRNL                                                    738

SEQ ID NO: 441           moltype = AA  length = 738
FEATURE                  Location/Qualifiers
REGION                   1..738
```

```
                         note = AAV capsid variant
source                   1..738
                         mol_type = protein
                         organism = synthetic construct
SEQUENCE: 441
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLASGS GNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 442           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 442
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLLGKE QNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 443           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 443
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLSGTN QNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 444           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 444
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
```

```
LPGPCYRQQR VSTYPLRDGQ LNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 445           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 445
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLADTG TNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 446           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 446
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLQNNN SNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 447           moltype = AA  length = 737
FEATURE                  Location/Qualifiers
REGION                   1..737
                         note = AAV capsid variant
source                   1..737
                         mol_type = protein
                         organism = synthetic construct
SEQUENCE: 447
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLQNNNS NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 448           moltype = AA  length = 737
FEATURE                  Location/Qualifiers
REGION                   1..737
                         note = AAV capsid variant
source                   1..737
                         mol_type = protein
                         organism = synthetic construct
```

```
SEQUENCE: 448
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLENFKY NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 449            moltype = AA  length = 737
FEATURE                   Location/Qualifiers
REGION                    1..737
                          note = AAV capsid variant
source                    1..737
                          mol_type = protein
                          organism = synthetic construct
SEQUENCE: 449
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLGDHSA NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 450            moltype = AA  length = 737
FEATURE                   Location/Qualifiers
REGION                    1..737
                          note = AAV capsid variant
source                    1..737
                          mol_type = protein
                          organism = synthetic construct
SEQUENCE: 450
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLASGSG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 451            moltype = AA  length = 737
FEATURE                   Location/Qualifiers
REGION                    1..737
                          note = AAV capsid variant
source                    1..737
                          mol_type = protein
                          organism = synthetic construct
SEQUENCE: 451
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLLGKEQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
```

```
VYSEPRPIGT RYLTRNL                                                         737

SEQ ID NO: 452          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 452
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLSGTNQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 453          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 453
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLRDGQL NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 454          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 454
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLADTGT NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 455          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 455
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
```

```
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLENFK YNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 456          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 456
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLGDHS ANFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 457          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 457
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLASGS GNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 458          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 458
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLLGKE QNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 459          moltype = AA  length = 738
FEATURE                 Location/Qualifiers
```

```
REGION                  1..738
                        note = AAV capsid variant
source                  1..738
                        mol_type = protein
                        organism = synthetic construct
SEQUENCE: 459
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLSGTN QNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 460          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 460
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLRDGQ LNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 461          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 461
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLADTG TNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 462          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 462
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
```

```
VPFHSSYAHS QSLDRLMNPL IDQYLYYLSR TQTTSNGRGV TLGFSQGGPN TMANQAKNWL    480
PGPCYRQQRV STYPLENFKY NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 463         moltype = AA  length = 737
FEATURE                Location/Qualifiers
REGION                 1..737
                       note = AAV capsid variant
source                 1..737
                       mol_type = protein
                       organism = synthetic construct
SEQUENCE: 463
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLGDHSA NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 464         moltype = AA  length = 737
FEATURE                Location/Qualifiers
REGION                 1..737
                       note = AAV capsid variant
source                 1..737
                       mol_type = protein
                       organism = synthetic construct
SEQUENCE: 464
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLASGSG NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 465         moltype = AA  length = 737
FEATURE                Location/Qualifiers
REGION                 1..737
                       note = AAV capsid variant
source                 1..737
                       mol_type = protein
                       organism = synthetic construct
SEQUENCE: 465
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLLGKEQ NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 466         moltype = AA  length = 737
FEATURE                Location/Qualifiers
REGION                 1..737
                       note = AAV capsid variant
source                 1..737
                       mol_type = protein
```

```
                      organism = synthetic construct
SEQUENCE: 466
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTSNGRGV TLGFSQGGPN TMANQAKNWL  480
PGPCYRQQRV STYPLSGTNQ NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                 737

SEQ ID NO: 467         moltype = AA  length = 737
FEATURE                Location/Qualifiers
REGION                 1..737
                       note = AAV capsid variant
source                 1..737
                       mol_type = protein
                       organism = synthetic construct
SEQUENCE: 467
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTSNGRGV TLGFSQGGPN TMANQAKNWL  480
PGPCYRQQRV STYPLRDGQL NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                 737

SEQ ID NO: 468         moltype = AA  length = 737
FEATURE                Location/Qualifiers
REGION                 1..737
                       note = AAV capsid variant
source                 1..737
                       mol_type = protein
                       organism = synthetic construct
SEQUENCE: 468
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTSNGRGV TLGFSQGGPN TMANQAKNWL  480
PGPCYRQQRV STYPLADTGT NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                 737

SEQ ID NO: 469         moltype = AA  length = 737
FEATURE                Location/Qualifiers
REGION                 1..737
                       note = AAV capsid variant
source                 1..737
                       mol_type = protein
                       organism = synthetic construct
SEQUENCE: 469
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STYPLQNNNS NFAWTAGTKY HLNGRNSLAN PGIAMATHKD DEERFFPSNG  540
ILIFGKQNAA RDNADYSDVM LTSEEEIKTT NPVATEEYGI VADNLQQNT  APQIGTVNSQ  600
GALPGMVWQN RDVYLQGPIW AKIPHTDGNF HPSPLMGGFG LKHPPPQILI KNTPVPADPP  660
```

```
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 470         moltype = AA   length = 736
FEATURE                Location/Qualifiers
REGION                 1..736
                       note = AAV capsid variant
source                 1..736
                       mol_type = protein
                       organism = synthetic construct
SEQUENCE: 470
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLQNNNSN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                   736

SEQ ID NO: 471         moltype = AA   length = 737
FEATURE                Location/Qualifiers
REGION                 1..737
                       note = AAV capsid variant
source                 1..737
                       mol_type = protein
                       organism = synthetic construct
SEQUENCE: 471
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLENFKY NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 472         moltype = AA   length = 737
FEATURE                Location/Qualifiers
REGION                 1..737
                       note = AAV capsid variant
source                 1..737
                       mol_type = protein
                       organism = synthetic construct
SEQUENCE: 472
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLGDHSA NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 473         moltype = AA   length = 737
FEATURE                Location/Qualifiers
REGION                 1..737
                       note = AAV capsid variant
source                 1..737
                       mol_type = protein
                       organism = synthetic construct
SEQUENCE: 473
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
```

```
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLASGSG NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 474          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 474
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLLGKEQ NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 475          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 475
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLSGTNQ NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 476          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 476
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLRDGQL NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 477          moltype = AA   length = 737
```

```
FEATURE                 Location/Qualifiers
REGION                  1..737
                        note = AAV capsid variant
source                  1..737
                        mol_type = protein
                        organism = synthetic construct
SEQUENCE: 477
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLADTGT NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 478          moltype = AA length = 737
FEATURE                 Location/Qualifiers
REGION                  1..737
                        note = AAV capsid variant
source                  1..737
                        mol_type = protein
                        organism = synthetic construct
SEQUENCE: 478
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLQNNNS NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 479          moltype = AA length = 736
FEATURE                 Location/Qualifiers
REGION                  1..736
                        note = AAV capsid variant
source                  1..736
                        mol_type = protein
                        organism = synthetic construct
SEQUENCE: 479
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLQNNNSN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 480          moltype = AA length = 736
FEATURE                 Location/Qualifiers
REGION                  1..736
                        note = AAV capsid variant
source                  1..736
                        mol_type = protein
                        organism = synthetic construct
SEQUENCE: 480
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
```

```
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLENFKYN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 481         moltype = AA  length = 736
FEATURE                Location/Qualifiers
REGION                 1..736
                       note = AAV capsid variant
source                 1..736
                       mol_type = protein
                       organism = synthetic construct
SEQUENCE: 481
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLGDHSAN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 482         moltype = AA  length = 736
FEATURE                Location/Qualifiers
REGION                 1..736
                       note = AAV capsid variant
source                 1..736
                       mol_type = protein
                       organism = synthetic construct
SEQUENCE: 482
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLASGSGN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 483         moltype = AA  length = 736
FEATURE                Location/Qualifiers
REGION                 1..736
                       note = AAV capsid variant
source                 1..736
                       mol_type = protein
                       organism = synthetic construct
SEQUENCE: 483
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLLGKEQN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 484         moltype = AA  length = 736
FEATURE                Location/Qualifiers
REGION                 1..736
                       note = AAV capsid variant
source                 1..736
```

```
                    mol_type = protein
                    organism = synthetic construct
SEQUENCE: 484
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLSGTNQN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 485          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 485
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLRDGQLN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 486          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 486
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLADTGTN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 487          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 487
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLENFKY NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
```

```
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 488           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 488
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STYPLGDHSA NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 489           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 489
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STYPLASGSG NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 490           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 490
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTANTQ TLGFSQGGPN TMANQAKNWL  480
PGPCYRQQRV STYPLLGKEQ NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                737

SEQ ID NO: 491           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 491
MAADGYLPDW LEDNLSEGIR EWWALKPGAP QPKANQQHQD NARGLVLPGY KYLGPGNGLD  60
```

```
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLSGTNQ NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 492          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 492
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLRDGQL NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 493          moltype = AA   length = 737
FEATURE                 Location/Qualifiers
REGION                  1..737
                        note = AAV capsid variant
source                  1..737
                        mol_type = protein
                        organism = synthetic construct
SEQUENCE: 493
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLADTGT NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 494          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 494
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLENFKYN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                  736
```

| SEQ ID NO: 495 | moltype = AA length = 736 |
| --- | --- |
| FEATURE | Location/Qualifiers |
| REGION | 1..736 |
| | note = AAV capsid variant |
| source | 1..736 |
| | mol_type = protein |
| | organism = synthetic construct |

SEQUENCE: 495
```
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TIQVFTDSEY QLPYVLGSAH 360
QGCLPPFPAD VFMIPQYGYL TLNNGSQAVG RSSFYCLEYF PSQMLRTGNN FQFTYTFEDV 420
PFHSSYAHSQ SLDRLMNPLI DQYLYYLSRT QTTSNGRGVT LGFSQGGPNT MANQAKNWLP 480
GPCYRQQRVS TYPLGDHSAN FAWTAGTKYH LNGRNSLANP GIAMATHKDD EERFFPSNGI 540
LIFGKQNAAR DNADYSDVML TSEEEIKTTN PVATEEYGIV ADNVMEPTRA PQIGTVNSQG 600
ALPGMVWQNR DVYLQGPIWA KIPHTDGNFH PSPLMGGFGL KHPPPQILIK NTPVPADPPT 660
TFNQSKLNSF ITQYSTGQVS VEIEWELQKE NSKRWNPEIQ YTSNYYKSTS VDFAVNTEGV 720
YSEPRPIGTR YLTRNL                                                736
```

| SEQ ID NO: 496 | moltype = AA length = 736 |
| --- | --- |
| FEATURE | Location/Qualifiers |
| REGION | 1..736 |
| | note = AAV capsid variant |
| source | 1..736 |
| | mol_type = protein |
| | organism = synthetic construct |

SEQUENCE: 496
```
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TIQVFTDSEY QLPYVLGSAH 360
QGCLPPFPAD VFMIPQYGYL TLNNGSQAVG RSSFYCLEYF PSQMLRTGNN FQFTYTFEDV 420
PFHSSYAHSQ SLDRLMNPLI DQYLYYLSRT QTTSNGRGVT LGFSQGGPNT MANQAKNWLP 480
GPCYRQQRVS TYPLASGSGN FAWTAGTKYH LNGRNSLANP GIAMATHKDD EERFFPSNGI 540
LIFGKQNAAR DNADYSDVML TSEEEIKTTN PVATEEYGIV ADNVMEPTRA PQIGTVNSQG 600
ALPGMVWQNR DVYLQGPIWA KIPHTDGNFH PSPLMGGFGL KHPPPQILIK NTPVPADPPT 660
TFNQSKLNSF ITQYSTGQVS VEIEWELQKE NSKRWNPEIQ YTSNYYKSTS VDFAVNTEGV 720
YSEPRPIGTR YLTRNL                                                736
```

| SEQ ID NO: 497 | moltype = AA length = 736 |
| --- | --- |
| FEATURE | Location/Qualifiers |
| REGION | 1..736 |
| | note = AAV capsid variant |
| source | 1..736 |
| | mol_type = protein |
| | organism = synthetic construct |

SEQUENCE: 497
```
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TIQVFTDSEY QLPYVLGSAH 360
QGCLPPFPAD VFMIPQYGYL TLNNGSQAVG RSSFYCLEYF PSQMLRTGNN FQFTYTFEDV 420
PFHSSYAHSQ SLDRLMNPLI DQYLYYLSRT QTTSNGRGVT LGFSQGGPNT MANQAKNWLP 480
GPCYRQQRVS TYPLLGKEQN FAWTAGTKYH LNGRNSLANP GIAMATHKDD EERFFPSNGI 540
LIFGKQNAAR DNADYSDVML TSEEEIKTTN PVATEEYGIV ADNVMEPTRA PQIGTVNSQG 600
ALPGMVWQNR DVYLQGPIWA KIPHTDGNFH PSPLMGGFGL KHPPPQILIK NTPVPADPPT 660
TFNQSKLNSF ITQYSTGQVS VEIEWELQKE NSKRWNPEIQ YTSNYYKSTS VDFAVNTEGV 720
YSEPRPIGTR YLTRNL                                                736
```

| SEQ ID NO: 498 | moltype = AA length = 736 |
| --- | --- |
| FEATURE | Location/Qualifiers |
| REGION | 1..736 |
| | note = AAV capsid variant |
| source | 1..736 |
| | mol_type = protein |
| | organism = synthetic construct |

SEQUENCE: 498
```
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
```

```
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLSGTNQN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 499          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 499
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLRDGQLN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 500          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 500
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLADTGTN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 501          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 501
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLNGGV VNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                 738

SEQ ID NO: 502          moltype = AA   length = 738
FEATURE                 Location/Qualifiers
REGION                  1..738
                        note = AAV capsid variant
```

```
source                     1..738
                           mol_type = protein
                           organism = synthetic construct
SEQUENCE: 502
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLEMPI GNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 503             moltype = AA  length = 739
FEATURE                    Location/Qualifiers
REGION                     1..739
                           note = AAV capsid variant
source                     1..739
                           mol_type = protein
                           organism = synthetic construct
SEQUENCE: 503
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLEDMG TINFAWTAGT KYHLNGRNSL ANPGIAMATH KDDEERFFPS   540
NGILIFGKQN AARDNADYSD VMLTSEEEIK TTNPVATEEY GIVADNLQQQ NTAPQIGTVN   600
SQGALPGMVW QNRDVYLQGP IWAKIPHTDG NFHPSPLMGG FGLKHPPPQI LIKNTPVPAD   660
PPTTFNQSKL NSFITQYSTG QVSVEIEWEL QKENSKRWNP EIQYTSNYYK STSVDFAVNT   720
EGVYSEPRPI GTRYLTRNL                                                739

SEQ ID NO: 504             moltype = AA  length = 737
FEATURE                    Location/Qualifiers
REGION                     1..737
                           note = AAV capsid variant
source                     1..737
                           mol_type = protein
                           organism = synthetic construct
SEQUENCE: 504
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLNGGVV NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 505             moltype = AA  length = 737
FEATURE                    Location/Qualifiers
REGION                     1..737
                           note = AAV capsid variant
source                     1..737
                           mol_type = protein
                           organism = synthetic construct
SEQUENCE: 505
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLEMPIG NFAWTAGTKY HLNGRNSLAN PGIAMATHKD DEERFFPSNG   540
```

```
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                   737

SEQ ID NO: 506          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 506
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLEDMGT INFAWTAGTK YHLNGRNSLA NPGIAMATHK DDEERFPSN     540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 507          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 507
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
LPGPCYRQQR VSTYPLNGGV VNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 508          moltype = AA   length = 738
FEATURE                 Location/Qualifiers
REGION                  1..738
                        note = AAV capsid variant
source                  1..738
                        mol_type = protein
                        organism = synthetic construct
SEQUENCE: 508
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLEMPI GNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                  738

SEQ ID NO: 509          moltype = AA   length = 739
FEATURE                 Location/Qualifiers
REGION                  1..739
                        note = AAV capsid variant
source                  1..739
                        mol_type = protein
                        organism = synthetic construct
SEQUENCE: 509
```

```
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLEDMG TINFAWTAGT KYHLNGRNSL ANPGIAMATH KDDEERFFPS   540
NGILIFGKQN AARDNADYSD VMLTSEEEIK TTNPVATEEY GIVADNVMEP TRAPQIGTVN   600
SQGALPGMVW QNRDVYLQGP IWAKIPHTDG NFHPSPLMGG FGLKHPPPQI LIKNTPVPAD   660
PPTTFNQSKL NSFITQYSTG QVSVEIEWEL QKENSKRWNP EIQYTSNYYK STSVDFAVNT   720
EGVYSEPRPI GTRYLTRNL                                               739

SEQ ID NO: 510           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 510
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLNGGVV NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 511           moltype = AA   length = 737
FEATURE                  Location/Qualifiers
REGION                   1..737
                         note = AAV capsid variant
source                   1..737
                         mol_type = protein
                         organism = synthetic construct
SEQUENCE: 511
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLEMPIG NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 512           moltype = AA   length = 738
FEATURE                  Location/Qualifiers
REGION                   1..738
                         note = AAV capsid variant
source                   1..738
                         mol_type = protein
                         organism = synthetic construct
SEQUENCE: 512
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLEDMGT INFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738
```

```
SEQ ID NO: 513            moltype = AA   length = 737
FEATURE                   Location/Qualifiers
REGION                    1..737
                          note = AAV capsid variant
source                    1..737
                          mol_type = protein
                          organism = synthetic construct
SEQUENCE: 513
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLNGGVV NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 514            moltype = AA   length = 737
FEATURE                   Location/Qualifiers
REGION                    1..737
                          note = AAV capsid variant
source                    1..737
                          mol_type = protein
                          organism = synthetic construct
SEQUENCE: 514
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLEMPIG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 515            moltype = AA   length = 738
FEATURE                   Location/Qualifiers
REGION                    1..738
                          note = AAV capsid variant
source                    1..738
                          mol_type = protein
                          organism = synthetic construct
SEQUENCE: 515
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLEDMGT INFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                738

SEQ ID NO: 516            moltype = AA   length = 736
FEATURE                   Location/Qualifiers
REGION                    1..736
                          note = AAV capsid variant
source                    1..736
                          mol_type = protein
                          organism = synthetic construct
SEQUENCE: 516
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
```

```
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLNGGVVN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                   736

SEQ ID NO: 517          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 517
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLEMPIGN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                   736

SEQ ID NO: 518          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 518
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLEDMGTI NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 519          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 519
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLNGGVV NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 520          moltype = AA  length = 737
FEATURE                 Location/Qualifiers
REGION                  1..737
```

```
                          note = AAV capsid variant
source                    1..737
                          mol_type = protein
                          organism = synthetic construct
SEQUENCE: 520
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLEMPIG NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                  737

SEQ ID NO: 521            moltype = AA   length = 738
FEATURE                   Location/Qualifiers
REGION                    1..738
                          note = AAV capsid variant
source                    1..738
                          mol_type = protein
                          organism = synthetic construct
SEQUENCE: 521
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLEDMGT INFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 522            moltype = AA   length = 736
FEATURE                   Location/Qualifiers
REGION                    1..736
                          note = AAV capsid variant
source                    1..736
                          mol_type = protein
                          organism = synthetic construct
SEQUENCE: 522
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLNGGVVN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPPT   660
TFNQSKLNSF ITQYSTGQVS VEIEWELQKE NSKRWNPEIQ YTSNYYKSTS VDFAVNTEGV   720
YSEPRPIGTR YLTRNL                                                   736

SEQ ID NO: 523            moltype = AA   length = 736
FEATURE                   Location/Qualifiers
REGION                    1..736
                          note = AAV capsid variant
source                    1..736
                          mol_type = protein
                          organism = synthetic construct
SEQUENCE: 523
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
```

```
GPCYRQQRVS TYPLEMPIGN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPPT    660
TFNQSKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 524          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 524
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRVT LGFSQGGPNT MANQAKNWLP    480
GPCYRQQRVS TYPLEDMGTI NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPP    660
TTFNQSKLNS FITQYSTGQV SVEIEWELQK ENSKRWNPEI QYTSNYYKST SVDFAVNTEG    720
VYSEPRPIGT RYLTRNL                                                  737

SEQ ID NO: 525          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 525
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLQNNNS NFAWTAGTKY HLNGRNSLAN PGIAMATHKD DEERFFPSNG    540
ILIFGKQNAA RDNADYSDVM LTSEEEIKTT NPVATEEYGI VADNLQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 526          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 526
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLENFK YNFAWTAGTK YHLNGRNSLA NPGIAMATHK DDEERFFPSN    540
GILIFGKQNA ARDNADYSDV MLTSEEEIKT NPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 527          moltype = AA  length = 738
FEATURE                 Location/Qualifiers
REGION                  1..738
                        note = AAV capsid variant
source                  1..738
                        mol_type = protein
                        organism = synthetic construct
```

```
SEQUENCE: 527
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLGDHS ANFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 528         moltype = AA  length = 738
FEATURE                Location/Qualifiers
REGION                 1..738
                       note = AAV capsid variant
source                 1..738
                       mol_type = protein
                       organism = synthetic construct
SEQUENCE: 528
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLASGS GNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 529         moltype = AA  length = 738
FEATURE                Location/Qualifiers
REGION                 1..738
                       note = AAV capsid variant
source                 1..738
                       mol_type = protein
                       organism = synthetic construct
SEQUENCE: 529
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLLGKE QNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 530         moltype = AA  length = 738
FEATURE                Location/Qualifiers
REGION                 1..738
                       note = AAV capsid variant
source                 1..738
                       mol_type = protein
                       organism = synthetic construct
SEQUENCE: 530
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLSGTN QNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
```

```
GVYSEPRPIG TRYLTRNL                                                      738

SEQ ID NO: 531          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 531
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTGGTANT QTLGFSQGGP NTMANQAKNW 480
LPGPCYRQQR VSTYPLRDGQ LNFAWTAGTK YHLNGRNSLA NPGIAMATHK DDEERFFPSN 540
GILIFGKQNA ARDNADYSDV MLTSEEEIKT TNPVATEEYG IVADNLQQQN TAPQIGTVNS 600
QGALPGMVWQ NRDVYLQGPI WAKIPHTDGN FHPSPLMGGF GLKHPPPQIL IKNTPVPADP 660
RSTFNGDKLN SFITQYSTGQ VSVEIEWELQ KENSKRWNPE IQYTSNYYKS TSVDFAVNTE 720
GVYSEPRPIG TRYLTRNL                                                  738

SEQ ID NO: 532          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 532
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTGGTANT QTLGFSQGGP NTMANQAKNW 480
LPGPCYRQQR VSTYPLADTG TNFAWTAGTK YHLNGRNSLA NPGIAMATHK DDEERFFPSN 540
GILIFGKQNA ARDNADYSDV MLTSEEEIKT TNPVATEEYG IVADNLQQQN TAPQIGTVNS 600
QGALPGMVWQ NRDVYLQGPI WAKIPHTDGN FHPSPLMGGF GLKHPPPQIL IKNTPVPADP 660
RSTFNGDKLN SFITQYSTGQ VSVEIEWELQ KENSKRWNPE IQYTSNYYKS TSVDFAVNTE 720
GVYSEPRPIG TRYLTRNL                                                  738

SEQ ID NO: 533          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 533
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
ESVPDPQPLG EPPAAPSGVG PNTMAAGGGA PMADNNEGAD GVGSSSGNWH CDSTWLGDRV 240
ITTSTRTWAL PTYNNHLYKQ ISNGTSGGAT NDNTYFGYST PWGYFDFNRF HCHFSPRDWQ 300
RLINNNWGFR PKRLSFKLFN IQVKEVTQNE GTKTIANNLT STIQVFTDSE YQLPYVLGSA 360
HQGCLPPFPA DVFMIPQYGY LTLNNGSQAV GRSSFYCLEY FPSQMLRTGN NFQFTYTFED 420
VPFHSSYAHS QSLDRLMNPL IDQYLYYLSR TQTTGGTANT QTLGFSQGGP NTMANQAKNW 480
LPGPCYRQQR VSTYPLQNNN SNFAWTAGTK YHLNGRNSLA NPGIAMATHK DDEERFFPSN 540
GILIFGKQNA ARDNADYSDV MLTSEEEIKT TNPVATEEYG IVADNVMEPT RAPQIGTVNS 600
QGALPGMVWQ NRDVYLQGPI WAKIPHTDGN FHPSPLMGGF GLKHPPPQIL IKNTPVPADP 660
RSTFNGDKLN SFITQYSTGQ VSVEIEWELQ KENSKRWNPE IQYTSNYYKS TSVDFAVNTE 720
GVYSEPRPIG TRYLTRNL                                                  738

SEQ ID NO: 534          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 534
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ 120
AKKRVLEPLG LVEEGAKTAP GKKRPVEPSP QRSPDSSTGI GKKGQQPARK RLNFGQTGDS 180
```

```
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLQNNNS NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 535          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 535
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLENFKY NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 536          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 536
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLGDHSA NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 537          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 537
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLASGSG NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 538          moltype = AA  length = 737
FEATURE                 Location/Qualifiers
```

```
REGION                      1..737
                            note = AAV capsid variant
source                      1..737
                            mol_type = protein
                            organism = synthetic construct
SEQUENCE: 538
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLLGKEQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 539              moltype = AA  length = 737
FEATURE                     Location/Qualifiers
REGION                      1..737
                            note = AAV capsid variant
source                      1..737
                            mol_type = protein
                            organism = synthetic construct
SEQUENCE: 539
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLSGTNQ NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 540              moltype = AA  length = 737
FEATURE                     Location/Qualifiers
REGION                      1..737
                            note = AAV capsid variant
source                      1..737
                            mol_type = protein
                            organism = synthetic construct
SEQUENCE: 540
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLRDGQL NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 541              moltype = AA  length = 737
FEATURE                     Location/Qualifiers
REGION                      1..737
                            note = AAV capsid variant
source                      1..737
                            mol_type = protein
                            organism = synthetic construct
SEQUENCE: 541
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
```

```
VPFHSSYAHS QSLDRLMNPL IDQYLYYLSR TQTTSNGRGV TLGFSQGGPN TMANQAKNWL    480
PGPCYRQQRV STYPLADTGT NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 542          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 542
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLENFK YNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 543          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 543
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLGDHS ANFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 544          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 544
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLASGS GNFAWTAGTK YHLNGRNSLA NPGIAMATHK DDEERFFPSN    540
GILIFGKQNA ARDNADYSDV MLTSEEEIKT TNPVATEEYG IVADNVMEPT RAPQIGTVNS    600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                 738

SEQ ID NO: 545          moltype = AA  length = 738
FEATURE                 Location/Qualifiers
REGION                  1..738
                        note = AAV capsid variant
source                  1..738
                        mol_type = protein
```

```
                        organism = synthetic construct
SEQUENCE: 545
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLLGKE QNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 546           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 546
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLSGTN QNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 547           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 547
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLRDGQ LNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 548           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 548
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLADTG TNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
```

```
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 549          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 549
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLENFKY NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 550          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 550
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLGDHSA NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 551          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 551
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLASGSG NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 552          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 552
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
```

```
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLLGKEQ NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 553         moltype = AA  length = 737
FEATURE                Location/Qualifiers
REGION                 1..737
                       note = AAV capsid variant
source                 1..737
                       mol_type = protein
                       organism = synthetic construct
SEQUENCE: 553
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLSGTNQ NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 554         moltype = AA  length = 737
FEATURE                Location/Qualifiers
REGION                 1..737
                       note = AAV capsid variant
source                 1..737
                       mol_type = protein
                       organism = synthetic construct
SEQUENCE: 554
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLRDGQL NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 555         moltype = AA  length = 737
FEATURE                Location/Qualifiers
REGION                 1..737
                       note = AAV capsid variant
source                 1..737
                       mol_type = protein
                       organism = synthetic construct
SEQUENCE: 555
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLADTGT NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                  737

SEQ ID NO: 556         moltype = AA  length = 737
```

```
FEATURE                 Location/Qualifiers
REGION                  1..737
                        note = AAV capsid variant
source                  1..737
                        mol_type = protein
                        organism = synthetic construct
SEQUENCE: 556
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLQNNNS NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 557          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 557
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLQNNNSN FAWTAGTKYH LNGRNSLANP GIAMATHKDD EERFFPSNGI   540
LIFGKQNAAR DNADYSDVML TSEEEIKTTN PVATEEYGIV ADNLQQQNTA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 558          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 558
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLENFKY NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 559          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 559
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
```

```
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTGGTANTQ TLGFSQGGPN TMANQAKNWL     480
PGPCYRQQRV STYPLGDHSA NFAWTAGTKY HLNGRNSLAN PGIAMATHKD DEERFFPSNG     540
ILIFGKQNAA RDNADYSDVM LTSEEEIKTT NPVATEEYGI VADNLQQQNT APQIGTVNSQ     600
GALPGMVWQN RDVYLQGPIW AKIPHTDGNF HPSPLMGGFG LKHPPPQILI KNTPVPADPR     660
STFNGDKLNS FITQYSTGQV SVEIEWELQK ENSKRWNPEI QYTSNYYKST SVDFAVNTEG     720
VYSEPRPIGT RYLTRNL                                                   737

SEQ ID NO: 560          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 560
MAADGYLPDW LEDNLSEGIR EWWALKPGAP QPKANQQHQD NARGLVLPGY KYLGPGNGLD      60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDSE     180
SVPDPQPLGE PPAAPSGVGP NTMAAGGGAP MADNNEGADG VGSSSGNWHC DSTWLGDRVI     240
TTSTRTWALP TYNNHLYKQI SNGTSGGATN DNTYFGYSTP WGYFDFNRFH CHFSPRDWQR     300
LINNNWGFRP KRLSFKLFNI QVKEVTQNEG TKTIANNLTS TIQVFTDSEY QLPYVLGSAH     360
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTGGTANTQ TLGFSQGGPN TMANQAKNWL     480
PGPCYRQQRV STYPLASGSG NFAWTAGTKY HLNGRNSLAN PGIAMATHKD DEERFFPSNG     540
ILIFGKQNAA RDNADYSDVM LTSEEEIKTT NPVATEEYGI VADNLQQQNT APQIGTVNSQ     600
GALPGMVWQN RDVYLQGPIW AKIPHTDGNF HPSPLMGGFG LKHPPPQILI KNTPVPADPR     660
STFNGDKLNS FITQYSTGQV SVEIEWELQK ENSKRWNPEI QYTSNYYKST SVDFAVNTEG     720
VYSEPRPIGT RYLTRNL                                                   737

SEQ ID NO: 561          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 561
MAADGYLPDW LEDNLSEGIR EWWALKPGAP QPKANQQHQD NARGLVLPGY KYLGPGNGLD      60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDSE     180
SVPDPQPLGE PPAAPSGVGP NTMAAGGGAP MADNNEGADG VGSSSGNWHC DSTWLGDRVI     240
TTSTRTWALP TYNNHLYKQI SNGTSGGATN DNTYFGYSTP WGYFDFNRFH CHFSPRDWQR     300
LINNNWGFRP KRLSFKLFNI QVKEVTQNEG TKTIANNLTS TIQVFTDSEY QLPYVLGSAH     360
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTGGTANTQ TLGFSQGGPN TMANQAKNWL     480
PGPCYRQQRV STYPLLGKEQ NFAWTAGTKY HLNGRNSLAN PGIAMATHKD DEERFFPSNG     540
ILIFGKQNAA RDNADYSDVM LTSEEEIKTT NPVATEEYGI VADNLQQQNT APQIGTVNSQ     600
GALPGMVWQN RDVYLQGPIW AKIPHTDGNF HPSPLMGGFG LKHPPPQILI KNTPVPADPR     660
STFNGDKLNS FITQYSTGQV SVEIEWELQK ENSKRWNPEI QYTSNYYKST SVDFAVNTEG     720
VYSEPRPIGT RYLTRNL                                                   737

SEQ ID NO: 562          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 562
MAADGYLPDW LEDNLSEGIR EWWALKPGAP QPKANQQHQD NARGLVLPGY KYLGPGNGLD      60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDSE     180
SVPDPQPLGE PPAAPSGVGP NTMAAGGGAP MADNNEGADG VGSSSGNWHC DSTWLGDRVI     240
TTSTRTWALP TYNNHLYKQI SNGTSGGATN DNTYFGYSTP WGYFDFNRFH CHFSPRDWQR     300
LINNNWGFRP KRLSFKLFNI QVKEVTQNEG TKTIANNLTS TIQVFTDSEY QLPYVLGSAH     360
QGCLPPFPAD VFMIPQYGYL TLNNGSQAVG RSSFYCLEYF PSQMLRTGNN FQFTYTFEDV     420
PFHSSYAHSQ SLDRLMNPLI DQYLYYLSRT QTTGGTANTQ TLGFSQGGPN TMANQAKNWL     480
PGPCYRQQRV STYPLSGTNQ NFAWTAGTKY HLNGRNSLAN PGIAMATHKD DEERFFPSNG     540
ILIFGKQNAA RDNADYSDVM LTSEEEIKTT NPVATEEYGI VADNLQQQNT APQIGTVNSQ     600
GALPGMVWQN RDVYLQGPIW AKIPHTDGNF HPSPLMGGFG LKHPPPQILI KNTPVPADPR     660
STFNGDKLNS FITQYSTGQV SVEIEWELQK ENSKRWNPEI QYTSNYYKST SVDFAVNTEG     720
VYSEPRPIGT RYLTRNL                                                   737

SEQ ID NO: 563          moltype = AA  length = 737
FEATURE                 Location/Qualifiers
REGION                  1..737
                        note = AAV capsid variant
source                  1..737
```

```
                        mol_type = protein
                        organism = synthetic construct
SEQUENCE: 563
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TIQVFTDSEY QLPYVLGSAH 360
QGCLPPFPAD VFMIPQYGYL TLNNGSQAVG RSSFYCLEYF PSQMLRTGNN FQFTYTFEDV 420
PFHSSYAHSQ SLDRLMNPLI DQYLYYLSRT QTTGGTANTQ TLGFSQGGPN TMANQAKNWL 480
PGPCYRQQRV STYPLRDGQL NFAWTAGTKY HLNGRNSLAN PGIAMATHKD DEERFFPSNG 540
ILIFGKQNAA RDNADYSDVM LTSEEEIKTT NPVATEEYGI VADNLQQQNT APQIGTVNSQ 600
GALPGMVWQN RDVYLQGPIW AKIPHTDGNF HPSPLMGGFG LKHPPPQILI KNTPVPADPR 660
STFNGDKLNS FITQYSTGQV SVEIEWELQK ENSKRWNPEI QYTSNYYKST SVDFAVNTEG 720
VYSEPRPIGT RYLTRNL                                                737

SEQ ID NO: 564          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 564
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TIQVFTDSEY QLPYVLGSAH 360
QGCLPPFPAD VFMIPQYGYL TLNNGSQAVG RSSFYCLEYF PSQMLRTGNN FQFTYTFEDV 420
PFHSSYAHSQ SLDRLMNPLI DQYLYYLSRT QTTGGTANTQ TLGFSQGGPN TMANQAKNWL 480
PGPCYRQQRV STYPLADTGT NFAWTAGTKY HLNGRNSLAN PGIAMATHKD DEERFFPSNG 540
ILIFGKQNAA RDNADYSDVM LTSEEEIKTT NPVATEEYGI VADNLQQQNT APQIGTVNSQ 600
GALPGMVWQN RDVYLQGPIW AKIPHTDGNF HPSPLMGGFG LKHPPPQILI KNTPVPADPR 660
STFNGDKLNS FITQYSTGQV SVEIEWELQK ENSKRWNPEI QYTSNYYKST SVDFAVNTEG 720
VYSEPRPIGT RYLTRNL                                                737

SEQ ID NO: 565          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 565
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TIQVFTDSEY QLPYVLGSAH 360
QGCLPPFPAD VFMIPQYGYL TLNNGSQAVG RSSFYCLEYF PSQMLRTGNN FQFTYTFEDV 420
PFHSSYAHSQ SLDRLMNPLI DQYLYYLSRT QTTGGTANTQ TLGFSQGGPN TMANQAKNWL 480
PGPCYRQQRV STYPLQNNNS NFAWTAGTKY HLNGRNSLAN PGIAMATHKD DEERFFPSNG 540
ILIFGKQNAA RDNADYSDVM LTSEEEIKTT NPVATEEYGI VADNVMEPTR APQIGTVNSQ 600
GALPGMVWQN RDVYLQGPIW AKIPHTDGNF HPSPLMGGFG LKHPPPQILI KNTPVPADPR 660
STFNGDKLNS FITQYSTGQV SVEIEWELQK ENSKRWNPEI QYTSNYYKST SVDFAVNTEG 720
VYSEPRPIGT RYLTRNL                                                737

SEQ ID NO: 566          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 566
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDSE 180
SVPDPQPLGE PPAAPSGVGP NTMAAGGGAP MADNNEGADG VGSSSGNWHC DSTWLGDRVI 240
TTSTRTWALP TYNNHLYKQI SNGTSGGATN DNTYFGYSTP WGYFDFNRFH CHFSPRDWQR 300
LINNNWGFRP KRLSFKLFNI QVKEVTQNEG TKTIANNLTS TIQVFTDSEY QLPYVLGSAH 360
QGCLPPFPAD VFMIPQYGYL TLNNGSQAVG RSSFYCLEYF PSQMLRTGNN FQFTYTFEDV 420
PFHSSYAHSQ SLDRLMNPLI DQYLYYLSRT QTTSNGRGVT LGFSQGGPNT MANQAKNWLP 480
GPCYRQQRVS TYPLQNNNSN FAWTAGTKYH LNGRNSLANP GIAMATHKDD EERFFPSNGI 540
LIFGKQNAAR DNADYSDVML TSEEEIKTTN PVATEEYGIV ADNVMEPTRA PQIGTVNSQG 600
```

```
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 567          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 567
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLENFKYN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 568          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 568
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLGDHSAN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 569          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 569
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLASGSGN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 570          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 570
MAADGYLPDW LEDNLSEGIR EWWALKPGAP QPKANQQHQD NARGLVLPGY KYLGPGNGLD    60
```

```
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLLGKEQN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 571          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 571
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLSGTNQN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 572          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 572
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLRDGQLN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 573          moltype = AA   length = 736
FEATURE                 Location/Qualifiers
REGION                  1..736
                        note = AAV capsid variant
source                  1..736
                        mol_type = protein
                        organism = synthetic construct
SEQUENCE: 573
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLADTGTN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                    736
```

```
SEQ ID NO: 574          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 574
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLENFKY NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 575          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 575
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLGDHSA NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 576          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 576
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLASGSG NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 577          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 577
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
```

```
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLLGKEQ NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 578           moltype = AA  length = 737
FEATURE                  Location/Qualifiers
REGION                   1..737
                         note = AAV capsid variant
source                   1..737
                         mol_type = protein
                         organism = synthetic construct
SEQUENCE: 578
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLSGTNQ NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 579           moltype = AA  length = 737
FEATURE                  Location/Qualifiers
REGION                   1..737
                         note = AAV capsid variant
source                   1..737
                         mol_type = protein
                         organism = synthetic construct
SEQUENCE: 579
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLRDGQL NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 580           moltype = AA  length = 737
FEATURE                  Location/Qualifiers
REGION                   1..737
                         note = AAV capsid variant
source                   1..737
                         mol_type = protein
                         organism = synthetic construct
SEQUENCE: 580
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTGGTANTQ TLGFSQGGPN TMANQAKNWL    480
PGPCYRQQRV STYPLADTGT NFAWTAGTKY HLNGRNSLAN PGIAMATHKD DEERFFPSNG    540
ILIFGKQNAA RDNADYSDVM LTSEEEIKTT NPVATEEYGI VADNVMEPTR APQIGTVNSQ    600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 581           moltype = AA  length = 736
FEATURE                  Location/Qualifiers
REGION                   1..736
                         note = AAV capsid variant
```

```
source                  1..736
                        mol_type = protein
                        organism = synthetic construct
SEQUENCE: 581
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLENFKYN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 582          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 582
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLGDHSAN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 583          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 583
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLASGSGN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
YSEPRPIGTR YLTRNL                                                  736

SEQ ID NO: 584          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 584
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNGRGVT LGFSQGGPNT MANQAKNWLP   480
GPCYRQQRVS TYPLLGKEQN FAWTAGTKYH LNGRNSLANP GIAMATHKDD EERFFPSNGI   540
```

```
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 585           moltype = AA  length = 736
FEATURE                  Location/Qualifiers
REGION                   1..736
                         note = AAV capsid variant
source                   1..736
                         mol_type = protein
                         organism = synthetic construct
SEQUENCE: 585
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLSGTNQN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 586           moltype = AA  length = 736
FEATURE                  Location/Qualifiers
REGION                   1..736
                         note = AAV capsid variant
source                   1..736
                         mol_type = protein
                         organism = synthetic construct
SEQUENCE: 586
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLRDGQLN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 587           moltype = AA  length = 736
FEATURE                  Location/Qualifiers
REGION                   1..736
                         note = AAV capsid variant
source                   1..736
                         mol_type = protein
                         organism = synthetic construct
SEQUENCE: 587
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLADTGTN FAWTAGTKYH LNGRNSLANP GIAMATHKDD EERFFPSNGI    540
LIFGKQNAAR DNADYSDVML TSEEEIKTTN PVATEEYGIV ADNVMEPTRA PQIGTVNSQG    600
ALPGMVWQNR DVYLQGPIWA KIPHTDGNFH PSPLMGGFGL KHPPPQILIK NTPVPADPRS    660
TFNGDKLNSF ITQYSTGQVS VEIEWELQKE NSKRWNPEIQ YTSNYYKSTS VDFAVNTEGV    720
YSEPRPIGTR YLTRNL                                                   736

SEQ ID NO: 588           moltype = AA  length = 738
FEATURE                  Location/Qualifiers
REGION                   1..738
                         note = AAV capsid variant
source                   1..738
                         mol_type = protein
                         organism = synthetic construct
SEQUENCE: 588
```

```
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLNGGV VNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 589         moltype = AA  length = 738
FEATURE                Location/Qualifiers
REGION                 1..738
                       note = AAV capsid variant
source                 1..738
                       mol_type = protein
                       organism = synthetic construct
SEQUENCE: 589
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLEMPI GNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 590         moltype = AA  length = 739
FEATURE                Location/Qualifiers
REGION                 1..739
                       note = AAV capsid variant
source                 1..739
                       mol_type = protein
                       organism = synthetic construct
SEQUENCE: 590
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLEDMG TINFAWTAGT KYHLNGRNSL ANPGIAMATH KDDEERFFPS   540
NGILIFGKQN AARDNADYSD VMLTSEEEIK TTNPVATEEY GIVADNLQQQ NTAPQIGTVN   600
SQGALPGMVW QNRDVYLQGP IWAKIPHTDG NFHPSPLMGG FGLKHPPPQI LIKNTPVPAD   660
PRSTFNGDKL NSFITQYSTG QVSVEIEWEL QKENSKRWNP EIQYTSNYYK STSVDFAVNT   720
EGVYSEPRPI GTRYLTRNL                                               739

SEQ ID NO: 591         moltype = AA  length = 737
FEATURE                Location/Qualifiers
REGION                 1..737
                       note = AAV capsid variant
source                 1..737
                       mol_type = protein
                       organism = synthetic construct
SEQUENCE: 591
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLNGGVV NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737
```

```
SEQ ID NO: 592          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 592
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLEMPIG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                 737

SEQ ID NO: 593          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 593
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLEDMGT INFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 594          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 594
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTYPLNGGV VNFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                738

SEQ ID NO: 595          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 595
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
```

```
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLEMPI GNFAWTAGTK YHLNGRNSLA NPGIAMATHK DDEERFFPSN    540
GILIFKQNA ARDNADYSDV MLTSEEEIKT TNPVATEEYG IVADNVMEPT RAPQIGTVNS     600
QGALPGMVWQ NRDVYLQGPI WAKIPHTDGN FHPSPLMGGF GLKHPPPQIL IKNTPVPADP    660
RSTFNGDKLN SFITQYSTGQ VSVEIEWELQ KENSKRWNPE IQYTSNYYKS TSVDFAVNTE    720
GVYSEPRPIG TRYLTRNL                                                  738

SEQ ID NO: 596          moltype = AA  length = 739
FEATURE                 Location/Qualifiers
REGION                  1..739
                        note = AAV capsid variant
source                  1..739
                        mol_type = protein
                        organism = synthetic construct
SEQUENCE: 596
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYRQQR VSTYPLEDMG TINFAWTAGT KYHLNGRNSL ANPGIAMATH KDDEERFFPS    540
NGILIFKQN AARDNADYSD VMLTSEEEIK TTNPVATEEY GIVADNVMEP TRAPQIGTVN     600
SQGALPGMVW QNRDVYLQGP IWAKIPHTDG NFHPSPLMGG FGLKHPPPQI LIKNTPVPAD    660
PRSTFNGDKL NSFITQYSTG QVSVEIEWEL QKENSKRWNP EIQYTSNYYK STSVDFAVNT    720
EGVYSEPRPI GTRYLTRNL                                                 739

SEQ ID NO: 597          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 597
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLNGGVV NFAWTAGTKY HLNGRNSLAN PGIAMATHKD DEERFFPSNG    540
ILIFKQNAA RDNADYSDVM LTSEEEIKTT NPVATEEYGI VADNVMEPTR APQIGTVNSQ     600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 598          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 598
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTSNGRGV TLGFSQGGPN TMANQAKNWL    480
PGPCYRQQRV STYPLEMPIG NFAWTAGTKY HLNGRNSLAN PGIAMATHKD DEERFFPSNG    540
ILIFKQNAA RDNADYSDVM LTSEEEIKTT NPVATEEYGI VADNVMEPTR APQIGTVNSQ     600
GALPGMVWQN RDVYLQGPIW AKIPHTDGNF HPSPLMGGFG LKHPPPQILI KNTPVPADPR    660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 599          moltype = AA  length = 738
FEATURE                 Location/Qualifiers
REGION                  1..738
```

| | | |
|---|---|---|
| | note = AAV capsid variant | |
| source | 1..738 | |
| | mol_type = protein | |
| | organism = synthetic construct | |

SEQUENCE: 599
```
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTSNGRGV TLGFSQGGPN TMANQAKNWL   480
PGPCYRQQRV STYPLEDMGT INFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738
```

| | | |
|---|---|---|
| SEQ ID NO: 600 | moltype = AA length = 737 | |
| FEATURE | Location/Qualifiers | |
| REGION | 1..737 | |
| | note = AAV capsid variant | |
| source | 1..737 | |
| | mol_type = protein | |
| | organism = synthetic construct | |

SEQUENCE: 600
```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLNGGVV NFAWTAGTKY HLNGRNSLAN PGIAMATHKD DEERFFPSNG   540
ILIFGKQNAR DNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737
```

| | | |
|---|---|---|
| SEQ ID NO: 601 | moltype = AA length = 737 | |
| FEATURE | Location/Qualifiers | |
| REGION | 1..737 | |
| | note = AAV capsid variant | |
| source | 1..737 | |
| | mol_type = protein | |
| | organism = synthetic construct | |

SEQUENCE: 601
```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLEMPIG NFAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737
```

| | | |
|---|---|---|
| SEQ ID NO: 602 | moltype = AA length = 738 | |
| FEATURE | Location/Qualifiers | |
| REGION | 1..738 | |
| | note = AAV capsid variant | |
| source | 1..738 | |
| | mol_type = protein | |
| | organism = synthetic construct | |

SEQUENCE: 602
```
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
```

```
PGPCYRQQRV STYPLEDMGT INFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVADP     660
RSTFNGDKLN SFITQYSTGQ VSVEIEWELQ KENSKRWNPE IQYTSNYYKS TSVDFAVNTE    720
GVYSEPRPIG TRYLTRNL                                                  738

SEQ ID NO: 603            moltype = AA   length = 736
FEATURE                   Location/Qualifiers
REGION                    1..736
                          note = AAV capsid variant
source                    1..736
                          mol_type = protein
                          organism = synthetic construct
SEQUENCE: 603
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLNGGVVN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVADPRS     660
TFNGDKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 604            moltype = AA   length = 736
FEATURE                   Location/Qualifiers
REGION                    1..736
                          note = AAV capsid variant
source                    1..736
                          mol_type = protein
                          organism = synthetic construct
SEQUENCE: 604
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLEMPIGN FAWTAGTKYH LNGRNSLANP GIAMATHKDD EERFFPSNGI    540
LIFGKQNAAR DNADYSDVML TSEEEIKTTN PVATEEYGIV ADNLQQQNTA PQIGTVNSQG    600
ALPGMVWQNR DVYLQGPIWA KIPHTDGNFH PSPLMGGFGL KHPPPQILIK NTPVADPRS     660
TFNGDKLNSF ITQYSTGQVS VEIEWELQKE NSKRWNPEIQ YTSNYYKSTS VDFAVNTEGV    720
YSEPRPIGTR YLTRNL                                                    736

SEQ ID NO: 605            moltype = AA   length = 737
FEATURE                   Location/Qualifiers
REGION                    1..737
                          note = AAV capsid variant
source                    1..737
                          mol_type = protein
                          organism = synthetic construct
SEQUENCE: 605
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDSE    180
SVPDPQPLGE PPAAPSGVGP NTMAAGGGAP MADNNEGADG VGSSSGNWHC DSTWLGDRVI    240
TTSTRTWALP TYNNHLYKQI SNGTSGGATN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FQFTYTFEDV    420
PFHSSYAHSQ SLDRLMNPLI DQYLYYLSRT QTTSNGRGVT LGFSQGGPNT MANQAKNWLP    480
GPCYRQQRVS TYPLEDMGTI NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQN RDVYLQGPIW AKIPHTDGNF HPSPLMGGFG LKHPPPQILI KNTPVADPR     660
STFNGDKLNS FITQYSTGQV SVEIEWELQK ENSKRWNPEI QYTSNYYKST SVDFAVNTEG    720
VYSEPRPIGT RYLTRNL                                                   737

SEQ ID NO: 606            moltype = AA   length = 737
FEATURE                   Location/Qualifiers
REGION                    1..737
                          note = AAV capsid variant
source                    1..737
                          mol_type = protein
                          organism = synthetic construct
```

```
SEQUENCE: 606
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLNGGVV NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 607          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 607
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLEMPIG NFAWTAGTKY HLNGRNSLAN PGIAMATHKD DEERFFPSNG   540
ILIFGKQNAA RDNADYSDVM LTSEEEIKTT NPVATEEYGI VADNVMEPTR APQIGTVNSQ   600
GALPGMVWQN RDVYLQGPIW AKIPHTDGNF HPSPLMGGFG LKHPPPQILI KNTPVPADPR   660
STFNGDKLNS FITQYSTGQV SVEIEWELQK ENSKRWNPEI QYTSNYYKST SVDFAVNTEG   720
VYSEPRPIGT RYLTRNL                                                  737

SEQ ID NO: 608          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 608
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTGGTANTQ TLGFSQGGPN TMANQAKNWL   480
PGPCYRQQRV STYPLEDMGT INFAWTAGTK YHLNGRNSLA NPGIAMATHK DDEERFFPSN   540
GILIFGKQNA ARDNADYSDV MLTSEEEIKT TNPVATEEYG IVADNVMEPT RAPQIGTVNS   600
QGALPGMVWQ NRDVYLQGPI WAKIPHTDGN FHPSPLMGGF GLKHPPPQIL IKNTPVPADP   660
RSTFNGDKLN SFITQYSTGQ VSVEIEWELQ KENSKRWNPE IQYTSNYYKS TSVDFAVNTE   720
GVYSEPRPIG TRYLTRNL                                                 738

SEQ ID NO: 609          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 609
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDSE   180
SVPDPQPLGE PPAAPSGVGP NTMAAGGGAP MADNNEGADG VGSSSGNWHC DSTWLGDRVI   240
TTSTRTWALP TYNNHLYKQI SNGTSGGATN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FQFTYTFEDV   420
PFHSSYAHSQ SLDRLMNPLI DQYLYYLSRT QTTSNRGVT LGFSQGGPNT MANQAKNWLP   480
GPCYRQQRVS TYPLNGGVVN FAWTAGTKYH LNGRNSLANP GIAMATHKDD EERFFPSNGI   540
LIFGKQNAAR DNADYSDVML TSEEEIKTTN PVATEEYGIV ADNVMEPTRA PQIGTVNSQG   600
ALPGMVWQNR DVYLQGPIWA KIPHTDGNFH PSPLMGGFGL KHPPPQILIK NTPVPADPRS   660
TFNGDKLNSF ITQYSTGQVS VEIEWELQKE NSKRWNPEIQ YTSNYYKSTS VDFAVNTEGV   720
```

-continued

```
YSEPRPIGTR YLTRNL                                                             736

SEQ ID NO: 610          moltype = AA  length = 736
FEATURE                 Location/Qualifiers
REGION                  1..736
                        note = AAV capsid variant
source                  1..736
                        mol_type = protein
                        organism = synthetic construct
SEQUENCE: 610
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTSNGRGVT LGFSQGGPNT MANQAKNWLP  480
GPCYRQQRVS TYPLEMPIGN FAWTAGTKYH LNGRNSLANP GIAMATHKDD EERFFPSNGI  540
LIFGKQNAAR DNADYSDVML TSEEEIKTTN PVATEEYGIV ADNVMEPTRA PQIGTVNSQG  600
ALPGMVWQNR DVYLQGPIWA KIPHTDGNFH PSPLMGGFGL KHPPPQILIK NTPVPADPRS  660
TFNGDKLNSF ITQYSTGQVS VEIEWELQKE NSKRWNPEIQ YTSNYYKSTS VDFAVNTEGV  720
YSEPRPIGTR YLTRNL                                                  736

SEQ ID NO: 611          moltype = AA  length = 737
FEATURE                 Location/Qualifiers
REGION                  1..737
                        note = AAV capsid variant
source                  1..737
                        mol_type = protein
                        organism = synthetic construct
SEQUENCE: 611
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFN IQVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTSNGRGVT LGFSQGGPNT MANQAKNWLP  480
GPCYRQQRVS TYPLEDMGTI NFAWTAGTKY HLNGRNSLAN PGIAMATHKD DEERFFPSNG  540
ILIFGKQNAA RDNADYSDVM LTSEEEIKTT NPVATEEYGI VADNVMEPTR APQIGTVNSQ  600
GALPGMVWQN RDVYLQGPIW AKIPHTDGNF HPSPLMGGFG LKHPPPQILI KNTPVPADPR  660
STFNGDKLNS FITQYSTGQV SVEIEWELQK ENSKRWNPEI QYTSNYYKST SVDFAVNTEG  720
VYSEPRPIGT RYLTRNL                                                 737

SEQ ID NO: 612          moltype = AA  length = 738
FEATURE                 Location/Qualifiers
REGION                  1..738
                        note = AAV capsid variant
source                  1..738
                        mol_type = protein
                        organism = synthetic construct
SEQUENCE: 612
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTYPLQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738

SEQ ID NO: 613          moltype = AA  length = 7
FEATURE                 Location/Qualifiers
source                  1..7
                        mol_type = protein
                        note = Parvovirus Adeno-associated virus
                        organism = unidentified
SEQUENCE: 613
SASTGAS                                                              7

SEQ ID NO: 614          moltype = AA  length = 10
FEATURE                 Location/Qualifiers
```

```
source                    1..10
                          mol_type = protein
                          note = Parvovirus Adeno-associated virus
                          organism = unidentified
SEQUENCE: 614
VFMIPQYGYL                                                              10

SEQ ID NO: 615            moltype = AA  length = 9
FEATURE                   Location/Qualifiers
source                    1..9
                          mol_type = protein
                          note = Parvovirus Adeno-associated virus
                          organism = unidentified
SEQUENCE: 615
NQSGSAQNK                                                                9

SEQ ID NO: 616            moltype =   length =
SEQUENCE: 616
000

SEQ ID NO: 617            moltype = AA  length = 8
FEATURE                   Location/Qualifiers
source                    1..8
                          mol_type = protein
                          note = Parvovirus Adeno-associated virus
                          organism = unidentified
SEQUENCE: 617
KTDNNNSN                                                                 8

SEQ ID NO: 618            moltype = AA  length = 7
FEATURE                   Location/Qualifiers
source                    1..7
                          mol_type = protein
                          note = Parvovirus Adeno-associated virus
                          organism = unidentified
SEQUENCE: 618
KDDEDKF                                                                  7

SEQ ID NO: 619            moltype = AA  length = 6
FEATURE                   Location/Qualifiers
source                    1..6
                          mol_type = protein
                          note = Parvovirus Adeno-associated virus
                          organism = unidentified
SEQUENCE: 619
SAGASN                                                                   6

SEQ ID NO: 620            moltype = AA  length = 10
FEATURE                   Location/Qualifiers
source                    1..10
                          mol_type = protein
                          note = Parvovirus Adeno-associated virus
                          organism = unidentified
SEQUENCE: 620
STDPATGDVH                                                              10

SEQ ID NO: 621            moltype =   length =
SEQUENCE: 621
000

SEQ ID NO: 622            moltype = AA  length = 7
FEATURE                   Location/Qualifiers
source                    1..7
                          mol_type = protein
                          note = Parvovirus Adeno-associated virus
                          organism = unidentified
SEQUENCE: 622
DNNGLYT                                                                  7

SEQ ID NO: 623            moltype = AA  length = 6
FEATURE                   Location/Qualifiers
source                    1..6
                          mol_type = protein
                          note = Parvovirus Adeno-associated virus
                          organism = unidentified
SEQUENCE: 623
SQSGAS                                                                   6

SEQ ID NO: 624            moltype = AA  length = 10
```

```
FEATURE              Location/Qualifiers
source               1..10
                     mol_type = protein
                     note = Parvovirus Adeno-associated virus
                     organism = unidentified
SEQUENCE: 624
VFMVPQYGYL                                                              10

SEQ ID NO: 625       moltype = AA  length = 9
FEATURE              Location/Qualifiers
source               1..9
                     mol_type = protein
                     note = Parvovirus Adeno-associated virus
                     organism = unidentified
SEQUENCE: 625
TPSGTTTQS                                                                9

SEQ ID NO: 626       moltype =     length =
SEQUENCE: 626
000

SEQ ID NO: 627       moltype = AA  length = 8
FEATURE              Location/Qualifiers
source               1..8
                     mol_type = protein
                     note = Parvovirus Adeno-associated virus
                     organism = unidentified
SEQUENCE: 627
SADNNNSE                                                                 8

SEQ ID NO: 628       moltype = AA  length = 7
FEATURE              Location/Qualifiers
source               1..7
                     mol_type = protein
                     note = Parvovirus Adeno-associated virus
                     organism = unidentified
SEQUENCE: 628
KDDEEKF                                                                  7

SEQ ID NO: 629       moltype = AA  length = 6
FEATURE              Location/Qualifiers
source               1..6
                     mol_type = protein
                     note = Parvovirus Adeno-associated virus
                     organism = unidentified
SEQUENCE: 629
GSEKTN                                                                   6

SEQ ID NO: 630       moltype = AA  length = 10
FEATURE              Location/Qualifiers
source               1..10
                     mol_type = protein
                     note = Parvovirus Adeno-associated virus
                     organism = unidentified
SEQUENCE: 630
NRQAATADVN                                                              10

SEQ ID NO: 631       moltype =     length =
SEQUENCE: 631
000

SEQ ID NO: 632       moltype = AA  length = 7
FEATURE              Location/Qualifiers
source               1..7
                     mol_type = protein
                     note = Parvovirus Adeno-associated virus
                     organism = unidentified
SEQUENCE: 632
DTNGVYS                                                                  7

SEQ ID NO: 633       moltype = AA  length = 6
FEATURE              Location/Qualifiers
source               1..6
                     mol_type = protein
                     note = Parvovirus Adeno-associated virus
                     organism = unidentified
SEQUENCE: 633
SQSGAS                                                                   6
```

-continued

| | | |
|---|---|---|
| SEQ ID NO: 634<br>FEATURE<br>source | moltype = AA   length = 10<br>Location/Qualifiers<br>1..10<br>mol_type = protein<br>note = Parvovirus Adeno-associated virus<br>organism = unidentified | |
| SEQUENCE: 634<br>VFMVPQYGYL | | 10 |
| SEQ ID NO: 635<br>FEATURE<br>source | moltype = AA   length = 9<br>Location/Qualifiers<br>1..9<br>mol_type = protein<br>note = Parvovirus Adeno-associated virus<br>organism = unidentified | |
| SEQUENCE: 635<br>TTSGTTNQS | | 9 |
| SEQ ID NO: 636<br>SEQUENCE: 636<br>000 | moltype =    length = | |
| SEQ ID NO: 637<br>FEATURE<br>source | moltype = AA   length = 8<br>Location/Qualifiers<br>1..8<br>mol_type = protein<br>note = Parvovirus Adeno-associated virus<br>organism = unidentified | |
| SEQUENCE: 637<br>ANDNNNSN | | 8 |
| SEQ ID NO: 638<br>FEATURE<br>source | moltype = AA   length = 7<br>Location/Qualifiers<br>1..7<br>mol_type = protein<br>note = Parvovirus Adeno-associated virus<br>organism = unidentified | |
| SEQUENCE: 638<br>KDDEEKF | | 7 |
| SEQ ID NO: 639<br>FEATURE<br>source | moltype = AA   length = 6<br>Location/Qualifiers<br>1..6<br>mol_type = protein<br>note = Parvovirus Adeno-associated virus<br>organism = unidentified | |
| SEQUENCE: 639<br>GTTASN | | 6 |
| SEQ ID NO: 640<br>FEATURE<br>source | moltype = AA   length = 10<br>Location/Qualifiers<br>1..10<br>mol_type = protein<br>note = Parvovirus Adeno-associated virus<br>organism = unidentified | |
| SEQUENCE: 640<br>NTAPTTGTVN | | 10 |
| SEQ ID NO: 641<br>SEQUENCE: 641<br>000 | moltype =    length = | |
| SEQ ID NO: 642<br>FEATURE<br>source | moltype = AA   length = 7<br>Location/Qualifiers<br>1..7<br>mol_type = protein<br>note = Parvovirus Adeno-associated virus<br>organism = unidentified | |
| SEQUENCE: 642<br>DTNGVYS | | 7 |
| SEQ ID NO: 643<br>FEATURE<br>source | moltype = AA   length = 8<br>Location/Qualifiers<br>1..8<br>mol_type = protein<br>note = Parvovirus Adeno-associated virus<br>organism = unidentified | |
| SEQUENCE: 643<br>RLGESLQS | | 8 |

-continued

| | | |
|---|---|---|
| SEQ ID NO: 644<br>FEATURE<br>source | moltype = AA  length = 10<br>Location/Qualifiers<br>1..10<br>mol_type = protein<br>note = Parvovirus Adeno-associated virus<br>organism = unidentified | |
| SEQUENCE: 644<br>VFMVPQYGYC | | 10 |
| SEQ ID NO: 645<br>FEATURE<br>source | moltype = AA  length = 9<br>Location/Qualifiers<br>1..9<br>mol_type = protein<br>note = Parvovirus Adeno-associated virus<br>organism = unidentified | |
| SEQUENCE: 645<br>GTTLNAGTA | | 9 |
| SEQ ID NO: 646<br>SEQUENCE: 646<br>000 | moltype =   length = | |
| SEQ ID NO: 647<br>FEATURE<br>source | moltype = AA  length = 12<br>Location/Qualifiers<br>1..12<br>mol_type = protein<br>note = Parvovirus Adeno-associated virus<br>organism = unidentified | |
| SEQUENCE: 647<br>ANQNYKIPAT GS | | 12 |
| SEQ ID NO: 648<br>FEATURE<br>source | moltype = AA  length = 7<br>Location/Qualifiers<br>1..7<br>mol_type = protein<br>note = Parvovirus Adeno-associated virus<br>organism = unidentified | |
| SEQUENCE: 648<br>GPADSKF | | 7 |
| SEQ ID NO: 649<br>FEATURE<br>source | moltype = AA  length = 6<br>Location/Qualifiers<br>1..6<br>mol_type = protein<br>note = Parvovirus Adeno-associated virus<br>organism = unidentified | |
| SEQUENCE: 649<br>QNGNTA | | 6 |
| SEQ ID NO: 650<br>FEATURE<br>source | moltype = AA  length = 10<br>Location/Qualifiers<br>1..10<br>mol_type = protein<br>note = Parvovirus Adeno-associated virus<br>organism = unidentified | |
| SEQUENCE: 650<br>SNLPTVDRLT | | 10 |
| SEQ ID NO: 651<br>SEQUENCE: 651<br>000 | moltype =   length = | |
| SEQ ID NO: 652<br>FEATURE<br>source | moltype = AA  length = 7<br>Location/Qualifiers<br>1..7<br>mol_type = protein<br>note = Parvovirus Adeno-associated virus<br>organism = unidentified | |
| SEQUENCE: 652<br>DAAGKYT | | 7 |
| SEQ ID NO: 653<br>FEATURE<br>source | moltype = AA  length = 10<br>Location/Qualifiers<br>1..10<br>mol_type = protein<br>note = Parvovirus Adeno-associated virus<br>organism = unidentified | |
| SEQUENCE: 653 | | |

```
SEQ ID NO: 654        moltype = AA  length = 10
FEATURE               Location/Qualifiers
source                1..10
                      mol_type = protein
                      note = Parvovirus Adeno-associated virus
                      organism = unidentified
SEQUENCE: 654
VFTLPQYGYA                                                          10

SEQ ID NO: 655        moltype = AA  length = 9
FEATURE               Location/Qualifiers
source                1..9
                      mol_type = protein
                      note = Parvovirus Adeno-associated virus
                      organism = unidentified
SEQUENCE: 655
STNNTGGVQ                                                            9

SEQ ID NO: 656        moltype =     length =
SEQUENCE: 656
000

SEQ ID NO: 657        moltype = AA  length = 7
FEATURE               Location/Qualifiers
source                1..7
                      mol_type = protein
                      note = Parvovirus Adeno-associated virus
                      organism = unidentified
SEQUENCE: 657
SGVNRAS                                                              7

SEQ ID NO: 658        moltype = AA  length = 7
FEATURE               Location/Qualifiers
source                1..7
                      mol_type = protein
                      note = Parvovirus Adeno-associated virus
                      organism = unidentified
SEQUENCE: 658
LQGSNTY                                                              7

SEQ ID NO: 659        moltype = AA  length = 8
FEATURE               Location/Qualifiers
source                1..8
                      mol_type = protein
                      note = Parvovirus Adeno-associated virus
                      organism = unidentified
SEQUENCE: 659
ANPGTTAT                                                             8

SEQ ID NO: 660        moltype = AA  length = 10
FEATURE               Location/Qualifiers
source                1..10
                      mol_type = protein
                      note = Parvovirus Adeno-associated virus
                      organism = unidentified
SEQUENCE: 660
TTAPATGTYN                                                          10

SEQ ID NO: 661        moltype =     length =
SEQUENCE: 661
000

SEQ ID NO: 662        moltype = AA  length = 7
FEATURE               Location/Qualifiers
source                1..7
                      mol_type = protein
                      note = Parvovirus Adeno-associated virus
                      organism = unidentified
SEQUENCE: 662
DSTGEYR                                                              7

SEQ ID NO: 663        moltype = AA  length = 7
FEATURE               Location/Qualifiers
source                1..7
                      mol_type = protein
                      note = Parvovirus Adeno-associated virus
                      organism = unidentified
```

| | | |
|---|---|---|
| SEQUENCE: 663<br>SASTGAS | | 7 |
| SEQ ID NO: 664<br>FEATURE<br>source | moltype = AA  length = 10<br>Location/Qualifiers<br>1..10<br>mol_type = protein<br>note = Parvovirus Adeno-associated virus<br>organism = unidentified | |
| SEQUENCE: 664<br>VFMIPQYGYL | | 10 |
| SEQ ID NO: 665<br>FEATURE<br>source | moltype = AA  length = 9<br>Location/Qualifiers<br>1..9<br>mol_type = protein<br>note = Parvovirus Adeno-associated virus<br>organism = unidentified | |
| SEQUENCE: 665<br>NQSGSAQNK | | 9 |
| SEQ ID NO: 666<br>SEQUENCE: 666<br>000 | moltype =    length = | |
| SEQ ID NO: 667<br>FEATURE<br>source | moltype = AA  length = 8<br>Location/Qualifiers<br>1..8<br>mol_type = protein<br>note = Parvovirus Adeno-associated virus<br>organism = unidentified | |
| SEQUENCE: 667<br>KTDNNNSN | | 8 |
| SEQ ID NO: 668<br>FEATURE<br>source | moltype = AA  length = 7<br>Location/Qualifiers<br>1..7<br>mol_type = protein<br>note = Parvovirus Adeno-associated virus<br>organism = unidentified | |
| SEQUENCE: 668<br>KDDKDKF | | 7 |
| SEQ ID NO: 669<br>FEATURE<br>source | moltype = AA  length = 6<br>Location/Qualifiers<br>1..6<br>mol_type = protein<br>note = Parvovirus Adeno-associated virus<br>organism = unidentified | |
| SEQUENCE: 669<br>SAGASN | | 6 |
| SEQ ID NO: 670<br>FEATURE<br>source | moltype = AA  length = 10<br>Location/Qualifiers<br>1..10<br>mol_type = protein<br>note = Parvovirus Adeno-associated virus<br>organism = unidentified | |
| SEQUENCE: 670<br>STDPATGDVH | | 10 |
| SEQ ID NO: 671<br>SEQUENCE: 671<br>000 | moltype =    length = | |
| SEQ ID NO: 672<br>FEATURE<br>source | moltype = AA  length = 7<br>Location/Qualifiers<br>1..7<br>mol_type = protein<br>note = Parvovirus Adeno-associated virus<br>organism = unidentified | |
| SEQUENCE: 672<br>DNNGLYT | | 7 |
| SEQ ID NO: 673<br>FEATURE<br>source | moltype = AA  length = 7<br>Location/Qualifiers<br>1..7<br>mol_type = protein<br>note = Parvovirus Adeno-associated virus | |

```
                                organism = unidentified
SEQUENCE: 673
SETAGST                                                                 7

SEQ ID NO: 674              moltype = AA  length = 10
FEATURE                     Location/Qualifiers
source                      1..10
                            mol_type = protein
                            note = Parvovirus Adeno-associated virus
                            organism = unidentified
SEQUENCE: 674
VFMIPQYGYL                                                              10

SEQ ID NO: 675              moltype = AA  length = 9
FEATURE                     Location/Qualifiers
source                      1..9
                            mol_type = protein
                            note = Parvovirus Adeno-associated virus
                            organism = unidentified
SEQUENCE: 675
NPGGTAGNR                                                               9

SEQ ID NO: 676              moltype =     length =
SEQUENCE: 676
000

SEQ ID NO: 677              moltype = AA  length = 8
FEATURE                     Location/Qualifiers
source                      1..8
                            mol_type = protein
                            note = Parvovirus Adeno-associated virus
                            organism = unidentified
SEQUENCE: 677
LDQNNNSN                                                                8

SEQ ID NO: 678              moltype = AA  length = 7
FEATURE                     Location/Qualifiers
source                      1..7
                            mol_type = protein
                            note = Parvovirus Adeno-associated virus
                            organism = unidentified
SEQUENCE: 678
KDDEDRF                                                                 7

SEQ ID NO: 679              moltype = AA  length = 6
FEATURE                     Location/Qualifiers
source                      1..6
                            mol_type = protein
                            note = Parvovirus Adeno-associated virus
                            organism = unidentified
SEQUENCE: 679
GATNKT                                                                  6

SEQ ID NO: 680              moltype = AA  length = 10
FEATURE                     Location/Qualifiers
source                      1..10
                            mol_type = protein
                            note = Parvovirus Adeno-associated virus
                            organism = unidentified
SEQUENCE: 680
NTAAQTQVVN                                                              10

SEQ ID NO: 681              moltype =     length =
SEQUENCE: 681
000

SEQ ID NO: 682              moltype = AA  length = 7
FEATURE                     Location/Qualifiers
source                      1..7
                            mol_type = protein
                            note = Parvovirus Adeno-associated virus
                            organism = unidentified
SEQUENCE: 682
DSQGVYS                                                                 7

SEQ ID NO: 683              moltype = AA  length = 8
FEATURE                     Location/Qualifiers
source                      1..8
                            mol_type = protein
```

```
                                note = Parvovirus Adeno-associated virus
                                organism = unidentified
SEQUENCE: 683
NGTSGGAT                                                                    8

SEQ ID NO: 684                  moltype = AA   length = 10
FEATURE                         Location/Qualifiers
source                          1..10
                                mol_type = protein
                                note = Parvovirus Adeno-associated virus
                                organism = unidentified
SEQUENCE: 684
VFMIPQYGYL                                                                 10

SEQ ID NO: 685                  moltype = AA   length = 9
FEATURE                         Location/Qualifiers
source                          1..9
                                mol_type = protein
                                note = Parvovirus Adeno-associated virus
                                organism = unidentified
SEQUENCE: 685
TTGGTANTQ                                                                   9

SEQ ID NO: 686                  moltype =   length =
SEQUENCE: 686
000

SEQ ID NO: 687                  moltype = AA   length = 8
FEATURE                         Location/Qualifiers
source                          1..8
                                mol_type = protein
                                note = Parvovirus Adeno-associated virus
                                organism = unidentified
SEQUENCE: 687
TGQNNNSN                                                                    8

SEQ ID NO: 688                  moltype = AA   length = 7
FEATURE                         Location/Qualifiers
source                          1..7
                                mol_type = protein
                                note = Parvovirus Adeno-associated virus
                                organism = unidentified
SEQUENCE: 688
KDDEERF                                                                     7

SEQ ID NO: 689                  moltype = AA   length = 6
FEATURE                         Location/Qualifiers
source                          1..6
                                mol_type = protein
                                note = Parvovirus Adeno-associated virus
                                organism = unidentified
SEQUENCE: 689
NAARDN                                                                      6

SEQ ID NO: 690                  moltype = AA   length = 11
FEATURE                         Location/Qualifiers
source                          1..11
                                mol_type = protein
                                note = Parvovirus Adeno-associated virus
                                organism = unidentified
SEQUENCE: 690
NTAPQIGTVN S                                                               11

SEQ ID NO: 691                  moltype =   length =
SEQUENCE: 691
000

SEQ ID NO: 692                  moltype = AA   length = 7
FEATURE                         Location/Qualifiers
source                          1..7
                                mol_type = protein
                                note = Parvovirus Adeno-associated virus
                                organism = unidentified
SEQUENCE: 692
NTEGVYS                                                                     7

SEQ ID NO: 693                  moltype = AA   length = 8
FEATURE                         Location/Qualifiers
source                          1..8
```

```
                                    mol_type = protein
                                    note = Parvovirus Adeno-associated virus
                                    organism = unidentified
SEQUENCE: 693
NSTSGGSS                                                                      8

SEQ ID NO: 694                      moltype = AA  length = 10
FEATURE                             Location/Qualifiers
source                              1..10
                                    mol_type = protein
                                    note = Parvovirus Adeno-associated virus
                                    organism = unidentified
SEQUENCE: 694
VFMIPQYGYL                                                                   10

SEQ ID NO: 695                      moltype = AA  length = 9
FEATURE                             Location/Qualifiers
source                              1..9
                                    mol_type = protein
                                    note = Parvovirus Adeno-associated virus
                                    organism = unidentified
SEQUENCE: 695
INGSGQNQQ                                                                     9

SEQ ID NO: 696                      moltype =     length =
SEQUENCE: 696
000

SEQ ID NO: 697                      moltype = AA  length = 8
FEATURE                             Location/Qualifiers
source                              1..8
                                    mol_type = protein
                                    note = Parvovirus Adeno-associated virus
                                    organism = unidentified
SEQUENCE: 697
VTQNNNSE                                                                      8

SEQ ID NO: 698                      moltype = AA  length = 7
FEATURE                             Location/Qualifiers
source                              1..7
                                    mol_type = protein
                                    note = Parvovirus Adeno-associated virus
                                    organism = unidentified
SEQUENCE: 698
KEGEDRF                                                                       7

SEQ ID NO: 699                      moltype = AA  length = 6
FEATURE                             Location/Qualifiers
source                              1..6
                                    mol_type = protein
                                    note = Parvovirus Adeno-associated virus
                                    organism = unidentified
SEQUENCE: 699
GTGRDN                                                                        6

SEQ ID NO: 700                      moltype = AA  length = 10
FEATURE                             Location/Qualifiers
source                              1..10
                                    mol_type = protein
                                    note = Parvovirus Adeno-associated virus
                                    organism = unidentified
SEQUENCE: 700
QAQAQTGWVQ                                                                   10

SEQ ID NO: 701                      moltype =     length =
SEQUENCE: 701
000

SEQ ID NO: 702                      moltype = AA  length = 7
FEATURE                             Location/Qualifiers
source                              1..7
                                    mol_type = protein
                                    note = Parvovirus Adeno-associated virus
                                    organism = unidentified
SEQUENCE: 702
NTEGVYS                                                                       7

SEQ ID NO: 703                      moltype = AA  length = 8
FEATURE                             Location/Qualifiers
```

| | | |
|---|---|---|
| source | 1..8<br>mol_type = protein<br>note = Parvovirus Adeno-associated virus<br>organism = unidentified | |
| SEQUENCE: 703<br>NGTSGGST | | 8 |
| SEQ ID NO: 704<br>FEATURE<br>source | moltype = AA length = 10<br>Location/Qualifiers<br>1..10<br>mol_type = protein<br>note = Parvovirus Adeno-associated virus<br>organism = unidentified | |
| SEQUENCE: 704<br>VFMVPQYGYL | | 10 |
| SEQ ID NO: 705<br>FEATURE<br>source | moltype = AA length = 9<br>Location/Qualifiers<br>1..9<br>mol_type = protein<br>note = Parvovirus Adeno-associated virus<br>organism = unidentified | |
| SEQUENCE: 705<br>QTTGTGGTQ | | 9 |
| SEQ ID NO: 706<br>SEQUENCE: 706<br>000 | moltype = length = | |
| SEQ ID NO: 707<br>FEATURE<br>source | moltype = AA length = 8<br>Location/Qualifiers<br>1..8<br>mol_type = protein<br>note = Parvovirus Adeno-associated virus<br>organism = unidentified | |
| SEQUENCE: 707<br>TNQNNNSN | | 8 |
| SEQ ID NO: 708<br>FEATURE<br>source | moltype = AA length = 7<br>Location/Qualifiers<br>1..7<br>mol_type = protein<br>note = Parvovirus Adeno-associated virus<br>organism = unidentified | |
| SEQUENCE: 708<br>KDDDDRF | | 7 |
| SEQ ID NO: 709<br>FEATURE<br>source | moltype = AA length = 6<br>Location/Qualifiers<br>1..6<br>mol_type = protein<br>note = Parvovirus Adeno-associated virus<br>organism = unidentified | |
| SEQUENCE: 709<br>GAGNDG | | 6 |
| SEQ ID NO: 710<br>FEATURE<br>source | moltype = AA length = 10<br>Location/Qualifiers<br>1..10<br>mol_type = protein<br>note = Parvovirus Adeno-associated virus<br>organism = unidentified | |
| SEQUENCE: 710<br>NTQAQTGLVH | | 10 |
| SEQ ID NO: 711<br>SEQUENCE: 711<br>000 | moltype = length = | |
| SEQ ID NO: 712<br>FEATURE<br>source | moltype = AA length = 7<br>Location/Qualifiers<br>1..7<br>mol_type = protein<br>note = Parvovirus Adeno-associated virus<br>organism = unidentified | |
| SEQUENCE: 712<br>NTEGVYS | | 7 |
| SEQ ID NO: 713 | moltype = AA length = 8 | |

```
FEATURE                 Location/Qualifiers
source                  1..8
                        mol_type = protein
                        note = Parvovirus Adeno-associated virus
                        organism = unidentified SEQUENCE: 713
NGTSGGST                                                                         8

SEQ ID NO: 714          moltype = AA  length = 10
FEATURE                 Location/Qualifiers
source                  1..10
                        mol_type = protein
                        note = Parvovirus Adeno-associated virus
                        organism = unidentified SEQUENCE: 714
VFMIPQYGYL                                                                      10

SEQ ID NO: 715          moltype = AA  length = 9
FEATURE                 Location/Qualifiers
source                  1..9
                        mol_type = protein
                        note = Parvovirus Adeno-associated virus
                        organism = unidentified SEQUENCE: 715
STGGTAGTQ                                                                        9

SEQ ID NO: 716          moltype =     length =
SEQUENCE: 716
000

SEQ ID NO: 717          moltype = AA  length = 8
FEATURE                 Location/Qualifiers
source                  1..8
                        mol_type = protein
                        note = Parvovirus Adeno-associated virus
                        organism = unidentified SEQUENCE: 717
LSQNNNSN                                                                         8

SEQ ID NO: 718          moltype = AA  length = 7
FEATURE                 Location/Qualifiers
source                  1..7
                        mol_type = protein
                        note = Parvovirus Adeno-associated virus
                        organism = unidentified SEQUENCE: 718
KDDEERF                                                                          7

SEQ ID NO: 719          moltype = AA  length = 6
FEATURE                 Location/Qualifiers
source                  1..6
                        mol_type = protein
                        note = Parvovirus Adeno-associated virus
                        organism = unidentified SEQUENCE: 719
GAGKDN                                                                           6

SEQ ID NO: 720          moltype = AA  length = 10
FEATURE                 Location/Qualifiers
source                  1..10
                        mol_type = protein
                        note = Parvovirus Adeno-associated virus
                        organism = unidentified SEQUENCE: 720
NAAPIVGAVN                                                                      10

SEQ ID NO: 721          moltype =     length =
SEQUENCE: 721
000

SEQ ID NO: 722          moltype = AA  length = 7
FEATURE                 Location/Qualifiers
source                  1..7
                        mol_type = protein
                        note = Parvovirus Adeno-associated virus
                        organism = unidentified SEQUENCE: 722
NTDGTYS                                                                          7
```

| | | |
|---|---|---|
| SEQ ID NO: 723<br>FEATURE<br>source<br><br>SEQUENCE: 723<br>NGTSGGST | moltype = AA length = 8<br>Location/Qualifiers<br>1..8<br>mol_type = protein<br>note = Parvovirus Adeno-associated virus<br>organism = unidentified | 8 |
| SEQ ID NO: 724<br>FEATURE<br>source<br><br>SEQUENCE: 724<br>VFMIPQYGYL | moltype = AA length = 10<br>Location/Qualifiers<br>1..10<br>mol_type = protein<br>note = Parvovirus Adeno-associated virus<br>organism = unidentified | 10 |
| SEQ ID NO: 725<br>FEATURE<br>source<br><br>SEQUENCE: 725<br>STGGTQGTQ | moltype = AA length = 9<br>Location/Qualifiers<br>1..9<br>mol_type = protein<br>note = Parvovirus Adeno-associated virus<br>organism = unidentified | 9 |
| SEQ ID NO: 726<br>SEQUENCE: 726<br>000 | moltype = length = | |
| SEQ ID NO: 727<br>FEATURE<br>source<br><br>SEQUENCE: 727<br>LSQNNNSN | moltype = AA length = 8<br>Location/Qualifiers<br>1..8<br>mol_type = protein<br>note = Parvovirus Adeno-associated virus<br>organism = unidentified | 8 |
| SEQ ID NO: 728<br>FEATURE<br>source<br><br>SEQUENCE: 728<br>KDDEERF | moltype = AA length = 7<br>Location/Qualifiers<br>1..7<br>mol_type = protein<br>note = Parvovirus Adeno-associated virus<br>organism = unidentified | 7 |
| SEQ ID NO: 729<br>FEATURE<br>source<br><br>SEQUENCE: 729<br>GAGRDN | moltype = AA length = 6<br>Location/Qualifiers<br>1..6<br>mol_type = protein<br>note = Parvovirus Adeno-associated virus<br>organism = unidentified | 6 |
| SEQ ID NO: 730<br>FEATURE<br>source<br><br>SEQUENCE: 730<br>NTGPIVGNVN | moltype = AA length = 10<br>Location/Qualifiers<br>1..10<br>mol_type = protein<br>note = Parvovirus Adeno-associated virus<br>organism = unidentified | 10 |
| SEQ ID NO: 731<br>SEQUENCE: 731<br>000 | moltype = length = | |
| SEQ ID NO: 732<br>FEATURE<br>source<br><br>SEQUENCE: 732<br>NTEGTYS | moltype = AA length = 7<br>Location/Qualifiers<br>1..7<br>mol_type = protein<br>note = Parvovirus Adeno-associated virus<br>organism = unidentified | 7 |

```
SEQ ID NO: 733            moltype = AA  length = 8
FEATURE                   Location/Qualifiers
source                    1..8
                          mol_type = protein
                          note = Parvovirus Adeno-associated virus
                          organism = unidentified
SEQUENCE: 733
RLGTTSSS                                                                    8

SEQ ID NO: 734            moltype = AA  length = 10
FEATURE                   Location/Qualifiers
source                    1..10
                          mol_type = protein
                          note = Parvovirus Adeno-associated virus
                          organism = unidentified
SEQUENCE: 734
VFMVPQYGYC                                                                 10

SEQ ID NO: 735            moltype = AA  length = 9
FEATURE                   Location/Qualifiers
source                    1..9
                          mol_type = protein
                          note = Parvovirus Adeno-associated virus
                          organism = unidentified
SEQUENCE: 735
GETLNQGNA                                                                   9

SEQ ID NO: 736            moltype =     length =
SEQUENCE: 736
000

SEQ ID NO: 737            moltype = AA  length = 12
FEATURE                   Location/Qualifiers
source                    1..12
                          mol_type = protein
                          note = Parvovirus Adeno-associated virus
                          organism = unidentified
SEQUENCE: 737
ASQNYKIPAS GG                                                              12

SEQ ID NO: 738            moltype = AA  length = 7
FEATURE                   Location/Qualifiers
source                    1..7
                          mol_type = protein
                          note = Parvovirus Adeno-associated virus
                          organism = unidentified
SEQUENCE: 738
GPSDGDF                                                                     7

SEQ ID NO: 739            moltype = AA  length = 6
FEATURE                   Location/Qualifiers
source                    1..6
                          mol_type = protein
                          note = Parvovirus Adeno-associated virus
                          organism = unidentified
SEQUENCE: 739
VTGNTT                                                                      6

SEQ ID NO: 740            moltype = AA  length = 10
FEATURE                   Location/Qualifiers
source                    1..10
                          mol_type = protein
                          note = Parvovirus Adeno-associated virus
                          organism = unidentified
SEQUENCE: 740
TTAPITGNVT                                                                 10

SEQ ID NO: 741            moltype =     length =
SEQUENCE: 741
000

SEQ ID NO: 742            moltype = AA  length = 7
FEATURE                   Location/Qualifiers
source                    1..7
                          mol_type = protein
                          note = Parvovirus Adeno-associated virus
                          organism = unidentified
SEQUENCE: 742
```

-continued

| | |
|---|---|
| DTTGKYT | 7 |
| SEQ ID NO: 743<br>FEATURE<br>source<br><br>SEQUENCE: 743 | moltype = AA  length = 8<br>Location/Qualifiers<br>1..8<br>mol_type = protein<br>note = Parvovirus Adeno-associated virus<br>organism = unidentified |
| RIGTTANS | 8 |
| SEQ ID NO: 744<br>FEATURE<br>source<br><br>SEQUENCE: 744 | moltype = AA  length = 10<br>Location/Qualifiers<br>1..10<br>mol_type = protein<br>note = Parvovirus Adeno-associated virus<br>organism = unidentified |
| VFMVPQYGYC | 10 |
| SEQ ID NO: 745<br>FEATURE<br>source<br><br>SEQUENCE: 745 | moltype = AA  length = 9<br>Location/Qualifiers<br>1..9<br>mol_type = protein<br>note = Parvovirus Adeno-associated virus<br>organism = unidentified |
| GNSLNQGTA | 9 |
| SEQ ID NO: 746<br>SEQUENCE: 746<br>000 | moltype =   length = |
| SEQ ID NO: 747<br>FEATURE<br>source<br><br>SEQUENCE: 747 | moltype = AA  length = 12<br>Location/Qualifiers<br>1..12<br>mol_type = protein<br>note = Parvovirus Adeno-associated virus<br>organism = unidentified |
| ANQNYKIPAS GG | 12 |
| SEQ ID NO: 748<br>FEATURE<br>source<br><br>SEQUENCE: 748 | moltype = AA  length = 7<br>Location/Qualifiers<br>1..7<br>mol_type = protein<br>note = Parvovirus Adeno-associated virus<br>organism = unidentified |
| GAGDSDF | 7 |
| SEQ ID NO: 749<br>FEATURE<br>source<br><br>SEQUENCE: 749 | moltype = AA  length = 6<br>Location/Qualifiers<br>1..6<br>mol_type = protein<br>note = Parvovirus Adeno-associated virus<br>organism = unidentified |
| PSGNTT | 6 |
| SEQ ID NO: 750<br>FEATURE<br>source<br><br>SEQUENCE: 750 | moltype = AA  length = 10<br>Location/Qualifiers<br>1..10<br>mol_type = protein<br>note = Parvovirus Adeno-associated virus<br>organism = unidentified |
| TTAPHIANLD | 10 |
| SEQ ID NO: 751<br>SEQUENCE: 751<br>000 | moltype =   length = |
| SEQ ID NO: 752<br>FEATURE<br>source | moltype = AA  length = 7<br>Location/Qualifiers<br>1..7<br>mol_type = protein<br>note = Parvovirus Adeno-associated virus<br>organism = unidentified |

```
SEQUENCE: 752
DNAGNYH                                                                 7

SEQ ID NO: 753          moltype = AA  length = 8
FEATURE                 Location/Qualifiers
source                  1..8
                        mol_type = protein
                        note = Parvovirus Adeno-associated virus
                        organism = unidentified
SEQUENCE: 753
RLGTTSNS                                                                8

SEQ ID NO: 754          moltype = AA  length = 10
FEATURE                 Location/Qualifiers
source                  1..10
                        mol_type = protein
                        note = Parvovirus Adeno-associated virus
                        organism = unidentified
SEQUENCE: 754
VFMVPQYGYC                                                              10

SEQ ID NO: 755          moltype = AA  length = 9
FEATURE                 Location/Qualifiers
source                  1..9
                        mol_type = protein
                        note = Parvovirus Adeno-associated virus
                        organism = unidentified
SEQUENCE: 755
GETLNQGNA                                                               9

SEQ ID NO: 756          moltype =     length =
SEQUENCE: 756
000

SEQ ID NO: 757          moltype = AA  length = 12
FEATURE                 Location/Qualifiers
source                  1..12
                        mol_type = protein
                        note = Parvovirus Adeno-associated virus
                        organism = unidentified
SEQUENCE: 757
ASQNYKIPAS GG                                                           12

SEQ ID NO: 758          moltype = AA  length = 7
FEATURE                 Location/Qualifiers
source                  1..7
                        mol_type = protein
                        note = Parvovirus Adeno-associated virus
                        organism = unidentified
SEQUENCE: 758
GPSDGDF                                                                 7

SEQ ID NO: 759          moltype = AA  length = 6
FEATURE                 Location/Qualifiers
source                  1..6
                        mol_type = protein
                        note = Parvovirus Adeno-associated virus
                        organism = unidentified
SEQUENCE: 759
VTGNTT                                                                  6

SEQ ID NO: 760          moltype = AA  length = 10
FEATURE                 Location/Qualifiers
source                  1..10
                        mol_type = protein
                        note = Parvovirus Adeno-associated virus
                        organism = unidentified
SEQUENCE: 760
TTAPITGNVT                                                              10

SEQ ID NO: 761          moltype =     length =
SEQUENCE: 761
000

SEQ ID NO: 762          moltype = AA  length = 7
FEATURE                 Location/Qualifiers
source                  1..7
                        mol_type = protein
                        note = Parvovirus Adeno-associated virus
```

-continued

```
SEQUENCE: 762
DTTGKYT                                                                 7

SEQ ID NO: 763          moltype = AA   length = 8
FEATURE                 Location/Qualifiers
source                  1..8
                        mol_type = protein
                        note = Parvovirus Adeno-associated virus
                        organism = unidentified
SEQUENCE: 763
RLGSSNAS                                                                8

SEQ ID NO: 764          moltype = AA   length = 10
FEATURE                 Location/Qualifiers
source                  1..10
                        mol_type = protein
                        note = Parvovirus Adeno-associated virus
                        organism = unidentified
SEQUENCE: 764
VFMVPQYGYC                                                              10

SEQ ID NO: 765          moltype = AA   length = 9
FEATURE                 Location/Qualifiers
source                  1..9
                        mol_type = protein
                        note = Parvovirus Adeno-associated virus
                        organism = unidentified
SEQUENCE: 765
GGTLNQGNS                                                               9

SEQ ID NO: 766          moltype =      length =
SEQUENCE: 766
000

SEQ ID NO: 767          moltype = AA   length = 12
FEATURE                 Location/Qualifiers
source                  1..12
                        mol_type = protein
                        note = Parvovirus Adeno-associated virus
                        organism = unidentified
SEQUENCE: 767
ASQNYKIPQG RN                                                           12

SEQ ID NO: 768          moltype = AA   length = 7
FEATURE                 Location/Qualifiers
source                  1..7
                        mol_type = protein
                        note = Parvovirus Adeno-associated virus
                        organism = unidentified
SEQUENCE: 768
ANDATDF                                                                 7

SEQ ID NO: 769          moltype = AA   length = 6
FEATURE                 Location/Qualifiers
source                  1..6
                        mol_type = protein
                        note = Parvovirus Adeno-associated virus
                        organism = unidentified
SEQUENCE: 769
ITGNTT                                                                  6

SEQ ID NO: 770          moltype = AA   length = 10
FEATURE                 Location/Qualifiers
source                  1..10
                        mol_type = protein
                        note = Parvovirus Adeno-associated virus
                        organism = unidentified
SEQUENCE: 770
TTVPTVDDVD                                                              10

SEQ ID NO: 771          moltype =      length =
SEQUENCE: 771
000

SEQ ID NO: 772          moltype = AA   length = 7
FEATURE                 Location/Qualifiers
source                  1..7
                        mol_type = protein
```

```
                               note = Parvovirus Adeno-associated virus
                               organism = unidentified
SEQUENCE: 772
DNAGAYK                                                                       7

SEQ ID NO: 773                 moltype = AA   length = 8
FEATURE                        Location/Qualifiers
source                         1..8
                               mol_type = protein
                               note = Parvovirus Adeno-associated virus
                               organism = unidentified
SEQUENCE: 773
RIQGPSGG                                                                      8

SEQ ID NO: 774                 moltype = AA   length = 10
FEATURE                        Location/Qualifiers
source                         1..10
                               mol_type = protein
                               note = Parvovirus Adeno-associated virus
                               organism = unidentified
SEQUENCE: 774
IYTIPQYGYC                                                                   10

SEQ ID NO: 775                 moltype = AA   length = 9
FEATURE                        Location/Qualifiers
source                         1..9
                               mol_type = protein
                               note = Parvovirus Adeno-associated virus
                               organism = unidentified
SEQUENCE: 775
VSQAGSSGR                                                                     9

SEQ ID NO: 776                 moltype =     length =
SEQUENCE: 776
000

SEQ ID NO: 777                 moltype = AA   length = 12
FEATURE                        Location/Qualifiers
source                         1..12
                               mol_type = protein
                               note = Parvovirus Adeno-associated virus
                               organism = unidentified
SEQUENCE: 777
ASNITKNNVF SV                                                                12

SEQ ID NO: 778                 moltype = AA   length = 7
FEATURE                        Location/Qualifiers
source                         1..7
                               mol_type = protein
                               note = Parvovirus Adeno-associated virus
                               organism = unidentified
SEQUENCE: 778
FSGEPDR                                                                       7

SEQ ID NO: 779                 moltype = AA   length = 8
FEATURE                        Location/Qualifiers
source                         1..8
                               mol_type = protein
                               note = Parvovirus Adeno-associated virus
                               organism = unidentified
SEQUENCE: 779
VYDQTTAT                                                                      8

SEQ ID NO: 780                 moltype = AA   length = 10
FEATURE                        Location/Qualifiers
source                         1..10
                               mol_type = protein
                               note = Parvovirus Adeno-associated virus
                               organism = unidentified
SEQUENCE: 780
VTPGTRAAVN                                                                   10

SEQ ID NO: 781                 moltype =     length =
SEQUENCE: 781
000

SEQ ID NO: 782                 moltype = AA   length = 7
FEATURE                        Location/Qualifiers
source                         1..7
```

```
                        mol_type = protein
                        note = Parvovirus Adeno-associated virus
                        organism = unidentified
SEQUENCE: 782
SDTGSYS                                                                    7

SEQ ID NO: 783          moltype = AA  length = 736
FEATURE                 Location/Qualifiers
REGION                  1..736
                        note = Recombinant AAV capsid protein
source                  1..736
                        mol_type = protein
                        organism = synthetic construct
SEQUENCE: 783
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTSNGRGVT LGFSQGGPNT MANQAKNWLP  480
GPCYRQQRVS TGTNLGKEQN FAWTAGTKYH LNGRNSLANP GIAMATHKDD EERFFPSNGI  540
LIFGKQNAAR DNADYSDVML TSEEEIKTTN PVATEEYGIV ADNVMEPTRA PQIGTVNSQG  600
ALPGMVWQNR DVYLQGPIWA KIPHTDGNFH PSPLMGGFGL KHPPPQILIK NTPVPADPRS  660
TFNGDKLNSF ITQYSTGQVS VEIEWELQKE NSKRWNPEIQ YTSNYYKSTS VDFAVNTEGV  720
YSEPRPIGTR YLTRNL                                                 736

SEQ ID NO: 784          moltype = AA  length = 736
FEATURE                 Location/Qualifiers
REGION                  1..736
                        note = Recombinant AAV capsid protein
source                  1..736
                        mol_type = protein
                        organism = synthetic construct
SEQUENCE: 784
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTSNGRGVT LGFSQGGPNT MANQAKNWLP  480
GPCYRQQRVS TMSAASGSGN FAWTAGTKYH LNGRNSLANP GIAMATHKDD EERFFPSNGI  540
LIFGKQNAAR DNADYSDVML TSEEEIKTTN PVATEEYGIV ADNVMEPTRA PQIGTVNSQG  600
ALPGMVWQNR DVYLQGPIWA KIPHTDGNFH PSPLMGGFGL KHPPPQILIK NTPVPADPRS  660
TFNGDKLNSF ITQYSTGQVS VEIEWELQKE NSKRWNPEIQ YTSNYYKSTS VDFAVNTEGV  720
YSEPRPIGTR YLTRNL                                                 736

SEQ ID NO: 785          moltype = AA  length = 736
FEATURE                 Location/Qualifiers
REGION                  1..736
                        note = Recombinant AAV capsid protein
source                  1..736
                        mol_type = protein
                        organism = synthetic construct
SEQUENCE: 785
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDSE  180
SVPDPQPLGE PPAAPSGVGP NTMAAGGGAP MADNNEGADG VGSSSGNWHC DSTWLGDRVI  240
TTSTRTWALP TYNNHLYKQI SNGTSGGATN DNTYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTSNGRGVT LGFSQGGPNT MANQAKNWLP  480
GPCYRQQRVS TVATRDGQLN FAWTAGTKYH LNGRNSLANP GIAMATHKDD EERFFPSNGI  540
LIFGKQNAAR DNADYSDVML TSEEEIKTTN PVATEEYGIV ADNVMEPTRA PQIGTVNSQG  600
ALPGMVWQNR DVYLQGPIWA KIPHTDGNFH PSPLMGGFGL KHPPPQILIK NTPVPADPRS  660
TFNGDKLNSF ITQYSTGQVS VEIEWELQKE NSKRWNPEIQ YTSNYYKSTS VDFAVNTEGV  720
YSEPRPIGTR YLTRNL                                                 736
```